US012630594B2

(12) United States Patent
Matsunaga et al.

(10) Patent No.: US 12,630,594 B2
(45) **Date of Patent: *May 19, 2026**

(54) ALLERGY ANTIGEN AND EPITOPE FOR SAME

(71) Applicant: HOYU CO., LTD., Aichi (JP)

(72) Inventors: Kayoko Matsunaga, Aichi (JP); Akiko Yagami, Aichi (JP); Naoshi Shimojo, Aichi (JP); Fumiaki Ohno, Aichi (JP)

(73) Assignee: HOYU CO., LTD., Nagoya (JP)

( * ) Notice: Subject to any disclaimer, the term of this patent is extended or adjusted under 35 U.S.C. 154(b) by 51 days.

This patent is subject to a terminal disclaimer.

(21) Appl. No.: 18/147,789

(22) Filed: Dec. 29, 2022

(65) Prior Publication Data

US 2023/0295251 A1      Sep. 21, 2023

Related U.S. Application Data

(62) Division of application No. 16/608,361, filed as application No. PCT/JP2017/045832 on Dec. 20, 2017, now abandoned.

(30) Foreign Application Priority Data

Apr. 28, 2017      (WO) .................. PCT/JP2017/017018

(51) Int. Cl.
| | |
|---|---|
| *C07K 14/46* | (2006.01) |
| *A23L 17/00* | (2016.01) |
| *A23L 17/30* | (2016.01) |
| *A23L 33/00* | (2016.01) |
| *A61K 39/00* | (2006.01) |
| *A61K 39/35* | (2006.01) |
| *A61P 37/08* | (2006.01) |
| *C12N 15/09* | (2006.01) |
| *C12Q 1/48* | (2006.01) |
| *C12Q 1/6888* | (2018.01) |
| *G01N 33/53* | (2006.01) |
| *G01N 33/68* | (2006.01) |
| *C07K 14/47* | (2006.01) |

(52) U.S. Cl.
CPC ............ *C07K 14/461* (2013.01); *A23L 17/00* (2016.08); *A23L 17/30* (2016.08); *A23L 33/40* (2016.08); *A61K 39/00* (2013.01); *A61K 39/35* (2013.01); *A61P 37/08* (2018.01); *C12Q 1/48* (2013.01); *C12Q 1/6888* (2013.01); *G01N 33/53* (2013.01); *G01N 33/6854* (2013.01); *G01N 33/6893* (2013.01); *A23V 2002/00* (2013.01); *C07K 14/47* (2013.01); *C12N 15/09* (2013.01); *G01N 2800/24* (2013.01)

(58) Field of Classification Search
None
See application file for complete search history.

(56) References Cited

U.S. PATENT DOCUMENTS

| | | |
|---|---|---|
| 2006/0121478 A1 | 6/2006 | North |
| 2011/0071043 A1 | 3/2011 | Sampson et al. |
| 2019/0256566 A1 | 8/2019 | Matsunaga et al. |
| 2020/0268877 A1 | 8/2020 | Matsunaga et al. |

FOREIGN PATENT DOCUMENTS

| | | |
|---|---|---|
| CN | 103931936 A | 7/2014 |
| JP | 2000-125775 A | 5/2000 |
| JP | 2002-286716 A | 10/2002 |
| JP | 2005-538710 A | 12/2005 |
| JP | 2011-033544 A | 2/2011 |
| JP | 2011-033546 A | 2/2011 |
| JP | 2011-033547 A | 2/2011 |
| JP | 2011-033548 A | 2/2011 |
| JP | 5894695 B1 | 3/2016 |
| WO | 2002/50269 A1 | 6/2002 |
| WO | 2009/078806 A2 | 6/2009 |
| WO | 2015/048340 A2 | 4/2015 |
| WO | 2015/048342 A2 | 4/2015 |
| WO | 2016/190376 A1 | 12/2016 |

OTHER PUBLICATIONS

Abaza et al., Effects of amino acid substitutions outside an antigenic site on protein binding to monoclonal antibodies of predetermined specificity obtained by peptide immunization: demonstration with region 94-100 (antigenic site 3) of myoglobin. J Protein Chem. Oct. 1992;11(5):433-44.
Agrisera, Product No. AS05 062, HSC70 / salmon heat shock cognate protein 70. www.agrisera.com, 1 page, downloaded Jun. 16, 2022.
An et al., Alpha-actinin is a new type of house dust mite allergen. PLoS One. Dec. 6, 2013;8(12):e81377, 9 pages.
Blumenthal et al., Definition of an Allergen (Immunobiology). Allergens and Allergen Immunotherapy, Third Edition, Revised and Expanded. Marcel Dekker, Inc., New York. Richard F. Lockey (Ed.). Chapter 2, pp. 37-50, (2004).

(Continued)

*Primary Examiner* — Nora M Rooney
(74) *Attorney, Agent, or Firm* — McCarter & English, LLP; Yu Lu

(57) ABSTRACT

The present invention provides novel antigens of an allergy to fish, methods and kits for diagnosing an allergy to fish, pharmaceutical compositions comprising such an antigen, fishes, fish eggs or processed products of such fish or fish egg in which such an antigen is eliminated, fishes that deliver such fish eggs or are born from such fish egg, and a tester for determining the presence or absence of a fish antigen in an object of interest. The present invention also relates to polypeptides comprising an epitope of an antigen, kits, compositions and methods for diagnosing an allergy, comprising such a polypeptide, pharmaceutical compositions comprising such a polypeptide, and raw materials or processed products in which an antigen comprising such a polypeptide is eliminated or reduced. The present invention further relates to a tester for determining the presence or absence of an antigen in an object of interest.

4 Claims, 6 Drawing Sheets

Specification includes a Sequence Listing.

(56) References Cited

OTHER PUBLICATIONS

Campbell, General properties and applications of monoclonal antibodies. Monoclonal Antibody Technology. Elsevier Science Publishers B.V., Amsterdam. Chapter 1, pp. 1-32, (1985).

Colman et al., Effects of amino acid sequence changes on antibody-antigen interactions. Res Immunol. Jan. 1994;145(1):33-6.

Elsayed et al., Characterization of a major allergen (cod). Observations on effect of denaturation on the allergenic activity. J Allergy. May 1971;47(5):283-91.

Gamez et al., New shrimp IgE-binding proteins involved in mite-seafood cross-reactivity. Mol Nutr Food Res. Sep. 2014;58(9):1915-25.

Gonzalez-Mancebo et al., Identification of a novel protein allergen in Mediterranean silverside fish species. Ann Allergy Asthma Immunol. Jul. 2014;113(1):114-5.

Harlow et al., Antibodies, A Laboratory Manual. Cold Spring Harbor Laboratory. Chapters 5-6, pp. 53-157, (1988).

Hart et al., Vertebrate isoforms of actin capping protein beta have distinct functions In vivo. J Cell Biol. Dec. 13, 1999;147(6):1287-98.

Homaei et al., Enzyme immobilization: an update. J Chem Biol. Aug. 29, 2013;6(4):185-205.

Kobayashi et al., Study of the cross-reactivity of fish allergens based on a questionnaire and blood testing. Allergol Int. Jul. 2016;65(3):272-9.

Kobayashi et al., Study of the cross-reactivity of fish allergens based on a questionnaire and blood testing. Allergol Int. Feb. 2016, pp. 1-8, prepublication version.

Kuehn et al., Identification of enolases and aldolases as important fish allergens in cod, salmon and tuna: component resolved diagnosis using parvalbumin and the new allergens. Clin Exp Allergy. Jul. 2013;43(7):811-22.

Lederman et al., A single amino acid substitution in a common African allele of the CD4 molecule ablates binding of the monoclonal antibody, OKT4. Mol Immunol. Nov. 1991;28(11):1171-81.

Lee et al., Proteomic profiling of lymphedema development in mouse model. Cell Biochem Funct. Jul. 2016;34 (5):317-25.

Lee et al., Proteomic profiling of lymphedema development in mouse model. Cell Biochem Funct. Jul. 2016;34 (5):317-25. Published online May 5, 2016, DOI: 10.1002/cbf.3192.

Matsuo et al., Identification of the IgE-binding epitope in omega-5 gliadin, a major allergen in wheat-dependent exercise-induced anaphylaxis. J Biol Chem. Mar. 26, 2004;279(13):12135-40.

Mermelstein, Allergen Detectives. Food Technology. Jan. 2014;68(1):68-71.

Mills et al., Differential expression of the actin-binding proteins, alpha-actinin-2 and -3, in different species: implications for the evolution of functional redundancy. Hum Mol Genet. Jun. 15, 2001;10(13):1335-46.

Nakamura et al., Antigen analysis of shrimp allergy using clinical research system for allergic disease "Minerva." The Journal of Allergy and Clinical Immunology. Feb. 1, 2020;145(2):Abstract 721, 1 page. DOI: https://doi.org/10.1016/iaci.2019.12.177.

Nilsson et al., Intrasplenic immunization with minute amounts of antigen. Immunol Today. Jan. 1990;11(1):10-2.

Perez-Gordo et al., Epitope mapping of Atlantic salmon major allergen by peptide microarray immunoassay. Int Arch Allergy Immunol. 2012;157(1):31-40.

Polymeropoulo et al., Growth hormone transgenesis and polyploidy increase metabolic rate, alter the cardiorespiratory response and influence HSP expression in response to acute hypoxia in Atlantic salmon (*Salmo salar*) yolk-sac alevins. The Journal of Experimental Biology. 2014;217:2268-2276.

Sakaguchi et al., IgE antibody to fish gelatin (type I collagen) in patients with fish allergy. J Allergy Clin Immunol. Sep. 2000;106(3):579-84.

Shimojo et al., Occupational fish allergy caused by percutaneous sensitization with a-actinin-3. Contact Dermatitis. May 2017;76(5):322-323.

UniProt Accession No. B5RIA0, Full=Putative uncharacterized protein. 1 page, Nov. 4, 2008.

UniProtKB Accession No. B5X3U6, Heat shock cognate 70 kDa protein. 5 pages, (2018).

UniProtKB Accession No. Q8AW95, 1 page, Mar. 1, 2003.

UniProtKB B5RI29, EEF1A2 binding protein-like. Retrieved online at: https://www.uniprot.org/uniprot/B5RI29. 6 pages, Aug. 12, 2020.

Van Der Ventel et al., Differential responses to natural and recombinant allergens in a murine model of fish allergy. Mol Immunol. Jan. 2011;48(4):637-46.

Van Do et al., Allergy to fish parvalbumins: studies on the cross-reactivity of allergens from 9 commonly consumed fish. J Allergy Clin Immunol. Dec. 2005;116(6):1314-20.

Virel et al., Molecular evolution and structure of alpha-actinin. Mol Biol Evol. Jun. 2004;21(6):1024-31.

WHO/IUIS Allergen Nomenclature Sub-Committee, Allergen Nomenclature. 3 pages, Jun. 9, 2016.

Xing et al., Effects of atrazine and chlorpyrifos on the mRNA levels of HSP70 and HSC70 in the liver, brain, kidney and gill of common carp (*Cyprinus carpio* L.). Chemosphere. Jan. 2013;90(3):910-6.

Yasuda et al., Allergic study of food urticaria. (1). Allergic food urticaria due to fish. Arerugi. Dec. 1984;33 (12):1016-24.

International Search Report for Application No. PCT/JP2017/017018, dated Aug. 1, 2017, 4 pages.

International Search Report for Application No. PCT/JP2017/045832, dated Mar. 27, 2018, 4 pages.

Supplementary Partial European Search Report for Application No. 17813033.2, dated Oct. 15, 2019, 12 pages.

Supplementary Partial European Search Report for Application No. 17907256.6, dated Feb. 26, 2021, 14 pages.

2 D – P A G E (Salmon)

Immunoblot using serum of fish-allergic patient 1

| No. | Protein name |
|---|---|
| 1 | Alpha-actinin-3 |
| 2 | EEF1A2 binding protein-like |
| 3 | Alpha-1,4-glucan phosphorylase |
| 4 | Elongation factor 2 |
| 5 | Heat shock cognate 70 kDa protein |
| 6 | Serotransferrin |
| 7 | Myosin binding protein H-like |
| 8 | Desmin (fragment) |
| 9 | Capping protein (actin filament) muscle Z-line beta |

Fig. 1B

Immunoblot using serum of fish-allergic patient 2

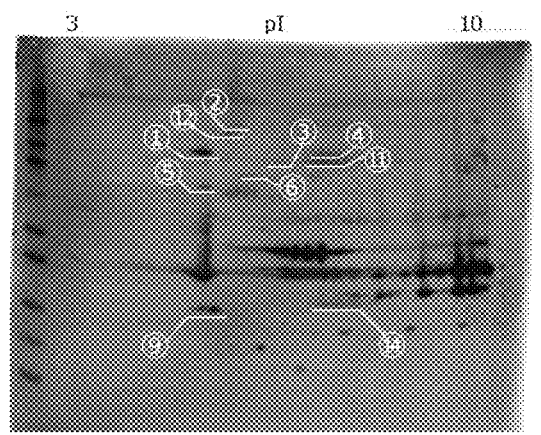

Immunoblot using serum of fish-allergic patient 3

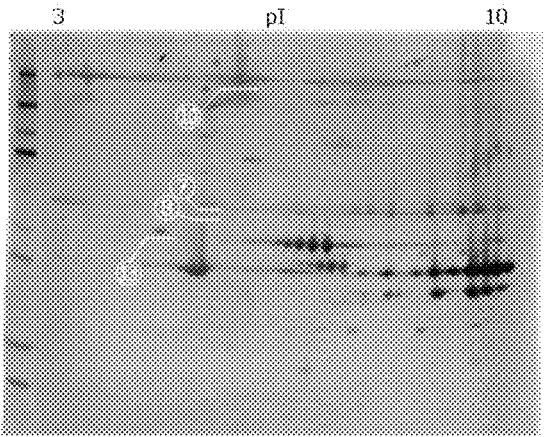

| No. | Protein name |
|---|---|
| 1 | Alpha-actinin-3 |
| 2 | EEF1A2 binding protein-like |
| 3 | Alpha-1,4-glucan phosphorylase |
| 4 | Elongation factor 2 |
| 5 | Heat shock cognate 70 kDa protein |
| 6 | Serotransferrin |
| 7 | Myosin binding protein H-like |
| 8 | Desmin (fragment) |
| 9 | Capping protein (actin filament) muscle Z-line beta |
| 10 | Myosin heavy chain, fast skeletal muscle-like |
| 11 | Glycogen phosphorylase, muscle form-like |
| 12 | Myosin-binding protein C, fast-type-like |
| 13 | ATP synthase subunit beta, mitochondrial |
| 14 | L-lactate dehydrogenase A chain-like |

Results of immunoblot of 10 fish species using serum of fish-allergic patient 1

Results of immunoblot of 10 fish species using serum of non-fish-allergic subject Results of immunoblot of 6 fish species using serum of fish-allergic patient 4

SEQUENCE LISTING

```
Sequence total quantity: 451
SEQ ID NO: 1          moltype = DNA  length = 2685
FEATURE               Location/Qualifiers
misc_feature          1..2685
                      note = PREDICTED: alpha-actinin-3
source                1..2685
                      mol_type = other DNA
```

```
                    organism = synthetic construct
SEQUENCE: 1
atgacggcaa tcgaaactca ggtgcaatat ggctcctaca tgacttcgga gcaagtctac   60
atgacccaag aggatgattg ggacagggac cttctgttgg accctgcctg ggagaaacag  120
cagcgcaaga ccttcaccgc ctggtgcaac tctcacctgc gtaaagcggg cacacagatt  180
gagaacattg aggaggactt caggaatggg ctcaagctca tgttgctgtt agaggtcatc  240
tcaggtgaaa ggcttcccaa accagacaaa ggcaaaatgc gtttccacaa aatcgccaac  300
gtgaacaagg ccctggattt catctgcagc aagggagtca agctggtgtc catcggtgcc  360
gaggagattg tggatggtaa tgtgaagatg accctgggga tgatctggac catcattctg  420
cgtttcgcca tccaggacat ctctgtagag gagacctctg ctaaggaggg tctgttgctg  480
tggtgccaga ggaagactgc cccctacagg aatgtcaatg tgcagaactt ccacatcagt  540
tggaaggatg gcctggcact gtgtgccctc atccacagac acagacctga cctcattgac  600
tactccaaac tgcgcaagga tgaccccatg ggcaatctca cactgtgcctt tgaggtggca  660
gagaagtacc tggacatccc caagatgttg gatgcagaag atattgtgaa cacccccgag  720
cccgacgaga aagccatcat gacctatgtg tcctgcttct atcatgcctt cgctggagcc  780
gagcaggccg agacagctgc caataggatc tgcaaggtgt tggctgtcaa ccaggagaac  840
gagaagctca tggaggagta tgagaagctg gccagtgagc tgctggagtg gatccgtcgc  900
accatcccct ggctggagaa ccgcgtggct gagcagacca tgcgcgccat gcagcagaag  960
ctggaggact tccgtgacta ccgtcgcgtc cacaagcctc ccaaggtgca ggagaagtgt  1020
cagctggaga ttaacttcaa caccctgcag accaagctga ggctgagcaa caggcccgcc  1080
ttcatgccct ccgagggcaa gatggtgtcg gacattgcca tgcctggaa gggtctggag  1140
caggtaggac agggctatga ggagtggctg ctcactgaga tcagacgcct agaggctg     1200
gaccacctgg ctgagaagtt caagcagaag tcttccctgc atgagtcctg gacctcaggt  1260
aaggtggagc tgctgtccat gaaggactat gagtctgcct cactgatgga gatccgtgcc  1320
ctgatgagga agcacgaggc gtttgagagc gacctggctg cccaccagga cagagtggag  1380
cagattgctg ccatcgccca ggagctcaat gagctggact atcatgatgc cgtcaccatc  1440
aacgcccgct gccagggtat ttgtgaccag tgggacaacc tgggcacctt gacccagaag  1500
aggagagact cactggagcg tgtggagaag ctgtgggaga ccatcgacca gctgtacctg  1560
gagtttgcca gagagcagc ccccttcaac aactggatgg acggagccat ggaggactta  1620
caggacatgt tcattgtgca cagcattgag gagatccaga gtctgatcac agcccatgac  1680
cagttcaagg ccaccctgcc agaggcagat aaggagcgcg ttgcaaccat gggaatccag  1740
aatgagatcg tgaagatcgc tcagacctac ggcatcaagc tgtcaggagt caacccctac  1800
accaaccttt ccccccagga catcaccgac aaatggggat ctgtgaaaca cctggtgccc  1860
ctcagggatc agatgctgca ggaggaggtg gccaggcagc agtccaacga gaggctgagg  1920
cgccagttcg ctgcccaggc caacatcatc ggacctgga tccagaccaa gatggaggag   1980
atcagccatg tgtctgtgga tatcgccggc tccctggagg aacagatgag caacctgaag  2040
cagtacgagc agaacatcat caactacaag tgcaacatcg acaagctgga gggagaccac  2100
caactcagcc aggagtccct catctttgac aacaagcaca ccaactacac catggagcat  2160
gtgcgtgtgg gctgggagca gctcctcacc accatcgcc gcaccatcaa cgaggtggag   2220
aaccagatcc tgacccgaga tgccaagggc atcagccagg agcagctcaa cgagttcaga  2280
gcctccttca accactttga caggaagaga aatggtatga tggacccaga tgacttccgt  2340
gcctgtctca tctccatggg ctacgatctg ggtgaggtgg agtttgcccg catcatgacg  2400
ctggtggatt ccaacaacac aggtgtggta accttccagg ccttcatcga cttcatgacc  2460
cgcgagacgg ccgagacaga caccgccgat caggtcatgg cctcattcaa gatcctggcc  2520
tctgacaaga catacatcac agtggaagaa ctgcgcaggg agctgccccc agagcaggcc  2580
gactactgca tcagccgcat gaccagttac atcggcagcg gcgcacccccc aggcgccctg  2640
gactacatct ccttctccag tgccctgtac ggagagagcg actta              2685
```

```
SEQ ID NO: 2              moltype = AA  length = 895
FEATURE                   Location/Qualifiers
REGION                    1..895
                          note = PREDICTED: alpha-actinin-3
source                    1..895
                          mol_type = protein
                          organism = synthetic construct
SEQUENCE: 2
MTAIETQVQY GSYMTSEQVY MTQEDDWDRD LLLDPAWEKQ QRKTFTAWCN SHLRKAGTQI   60
ENIEEDFRNG LKLMLLLEVI SGERLPKPDK GKMRFHKIAN VNKALDFICS KGVKLVSIGA  120
EEIVDGNVKM TLGMIWTIIL RFAIQDISVE ETSAKEGLLL WCQRKTAPYR NVNVQNFHIS  180
WKDGLALCAL IHRHRPDLID YSKLRKDDPM GNLNTAFEVA EKYLDIPKML DAEDIVNTPK  240
PDEKAIMTYV SCFYHAFAGA EQAETAANRI CKVLAVNQEN EKLMEEYEKL ASELLEWIRR  300
TIPWLENRVA EQTMRAMQQK LEDFRDYRRV HKPPKVQEKC QLEINFNTLQ TKLRLSNRPA  360
FMPSEGKMVS DIANAWKGLE QVEKGYEEWL LTEIRRLERL DHLAEKFKQK SSLHESWTSG  420
KVELLSMKDY ESASLMEIRA LMRKHEAFES DLAAHQDRVE QIAAIAQELN ELDYHDAVTI  480
NARCQGICDQ WDNLGTLTQK RRDSLERVEK LWETIDQLYL EFAKRAAPFN NWMDGAMEDL  540
QDMFIVHSIE EIQSLITAHD QFKATLPEAD KERVATMGIQ NEIVKIAQTY GIKLSGVNPY  600
TNLSPQDITD KWDAVKHLVP LRDQMLQEEV ARQQSNERLR RQFAAQANII GPWIQTKMEE  660
ISHVSVDIAG SLEEQMSNLK QYEQNIINYK CNIDKLEGDH QLSQESLIFD NKHTNYTMEH  720
VRVGWEQLLT TIARTINEVE NQILTRDAKG ISQEQLNEFR ASFNHFDRKR NGMMDPDDFR  780
ACLISMGYDL GEVEFARIMT LVDSNNTGVV TFQAFIDFMT RETAETDTAD QVMASFKILA  840
SDKTYITVEE LRRELPPEQA DYCISRMTSY IGSGAPPGAL DYISFSSALY GESDL       895
```

```
SEQ ID NO: 3              moltype = AA  length = 14
FEATURE                   Location/Qualifiers
REGION                    1..14
                          note = PREDICTED: alpha-actinin-3 fragment
source                    1..14
                          mol_type = protein
                          organism = synthetic construct
```

```
SEQUENCE: 3
ERVATMGIQN EIVK                                                              14

SEQ ID NO: 4              moltype = DNA  length = 3591
FEATURE                  Location/Qualifiers
misc_feature             1..3591
                         note = EEF1A2 binding protein-like
source                   1..3591
                         mol_type = other DNA
                         organism = synthetic construct
SEQUENCE: 4
atgtggaaaa agaaatcaaa gctcacggac cagacggcca ctggccaagt tgggatcaag   60
aagagatcaa aagtccctgg agttatgatc acgcagtatg tggagaaaat accagatggg  120
aaaagccacc ctgacttcac ccgcaagcct atcgcgttga ccattcagga gggtaaattc  180
gccttcttca aagccctggt tattggagat ccagaaccaa ccgtgacatg gggcagaaat  240
aatggagatg tgtcagatac atcaaaatat gtgacaaaat atgaccctgc tacacgtgag  300
cacttatttg agatggccaa tgtaaaacca gaacaagcag acacctacaa atgctttgca  360
gctaatgagt ttggaagagc agtggtcaca gtggtcctca atgttattga agttgggttc  420
aagaaagcac aagcggactc acaggtgcaa ccagaggcag ctgttgcaga tttttaaatct  480
gtattgaaga gaaaaagtaa aattcagccc aaaatggaaa agaaagaaga tggagaaata  540
gatccaagat tttgggaact cttgataagt gctgacaaga aagactatga gagcctcatg  600
ttggagtttg gagtcactga cttccgcttt atgctgaaga cactgaatga gattaagaag  660
gaaagagagg aagagcaagc acagttcatt gaaaacctag ctaacctgaa acctattgaa  720
gttgacccg atggctgtgc aacctttttca atagacatgg atctcattga acaaagcagc  780
aggatcttcc tctacaagga tggagtgatg attccataca gcaaggagtt gggagataca  840
atcaaacaca gcctaaagat agtgggccga aagtatcagt tcagcataag ggatctgttt  900
cctgatgatg ctgggctcta ccaggtggat gttgaggacg taaatgtatt ctccaccgat  960
tttaagattc ccatggtgga cttcctggtc aagattcagg agtgtaaggc catggagaga 1020
gaggatgctg tgtttgagtg tgtcctgtca cagcccttcg gcaagatcat gtgggttggc 1080
aagaacttac cattggaggc aggggataaa tatgatattg aggtttcaga agacaagctc 1140
atccacagac taatcattaa agacgttgct atggtggaca aaggcatcta tgccgctgtg 1200
gcaggaatca aatcttgcaa tgcctttctt gtggttgaag ccgacaaggg tgaacccggc 1260
aaaaagaaac aacgtaaaac cacaagggca ggaggagctg gagttgacct gacggcgatt 1320
gcccaagagc aggcagttaa aaacacggca gacagagagg tgctgaagga gaaggtgaaa 1380
gcaatcaatg acgagagagc ggctaatgcc actgcagcac ctgagacttc agctgaagct 1440
aaagctaaag ttaaggtggt agaggcttcc caaacaggag ctccaaaaca gggaccggca 1500
gttaaagggt ctgaccataa atccgtggat aatgagggat acagcattaa gagtggactc 1560
tcagatgtct ttgctctccg tggcaagaaa ggtgaactgg tttgtgagat gagccatgaa 1620
gttgatgggg cctggttcaa ggatgggag aagttatcca ccacagatgg aatagccata 1680
gtgaaagatg gaacgagaca cacgatgacc attcatagca gtagtgaaga cgacactgga 1740
gtctatcaca ttgaagcggg gggatttaaa tcagaggcaa aagtcactgt gggagaatta 1800
cctgccattg atgctgatga cctccacaag tttttctaagc ctgtgacaat aaaagtgggc 1860
cagaatgcat cctggaagat gccttataca ccacaggaca acttggaggt gaaatgtttt 1920
aaggatggca aagagttgaa ggatggtggt ggggtgaagt tggtgaagga ggtcaagcac 1980
agccggctgc tgctccggga gtgtctgcgt tctgacgctg gggagatcaa gattcaactc 2040
aaaaaccct ttggcactat agaggccaca tctcgactga ttgtccttga caagcccggc 2100
ccaccagaag gcccggtgga aatcttggag accacctcca ctgtgattga gctgcagtgg 2160
ggcgctccta aggacgacgg tggctcccccg gtgactaact acatcattga gcgcagcag 2220
ctgggacaga ccgtgtggaa gaagatgggg gatgtcgcag ctgacaaaac cacctacagg 2280
gacaggaatg tggtccatgg gaaactgtac atctacaata tctacgcagt gaacccagag 2340
gggaccagtg atgcactgca gactgaggaa acaatggcag gcgtattgat atttgctgct 2400
cgacctggag caccaaaagt ggtcagcgca tcaaagacct gcatcaacct gaaatgggag 2460
cccccagaag atgacggagg aattaagatt gatggctatc aactggaaaa acgcaaaaag 2520
gacacagctc agtggattgc tttgaaccca gtaactgagc ctattgaagt gctggagtac 2580
gcagtgaagg atgttgttga gggggcggag tatgagttca gggtatcggc catcaacgtt 2640
tctggggcgg gagagttcag tctcccctct gtgatggtga ctgcaaagaa tcccaacatg 2700
aggcctacat tcaaagatcc agaggacttc atggtgatca gggcgggaaa ctctgtgaga 2760
atcaaagttc tctatgaggc tgagcctcca ccggagatca cttggatgaa ggacaatgag 2820
cctgtatcca gttttataca gatcatcaac acagagggct gttcccagct tgtgatcccc 2880
tcaacaaaac gctctgattc aggaaattac accattgtgg ctaagaataa agttggaaag 2940
gccagctttg acattgaggt cctagtcaca gatgagccaa agcctcctgg tgcagtggag 3000
ctggagcaga ttgtccatgg caaagttatt gtgtcctggg aggcctctcc agaccaggag 3060
ctggacaaca ggctgtatta catggtggcc gagcacgact ccagcacacg catgtggcac 3120
actgtggcag accgcatctt tgacaattca tacacagcca ataacatcat gcctgggaag 3180
gagtaccact tcaaaatcta tgccaagaac gacatgggca tgtcagaccc ctccatgtca 3240
cccacctggg gcatcaacag caacagaatt cctataaaca caaacacgcc agtggaagtc 3300
agctttgaga aaccaccatc tgtcctggtc cctctgaaga tgcactcgcc accaaaagga 3360
ttccagatgt acatgacctg cgccatccgg ggatgcccca cacccagcgt cacgtggcac 3420
ctgaacaacg tctgcatcaa tggtgacagc aactactaca tcacccaactc gtatggctgg 3480
tgctccatgt acatccttag ggtcaggccc aaggacgccg agaatacaa agttgtcgca 3540
gttaactcct tcggcaaggc agaatgctcc actaaacttg ttgttaaaga c             3591

SEQ ID NO: 5              moltype = AA  length = 1197
FEATURE                  Location/Qualifiers
REGION                   1..1197
                         note = EEF1A2 binding protein-like
source                   1..1197
                         mol_type = protein
                         organism = synthetic construct
```

```
SEQUENCE: 5
MWKKKSKLTD QTATGQVGIK KRSKVPGVMI TQYVEKIPDG KSHPDFTRKP IALTIQEGKF   60
AFFKALVIGD PEPTVTWGRN NGDVSDTSKY VTKYDPATRE HLFEMANVKP EQADTYKCFA  120
ANEFGRAVVT VVLNVIEVGF KKAQADSQVQ PEAAVADFKS VLKRKSKIQP KMEKKEDGEI  180
DPRFWELLIS ADKKDYESLM LEFGVTDFRF MLKTLNEIKK EREEEQAQFI ENLANLKPIE  240
VGPDGCATFS IDMDLIEQSS RIFLYKDGVM IPYSKELGDT IKHSLKIVGR KYQFSIRDLF  300
PDDAGLYQVD VEDVNVFSTD FKIPMVDFLV KIQECKAMER EDAVFECVLS QPFGKIMWVG  360
KNLPLEAGDK YDIEVSEDKL IHRLIIKDVA MVDKGIYAAV AGIKSCNAFL VVEADKGEPG  420
KKKQRKTTRA GGAGVDLTAI AQEQAVKNTA DREVLKEKVK AINDERAANA TAAPETSAEA  480
KAKVKVVEAS QTGAPKQGPA VKGSDHKSVD NEGYSIKSGL SDVFALRGKK GELVCEMSHE  540
VDGAWFKDGE KLSTTDGIAI VKDGTRHTMT IHSSSEDDTG VYHIEAGGFK SEAKVTVGEL  600
PAIDADDLHK FSKPVTIKVG QNASWKMPYT PQDNLEVKWF KDGKELKDGG GVKLVKEVKH  660
SRLLLRECLR SDAGEIKIQL KNPFGTIEAT SRLIVLDKPG PPEGPVEILE TTSTVIELQW  720
GAPKDDGGSP VTNYIIERQQ LGQTVWKKMG DVAADKTTYR DRNVVHGKLY IYNIYAVNPE  780
GTSDALQTEE TMAGVLIFAG RPGAPKVVSA SKTCINLKWE PPEDDGGIKI DGYQLEKRKK  840
DTAQWIALNP VTEPIEVLEY AVKDVVEGAE YEFRVSAINV SGAGEFSLPS VMVTAKNPNM  900
RPTFKDPEDF MVIRAGNSVR IKVLYEAEPP PEITWMKDNE PVSSFIQIIN TEGCSQLVIP  960
STKRSDSGNY TIVAKNKVGE ASFDIEVLVT DEPKPPGAVE LEQIVHGKVI VSWEASPDQE 1020
LDNRLYYMVA EHDSSTRMWH TVADRIFDNS YTANNIMPGR EYHFKIYAKN DMGMSDPSMS 1080
PTWGINSNRI PINTNTPVEV SFEKPPSVLV PLKMHSPPKG FQMYMTCAIR GCPTPSVTWH 1140
LNNVCINGDS NYYITNSYGV CSMYILRVRP KDAGEYKVVA VNSFGKAECS TKLVVKD    1197

SEQ ID NO: 6                moltype = AA  length = 17
FEATURE                     Location/Qualifiers
REGION                      1..17
                            note = EEF1A2 binding protein-like fragment
source                      1..17
                            mol_type = protein
                            organism = synthetic construct
SEQUENCE: 6
AQADSQVQPE AAVADFK                                                   17

SEQ ID NO: 7                moltype = AA  length = 10
FEATURE                     Location/Qualifiers
REGION                      1..10
                            note = EEF1A2 binding protein-like fragment
source                      1..10
                            mol_type = protein
                            organism = synthetic construct
SEQUENCE: 7
GIYAAVAGIK                                                           10

SEQ ID NO: 8                moltype = AA  length = 21
FEATURE                     Location/Qualifiers
REGION                      1..21
                            note = EEF1A2 binding protein-like fragment
source                      1..21
                            mol_type = protein
                            organism = synthetic construct
SEQUENCE: 8
TTRAGGAGVD LTAIAQEQAV K                                              21

SEQ ID NO: 9                moltype = DNA  length = 2532
FEATURE                     Location/Qualifiers
misc_feature                1..2532
                            note = Alpha-1,4 glucan phosphorylase
source                      1..2532
                            mol_type = other DNA
                            organism = synthetic construct
SEQUENCE: 9
atgtcaaaac cgttgtcaga tcacgataga aagaagcaga tctccgtgag aggtcttgct   60
ggtgtggaaa atgtggcaga actgaaggtc gctttcaaca ggcatctcca ttttacgctg  120
gtcaaggaca gaaatgtggc atccaaacgg gattactact ttgctctcgc caacaccgtg  180
cgtgaccact tggtgggcag gtggatcaga acccagcaat actactatga gaaagatccc  240
aaacgtgtgt actacatctc cctggagttc tacatgggtc gcaccctgca gaacaccatg  300
gtgaacctgg cgctggaaaa cgcctgtgat gaggccatat accagctggg tctggacatg  360
gaggagctga aggacatgga ggaggacgca ggcctgggaa acggtggtct tggacgtctt  420
gccgcctgct tcctggactc tatggcttct ctgggtctgg ctgcgtatgg ctacggtatc  480
cgctatgagt ttggcatctt taaccagaag atcgtcaatg gatggcaggt tgaggaggct  540
gatgactggc tgcgttacgg caaccccctg gagaaggccc gacccgagta catgcgcccc  600
gtcaagttct atggcagaac cgagcacacc ccagagggtg tgaaatgggt tgacactcag  660
gtagtgttgg ctctgccata tgacacccct atccccgggt acagaaacaa cattgtcaac  720
accatgagac tgtggtctgc aaaggcccca tgcgacttca acctgaaaga cttcaacgtt  780
ggtaggtaca ttcaggctgt gttggacaga aacctatgcg gaacatttc ccgtgtgcat  840
taccccaatg ataacttctt tgagggcaag agctgcgtc tgaagcagga gtactttgtg  900
gtggccgcca cccttcagga catcgtccgt cgtttcaagg cctctaagtt tggctccaga  960
gagatcgtcc gcacagactt cgcccagctg cccaacaaag ttgccatcca gctgaatgac 1020
actcaccctg ccatggccat tcctgagctg atgagggtac tggttgatga ggagaagctg 1080
gagtgggaca aggcctggga cgtgtgtgtc cgtacctgtg cctacacaaa ccacaccgtg 1140
```

-continued

```
ctgcctgagg ccctggagcg ctggcccatt gacctgttcc atcacctgct gccccgtcac   1200
ctggagatta tctacgagat caaccgtcgc ttcctgcagt acgtcgcctc gaagttccct   1260
ggcgacaacg accgtctgcg ccgcatgtcc ctgattgagg agggagaatg caagaaagtc   1320
aacatggctc atatgtgtat cgttggatcc catgctgtca acggcgtggc ccgcatccac   1380
tcgcagatcc tcgtcgccac tctgttcaag gactttttatg agttggacct cacacaagttc   1440
cagaacaaga ccaatggcat cacccccgt cgctggctgg ttatgtgcaa ccccggcttc   1500
gctgaggtca tcgcagagag aattggagag gagtttgtcc gtgaccttga ccagctgaag   1560
aaactgttga agttcattga tgatgatgct ttcatccgtg acatagccaa agtcaagcag   1620
gagaacaagc tgaagttcgc tgtgcacctg gaagaacact acaaagtaaa gatcaacccc   1680
cagtccatgt ttgacttcca agtcaaaaga atccacgagt acaagagaca gctgctcaac   1740
tgtctgcaca tgatcaccta ctacaaccgt atcaagaagg agccaaacaa gcactggacc   1800
ccaagaacca tcatggtcgg aggaaaggct gcccccaggct accacacagc caagatgatc   1860
attcgtctca tcaccgctat cggtgaggtt gtcaaccacg accccgtgat cggcgaccgc   1920
ctcaaagtca tcttcttgga gaactacaga gtcacccctg ctgagaaagc catcccctct   1980
gctgacctgt ctgagcagat ctctacagct ggcactgagg cctctggcac tggcaacatg   2040
aagttcatgc tgaatggcgc tctgaccatc ggcaccatgg acggagccaa cgtggagatg   2100
gccgaggagg ccgagagaa gaacctcttc atcttcggca tgagagtgga ggaagtggac   2160
gcaatgacg ccggcaaagg ataccacgcc tctgagtact acaaccgtat tcccgagctg   2220
aaacaggcca tggaccagat ctctggtggc ttcttcagca ataagcagcc agacctcttc   2280
aaggaacttg tggacctgct gatgcaccac gacaggttca aggtgtttgc tgactacgaa   2340
gcctacatca aaagtcagga taaggtcaac gaactgtaca agaaacccaa ggaatggacc   2400
aagatggtga tccataacat tgcaggctgt ggtaaattct ccagcgaccg caccattccc   2460
cagtacgccc gggagatctg gggcatggag cccagcctgg agaagatccc tgcccccgat   2520
gagcaactca aa                                                       2532
```

```
SEQ ID NO: 10           moltype = AA  length = 844
FEATURE                 Location/Qualifiers
REGION                  1..844
                        note = Alpha-1,4 glucan phosphorylase
source                  1..844
                        mol_type = protein
                        organism = synthetic construct
SEQUENCE: 10
MSKPLSDHDR KKQISVRGLA GVENVAELKV AFNRHLHFTL VKDRNVASKR DYYFALANTV   60
RDHLVGRWIR TQQYYYEKDP KRVYYISLEF YMGRTLQNTM VNLALENACD EAIYQLGLDM  120
EELEDMEEDA GLGNGGLGRL AACFLDSMAS LGLAAYGYGI RYEFGIFNQK IVNGWQVEEA  180
DDWLRYGNPW EKARPEYMRP VKFYGRTEHT PEGVKWVDTQ VVLALPYDTP IPGYRNNIVN  240
TMRLWSAKAP CDFNLKDFNV GGYIQAVLDR NLCENISRVL YPNDNFFEGK ELRLKQEYFV  300
VAATLQDIVR RFKASKFGSR EIVRTDFAQL PNKVAIQLND THPAMAIPEL MRVLVDEEKL  360
EWDKAWDVCV RTCAYTNHTV LPEALERWPI DLFHHLLPRH LEIIYEINRR FLQYVASKFP  420
GDNDRLRRMS LIEEGECKKV NMAHMCIVGS HAVNGVARIH SEILVATLFK DFYELDPHKF  480
QNKTNGITPR RWLVMCNPGL AEVIAERIGE EFVRDLDQLK KLLKFIDDDA FIRDIAKVKQ  540
ENKLKFAVHL EEHYKVKINP QSMFDFQVKR IHEYKRQLLN CLHMITYYNR IKKEPNKHWT  600
PRTIMVGGKA APGYHTAKMI IRLITAIGEV VNHDPVIGDR LKVIFLENYR VTLAEKAIPS  660
ADLSEQISTA GTEASGTGNM KFMLNGALTI GTMDGANVEM AEEAGEKNLF IFGMRVEEVD  720
AMDAGKGYHA SEYYNRIPEL KQAMDQISGG FFSHKQPDLF KELVDLLMHH DRFKVFADYE  780
AYIKSQDKVN ELYKKPKEWT KMVIHNIAGC GKFSSDRTIS QYAREIWGME PSLEKIPAPD  840
EQLK                                                               844
```

```
SEQ ID NO: 11           moltype = AA  length = 9
FEATURE                 Location/Qualifiers
REGION                  1..9
                        note = Alpha-1,4 glucan phosphorylase fragment
source                  1..9
                        mol_type = protein
                        organism = synthetic construct
SEQUENCE: 11
IPAPDEQLK                                                            9
```

```
SEQ ID NO: 12           moltype = AA  length = 17
FEATURE                 Location/Qualifiers
REGION                  1..17
                        note = Alpha-1,4 glucan phosphorylase fragment
source                  1..17
                        mol_type = protein
                        organism = synthetic construct
SEQUENCE: 12
QISVRGLAGV ENVAELK                                                  17
```

```
SEQ ID NO: 13           moltype = AA  length = 25
FEATURE                 Location/Qualifiers
REGION                  1..25
                        note = Alpha-1,4 glucan phosphorylase fragment
source                  1..25
                        mol_type = protein
                        organism = synthetic construct
SEQUENCE: 13
AIPSADLSEQ ISTAGTEASG TGNMK                                         25
```

-continued

```
SEQ ID NO: 14          moltype = AA   length = 9
FEATURE                Location/Qualifiers
REGION                 1..9
                       note = Alpha-1,4 glucan phosphorylase fragment
source                 1..9
                       mol_type = protein
                       organism = synthetic construct
SEQUENCE: 14
DFYELDPHK                                                              9

SEQ ID NO: 15          moltype = AA   length = 10
FEATURE                Location/Qualifiers
REGION                 1..10
                       note = Alpha-1,4 glucan phosphorylase fragment
source                 1..10
                       mol_type = protein
                       organism = synthetic construct
SEQUENCE: 15
FAVHLEEHYK                                                             10

SEQ ID NO: 16          moltype = AA   length = 15
FEATURE                Location/Qualifiers
REGION                 1..15
                       note = Alpha-1,4 glucan phosphorylase fragment
source                 1..15
                       mol_type = protein
                       organism = synthetic construct
SEQUENCE: 16
GYHASEYYNR IPELK                                                       15

SEQ ID NO: 17          moltype = AA   length = 9
FEATURE                Location/Qualifiers
REGION                 1..9
                       note = Alpha-1,4 glucan phosphorylase fragment
source                 1..9
                       mol_type = protein
                       organism = synthetic construct
SEQUENCE: 17
IPAPDEQLK                                                              9

SEQ ID NO: 18          moltype = DNA   length = 2574
FEATURE                Location/Qualifiers
misc_feature           1..2574
                       note = Elongation factor 2
source                 1..2574
                       mol_type = other DNA
                       organism = synthetic construct
SEQUENCE: 18
atggtgaact ttacagtgga ccagatccgt gccatcatgg acaagaaatc caacattcgt   60
aacatgtctg tgatcgctca cgtggaccac ggcaagtcca cgctgaccga ctccctggtg  120
tctaaagccg ggatcatcgc ggggtctcgc gccggagaga cacgcttcac agacacactcgc  180
aaagacgagc aggagcgctg tattaccatc aagtccacgg ctatctcgat gtactatgag  240
ctggggggaaa acgacatggc cttcatcaag cagtctaagg atgggcttgg cttcctcatc  300
aacctgattg actcaccggg ccatgtggac ttctcctctg aggtcacagc cgcccttagg  360
gtcaccgacg gcgccctggt ggtggttgac tgcgtctcaa gtgtgtgtgt gcagacagag  420
accgtgttga ggcaggccat tgctgagcgc atcaagccag tgctgatgat gaacaagatg  480
gaccgggccc tgctggagct gcagctggag cctgaggacc tgttccagac cttccagcgc  540
atcgtggaga atgtcaacgt catcattgcc acctacggag aggatgaagc gggaccaatg  600
ggtgccatca tgattgaccc tgtgattggt accgtggggt ttgggtctgg cctccacggc  660
tgggccttca ctctaaagca gtttgctgag atgtacgtga caaagttttc tgccggcaag  720
gacacccagc tgggatcggc ggagaggtgt aagaaggtgg aggacatgat gaagaagctg  780
tggggggaga ggttttttga cccagccact gggaagttca gtaagtccaa cctcggcct  840
gacggtaaga agctgcccg caccttctct cagctggtcc tggaccctat cttcaaggta  900
tttgatgcca tcatgaactt caagaaggat gagacagcca agctgataga gaagctggac  960
atcaagctgg actctgagga caaggagaag gagggcaagc ccctgttgaa ggcagtgatg  1020
cgtcgctggc tcccagccgg agaagccctg ctccagatga tcaccatcca cctgccctcc  1080
cccgtcacgc cccagaagta ccgctgtgag ctgctctacg agggaccagg agacgacgag  1140
gccgccatgg gtatcaagaa ctgcgacccc aaggctcccc tgatgatgta catatctaag  1200
atggtgccca ccacagacaa gggtcgcttc tatgcctttg gccgtgtgtt ctctggctgt  1260
gtgtccaccg gtctgaaggt gcgcatcatg ggaccaaact tcacccctgg aagaaggaa  1320
gacctctaca tcaagcccat ccagaggacc attctgatga tggggcgtta tgtggagccc  1380
attgaggatg taccatgtgg gaacatcgtt gggctggttg agttgaccga gtatctgatt  1440
aagactggga ccatcaccac ctttgaacag gcccacaaca tgcgtgtgat gaagttcagc  1500
gtcagccctg tggtgagggt ggctgtggag gccaagaacc ctgctgacct gccaagctg  1560
gtggagggggc tgaagcgtct ggccaagtct gaccccatgg tgcagtgtat catcgaggag  1620
tctggagagc acatcatcgc cggggccgga gagcttcatc tggagatctg tctcaaggat  1680
ctggaggagg accacgccgg cattcccctg aagaaatctg atccagtggt gtcctacagg  1740
gagactgtgt ctgaggagtc tgaagtgatg tgtctatcca gtcccctaa caagcacaac  1800
cgtctgtaca tgcgggctaa acctttccct gacggctggg ccgaggacat cgagaagggg  1860
```

```
gacgtcagcc cccgacagga gctgaaaatc cgcgcccgtt tcctggctga caagtacgag   1920
tgggacgtgt cggaggcccg taagatctgg tgcttcggcc ctgacggtac cggtcccaac   1980
ctgctgatgg atgttaccaa gggagtccag tacctgaatg agatcaagga cagtgttgtg   2040
gctggcttcc agtgggctgt caaggagggt gtgttgtgtg aggagaacat gcgtgcagtc   2100
cgcttcgaca tccacgacgt gacccttgcac acagacgcaa ttcaccgcgg tggcggacag   2160
atcatcccca cggccgcag agtgctgtat gcctgccagc tcaccgccca gccacgactc   2220
atggagccgg tctacttagt ggagatccag tgcccagagc aggtagtggg tgggatctac   2280
ggcgtgctga acaggaagcg aggccatgtg ttcgaggagt cccaggtgat gggcacgccc   2340
atgttcatcg tcaaggccta cctgcctgtc aacagtgcat ttgggttcac cgctgacctg   2400
cgctccaaca cgggcggcca ggctttcccc cagtgtgtgt ttgatcactg gcagatcctc   2460
caggagatc cccaggaccc caccaccaag accgccattg tggtggccga gaccaggaaa   2520
cgcaaggggc tgaaagaggg catcccggcc ctggacaact acctggacaa attg          2574
```

```
SEQ ID NO: 19          moltype = AA  length = 858
FEATURE                Location/Qualifiers
REGION                 1..858
                       note = Elongation factor 2
source                 1..858
                       mol_type = protein
                       organism = synthetic construct
SEQUENCE: 19
MVNFTVDQIR AIMDKKSNIR NMSVIAHVDH GKSTLTDSLV SKAGIIAGSR AGETRFTDTR   60
KDEQERCITI KSTAISMYYE LGENDMAFIK QSKDGLGFLI NLIDSPGHVD FSSEVTAALR   120
VTDGALVVVD CVSGVCVQTE TVLRQAIAER IKPVLMMNKM DRALLELQLE PEDLFQTFQR   180
IVENVNVIIA TYGEDEAGPM GAIMIDPVIG TVGFGSGLHG WAFTLKQFAE MYVTKFSAGK   240
DTQLGSAERC KKVEDMMKKL WGERFFDPAT GKFSKSNLGP DGKKLPRTFS QLVLDPIFKV   300
FDAIMNFKKD ETAKLIEKLD IKLDSEDKEK EGKPLLKAVM RRWLPAGEAL LQMITIHLPS   360
PVTAQKYRCE LLYEGPGDDE AAMGIKNCDP KAPLMMYISK MVPTTDKGRF YAFGRVFSGC   420
VSTGLKVRIM GPNFTPGKKE DLYIKPIQRT ILMMGRYVEP IEDVPCGNIV GLVGVDQYLI   480
KTGTITTFEQ AHNMRVMKFS VSPVVRVAVE AKNPADLPKL VEGLKRLAKS DPMVQCIIEE   540
SGEHIIAGAG ELHLEICLKD LEEDHAGIPL KKSDPVVSYR ETVSEESEVM CLSKSPNKHN   600
RLYMRAKPFP DGLAEDIEKG DVSPRQELKI RARFLADKYE WDVSEARKIW CFGPDGTGPN   660
LLMDVTKGVQ YLNEIKDSVV AGFQWAVKEG VLCEENMRAV RFDIHDVTLH TDAIHRGGGQ   720
IIPTARRVLY ACQLTAQPRL MEPVYLVEIQ CPEQVVGGIY GVLNRKRGHV FEESQVMGTP   780
MFIVKAYLPV NESFGFTADL RSNTGGQAFP QCVFDHWQIL QGDPQDPTTK TAIVVAETRK   840
RKGLKEGIPA LDNYLDKL                                                  858
```

```
SEQ ID NO: 20          moltype = AA  length = 10
FEATURE                Location/Qualifiers
REGION                 1..10
                       note = Elongation factor 2 fragment
source                 1..10
                       mol_type = protein
                       organism = synthetic construct
SEQUENCE: 20
TAIVVAETRK                                                            10
```

```
SEQ ID NO: 21          moltype = AA  length = 12
FEATURE                Location/Qualifiers
REGION                 1..12
                       note = Elongation factor 2 fragment
source                 1..12
                       mol_type = protein
                       organism = synthetic construct
SEQUENCE: 21
DLEEDHAGIP LK                                                         12
```

```
SEQ ID NO: 22          moltype = AA  length = 13
FEATURE                Location/Qualifiers
REGION                 1..13
                       note = Elongation factor 2 fragment
source                 1..13
                       mol_type = protein
                       organism = synthetic construct
SEQUENCE: 22
DLEEDHAGIP LKK                                                        13
```

```
SEQ ID NO: 23          moltype = AA  length = 12
FEATURE                Location/Qualifiers
REGION                 1..12
                       note = Elongation factor 2 fragment
source                 1..12
                       mol_type = protein
                       organism = synthetic construct
SEQUENCE: 23
DSVVAGFQWA VK                                                         12
```

```
SEQ ID NO: 24          moltype = AA  length = 10
FEATURE                Location/Qualifiers
```

-continued

```
REGION                   1..10
                         note = Elongation factor 2 fragment
source                   1..10
                         mol_type = protein
                         organism = synthetic construct
SEQUENCE: 24
GDVSPRQELK                                                                   10

SEQ ID NO: 25            moltype = DNA  length = 1989
FEATURE                  Location/Qualifiers
misc_feature             1..1989
                         note = Heat shock cognate 70 kDa protein
source                   1..1989
                         mol_type = other DNA
                         organism = synthetic construct SEQUENCE: 25
atgtcaaagg gaccagcagt tggcattgac ctgggcacca cctactcctg tgtgggtgtg      60
tttcagcatg gcaaagtgga gatcatagcc aacgaccagg gaaacaggac cacacccagt     120
tatgtcgcct tcacagacac agaaaggctg attggggacg cagccaagaa ccaagtggcc     180
atgaaccca caaacacagt gtttgatgct aagcggctga tagggcggaa gtttgacgac     240
agtgtcgtcc aggcagacat gaaacactgg ccgtttacag tgatcaacga ctcgacacgg     300
cccaagtcc aagtggagta caaggagag accaaggcct tctacccaga ggagatctcc     360
tccatggtgc tggtcaagat gaaggagatt gcagaggcct acctgggcaa gactataacc     420
aatgcagtgg tcactgtgcc agcttacttc aacgactctc agcgccaggc caccaaagat     480
gcagggacta tctcaggact caacgtactc cgcatcatca tgagccaac tgctgctgct     540
atcgcctatg gcctggacaa gaaggtggga gtggagagaa acgtcctaat ctttgaccta     600
ggcggaggta cgtttgatgt gtctatcctg accatcgaag acgggatctt tgaggtgaag     660
tccacggccg gagacacca tcttggagga gaggacttcg acaaccgcat ggtcaaccac     720
ttcatctctg agttcaagcg caaatacaag aaggacatca gcgataacaa gagggccgtg     780
cgtcgtctgc gcaccgcctg tgaacgtgcc aagcgcacc tgtcctccag tacccaggcc     840
agcattgaga ttgactctct gtatgagggc gtcgacttct acacctccat caccagggct     900
cgctttgagg agctgaacgc tgacctgttc agaggcaccc tggaccccgt ggagaagtct     960
ctgagggacg ccaagatgga caaggcccag gttcacgaca tcgtcctagt gggaggctcc    1020
acacgcatcc ccaagatcca aaagttgctg caggacttct tcaatgggaa ggagctcaac    1080
aagagcatca accctgatga ggcggttgcc tatggtgcag ctgttcaggc ggccatcttg    1140
tccggagaca agtctgagaa cgtgcaggac ctgctgctgc tggacgtcac gccactgtcc    1200
ctgggcattg agacggccgg aggggtcatg accgtgctca tcaagaggaa caccaccatc    1260
cccaccaagc agacgcagac cttcacaaca tactcagaca accagcctgg ggtgctcatt    1320
caggtatatg aggggaaag agccatgacc aagacaaca acctactgg gaagtttgag    1380
ttgtgtggga ttccaccagc ccccgggggt gtgcctcaga tcgaggtcac ctttgacatt    1440
gacgccaacg gcatcatgaa cgtgtctgcc gctgacaaga gcaccggcaa ggagaataag    1500
atcaccatca ccaatgacaa aggtcgtctg agtaaggagg acatagagcg catggtccag    1560
gaggctgaac agtacaaagc tgcggacgat gtccagagga aggaaggtgc gtccaagaat    1620
ggcctggagt catacgcctt caacatgaag tccaccgtgg aggacgagaa gctcaagggc    1680
aagctcagcg acgaggacaa acagaagatc ctggacaaat gcaatgaggt catcagctgg    1740
ctggacaaga accagtctgc agagaaggag gagtttgagc accaccagaa ggagctggag    1800
aaggtctgta cccccatcat caccaagctg taccagggtg ctggggggat gcctggaggg    1860
atgcctggag ggatgcctgg agggatgcct ggagggatgc ctggggggat gcctggaggg    1920
atgcccgggg ctggtggtgc cgcacccgga ggaggtggat cctctggacc aacaattgag    1980
gaagtcgac                                                             1989

SEQ ID NO: 26            moltype = AA  length = 663
FEATURE                  Location/Qualifiers
REGION                   1..663
                         note = Heat shock cognate 70 kDa protein
source                   1..663
                         mol_type = protein
                         organism = synthetic construct
SEQUENCE: 26
MSKGPAVGID LGTTYSCVGV FQHGKVEIIA NDQGNRTTPS YVAFTDTERL IGDAAKNQVA      60
MNPTNTVFDA KRLIGRKFDD SVVQADMKHW PFTVINDSTR PKVQVEYKGE TKAFYPEEIS     120
SMVLVKMKEI AEAYLGKTIT NAVVTVPAYF NDSQRQATKD AGTISGLNVL RIINEPTAAA     180
IAYGLDKKVG VERNVLIFDL GGGTFDVSIL TIEDGIFEVK STAGDTHLGG EDFDNRMVNH     240
FISEFKRKYK KDISDNKRAV RRLRTACERA KRTLSSSTQA SIEIDSLYEG VDFYTSITRA     300
RFEELNADLF RGTLDPVEKS LRDAKMDKAQ VHDIVLVGGS TRIPKIQKLL QDFFNGKELN     360
KSINPDEAVA YGAAVQAAIL SGDKSENVQD LLLLDVTPLS LGIETAGGVM TVLIKRNTTI     420
PTKQTQTFTT YSDNQPGVLI QVYEGERAMT KDNNLLGKFE LCGIPPAPRG VPQIEVTFDI     480
DANGIMNVSA ADKSTGKENK ITITNDKGRL SKEDIERMVQ EAEQYKAADD VQRDKVASKN     540
GLESYAFNMK STVEDEKLKG KLSDEDKQKI LDKCNEVISW LDKNQSAEKE EFEHHQKELE     600
KVCNPIITKL YQGAGGMPGG MPGGMPGGMP GGMPGGMPGG MPGAGGAAPG GGGSSGPTIE     660
EVD                                                                    663

SEQ ID NO: 27            moltype = AA  length = 14
FEATURE                  Location/Qualifiers
REGION                   1..14
                         note = Heat shock cognate 70 kDa protein fragment
source                   1..14
                         mol_type = protein
                         organism = synthetic construct
```

-continued

```
SEQUENCE: 27
AFYPEEISSM VLVK                                                                    14

SEQ ID NO: 28            moltype = AA  length = 14
FEATURE                  Location/Qualifiers
REGION                   1..14
                         note = Heat shock cognate 70 kDa protein fragment
source                   1..14
                         mol_type = protein
                         organism = synthetic construct
SEQUENCE: 28
EDIERMVQEA EQYK                                                                    14

SEQ ID NO: 29            moltype = AA  length = 14
FEATURE                  Location/Qualifiers
REGION                   1..14
                         note = Heat shock cognate 70 kDa protein fragment
source                   1..14
                         mol_type = protein
                         organism = synthetic construct
SEQUENCE: 29
HWPFTVINDS TRPK                                                                    14

SEQ ID NO: 30            moltype = AA  length = 14
FEATURE                  Location/Qualifiers
REGION                   1..14
                         note = Heat shock cognate 70 kDa protein fragment
source                   1..14
                         mol_type = protein
                         organism = synthetic construct
SEQUENCE: 30
NQSAEKEEFE HHQK                                                                    14

SEQ ID NO: 31            moltype = AA  length = 22
FEATURE                  Location/Qualifiers
REGION                   1..22
                         note = Heat shock cognate 70 kDa protein fragment
source                   1..22
                         mol_type = protein
                         organism = synthetic construct
SEQUENCE: 31
TITNAVVTVP AYFNDSQRQA TK                                                           22

SEQ ID NO: 32            moltype = DNA  length = 2061
FEATURE                  Location/Qualifiers
misc_feature             1..2061
                         note = Serotransferrin
source                   1..2061
                         mol_type = other DNA
                         organism = synthetic construct
SEQUENCE: 32
atgaaactgc ttctcgtctc agcgctgctg gggtgcttcg ctacggtgta tgctgcccca  60
gctgagggaa tggttagatg gtgcgtaaag tcggaaaaag agctgaagaa atgccacgat  120
ctcgcagcca atgtggcggg gttttcatgc gtgaggaggg acgactctct tgaatgcatc  180
caagccatca agaggaaga ggctgatgct atcactctgg atggaggaga tatttacata  240
gctggcctcc acaactacaa cctgcagccc atcattgcag aggactatgg tgaggactct  300
gacacctgct attatgctgt ggccgtggcc aaaaagggca ctgaatttgg gttcctcgac  360
ctccgtggca agaagtcctg ccacaccggg ttgggcaaat ctgcaggctg gaacattccc  420
atcggtaccc tggtgactgt gggccagatc caatgggccg gcatcgagga cagacctgtg  480
gagtcggcgg tgagcgactt cttcaatgcc agctgtgctc caggagccaa tagggattcc  540
caactgtgcc agttgtgtat gggagactgc tccagatctc acaacgagcc ctactatgac  600
tattccgggg ccttccagtg cctgaaggat ggagcaggag aggttgcctt catcaagcac  660
ctgactgtac ctgccgcaga gaaggcaagc tatgagttgc tgtgcaagga taacaccaga  720
gctcccatcg acagctacaa gacctgccac ctggccagca cccgcccca cgctgtggtc  780
agccgcaagg accccaggct ggccaatctc atctacagca agctgatggc cgtcacgaac  840
ttcaacctgt tctcctccga tggttatgct gccaagaacc tgatgttcaa ggactccact  900
cagaatctag tacagctgcc aatgaccacc gactccttcc tctacctggg agctgagtac  960
atgagcacta tacgctccct gacaaaagcg caggccacag tgtgtcacctc cagggccatc  1020
aaatggtgtg ccgtgggcca taggagaag gtcaagtgta acgcctggac aatcaacagc  1080
ttcacagatg gtgactccag gatcgaatgc caggacgcac ccacagtgga tgaatgcatc  1140
aagaagatca tgcgtaaaga ggcagatgcc atagcggtgg atggtgggga ggtgttcact  1200
gctggaaaat gtggtctggt ccctgtcatg gtggagcagt atgatgaagt tcggtgcagc  1260
gcccctggtg aggcgtcatc ctactttgcg gtggcggtgg caaagagggg atctgggttg  1320
acctggacaa ccctgaaggg caagaggtca tgccacaccg gcttgggcag gaccgcaggc  1380
tggaacatac ccatgggtct tatccatagg aggactatga actgcgactt caccacatac  1440
ttcagtaagg gctgtgctcc tggatttgag gtggactctc ccttctgtgc ccagtgtaag  1500
ggcagtggga agtccgtggg aggagatggg tccaagtgca agccagctc tgaagagcag  1560
tactacggct ataacggagc attcagatgt ctggttgaag atgctggaga tgttgccttc  1620
attaaacaca ctattgtacc agagatgact gatggtagtg gtccagtttg ggcacagaac  1680
```

-continued

```
ctgatgtcct ctgactttga actactctgc caggatggta ctaccaagcc agtcacacat   1740
ttccgtgagt gccacctggc caaggtgccc gcccatgctg tgataacacg cccagagtcc   1800
cgtggagagg ttgtgtccat ccttctggag cagcaggcca ggttcggctc aagcggcagc   1860
gattcctcat ttaatatgtt caagccagat tttggaaaga acttgctctt caaggattcc   1920
acaaagtgtc tccaggagat cccaagcggc accaaattcc agggtttcct ggggaagag    1980
tacatgatcg ccatgcaatc gctcagggag tgctccaaca gtacctcaga tttggagaag   2040
gcatgcactt tccattcctg c                                            2061
```

```
SEQ ID NO: 33            moltype = AA  length = 687
FEATURE                  Location/Qualifiers
REGION                   1..687
                         note = Serotransferrin
source                   1..687
                         mol_type = protein
                         organism = synthetic construct
SEQUENCE: 33
MKLLLVSALL GCFATVYAAP AEGMVRWCVK SEKELKKCHD LAANVAGFSC VRRDDSLECI    60
QAIKREEADA ITLDGGDIYI AGLHNYNLQP IIAEDYGEDS DTCYYAVAVA KKGTEFGFLD   120
LRGKKSCHTG LGKSAGWNIP IGTLVTVGQI QWAGIEDRPV ESAVSDFFNA SCAPGANRDS   180
QLCQLCMGDC SRSHNEPYYD YSGAFQCLKD GAGEVAFIKH LTVPAAEKAS YELLCKDNTR   240
APIDSYKTCH LARVPAHAVV SRKDPRLANL IYSKLMAVTN FNLFSSDGYA AKNLMFKDST   300
QNLVQLPMTT DSFLYLGAEY MSTIRSLTKA QATGVTSRAI KWCAVGHKEK VKCDAWTINS   360
FTDGDSRIEC QDAPTVDECI KKIMRKEADA IAVDGGEVFT AGKCGLVPVM VEQYDEVRCS   420
APGEASSYFA VAVAKRGSGL TWTTLKGKRS CHTGLGRTAG WNIPMGLIHR RTMNCDFTTY   480
FSKGCAPGFE VDSPFCAQCK GSGKSVGGDG SKCKASSEEQ YYGYNGAFRC LVEDAGDVAF   540
IKHTIVPEMT DGSGPVWAQN LMSSDFELLC QDGTTKPVTH FRECHLAKVP AHAVITRPES   600
RGEVVSILLE QQARFGSSGS DSSFNMFKPD FGKNLLFKDS TKCLQEIPSG TKFQGFLGEE   660
YMIAMQSLRE CSNSTSDLEK ACTFHSC                                       687
```

```
SEQ ID NO: 34            moltype = AA  length = 12
FEATURE                  Location/Qualifiers
REGION                   1..12
                         note = Serotransferrin fragment
source                   1..12
                         mol_type = protein
                         organism = synthetic construct
SEQUENCE: 34
AQATGVTSRA IK                                                        12
```

```
SEQ ID NO: 35            moltype = AA  length = 10
FEATURE                  Location/Qualifiers
REGION                   1..10
                         note = Serotransferrin fragment
source                   1..10
                         mol_type = protein
                         organism = synthetic construct
SEQUENCE: 35
ATGVTSRAIK                                                           10
```

```
SEQ ID NO: 36            moltype = AA  length = 11
FEATURE                  Location/Qualifiers
REGION                   1..11
                         note = Serotransferrin fragment
source                   1..11
                         mol_type = protein
                         organism = synthetic construct
SEQUENCE: 36
DPRLANLIYS K                                                         11
```

```
SEQ ID NO: 37            moltype = AA  length = 12
FEATURE                  Location/Qualifiers
REGION                   1..12
                         note = Serotransferrin fragment
source                   1..12
                         mol_type = protein
                         organism = synthetic construct
SEQUENCE: 37
GTEFGFLDLR GK                                                        12
```

```
SEQ ID NO: 38            moltype = AA  length = 13
FEATURE                  Location/Qualifiers
REGION                   1..13
                         note = Serotransferrin fragment
source                   1..13
                         mol_type = protein
                         organism = synthetic construct
SEQUENCE: 38
KGTEFGFLDL RGK                                                       13
```

-continued

```
SEQ ID NO: 39          moltype = AA   length = 14
FEATURE                Location/Qualifiers
REGION                 1..14
                       note = Serotransferrin fragment
source                 1..14
                       mol_type = protein
                       organism = synthetic construct
SEQUENCE: 39
KGTEFGFLDL RGKK                                               14

SEQ ID NO: 40          moltype = AA   length = 18
FEATURE                Location/Qualifiers
REGION                 1..18
                       note = Serotransferrin fragment
source                 1..18
                       mol_type = protein
                       organism = synthetic construct
SEQUENCE: 40
LMAVTNFNLF SSDGYAAK                                           18

SEQ ID NO: 41          moltype = AA   length = 11
FEATURE                Location/Qualifiers
REGION                 1..11
                       note = Serotransferrin fragment
source                 1..11
                       mol_type = protein
                       organism = synthetic construct
SEQUENCE: 41
RGSGLTWTTL K                                                  11

SEQ ID NO: 42          moltype = DNA   length = 1518
FEATURE                Location/Qualifiers
misc_feature           1..1518
                       note = Myosin binding protein H-like
source                 1..1518
                       mol_type = other DNA
                       organism = synthetic construct
SEQUENCE: 42
atgcctgcga agcctgcccc tatcaagaag gcagccccga aagagcctgc tcctaagaag   60
gaggaagcac ctgcacctgc acccgcggag gcggctcctg ctgaagttgc tcccctgcc   120
gaggtcgaag ctccaccggc agaggctgcc cctgccgaag cagctgcccc tgctgaggca   180
gctccaaccg aagaaaaggc tcccgcagaa cccgcgcctc agcagcccaa agcacccaca   240
ccccctcctc cagatgagcc caccagtgag cccctggaag tgacagtgga cgacaagagc   300
gacacttcag tgaccatcac ctggaggcct ccaaagacta ttccagccaa ctctggcctg   360
gatggataca ctgtggaaat caccaaggag ggaactgaag actggaaagc agccaacgag   420
gatctgaccg tgtcctgccg ttatgtcatc aagaaccaga ctaccggcga ccgtctgctg   480
atccgagtgg ttgctgtaaa ccctggtggc cgcagccccg ctgctaccat cgccgacccc   540
gttctggtca aggaggttgg ggctcgcccc aaagtccgcc tccctcgttt cctgaggcag   600
aggtatgtca agaaagtcgg cgagaagatc aacattgtca tcccgtactc tggcaaacct   660
aagccagtgg ttagctggtt aaaggatgga cagcccctcg actcaaagag ggccaacatc   720
cgtacatctg acagagacag catcctgttc atccgtcaag cagagagggt ggactctggc   780
tcatacgaaa tgtgcgtgaa ggtggacgac tttgaggaca aagctgctat catcatccag   840
attattgagt acccgggccc accagccagc attaagattg tggatgtctg gggattcaac   900
gttgctttgg agtggaccgt acccaaagat aatggaaaca cagagatcac aggctacact   960
gtccagaaag ctgacaagaa gaccggggac tggttcaaca ttttggagca ctacgccaga  1020
ctaaatgcca ccatctcaga cctcattatg ggcaacacct acaccttcag ggtctcttgca  1080
gagaacaagt gcgggactcag tgaggaatgt gccgtgacca agggagaagc caccattgtg  1140
aaggaggtta ttgactacaa aacctacccccg ttcgtggagc atgacttcac cgaggctccc  1200
aagttcacca ctgttctgaa cgacaggtcc accactgttg gctacagcac caagctgctg  1260
tgttctgtga ggggatgccc caagcctaag attatgtgga tgaagaacaa gatgattctc  1320
aacaacatgg acaaccccaa gtacaggatg atcagcacag ggggcatctg caccctggag  1380
atccgtaagc ctgccccata cgacggtggt gagtatgtct gcagagccga gaatacactg  1440
gggaaggtcg acaccggctg caagctggag gtcagaaagc ctgggcaagc agatgctgac  1500
aaagacaaga aggaacag                                               1518

SEQ ID NO: 43          moltype = AA   length = 506
FEATURE                Location/Qualifiers
REGION                 1..506
                       note = Myosin binding protein H-like
source                 1..506
                       mol_type = protein
                       organism = synthetic construct
SEQUENCE: 43
MPAKPAPIKK AAPKEPAPKK EEAPAPAPAE AAPAEVAPPA EVEAPPAEAA PAEAAAPAEA   60
APTEEKAPAE PAPEQPKAPT PPPPDEPTSE PLEVTVDDKS DTSVTITWRP PKTIPANSGL  120
DGYTVEITKE GTEDWKAANE DLTVSCRYVI KNQTTGDRLL IRVVAVNPGG RSPPATIADP  180
VLVKEVGARP KVRLPRFLRQ RYVKKVGEKI NIVIPYSGKP KPVVSWLKDG QPLDSKRANI  240
RTSDRDSILF IRQAERVDSG SYEMCVKVDD FEDKAAIIIQ IIELPGPPAS IKIVDVWGFN  300
VALEWTVPKD NGNTEITGYT VQKADKKTGD WFNILEHYAR LNATISDLIM GNTYTFRVFA  360
```

```
ENKCGLSEEC AVTKGEATIV KEVIDYKPTP FVEHDFTEAP KFTTVLNDRS TTVGYSTKLL    420
CSVRGCPKPK IMWMKNKMIL NNMDNPKYRM ISTGGICTLE IRKPGPYDGG EYVCRAENTL    480
GKVDTGCKLE VRKPGQADAD KDKKEQ                                        506

SEQ ID NO: 44              moltype = AA   length = 18
FEATURE                    Location/Qualifiers
REGION                     1..18
                           note = Myosin binding protein H-like fragment
source                     1..18
                           mol_type = protein
                           organism = synthetic construct
SEQUENCE: 44
AAIIQIIEL PGPPASIK                                                   18

SEQ ID NO: 45              moltype = AA   length = 18
FEATURE                    Location/Qualifiers
REGION                     1..18
                           note = Myosin binding protein H-like fragment
source                     1..18
                           mol_type = protein
                           organism = synthetic construct
SEQUENCE: 45
AAPAEAAAPA EAAPTEEK                                                  18

SEQ ID NO: 46              moltype = AA   length = 11
FEATURE                    Location/Qualifiers
REGION                     1..11
                           note = Myosin binding protein H-like fragment
source                     1..11
                           mol_type = protein
                           organism = synthetic construct
SEQUENCE: 46
APAEPAPEQP K                                                         11

SEQ ID NO: 47              moltype = AA   length = 14
FEATURE                    Location/Qualifiers
REGION                     1..14
                           note = Myosin binding protein H-like fragment
source                     1..14
                           mol_type = protein
                           organism = synthetic construct
SEQUENCE: 47
DNGNTEITGY TVQK                                                      14

SEQ ID NO: 48              moltype = AA   length = 20
FEATURE                    Location/Qualifiers
REGION                     1..20
                           note = Myosin binding protein H-like fragment
source                     1..20
                           mol_type = protein
                           organism = synthetic construct
SEQUENCE: 48
EVIDYKPTPF VEHDFTEAPK                                                20

SEQ ID NO: 49              moltype = AA   length = 17
FEATURE                    Location/Qualifiers
REGION                     1..17
                           note = Myosin binding protein H-like fragment
source                     1..17
                           mol_type = protein
                           organism = synthetic construct
SEQUENCE: 49
FTTVLNDRST TVGYSTK                                                   17

SEQ ID NO: 50              moltype = AA   length = 10
FEATURE                    Location/Qualifiers
REGION                     1..10
                           note = Myosin binding protein H-like fragment
source                     1..10
                           mol_type = protein
                           organism = synthetic construct
SEQUENCE: 50
INIVIPYSGK                                                          10

SEQ ID NO: 51              moltype = AA   length = 19
FEATURE                    Location/Qualifiers
REGION                     1..19
                           note = Myosin binding protein H-like fragment
source                     1..19
```

-continued

```
                        mol_type = protein
                        organism = synthetic construct
SEQUENCE: 51
INIVIPYSGK PKPVVSWLK                                          19

SEQ ID NO: 52           moltype = AA   length = 33
FEATURE                 Location/Qualifiers
REGION                  1..33
                        note = Myosin binding protein H-like fragment
source                  1..33
                        mol_type = protein
                        organism = synthetic construct
SEQUENCE: 52
NQTTGDRLLI RVVAVNPGGR SPPATIADPV LVK                          33

SEQ ID NO: 53           moltype = AA   length = 13
FEATURE                 Location/Qualifiers
REGION                  1..13
                        note = Myosin binding protein H-like fragment
source                  1..13
                        mol_type = protein
                        organism = synthetic construct
SEQUENCE: 53
SDTSVTITWR PPK                                                13

SEQ ID NO: 54           moltype = AA   length = 17
FEATURE                 Location/Qualifiers
REGION                  1..17
                        note = Myosin binding protein H-like fragment
source                  1..17
                        mol_type = protein
                        organism = synthetic construct
SEQUENCE: 54
TIPANSGLDG YTVEITK                                            17

SEQ ID NO: 55           moltype = DNA   length = 1377
FEATURE                 Location/Qualifiers
misc_feature            1..1377
                        note = Desmin (fragment)
source                  1..1377
                        mol_type = other DNA
                        organism = synthetic construct
SEQUENCE: 55
atttcctctt accgccgcac tttcggttct ggtattggat ccaccccagg catgtcctcc   60
atgttctccc acggtggacg cggctcctcc ggctcggccc acatgtcctc cagagtctac  120
gagatgacca aaagctccgc ccgccccagc tactcctccg gcagtattcg ctcctcctcc  180
ggcggccgcga tgcgctcgta cgccgggatg ggcgagaagc tggacttcaa cctggccgac  240
gccactaacc gcgacttcct ggacaccaga accaatgaga aggcagagtt gcagcacctg  300
aacgaccggt tcgccagcta catcgagaag gtccgtttcc tggagcagca gaacgctact  360
ctggtggtgg agatcgagag gctgaggggt cacgagccga cccgcgtggc cgagatgtac  420
gaggaggaga tgagagagct gaggcgtcag gtggacggca tgtccaatga ccgagcccgc  480
atggaggtgg agagagacaa cttggctgac gacctgcaga aactcaaact cagactgcag  540
gaggtgatcc accagaggga agaggcagag aacaacctgt ctgccttcag agctgacgtg  600
gactctgcca cgctggccag gctggacctg agagacgcga ttgaaagcct gcaggaggag  660
atcaccttcc tcaagaagat ccacgaggag gagatccatg agctgacgag ccagatgcag  720
gagacctcgg tgcaggtcca gatggacatg tccaaaccag acctgaccgt tgccctcagg  780
gacatccgta tgcagtacga gggtatcgca gccaagaaca tctctgaggc agaggactgg  840
tacaagtcca aggtgtcaga cctgaaccag gctgtgaaca agaacaacga tgctctgaga  900
caggccaaac aggagagcat ggagttcagg catcagatcc agtcctacac ctgtgagatc  960
gactctctca agggaaccaa cgagtctctg ctgaggcaga tgagggagat ggaggatcgt 1020
ctgggaaacg aggctggagg ttaccaggac tccgtcaccc gtctggaggc tgagatcgcc 1080
aagatgaagg atgagatggc tcgtcacctc agagagtacc aggacctcct caatgtcaag 1140
atggccctgg atatagagat cgctacctac aggaagctac tggagggaga ggagagccga 1200
atcactgtat ctggctccaa gtcttctcac tctggctccc actctgctgc ctcattatat 1260
tccactgttg gattcagaga gaccagccca gacgtcggac gatcagcaga ggtccactcc 1320
aagaagactg tcctgatcaa gaccatcgag acccgcgatg gagaggtcgt cagcgag     1377

SEQ ID NO: 56           moltype = AA   length = 459
FEATURE                 Location/Qualifiers
REGION                  1..459
                        note = Desmin (fragment)
source                  1..459
                        mol_type = protein
                        organism = synthetic construct
SEQUENCE: 56
ISSYRRTFGS GIGSTPGMSS MFSHGGRGSS GSAHMSSRVY EMTKSSARPS YSSGSIRSSS   60
GGAMRSYAGM GEKLDFNLAD ATNRDFLDTR TNEKAELQHL NDRFASYIEK VRFLEQQNAT  120
LVVEIERLRG HEPTRVAEMY EEEMRELRRQ VDGMSNDRAR MEVERDNLAD DLQKLKLRLQ  180
EVIHQREEAE NNLSAFRADV DSATLARLDL ERRIESLQEE ITFLKKIHEE EIHELTSQMQ  240
```

```
ETSVQVQMDM SKPDLTVALR DIRMQYEGIA AKNISEAEDW YKSKVSDLNQ AVNKNNDALR   300
QAKQESMEFR HQIQSYTCEI DSLKGTNESL LRQMREMEDR LGNEAGGYQD SVTRLEAEIA   360
KMKDEMARHL REYQDLLNVK MALDIEIATY RKLLEGEESR ITVSGSKSSH SGSHSAASLY   420
STVGFRETSP DVGRSAEVHS KKTVLIKTIE TRDGEVVSE                         459

SEQ ID NO: 57             moltype = AA  length = 17
FEATURE                   Location/Qualifiers
REGION                    1..17
                          note = A part of Desmin (fragment)
source                    1..17
                          mol_type = protein
                          organism = synthetic construct
SEQUENCE: 57
DEMARHLREY QDLLNVK                                                 17

SEQ ID NO: 58             moltype = AA  length = 21
FEATURE                   Location/Qualifiers
REGION                    1..21
                          note = A part of Desmin (fragment)
source                    1..21
                          mol_type = protein
                          organism = synthetic construct
SEQUENCE: 58
LDFNLADATN RDFLDTRTNE K                                            21

SEQ ID NO: 59             moltype = AA  length = 10
FEATURE                   Location/Qualifiers
REGION                    1..10
                          note = A part of Desmin (fragment)
source                    1..10
                          mol_type = protein
                          organism = synthetic construct
SEQUENCE: 59
NISEAEDWYK                                                         10

SEQ ID NO: 60             moltype = DNA  length = 822
FEATURE                   Location/Qualifiers
misc_feature              1..822
                          note = Capping protein (Actin filament) muscle Z-line beta
source                    1..822
                          mol_type = other DNA
                          organism = synthetic construct
SEQUENCE: 60
atgaatgacc agcagctgga ctgtgctctg gacctgatga ggcgtcttcc tccccagcag   60
atcgagaaga atctcagtga cctcatcgac ctggtgccca gtctgtgtga ggacctactc  120
tcctctgtgg accagcctct gaagatcgcc cgggacaagg tagtggggaa agactacctg  180
ctctgtgact ataacagaga cggtgactcc tacagatccc catggagtaa taagtatgag  240
ccacccatcg acgatggtgc catgccatct gcccgcctgc gcaaactaga ggtggaagcc  300
aacaatgcct ttgaccagta tagagacctg tactttgagg gtggcgtatc gtctgtgtat  360
ctgtgggact tggatcatgg ctttgctggg gtcatcctca tcaagaaggc tggagacggc  420
tccaagaaga tcaaaggctg ctgggactcc atccatgtgg tggaggtgca ggagaagtcc  480
agcggacgga ccgctcacta caaactcacc tccaccgtca tgctgtggct ccagacgacc  540
aaggccgggt ctggaaccat gaacctgggt ggcagtctga caagacagat ggagaaagac  600
gagacagttg gagagtcttc cccacatatt gccaacatcg gccgcctggt ggaggatatg  660
gagaataaga ttcgctccac tctcaacgag atctactttg ggaagaccaa ggacatcgtc  720
aatggtttaa gatctcattga ctctctgcct gataaccaaa agtaccggca gctccagaag  780
gagctgtctc aggtccttac ccagcgccag atcttcattg ac                     822

SEQ ID NO: 61             moltype = AA  length = 274
FEATURE                   Location/Qualifiers
REGION                    1..274
                          note = Capping protein (Actin filament) muscle Z-line beta
source                    1..274
                          mol_type = protein
                          organism = synthetic construct
SEQUENCE: 61
MNDQQLDCAL DLMRRLPPQQ IEKNLSDLID LVPSLCEDLL SSVDQPLKIA RDKVVGKDYL   60
LCDYNRDGDS YRSPWSNKYE PPIDDGAMPS ARLRKLEVEA NNAFDQYRDL YFEGGVSSVY  120
LWDLDHGFAG VILIKKAGDG SKKIKGCWDS IHVVEVQEKS SGRTAHYKLT STVMLWLQTT  180
KAGSGTMNLG GSLTRQMEKD ETVGESSPHI ANIGRLVEDM ENKIRSTLNE IYFGKTKDIV  240
NGLRSIDSLP DNQKYRQLQK ELSQVLTQRQ IFID                              274

SEQ ID NO: 62             moltype = AA  length = 24
FEATURE                   Location/Qualifiers
REGION                    1..24
                          note = Capping protein (Actin filament) muscle Z-line beta
                           fragment
source                    1..24
                          mol_type = protein
```

```
                        organism = synthetic construct
SEQUENCE: 62
DETVGESSPH IANIGRLVED MENK                                              24

SEQ ID NO: 63          moltype = AA   length = 17
FEATURE                Location/Qualifiers
REGION                 1..17
                       note = Capping protein (Actin filament) muscle Z-line beta
                        fragment
source                 1..17
                       mol_type = protein
                       organism = synthetic construct
SEQUENCE: 63
DIVNGLRSID SLPDNQK                                                      17

SEQ ID NO: 64          moltype = AA   length = 14
FEATURE                Location/Qualifiers
REGION                 1..14
                       note = Capping protein (Actin filament) muscle Z-line beta
                        fragment
source                 1..14
                       mol_type = protein
                       organism = synthetic construct
SEQUENCE: 64
ELSQVLTQRQ IFID                                                         14

SEQ ID NO: 65          moltype = AA   length = 12
FEATURE                Location/Qualifiers
REGION                 1..12
                       note = Capping protein (Actin filament) muscle Z-line beta
                        fragment
source                 1..12
                       mol_type = protein
                       organism = synthetic construct
SEQUENCE: 65
IRSTLNEIYF GK                                                           12

SEQ ID NO: 66          moltype = AA   length = 13
FEATURE                Location/Qualifiers
REGION                 1..13
                       note = Capping protein (Actin filament) muscle Z-line beta
                        fragment
source                 1..13
                       mol_type = protein
                       organism = synthetic construct
SEQUENCE: 66
LTSTVMLWLQ TTK                                                          13

SEQ ID NO: 67          moltype = AA   length = 10
FEATURE                Location/Qualifiers
REGION                 1..10
                       note = Capping protein (Actin filament) muscle Z-line beta
                        fragment
source                 1..10
                       mol_type = protein
                       organism = synthetic construct
SEQUENCE: 67
SIDSLPDNQK                                                              10

SEQ ID NO: 68          moltype = AA   length = 17
FEATURE                Location/Qualifiers
REGION                 1..17
                       note = Capping protein (Actin filament) muscle Z-line beta
                        fragment
source                 1..17
                       mol_type = protein
                       organism = synthetic construct
SEQUENCE: 68
YEPPIDDGAM PSARLRK                                                      17

SEQ ID NO: 69          moltype = DNA   length = 5799
FEATURE                Location/Qualifiers
misc_feature           1..5799
                       note = myosin heavy chain, fast skeletal muscle-like
source                 1..5799
                       mol_type = other DNA
                       organism = synthetic construct
SEQUENCE: 69
atgagtacgg acgcggagat gcaagtctac ggcaaggctg ccatataacct tcgtaagtct   60
```

-continued

```
gagaaggaga ggatggaggc acaagccatg ccctttgatt caaagaacgc ctgctatgtg    120
acagacaagg tggagctgta ccttaagggt ttagtcactg ccagggccga cgggaagtgt    180
actgtgacag ctttagactt tcgtgaagga aaagagttca aagatgcaga catctatgag    240
atgaaccccc ctaagtacga caagattgag gacatggcca tgatgaccta cctgaatgaa    300
gcctctgtgt tgtataacct caaagagcgt tatgcagcat ggatgatcta tacctactct    360
gggctcttct gtgccacggt gaacccctac aagtggctcc cagtgtacga cgaagaggtt    420
gtcaacgcct acagagggaa gaagaggggtg gaggctccac cacatatctt ctccgtctct    480
gacaacgcct ttcagttcat gatgattgat aaggagaacc agtccgtcct gattactgga    540
gaatccggtg caggaaagac tgtcaacacc aagcgtgtca tccagtactt tgccaccatt    600
gcagtgtctg gtggcaagaa ggaagcagac cccaacaaaa tgcagggggtc tcttgaggat    660
cagatcattg cagctaaccc tctgctagag tcttacggta atgccaagac agtgaggaac    720
gacaactcgt ctcgctttgg taaattcatc aggattcact tccaagctgg taaactggct    780
aaagctgaca ttgagaccta cctgctggag aagtccagag tgtccttcca actgcccgat    840
gagagaggct accacatctt cttccagatg atgacagcc acaaacctga gctagttgaa    900
ttggcactcc tcaccaccaa cccctacgac ttccccatgt gcagccaggg tcagattgct    960
gtggccagca tcaacgacaa tgaagagctg gatgccacag atgaagccat tacaatcctg   1020
ggcttcacta atgaggagaa gcttggaata tacaagctga caggagctgt agtgcaccat   1080
ggcaacttga aattcaagca gaagcacgt gaggagcagg ccggaccaga cggcacagag   1140
gtggctgata aaatcgccta cctgctgggc ctgaactcag ctgagatgtt gaaagctctg   1200
tgctaccca gagtgaaggt cggcaacgag tatgtgacca agggacgac tgtggctcag   1260
gttaataact cagtcagtgc tctggccaag tccatctatg agaggatgtt cttgtggatg   1320
gtcatccgta tcaatgagat gttggacacc aagaatccaa ggcagttcta tatcggtgtg   1380
cttgacattg ccgggtttga gatctttgat tacaacagca tggagcagct gtgcatcaac   1440
ttcaccaatg agaaactgca acagtttttc aaccacacca tgttcgtcct ggagcaagag   1500
gagtacaaga aggaggggaat cgtctgggcc ttcattgact tcggcatgga tttggctgcc   1560
tgcattgagc ttattgagaa gccattgggc atcttctcca tccttgaaga ggagtgcatg   1620
ttccccaagt cttcagacac taccttcaag gacaagctgt acgcccagca tcttggtaaa   1680
acaaaggcgt ttgagaagcc caagcctgcc aaaggcaagg cagaggccca cttctccctg   1740
gtgcattacg ccggtactgt ggactacaac atcactggct ggctggagaa gaacaaggac   1800
cccttgaacg actcagtttg tcaactgtat gggaagtccg gagtcaaaat tttggctgcc   1860
ctgtatcccc ctcccctcc tgaggataaa gccaagaaag gaggcaagaa gaagggtggt   1920
tccatgcaga ctgtgtcctc ccagttcagg gagaacttac ataagctgat gaccaacttg   1980
aggagcactc atcctcactt tgtgcgctgc ctgatcccca acgagtcaaa gactccaggt   2040
ctgatggaga acttcctggt tatccaccag ctcaggtgta atggtgtact ggagggtatc   2100
aggatctgca gaaagggctt ccccagcaga atcatctatg ctgacttcaa gcaaaggtac   2160
aaagtactga atgccagcgt catccctgag ggccagttca tggacaacaa gaaggcttct   2220
gagaagctgc ttggatccat tgatgtgaat cacgaggatt acaagtttgg acacaccaag   2280
gtgttcttca aagccggtct gctggggtgtc ctggaggaga tgagagatga gaagctggcc   2340
tctctagtcg gcatgctcca ggctctcagc cgtggatccc tcatgaggag agagttcacc   2400
aagatgatgg agaggagaga atcaatttac tccatccagt acaacatccg ctcattcatg   2460
aatgtgaaaa cctggccatg gatgaagttg tacttcaaga tcaagcccct gctgcagagc   2520
gctgagactg agaaggagct ggccaacatg aaggagaact atgagaaaat gaagacagac   2580
ctggccaagg ctctgtctac aaagaagcaa atggagggaga agttggtgtc cctgacgcag   2640
gagaagaacg acctggcact ccaagtcgca tctgaaggag agagtctgaa cgatgctgag   2700
gaaaggtgcg aggggctcat caagagcaag atccagcagg aggccaaact caaagagacg   2760
accgagaggc tggaggatga ggaggagatc aatgctgagt tgactgccaa gaagaggaag   2820
ctggagagga gtgctctga gctgaagaag gacattgatg atctggagct caccctggcc   2880
aaagtggaga aggagaagca cgccactgaa aacaaggtta aaaacctgac agaggagatg   2940
gcgtctatgg atgagagtgt tgccaagctg accaaggaga agaaagccct acaagaggcc   3000
caccagcaga cactggatga cctgcaggca gaggaggaca aagtcaacac tctgaccaag   3060
gccaagacca agctggaaca gcaagtggaa gaccttgagg gttctctgga acaagaagag   3120
aagctccgca tggaccttga gagatccaag agaaagctgg agggagatct gaaactggcc   3180
caggagtcca taatgaccct ggagaatgac aagcagcaag ctgatgagaa aatcaagaag   3240
aaggagtttg agaccactca gctcctcagc aaggttgagg atgagcagtc tctgggagct   3300
cagctgcagaa agaagatcaa ggaactccag gccccgtattg aggaactgga ggaggaaatt   3360
gaggctgagc gtgctgccag ggctaaggtt gagaagcaga gggctgatct ctccagggaa   3420
cttgaggaga tcagcgagag gctggaggag ccggaggcg ccactgctgc tcagattgag   3480
atgaacaaga gcgtgaggc tgagttccag aagctgcgtc gtgatcttga gagtccacc   3540
ctgcagcatg aggccacagc cgccgctctg cgcaagaagc aggccgacag tgtggctgag   3600
ctcggggggac agatcgacaa cctgcagcgc gtcaagcaga gctggagaa gggagaagagc   3660
gagtacaaga tggagattga tgacctctcc agcaacatgg aggccgttgc caaggctaag   3720
ggcaatctag agaagatgtg ccgtactctt gaggaccagc tgagcgagct caagactaag   3780
aatgatgaga atgttcgcca ggtcaacgac atcagcggac agagggccag actcctgaca   3840
gaaaatggtg agtttggtag gcagctggag gagaagaagg ccctggtgtc tcagctgacc   3900
agaggcaaac aggccttcac ccagcaggtg gaggagctga gagggcgat tgaggaggag   3960
gtcaaggcta aaaatgcact ggccacggga gttcagtctg cccgccatga ctgtgacctc   4020
ctgagggagc agtttgagga ggagcaggag gccaaggcag agctgcaacg cggcatgtcc   4080
aaggccaata gtgaggtggc tcagtggagg actaagtatg aaactgatgc catccagcgc   4140
acagaggccg tggaggaggc caagaagaag ctggccagc gtctgcagga tgccgaggag   4200
accattgagg cgaccaactc caagtgcgcc tccctggaga agaccaagca gagactacag   4260
ggagaggtgg aggacctcat gattgatgtt gagagagcca acgcattggc cgccaacctc   4320
gacaagaagc agagaggaactt tgacaaggtt ctggcagagt ggaagcagaa gtatgaggag   4380
ggtcaggctg agctggaagg agctcagaag gaggctcgct ctatgagcac tgagctcttc   4440
aagataaaga actcctacga ggaggctctg gatcatctga gaactcagaa gagagagaac   4500
aagaacctgc aacaggagat ctctgacctt actcagaaca ttggagagac tggcaagagc   4560
atccatgagc tggagaaggc caagaagacc gtggagacag agaagtctga gatccagacc   4620
gctctggagg aggctgaggg cacactggag cacgaggaat ccaagattct gcgtgtgcag   4680
ctggagctga accagatcaa gggtgaggtg gacaggaaga tcgctgagaa ggacgaggag   4740
atggagcaga tcaagaggaa cagccagagg atggttgact ccatgcagag caccctggac   4800
```

```
tctgaggtca ggagcaggaa tgatgccctg agggtgaaga agaagatgga gggagacctg   4860
aacgagatgg agatccagct gagccactcc aacaggcagg ccgctgaggc ccagaaacag   4920
ctgaggaatg tccagggaca gctcaaggat gcccaattgc accttgatga tgccgtccgt   4980
gtcgcagagg acatgaagga gcaggcagcc atggtggagc gcagaaacgg tctgatggtg   5040
gctggatcg aggagctgag agttgctctg gagcagacag agagaggccg caaagtggct   5100
gagactgagc tggtagacgc cagcgagcgt gttggactgc tgcactccca gaacaccagc   5160
cttctgaaca ccaagaagaa gctggagact gacctggtgc aggtgcaggg agaggtggat   5220
gacatcgtcc aggaggccag gaatgcagaa gagaaggcca agaaggcaat cactgatgcg   5280
gcaatgatgg ctgaggagct gaagaaggag caggacacca gctctcacct ggagagaatg   5340
aagaagaacc tggagatcac agtcaaggac ctgcagcacc gcctggatga ggctgagaat   5400
ctggccatga agggaggcaa gaaacaactc cagaaactgg aatccagggt gcgtgagctt   5460
gagactgagg tggaggctga gcagagaaga ggtgtagacg cggtaaaggg agtccgcaag   5520
tatgagcgca gagtcaagga gctcacttac cagactgagg aggataagaa gaatgttaac   5580
agacttcagg acctggtaga taagctgcag atgaaagtga aggcctacaa gaggcacgct   5640
gaggaagcgg aggaagcagc aaaccagcac atgtctaagt tcaggaaggt tcagcatgag   5700
ctggaggagg ctgaggagcg tgctgacatc gctgagactc aggtcaacaa gctcagagcc   5760
aagacccgtg actctggaaa gggaaaagaa gttgctgaa                            5799
```

SEQ ID NO: 70          moltype = AA   length = 1933
FEATURE                Location/Qualifiers
REGION                 1..1933
                       note = myosin heavy chain, fast skeletal muscle-like
source                 1..1933
                       mol_type = protein
                       organism = synthetic construct
SEQUENCE: 70
```
MSTDAEMQVY GKAAIYLRKS EKERMEAQAM PFDSKNACYV TDKVELYLKG LVTARADGKC   60
TVTALDFREG KEFKDADIYE MNPPKYDKIE DMAMMTYLNE ASVLYNLKER YAAWMIYTYS   120
GLFCATVNPY KWLPVYDEEV VNAYRGKKRV EAPPHIFSVS DNAFQFMMID KENQSVLITG   180
ESGAGKTVNT KRVIQYFATI AVSGGKKEAD PNKMQGSLED QIIAANPLLE SYGNAKTVRN   240
DNSSRFGKFI RIHFQAGKLA KADIETYLLE KSRVSFQLPD ERGYHIFFQM MTGHKPELVE   300
LALLTTNPYD FPMCSQGQIA VASINDNEEL DATDEAITIL GFTNEEKLGI YKLTGAVVHH   360
GNLKFKQKQR EEQAEPDGTE VADKIAYLLG LNSAEMLKAL CYPRVKVGNE YVTKGQTVAQ   420
VNNSVSALAK SIYERMFLWM VIRINEMLDT KNPRQFYIGV LDIAGFEIFD YNSMEQLCIN   480
FTNEKLQQFF NHTMFVLEQE EYKKEGIVWA FIDFGMDLAA CIELIEKPLG IFSILEEECM   540
FPKSSDTTFK DKLYAQHLGK TKAFEKPKPA KGKAEAHFSL VHYAGTVDYN ITGWLEKNKD   600
PLNDSVCQLY GKSGVKILAA LYPPPPPEDK AKKGGKKKGG SMQTVSSQFR ENLHKLMTNL   660
RSTHPHFVRC LIPNESKTPG LMENFLVIHQ LRCNGVLEGI RICRKGFPSR IIYADFKQRY   720
KVLNASVIPE GQFMDNKKAS EKLLGSIDVN HEDYKFGHTK VFFKAGLLGV LEEMRDEKLA   780
SLVGMLQALS RGFLMRREFT KMMERRESIY SIQYNIRSFM NVKTWPWMKL YFKIKPLLQS   840
AETEKELANM KENYEKMKTD LAKALSTKKQ MEEKLVSLTQ EKNDLALQVA SEGESLNDAE   900
ERCEGLIKSK IQQEAKLKET TERLEDEEEI NAELTAKKRK LEDECSELKK DIDDLELTLA   960
KVEKEKHATE NKVKNLTEEM ASMDESVAKL TKEKKALQEA HQQTLDDLQA EEDKVNTLTK   1020
AKTKLEQQVD DLEGSLEQEK KLRMDLERSK RKLEGDLKLA QESIMDLEND KQQADEKIKK   1080
KEFETTQLLS KVEDEQSLGA QLQKKIKELQ ARIEELEEEI EAERAARAKV EKQRADLSRE   1140
LEEISERLEE AGGATAAQIE MNKKREAEFQ KLRRDLEEST LQHEATAAAL RKKQADSVAE   1200
LGEQIDNLQR VKQKLEKEKS EYKMEIDDLS SNMEAVAKAK QNLEKMCRTL EDQLSELKTK   1260
NDENVRQVND ISGQRARLLT ENGEFGRQLE EKEALVSQLT RGKQAFTQQV EELKRAIEEE   1320
VKAKNALAHG VQSARHDCDL LREQFEEEQE AKAELQRGMS KANSEVAQWR TKYETDAIQR   1380
TEELEEAKKK LAQRLQDAEE TIEATNSKCA SLEKTKQRLQ GEVEDLMIDV ERANALAANL   1440
DKKQRNFDKV LAEWKQKYEE GQAELEGAQK EARSMSTELF KMKNSYEEAL DHLETLKREN   1500
KNLQQEISDL TEQIGETGKS IHELEKAKKT VETEKSEIQT ALEEAEGTLE HEESKILRVQ   1560
LELNQIKGEV DRKIAEKDEE MEQIKRNSQR MVDSMQSTLD SEVRSRNDAL RVKKKMEGDL   1620
NEMEIQLSHS NRQAAEAQKQ LRNVQGQLKD AQLHLDDAVR VAEDMKEQAA MVERRNGLMV   1680
AEIEELRVAL EQTERGRKVA ETELVDASER VGLLHSQNTS LLNTKKKLET DLVQVQGEVD   1740
DIVQEARNAE EKAKKAITDA AMMAEELKKE QDTSSHLERM KKNLEITVKD LQHRLDEAEN   1800
LAMKGGKKQL QKLESRVREL ETEVEAEQRR GVDAVKGVRK YERRVKELTY QTEEDKKNVN   1860
RLQDLVDKLQ MKVKAYKRHA EEAEEAANQH MSKFRKVQHE LEEAEERADI AETQVNKLRA   1920
KTRDSGKGKE VAE                                                      1933
```

SEQ ID NO: 71          moltype = AA   length = 7
FEATURE                Location/Qualifiers
REGION                 1..7
                       note = myosin heavy chain, fast skeletal muscle-like
                        fragment
source                 1..7
                       mol_type = protein
                       organism = synthetic construct
SEQUENCE: 71
```
AAIYLRK                                                               7
```

SEQ ID NO: 72          moltype = AA   length = 10
FEATURE                Location/Qualifiers
REGION                 1..10
                       note = myosin heavy chain, fast skeletal muscle-like
                        fragment
source                 1..10
                       mol_type = protein
                       organism = synthetic construct -continued

```
SEQUENCE: 72
ADIETYLLEK                                                          10

SEQ ID NO: 73        moltype = AA  length = 19
FEATURE              Location/Qualifiers
REGION               1..19
                     note = myosin heavy chain, fast skeletal muscle-like
                       fragment
source               1..19
                     mol_type = protein
                     organism = synthetic construct
SEQUENCE: 73
ALQEAHQQTL DDLQAEEDK                                                19

SEQ ID NO: 74        moltype = AA  length = 11
FEATURE              Location/Qualifiers
REGION               1..11
                     note = myosin heavy chain, fast skeletal muscle-like
                       fragment
source               1..11
                     mol_type = protein
                     organism = synthetic construct
SEQUENCE: 74
DIDDLELTLA K                                                        11

SEQ ID NO: 75        moltype = AA  length = 11
FEATURE              Location/Qualifiers
REGION               1..11
                     note = myosin heavy chain, fast skeletal muscle-like
                       fragment
source               1..11
                     mol_type = protein
                     organism = synthetic construct
SEQUENCE: 75
EALVSQLTRG K                                                        11

SEQ ID NO: 76        moltype = AA  length = 10
FEATURE              Location/Qualifiers
REGION               1..10
                     note = myosin heavy chain, fast skeletal muscle-like
                       fragment
source               1..10
                     mol_type = protein
                     organism = synthetic construct
SEQUENCE: 76
EFETTQLLSK                                                          10

SEQ ID NO: 77        moltype = AA  length = 10
FEATURE              Location/Qualifiers
REGION               1..10
                     note = myosin heavy chain, fast skeletal muscle-like
                       fragment
source               1..10
                     mol_type = protein
                     organism = synthetic construct
SEQUENCE: 77
ELTYQTEEDK                                                          10

SEQ ID NO: 78        moltype = AA  length = 15
FEATURE              Location/Qualifiers
REGION               1..15
                     note = myosin heavy chain, fast skeletal muscle-like
                       fragment
source               1..15
                     mol_type = protein
                     organism = synthetic construct
SEQUENCE: 78
ENQSVLITGE SGAGK                                                    15

SEQ ID NO: 79        moltype = AA  length = 19
FEATURE              Location/Qualifiers
REGION               1..19
                     note = myosin heavy chain, fast skeletal muscle-like
                       fragment
source               1..19
                     mol_type = protein
                     organism = synthetic construct
SEQUENCE: 79
ETTERLEDEE EINAELTAK                                                19
```

-continued

```
SEQ ID NO: 80          moltype = AA   length = 10
FEATURE                Location/Qualifiers
REGION                 1..10
                       note = myosin heavy chain, fast skeletal muscle-like
                        fragment
source                 1..10
                       mol_type = protein
                       organism = synthetic construct
SEQUENCE: 80
FIRIHFQAGK                                                          10

SEQ ID NO: 81          moltype = AA   length = 12
FEATURE                Location/Qualifiers
REGION                 1..12
                       note = myosin heavy chain, fast skeletal muscle-like
                        fragment
source                 1..12
                       mol_type = protein
                       organism = synthetic construct
SEQUENCE: 81
GFPSRIIYAD FK                                                       12

SEQ ID NO: 82          moltype = AA   length = 10
FEATURE                Location/Qualifiers
REGION                 1..10
                       note = myosin heavy chain, fast skeletal muscle-like
                        fragment
source                 1..10
                       mol_type = protein
                       organism = synthetic construct
SEQUENCE: 82
GLVTARADGK                                                          10

SEQ ID NO: 83          moltype = AA   length = 16
FEATURE                Location/Qualifiers
REGION                 1..16
                       note = myosin heavy chain, fast skeletal muscle-like
                        fragment
source                 1..16
                       mol_type = protein
                       organism = synthetic construct
SEQUENCE: 83
GQTVAQVNNS VSALAK                                                   16

SEQ ID NO: 84          moltype = AA   length = 12
FEATURE                Location/Qualifiers
REGION                 1..12
                       note = myosin heavy chain, fast skeletal muscle-like
                        fragment
source                 1..12
                       mol_type = protein
                       organism = synthetic construct
SEQUENCE: 84
IKPLLQSAET EK                                                       12

SEQ ID NO: 85          moltype = AA   length = 14
FEATURE                Location/Qualifiers
REGION                 1..14
                       note = myosin heavy chain, fast skeletal muscle-like
                        fragment
source                 1..14
                       mol_type = protein
                       organism = synthetic construct
SEQUENCE: 85
ILAALYPPPP PEDK                                                     14

SEQ ID NO: 86          moltype = AA   length = 12
FEATURE                Location/Qualifiers
REGION                 1..12
                       note = myosin heavy chain, fast skeletal muscle-like
                        fragment
source                 1..12
                       mol_type = protein
                       organism = synthetic construct
SEQUENCE: 86
ILRVQLELNQ IK                                                       12

SEQ ID NO: 87          moltype = AA   length = 18
```

-continued

```
FEATURE              Location/Qualifiers
REGION               1..18
                     note = myosin heavy chain, fast skeletal muscle-like
                       fragment
source               1..18
                     mol_type = protein
                     organism = synthetic construct
SEQUENCE: 87
LAQRLQDAEE TIEATNSK                                                      18

SEQ ID NO: 88        moltype = AA  length = 16
FEATURE              Location/Qualifiers
REGION               1..16
                     note = myosin heavy chain, fast skeletal muscle-like
                       fragment
source               1..16
                     mol_type = protein
                     organism = synthetic construct
SEQUENCE: 88
LEQQVDDLEG SLEQEK                                                        16

SEQ ID NO: 89        moltype = AA  length = 24
FEATURE              Location/Qualifiers
REGION               1..24
                     note = myosin heavy chain, fast skeletal muscle-like
                       fragment
source               1..24
                     mol_type = protein
                     organism = synthetic construct
SEQUENCE: 89
LESRVRELET EVEAEQRRGV DAVK                                               24

SEQ ID NO: 90        moltype = AA  length = 13
FEATURE              Location/Qualifiers
REGION               1..13
                     note = myosin heavy chain, fast skeletal muscle-like
                       fragment
source               1..13
                     mol_type = protein
                     organism = synthetic construct
SEQUENCE: 90
LLGSIDVNHE DYK                                                          13

SEQ ID NO: 91        moltype = AA  length = 21
FEATURE              Location/Qualifiers
REGION               1..21
                     note = myosin heavy chain, fast skeletal muscle-like
                       fragment
source               1..21
                     mol_type = protein
                     organism = synthetic construct
SEQUENCE: 91
LRRDLEESTL QHEATAAALR K                                                  21

SEQ ID NO: 92        moltype = AA  length = 12
FEATURE              Location/Qualifiers
REGION               1..12
                     note = myosin heavy chain, fast skeletal muscle-like
                       fragment
source               1..12
                     mol_type = protein
                     organism = synthetic construct
SEQUENCE: 92
LTGAVVHHGN LK                                                            12

SEQ ID NO: 93        moltype = AA  length = 32
FEATURE              Location/Qualifiers
REGION               1..32
                     note = myosin heavy chain, fast skeletal muscle-like
                       fragment
source               1..32
                     mol_type = protein
                     organism = synthetic construct
SEQUENCE: 93
NDENVRQVND ISGQRARLLT ENGEFGRQLE EK                                      32

SEQ ID NO: 94        moltype = AA  length = 7
FEATURE              Location/Qualifiers
REGION               1..7
```

-continued

```
                         note = myosin heavy chain, fast skeletal muscle-like
                           fragment
source                   1..7
                         mol_type = protein
                         organism = synthetic construct
SEQUENCE: 94
NLEITVK                                                                    7

SEQ ID NO: 95            moltype = AA  length = 18
FEATURE                  Location/Qualifiers
REGION                   1..18
                         note = myosin heavy chain, fast skeletal muscle-like
                           fragment
source                   1..18
                         mol_type = protein
                         organism = synthetic construct
SEQUENCE: 95
NLQQEISDLT EQIGETGK                                                        18

SEQ ID NO: 96            moltype = AA  length = 14
FEATURE                  Location/Qualifiers
REGION                   1..14
                         note = myosin heavy chain, fast skeletal muscle-like
                           fragment
source                   1..14
                         mol_type = protein
                         organism = synthetic construct
SEQUENCE: 96
NSYEEALDHL ETLK                                                           14

SEQ ID NO: 97            moltype = AA  length = 19
FEATURE                  Location/Qualifiers
REGION                   1..19
                         note = myosin heavy chain, fast skeletal muscle-like
                           fragment
source                   1..19
                         mol_type = protein
                         organism = synthetic construct
SEQUENCE: 97
QADSVAELGE QIDNLQRVK                                                       19

SEQ ID NO: 98            moltype = AA  length = 11
FEATURE                  Location/Qualifiers
REGION                   1..11
                         note = myosin heavy chain, fast skeletal muscle-like
                           fragment
source                   1..11
                         mol_type = protein
                         organism = synthetic construct
SEQUENCE: 98
QAFTQQVEEL K                                                              11

SEQ ID NO: 99            moltype = AA  length = 16
FEATURE                  Location/Qualifiers
REGION                   1..16
                         note = myosin heavy chain, fast skeletal muscle-like
                           fragment
source                   1..16
                         mol_type = protein
                         organism = synthetic construct
SEQUENCE: 99
QREEQAEPDG TEVADK                                                         16

SEQ ID NO: 100           moltype = AA  length = 8
FEATURE                  Location/Qualifiers
REGION                   1..8
                         note = myosin heavy chain, fast skeletal muscle-like
                           fragment
source                   1..8
                         mol_type = protein
                         organism = synthetic construct
SEQUENCE: 100
RAIEEEVK                                                                   8

SEQ ID NO: 101           moltype = AA  length = 20
FEATURE                  Location/Qualifiers
REGION                   1..20
                         note = myosin heavy chain, fast skeletal muscle-like
                           fragment
```

-continued

```
source                   1..20
                         mol_type = protein
                         organism = synthetic construct
SEQUENCE: 101
SEIQTALEEA EGTLEHEESK                                          20

SEQ ID NO: 102           moltype = AA   length = 12
FEATURE                  Location/Qualifiers
REGION                   1..12
                         note = myosin heavy chain, fast skeletal muscle-like
                           fragment
source                   1..12
                         mol_type = protein
                         organism = synthetic construct
SEQUENCE: 102
TVRNDNSSRF GK                                                  12

SEQ ID NO: 103           moltype = AA   length = 27
FEATURE                  Location/Qualifiers
REGION                   1..27
                         note = myosin heavy chain, fast skeletal muscle-like
                           fragment
source                   1..27
                         mol_type = protein
                         organism = synthetic construct
SEQUENCE: 103
VAETELVDAS ERVGLLHSQN TSLLNTK                                  27

SEQ ID NO: 104           moltype = AA   length = 13
FEATURE                  Location/Qualifiers
REGION                   1..13
                         note = myosin heavy chain, fast skeletal muscle-like
                           fragment
source                   1..13
                         mol_type = protein
                         organism = synthetic construct
SEQUENCE: 104
VEDEQSLGAQ LQK                                                 13

SEQ ID NO: 105           moltype = AA   length = 8
FEATURE                  Location/Qualifiers
REGION                   1..8
                         note = myosin heavy chain, fast skeletal muscle-like
                           fragment
source                   1..8
                         mol_type = protein
                         organism = synthetic construct
SEQUENCE: 105
VGNEYVTK                                                       8

SEQ ID NO: 106           moltype = AA   length = 21
FEATURE                  Location/Qualifiers
REGION                   1..21
                         note = myosin heavy chain, fast skeletal muscle-like
                           fragment
source                   1..21
                         mol_type = protein
                         organism = synthetic construct
SEQUENCE: 106
VQHELEEAEE RADIAETQVN K                                        21

SEQ ID NO: 107           moltype = AA   length = 13
FEATURE                  Location/Qualifiers
REGION                   1..13
                         note = myosin heavy chain, fast skeletal muscle-like
                           fragment
source                   1..13
                         mol_type = protein
                         organism = synthetic construct
SEQUENCE: 107
YEEGQAELEG AQK                                                 13

SEQ ID NO: 108           moltype = AA   length = 16
FEATURE                  Location/Qualifiers
REGION                   1..16
                         note = myosin heavy chain, fast skeletal muscle-like
                           fragment
source                   1..16
                         mol_type = protein
``` organism = synthetic construct

SEQUENCE: 108
YETDAIQRTE ELEEAK                                                                                                  16

SEQ ID NO: 109          moltype = DNA   length = 2532
FEATURE                 Location/Qualifiers
misc_feature            1..2532
                        note = glycogen phosphorylase, muscle form-like
source                  1..2532
                        mol_type = other DNA
                        organism = synthetic construct
SEQUENCE: 109
atgtcaaaac cattgtcaga ccacgataaa aggaagcaga tctccgtgag aggtcttgct  60
ggtgtggaaa atgtcgcaga actgaaggtc gctttcaaca ggcatctcca ttttacactg  120
gtcaaggaca gaaatgtggc aaacaaacgg gattactact ttgctctcgc caacaccgtg  180
cgtgaccact tggtgggcag gtggatcaga acccagcagt actactatga gaaagatccc  240
aaacgtgtgt actacatctc cctggagttt tatatgggtc gcaccctgca gaacactatg  300
gtgaacctgg ccctggagaa cgcttgtgat gaggccatat accagctggt tctggacatg  360
gaggagctgg aggacatgga agaggatgct ggcctgggaa acggtggtct tggccgtctt  420
gccgcatgct tcctggactc aatggcttct ctaggccttg ctgcctatgg ctatggtatc  480
cgctatgagt ttggcatctt caatcagaag atcgtcaatg gctggcaggt tgaggaggcc  540
gatgattggt tgcgttacgg caacccctgg gagaaggccc gcctggagta cagtcgcccc  600
gtcaagttct atggcaggac cgagcacacc ccagatggtg tgaaatgggt tgacactcag  660
gtagtgttgg ctctgccata tgacacccct attcccggct acagaaacaa cattgtcaac  720
accatgagac tgtggtctgc taaggcccca tgcgacttca acctgaaaga cttcaacgtt  780
ggtggctaca ttcaggctgt gttggacaga aacttgtgga gaacatttcc ccgcgtgctg  840
taccccaatg ataatttctt tgagggcaag gagctgcgtc tgaagcagga gtactttgtg  900
gtggccgcca ctctgcagga cgtcgtccgt cgtttcaagg cctctaagtt tggctccaga  960
gagattgtcc gcacagactt cgccgagcta ccaaacaaag ttgccatcca gctgaatgac  1020
actcaccctg ccatggctat tcctgagctg atgaggtctc tggttgatga ggagaagctg  1080
ggttgggaca aggcctggga cgtgtgtgtc cgtacctgtg cctacacaaa ccacaccgtg  1140
ctgcctgagg ccctggagcg ctggcccatt gacctgttcc atcacctgct gccacgtcac  1200
ctggagatca tctacgagat caaccgtcgc ttcatggagt atgttgcctc gaagttccct  1260
ggagacaacg accgtctgcg tcgcatgtcc ctgattgagg agggaggatg caagaaagtc  1320
aacatggctc atctgtgtat cgttggttcc catgctgtca acggcgtggc ccgcatccac  1380
tctgagatcc tcatcgccac tctgttcaag gacttctatg agttggaccc acacaagttt  1440
cagaacaaga ccaatgggat cacccccccgt cgctggctgg ttatgtgcaa ccccggcttg  1500
gcggaggtca tcgcagagaa aattggagag gagtttatcc gtgaccttga ccagcttaag  1560
cgactgttga agttcgttaa tgatgatgct ttcatccgtg acatcgccaa agtcaagcag  1620
gagaacaagc tgaagttcgc tgtgcacctg aagagcact acaaggtcaa gatcaacccc  1680
cagtccatgt ttgacttcca gttcaaaaga atccacgagt acaaaagaca gctgctcaac  1740
tgtctgcaca tgatcaccta ctacaaccgt atcaagaagg agcccaacaa gcactggacc  1800
ccaagaacca tcatggtcgg aggaaaggct gcaccaggct accacacagc caagatgatc  1860
atccgtctca tcacagctat cggtgaggtt gtcaaccacg accccgttgt cggcgaccgc  1920
ctcaaagtta tcttcctgga aactacagat gtcaccctgg ctgagaaagc catcccctct  1980
gccgacctgt ctgagcagat ctctacagct ggcaccgagg cctctggcac tggtaacatg  2040
aagttcatgc tgaacggtgc tcttaccatt ggcaccatgg atggagccaa tgtggagatg  2100
gccgaggagg ccggagagga aaacttcttc atcttcggta tgagagtgga ggatgtggac  2160
gcaatggacg ccggcaaagg ataccacgcc tctgagtact acaaccgtat ccccgagctg  2220
aagcaggcca tggaccagat tgctggcggc ttcttcagtc ccaagcagcc tgacctcttc  2280
aaggaacttg tggacctgct gatgcaccat gacaggttca aggtgtttgc tgactacgaa  2340
gcctacatca aatgccagga caaggtcaac caactgtaca agaatcccaa ggaatggacc  2400
aagatggtga tccataacat tgcgggctgt ggtaaattct ccagcgaccg caccattgcc  2460
cagtacgccc gagagatctg gggcatggag cccagcctgg agaagatccc tgcccccgat  2520
gagaaactca aa                                                       2532

SEQ ID NO: 110          moltype = AA   length = 844
FEATURE                 Location/Qualifiers
REGION                  1..844
                        note = glycogen phosphorylase, muscle form-like
source                  1..844
                        mol_type = protein
                        organism = synthetic construct
SEQUENCE: 110
MSKPLSDHDK RKQISVRGLA GVENVAELKV AFNRHLHFTL VKDRNVANKR DYYFALANTV  60
RDHLVGRWIR TQQYYYEKDP KRVYYISLEF YMGRTLQNTM VNLALENACD EAIYQLGLDM  120
EELEDMEEDA GLGNGGLGRL AACFLDSMAS LGLAAYGYGI RYEFGIFNQK IVNGWQVEEA  180
DDWLRYGNPW EKARPEYMRP VKFYGRTEHT PDGVKWVDTQ VVLALPYDTP IPGYRNNIVN  240
TMRLWSAKAP CDFNLKDFNV GGYIQAVLDR NLCENISRVL YPNDNFFEGK ELRLKQEYFV  300
VAATLQDVVR RFKASKFGSR EIVRTDFAEL PNKVAIQLND THPAMAIPEL MRVLVDEEKL  360
GWDKAWDVCV RTCAYTNHTV LPEALERWPI DLFHHLLPRH LEIIYEINRR FMEYVASKFP  420
GDNDRLRRMS LIEEGGCKKV NMAHLCIVGS HAVNGVARIH SEILIATLFK DFYELDPHKF  480
QNKTNGITPR RWLVMCNPGL AEVIAEKIGE EFIRDLDQLK RLLKFVNDDA FIRDIAKVKQ  540
ENKLKFAVHL EEHYKVKINP QSMFDFQVKR IHEYKRQLLN CLHMITYYNR IKKEPNKHWT  600
PRTIMVGGKA APGYHTAKMI IRLITAIGEV VNHDPVVGDR LKVIFLENYR VTLAEKAIPS  660
ADLSEQISTA GTEASGTGNM KFMLNGALTI GTMDGANVEM AEEAGEENFF IPGMRVEDVD  720
AMDAGKGYHA SEYYNRIPEL KQAMDQIAGG FFSPKQPDLF KELVDLLMHH DRFKVFADYE  780
AYIKCQDKVN QLYKNPKEWT KMVIHNIAGC GKFSSDRTIA QYAREIWGME PSLEKIPAPD  840
EKLK                                                                844

-continued

```
SEQ ID NO: 111          moltype = AA   length = 9
FEATURE                 Location/Qualifiers
REGION                  1..9
                        note = glycogen phosphorylase, muscle form-like fragment
source                  1..9
                        mol_type = protein
                        organism = synthetic construct SEQUENCE: 111
DFYELDPHK                                                              9

SEQ ID NO: 112          moltype = AA   length = 10
FEATURE                 Location/Qualifiers
REGION                  1..10
                        note = glycogen phosphorylase, muscle form-like fragment
source                  1..10
                        mol_type = protein
                        organism = synthetic construct SEQUENCE: 112
FAVHLEEHYK                                                             10

SEQ ID NO: 113          moltype = AA   length = 13
FEATURE                 Location/Qualifiers
REGION                  1..13
                        note = glycogen phosphorylase, muscle form-like fragment
source                  1..13
                        mol_type = protein
                        organism = synthetic construct SEQUENCE: 113
FYGRTEHTPD GVK                                                         13

SEQ ID NO: 114          moltype = AA   length = 15
FEATURE                 Location/Qualifiers
REGION                  1..15
                        note = glycogen phosphorylase, muscle form-like fragment
source                  1..15
                        mol_type = protein
                        organism = synthetic construct SEQUENCE: 114
GYHASEYYNR IPELK                                                       15

SEQ ID NO: 115          moltype = AA   length = 13
FEATURE                 Location/Qualifiers
REGION                  1..13
                        note = glycogen phosphorylase, muscle form-like fragment
source                  1..13
                        mol_type = protein
                        organism = synthetic construct SEQUENCE: 115
IGEEFIRDLD QLK                                                         13

SEQ ID NO: 116          moltype = AA   length = 14
FEATURE                 Location/Qualifiers
REGION                  1..14
                        note = glycogen phosphorylase, muscle form-like fragment
source                  1..14
                        mol_type = protein
                        organism = synthetic construct SEQUENCE: 116
QAMDQIAGGF FSPK                                                        14

SEQ ID NO: 117          moltype = AA   length = 17
FEATURE                 Location/Qualifiers
REGION                  1..17
                        note = glycogen phosphorylase, muscle form-like fragment
source                  1..17
                        mol_type = protein
                        organism = synthetic construct SEQUENCE: 117
QISVRGLAGV ENVAELK                                                     17

SEQ ID NO: 118          moltype = AA   length = 10
FEATURE                 Location/Qualifiers
REGION                  1..10
                        note = glycogen phosphorylase, muscle form-like fragment
source                  1..10
                        mol_type = protein
                        organism = synthetic construct

SEQUENCE: 118
```

-continued

```
VFADYEAYIK                                                                       10

SEQ ID NO: 119          moltype = AA  length = 14
FEATURE                 Location/Qualifiers
REGION                  1..14
                        note = glycogen phosphorylase, muscle form-like fragment
source                  1..14
                        mol_type = protein
                        organism = synthetic construct
SEQUENCE: 119
VIFLENYRVT LAEK                                                                   14

SEQ ID NO: 120          moltype = DNA  length = 3399
FEATURE                 Location/Qualifiers
misc_feature            1..3399
                        note = myosin-binding protein C, fast-type-like
source                  1..3399
                        mol_type = other DNA
                        organism = synthetic construct
SEQUENCE: 120
atgcctgaag ccgctgatgc agtgaagccg gagggcgagg agggagaagc accagcagaa   60
gccgaagaaa atactgcaga agatgatgag ccactgcctg agaggaggga gggtgcccat  120
cagtcacagg agattacagg actgtttctt cagcaccctg agactacggt tgccataaca  180
ggtacggaca ttgtgtttac tgccaaagtg gactctacta cactatcaag gaaacccacc  240
attaaatggc tgaaggggaa gtggctggac ctgggcagca agcaggaaa acacatgcag  300
ttcaaagaga cttttgacag agccacaaag atctcacct gggacatgaa gataatcaag  360
gtggtccctg gtgacgctgg ggcctacagg tgtgaggtca cctccaaaga caagtgtgac  420
agcagcgctt tcgacatctc cgtggaggct gtgcaaattg aggaggaaca tgattctttg  480
gccgcattca aaagaacgga tgctggagag gatgaaggca gtttggattt cagtgctttg  540
ctgaaagcta ccaagaagaa gaagaagcca gtcgtagatg aggagaaggc agacgtgtgg  600
gaaatcctga agaacgctca acccagcgag tatgagaaga ttgctttga gtacggcatt  660
acagacctga ggggtctgct caagcgactg aagaagatga agactgttga gcccaagcac  720
agcgacgctt tcctaaagag aatggagtct gcctactctg tggataaggg caagaaaatc  780
gtactgcagg tggaagtggt tgacccaaat gcccaggtca aatggttgaa gaacggtcag  840
gagataaaat catcagccaa gtacatcata gaatcagttg gcaacatcag gacgctcacc  900
atcaacaagt gtagcctggc tgacgacgct gcgtacgagt gtgtgattgg ggaagagaag  960
tccttcacag aggtgtttgt caaagagccc ccggtcacca tcaccaagct gctggatgat 1020
taccacgtgg tggtgggaga gagagtggag tttgaggtgg aggtgtctgt ggagggagca 1080
cacgttaact ggatgtttga ggaccaagaa ctctccaggg acacccataa gtaccgcttt 1140
aagaaggacc ggttgaagca catgctcatc atccaagagg ctacgctgga tgacattgga 1200
atgtactggt gcttcaccaa cggcgggcga accaaaggag agctagaagt tgaagagaaa 1260
gaactggagg tgttgcagaa catcgctgac ctgacggtga aggccgagga ccaggccatg 1320
ttcaagtgtg aggtgtctga tgagaaggta acagggaaat ggctcaaaga tggcgtgaca 1380
gtgctgccca gcagtcgcat caagctgacc cacatcggaa gaatccatcg gcttaccata 1440
gacgacgtca agcccgagga cgctggagac tataccttta tcccagacg atatgccctc 1500
tcactgtccg ccaaactcaa cttcctggaa attaagatcg actatgtccc ccgccaagag 1560
ccacccaaga tccatctaga caccaccggc aacatggttt cccagaacac catcattgtg 1620
gtggctggca acaagctgcg cctgacgtg gagatctctg agagcctcc tcccactgtc 1680
gtctgggcaa agggagacac ggcaatcaca gctgtggagg ggcgtgtgag gactgagagc 1740
cggaaggacc tgagctgctt cgtcatagag ggggcagaga gagaggatga gggcaactac 1800
accatcattg tcaccaaccc tgccggagag gacaaggctc atctgtttgt caagattgtt 1860
gatgtgcctg actgccctga gaatgtaaag tgtacctcgg tgggagaaga ctgtgccacc 1920
atggtctggg acccacccaa gttcgacgga ggcgcaccag tcacaggcta tctcatggag 1980
aggaagaaga agggctccac caggtggacg aagctcaact ttgacgtgta cgaggggtg 2040
acgtacgaag ccaagaggat gattgaggc gtgctctacg agatgagagt gtacgccgtc 2100
aatggcattg gcatgtccca gcccagcctc aattccaaac ccttcatgcc catcgctgca 2160
accagtgagc ctctgggcct caaggtgcat gatgtcacag acaccacatg taccctgaag 2220
tggctggccc ctgagaagat cggtgccgga ggcctggacg gatacgttat tgagtactgc 2280
aaggaggag acacggagtg ggtggtggcg aacaactgag tggtggagag acagaattac 2340
acagtccgca acctccccac cgcggagaag atcaacttca gagtggtggc cgtgaacatt 2400
gctggacgca gccccctac cggcctgagc cagcccgtca ctatccgcga gatcgtggaa 2460
ctgcccaaga tccgcctccc tcgctactta agacagaagt acattagaag agtgggcgac 2520
aaaatcaacc tgaccatccc cttccagggt aagccacgtc ccaaagtgca atggtacaag 2580
gatggggaag agcttgacac tcgagttgcc agcatacgca attccgaagt ggactctatc 2640
ctgttcatcc gctcggctga gagatcccac tctgggaagt acgagttggt cctgcagatt 2700
gagaacatgg aggccagggc tattctggaa atcaggatcg tagaggcacc tgggcctccc 2760
gaggtagtga aggtcacaga cgtttggggc ttcaacgctg cgctggagtg gaagccaccg 2820
aaggacgacg gcaactgcga gatcaccggt tacacaaatac agaaggcgga caagaagaca 2880
aatgaatggt tcactatcta cgagcacaac aggaggacaa actgcacgc ctcagacctg 2940
atcatgggaa atgagtacat gttccgtgtc ttcagcgaga acctcgttgg aaagagtgag 3000
gatttctgcc tcagcaagga cacagccatc atacctaaga taggattgga gtacaaccca 3060
cctccattca aggagaagga tatgcaaagc gcccccaagt tcatacagcc cctgcttgac 3120
aggtctgtgg tggcaggcta cagtaccacc atcagctctg ctgtcaagac ttgtcctaaa 3180
cctaagatca ggtggttgag gaataagatt ccctggaacg agaaccctag gttcctgatg 3240
cagaacaacc aggggtttt gaccctgaac atccgcaagc ccagtcagta tgacgggggc 3300
aagttcacct gcaaggctat caactctttg ggggaggacg tcgtggagtg caccctactc 3360
gtacgagctc tcaaggacaa ggaagatgga gacgagaaa                         3399

SEQ ID NO: 121          moltype = AA  length = 1133
```

-continued

```
FEATURE              Location/Qualifiers
REGION               1..1133
                     note = myosin-binding protein C, fast-type-like
source               1..1133
                     mol_type = protein
                     organism = synthetic construct
SEQUENCE: 121
MPEAADAVKP EGEEGEAPAE AEENTAEDDE PLPEGEEGAH QSQEITGLFL QHPETTVAIT  60
GTDIVFTAKV DSTTLSRKPT IKWLKGKWLD LGSKAGKHMQ FKETFDRATK IYTWDMKIIK  120
VVPGDAGAYR CEVTSKDKCD SSAFDISVEA VQIEEEHDSL AAFKRTDAGE DEGSLDFSAL  180
LKATKKKKKP VVDEEKADVW EILKNAQPSE YEKIAFEYGI TDLRGLLKRL KKMKTVEPKH  240
SDAFLKRMES AYSVDKGKKI VLQVEVVDPN AQVKWLKNGQ EIKSSAKYII ESVGNIRTLT  300
INKCSLADDA AYECVIGEEK SFTEVFVKEP PVTITKLLDD YHVVVGERVE FEVEVSVEGA  360
HVNWMFEDQE LSRDTHKYRF KKDGLKHMLI IQEATLDDIG MYWCFTNGGR TKGELEVEEK  420
ELEVLQNIAD LTVKAEDQAM FKCEVSDEKV TGKWLKDGVE VLPSSRIKLT HIGRIHRLTI  480
DDVKPEDAGD YTFIPDGYAL SLSAKLNFLE IKIDYVPRQE PPKIHLDTTG NMVSQNTIIV  540
VAGNKLRLDV EISGEPPPTV VWAKGDTAIT AVEGRVRTES RKDLSCFVIE GAEREDEGNY  600
TIIVTNPAGE DKAHLFVKIV DVPDCPENVK CTSVGEDCAT MVWDPPKFDG GAPVTGYLME  660
RKKKGSTRWT KLNFDVYEGV TYEAKRMIEG VLYEMRVYAV NGIGMSQPSL NSKPFMPIAA  720
TSEPLGLKVH DVTDTTCTLK WLAPEKIGAG GLDGYVIEYC KEGDTEWVVA NTELVERQNY  780
TVRNLPTAEK INFRVVAVNI AGRSPPTGLS QPVTIREIVE LPKIRLPRYL RQKYIRRVGD  840
KINLTIPFQG KPRPKVQWYK DGEELDTRVA SIRNSEVDSI LFIRSAERSH SGKYELVLQI  900
ENMEARAILE IRIVEAPGPP EVVKVTDVWG FNAALEWKPP KDDGNCEITG YTIQKADKKT  960
NEWFTIYEHN RRTNCTASDL IMGNEYMFRV FSENLVGKSE DFCLSKDTAI IPKIGLEYNP  1020
PPFKEKDMQS APKFIQPLLD RSVVAGYSTT ISSAVKTCPK PKIRWLRNKI PLDENPRFLM  1080
QNNQGVLTLN IRKPSQYDGG KFTCKAINSL GEDVVECTLL VRALKDKEDG DEK          1133

SEQ ID NO: 122         moltype = AA  length = 8
FEATURE                Location/Qualifiers
REGION                 1..8
                       note = myosin-binding protein C, fast-type-like fragment
source                 1..8
                       mol_type = protein
                       organism = synthetic construct
SEQUENCE: 122
ADVWEILK                                                           8

SEQ ID NO: 123         moltype = AA  length = 14
FEATURE                Location/Qualifiers
REGION                 1..14
                       note = myosin-binding protein C, fast-type-like fragment
source                 1..14
                       mol_type = protein
                       organism = synthetic construct
SEQUENCE: 123
ELEVLQNIAD LTVK                                                    14

SEQ ID NO: 124         moltype = AA  length = 8
FEATURE                Location/Qualifiers
REGION                 1..8
                       note = myosin-binding protein C, fast-type-like fragment
source                 1..8
                       mol_type = protein
                       organism = synthetic construct
SEQUENCE: 124
EPPVTITK                                                           8

SEQ ID NO: 125         moltype = AA  length = 8
FEATURE                Location/Qualifiers
REGION                 1..8
                       note = myosin-binding protein C, fast-type-like fragment
source                 1..8
                       mol_type = protein
                       organism = synthetic construct
SEQUENCE: 125
GELEVEEK                                                           8

SEQ ID NO: 126         moltype = AA  length = 7
FEATURE                Location/Qualifiers
REGION                 1..7
                       note = myosin-binding protein C, fast-type-like fragment
source                 1..7
                       mol_type = protein
                       organism = synthetic construct
SEQUENCE: 126
HSDAFLK                                                            7

SEQ ID NO: 127         moltype = AA  length = 15
FEATURE                Location/Qualifiers
```

```
REGION                    1..15
                          note = myosin-binding protein C, fast-type-like fragment
source                    1..15
                          mol_type = protein
                          organism = synthetic construct
SEQUENCE: 127
IAFEYGITDL RGLLK                                                    15

SEQ ID NO: 128            moltype = AA   length = 11
FEATURE                   Location/Qualifiers
REGION                    1..11
                          note = myosin-binding protein C, fast-type-like fragment
source                    1..11
                          mol_type = protein
                          organism = synthetic construct
SEQUENCE: 128
IGLEYNPPPF K                                                        11

SEQ ID NO: 129            moltype = AA   length = 14
FEATURE                   Location/Qualifiers
REGION                    1..14
                          note = myosin-binding protein C, fast-type-like fragment
source                    1..14
                          mol_type = protein
                          organism = synthetic construct
SEQUENCE: 129
INLTIPFQGK PRPK                                                     14

SEQ ID NO: 130            moltype = AA   length = 15
FEATURE                   Location/Qualifiers
REGION                    1..15
                          note = myosin-binding protein C, fast-type-like fragment
source                    1..15
                          mol_type = protein
                          organism = synthetic construct
SEQUENCE: 130
IVLQVEVVDP NAQVK                                                    15

SEQ ID NO: 131            moltype = AA   length = 14
FEATURE                   Location/Qualifiers
REGION                    1..14
                          note = myosin-binding protein C, fast-type-like fragment
source                    1..14
                          mol_type = protein
                          organism = synthetic construct
SEQUENCE: 131
LNFDVYEGVT YEAK                                                     14

SEQ ID NO: 132            moltype = AA   length = 7
FEATURE                   Location/Qualifiers
REGION                    1..7
                          note = myosin-binding protein C, fast-type-like fragment
source                    1..7
                          mol_type = protein
                          organism = synthetic construct
SEQUENCE: 132
LNFLEIK                                                             7

SEQ ID NO: 133            moltype = AA   length = 9
FEATURE                   Location/Qualifiers
REGION                    1..9
                          note = myosin-binding protein C, fast-type-like fragment
source                    1..9
                          mol_type = protein
                          organism = synthetic construct
SEQUENCE: 133
NAQPSEYEK                                                           9

SEQ ID NO: 134            moltype = AA   length = 18
FEATURE                   Location/Qualifiers
REGION                    1..18
                          note = myosin-binding protein C, fast-type-like fragment
source                    1..18
                          mol_type = protein
                          organism = synthetic construct
SEQUENCE: 134
RTDAGEDEGS LDFSALLK                                                 18

SEQ ID NO: 135            moltype = AA   length = 8
```

```
FEATURE              Location/Qualifiers
REGION               1..8
                     note = myosin-binding protein C, fast-type-like fragment
source               1..8
                     mol_type = protein
                     organism = synthetic construct
SEQUENCE: 135
SFTEVFVK                                                                        8

SEQ ID NO: 136       moltype = AA  length = 13
FEATURE              Location/Qualifiers
REGION               1..13
                     note = myosin-binding protein C, fast-type-like fragment
source               1..13
                     mol_type = protein
                     organism = synthetic construct
SEQUENCE: 136
VDSTTLSRKP TIK                                                                  13

SEQ ID NO: 137       moltype = DNA  length = 1551
FEATURE              Location/Qualifiers
misc_feature         1..1551
                     note = ATP synthase subunit beta, mitochondrial
source               1..1551
                     mol_type = other DNA
                     organism = synthetic construct
SEQUENCE: 137
atgttaggag ctgtgggacg ctgctgcacc ggggctctcc aggcacttaa gcctggggtc   60
cagcccctga aggcccttgt aggatcgcca tctgtccttg gacgcagaga ctactctgca   120
cctgctgctg ctgccgcctt cgcccatggc aggatcgtag cggtcatcgg tgccgtcgtc   180
gacgtccagt tcgatgaggg cctcccaccc atcctcaatg ccctggaagt tgctgggcgt   240
gagtccaggc tagttctgga ggtggcacag catcttggtg agaacactgt gcgtaccatt   300
gccatggatg gtactgaagg tcttgtccgt ggacagaagg ttgtggacac tggcgatccc   360
atcagaatcc cagtgggtcc cgagaccta ggcagaatca tgaatgtcat tggagagccc    420
attgatgaga gggggccaat ctccaccaag cagactgccg ccatccacgc tgaggcccca   480
gagttcactg acatgagtgt ggagcaggag atcctggtaa ctggcatcaa ggtggtagat   540
ctgctggctc cctatgccaa gggaggcaaa atcggtctgt tcggtggtgc tggtgtgggc   600
aagactgtgt tgatcatgga gctgatcaac aatgtggcca aggcccatgg tggttactct   660
gtgtttgccg gagtgggaga gcgtaccgc gagggaaatg acttgtacca cgagatgatt     720
gagtcgggtg tcatcaacct gaaggatgac acctccaagg tggcgctggt gtacggacaa   780
atgaacgagc cccaggcgc ccgtgcccgt gtggctctga ctggtctgac cgtggcagag    840
tatttccgtg accaggaggg tcaggatgtg ctgctcttca tcgataacat cttccgtttc   900
acccaggctg gctccgaggt gtctgccctg ctgggtcgta tccctccgc tgtgggttac     960
cagcccaccc tggccactga catgggtacc atgcaggaga gaatcaccac caccaagaag   1020
ggttccatca cctctgtgca ggccatctat gtgccggctg acgatttgac tgatcccgcc   1080
cctgccacca ccttcgctca cttggacgcc accactgtgc tgtcccgtgc aatcgctgag   1140
ctgggtatct accctgctgt ggatcccctg gattccaccct cccgtatcat ggaccccaac   1200
attgtcggcg ctgagcacta tgatgttgct cgtggcgtgc agaagatcct ccaggactac   1260
aagtccctgc aggatatcat tgccatcctg ggtatggatg agttgtctga ggaggacaag   1320
ctgattgtct ctcgcgcccg caagatccag cgtttcctgt cccagccctt ccaggtggcg   1380
gaggtattca ccggtcatgc tggcaagctg gtgccactca ggagaccat cagtggcttc    1440
cagagcattc taaatggtga gtacgatgcc ctgcccgagc aggctttcta catggttgga   1500
cccatcgagg aggtggttga gaaggctgca cagatggcca aggatctcgc a             1551

SEQ ID NO: 138       moltype = AA  length = 517
FEATURE              Location/Qualifiers
REGION               1..517
                     note = ATP synthase subunit beta, mitochondrial
source               1..517
                     mol_type = protein
                     organism = synthetic construct
SEQUENCE: 138
MLGAVGRCCT GALQALKPGV QPLKALVGSP SVLGRRDYSA PAAAAAFAHG RIVAVIGAVV   60
DVQFDEGLPP ILNALEVAGR ESRLVLEVAQ HLGENTVRTI AMDGTEGLVR GQKVVDTGDP   120
IRIPVGPETL GRIMNVIGEP IDERGPISTK QTAAIHAEAP EFTDMSVEQE ILVTGIKVVD   180
LLAPYAKGGK IGLFGGAGVG KTVLIMELIN NVAKAHGGYS VFAGVGERTR EGNDLYHEMI   240
ESGVINLKDD TSKVALVYGQ MNEPPGARAR VALTGLTVAE YFRDQEGQDV LLFIDNIFRF   300
TQAGSEVSAL LGRIPSAVGY QPTLATDMGT MQERITTTKK GSITSVQAIY VPADDLTDPA   360
PATTFAHLDA TTVLSRAIAE LGIYPAVDPL DSTSRIMDPN IVGAEHYDVA RGVQKILQDY   420
KSLQDIIAIL GMDELSEEDK LIVSRARKIQ RFLSQPFQVA EVFTGHAGKL VPLKETISGF   480
QSILNGEYDA LPEQAFYMVG PIEEVVEKAA QMAKDLA                             517

SEQ ID NO: 139       moltype = AA  length = 11
FEATURE              Location/Qualifiers
REGION               1..11
                     note = ATP synthase subunit beta, mitochondrial fragment
source               1..11
                     mol_type = protein
                     organism = synthetic construct
```

```
SEQUENCE: 139
IGLFGGAGVG K                                                          11

SEQ ID NO: 140       moltype = AA  length = 21
FEATURE              Location/Qualifiers
REGION               1..21
                     note = ATP synthase subunit beta, mitochondrial fragment
source               1..21
                     mol_type = protein
                     organism = synthetic construct
SEQUENCE: 140
IQRFLSQPFQ VAEVFTGHAG K                                               21

SEQ ID NO: 141       moltype = AA  length = 13
FEATURE              Location/Qualifiers
REGION               1..13
                     note = ATP synthase subunit beta, mitochondrial fragment
source               1..13
                     mol_type = protein
                     organism = synthetic construct
SEQUENCE: 141
TVLIMELINN VAK                                                        13

SEQ ID NO: 142       moltype = AA  length = 10
FEATURE              Location/Qualifiers
REGION               1..10
                     note = ATP synthase subunit beta, mitochondrial fragment
source               1..10
                     mol_type = protein
                     organism = synthetic construct
SEQUENCE: 142
VVDLLAPYAK                                                            10

SEQ ID NO: 143       moltype = DNA  length = 996
FEATURE              Location/Qualifiers
misc_feature         1..996
                     note = L-lactate dehydrogenase A chain-like
source               1..996
                     mol_type = other DNA
                     organism = synthetic construct
SEQUENCE: 143
atgactacca aggagaagct gatcacccat gtgttggctg gtgagcctgt tggctcccgg   60
agcaaggtga cagttgttgg cgtcggcatg gttggcatgg cctccgcagt cagcgtcctg  120
ctcaaggacc tgtgcgatga gctgtgcctg attgacgtga tggaagataa actgaagggt  180
gaggtcatgg acctgcagca tggcagcctc ttctgcaaga ctcacaagat tgtgggcgac  240
aaggactaca gtacgactgc ccactccaag gtggtggtgt tcacagccgg tgctcgtcag  300
caagagggtg agagccgtct gaacctggtg cagcgtaacg tcaacatctt caaattcata  360
attccccaga tcgtcaagta cagccccaac gccatcctgc tggtcgtctc caatcctgtt  420
gacatcctaa cctacgtggc cttggaagct gagtggtttc cccgtcaccg cgtcatcggt  480
tccggcacca acctggactc tggtcgtttc cgccacctga tgggcgagaa gctacacctt  540
cacccatcca gctgtcacgg ctggatcatt ggagaacacg gagactccag cgtgcccgta  600
tggagcggtg tgaatgttgc cggtgtttcc ctgaagggcc tgaacccaga catgggcaca  660
gacgcagaca aggaggactg gaagcacgtc cacaagatgg tggtcgacgg tgcctatgag  720
gtcatcaagc tgaagggtta cacctcctgg gctatcggca tgtccgtcgc tgacctggtt  780
gagagcatcc tgaagaacct ccacaaagtc caccctgtgt ccaccctggt caagggaatg  840
cacggtgtga aggaggaggt gtttctcagc gtgccctgcg tgctgggaaa cagcggtctg  900
accgacgtca tccacatgac tctgaagccc gaggaggaga agcagctgag caacagtgcc  960
gagaccctat ggggcgtaca gaaagagctc accttg                            996

SEQ ID NO: 144       moltype = AA  length = 332
FEATURE              Location/Qualifiers
REGION               1..332
                     note = L-lactate dehydrogenase A chain-like
source               1..332
                     mol_type = protein
                     organism = synthetic construct
SEQUENCE: 144
MTTKEKLITH VLAGEPVGSR SKVTVVGVGM VGMASAVSVL LKDLCDELCL IDVMEDKLKG   60
EVMDLQHGSL FCKTHKIVGD KDYSTTAHSK VVVVTAGARQ QEGESRLNLV QRNVNIFKFI  120
IPQIVKYSPN AILLVVSNPV DILTYVAWKL SGFPRHRVIG SGTNLDSGRF RHLMGEKLHL  180
HPSSCHGWII GEHGDSSVPV WSGVNVAGVS LKGLNPDMGT DADKEDWKHV HKMVVDGAYE  240
VIKLKGYTSW AIGMSVADLV ESILKNLHKV HPVSTLVKGM HGVKEEVFLS VPCVLGNSGL  300
TDVIHMTLKP EEEKQLSNSA ETLWGVQKEL TL                                 332

SEQ ID NO: 145       moltype = AA  length = 8
FEATURE              Location/Qualifiers
REGION               1..8
                     note = L-lactate dehydrogenase A chain-like fragment
source               1..8
```

-continued

```
                         mol_type = protein
                         organism = synthetic construct
SEQUENCE: 145
FIIPQIVK                                                        8

SEQ ID NO: 146          moltype = AA   length = 16
FEATURE                 Location/Qualifiers
REGION                  1..16
                        note = L-lactate dehydrogenase A chain-like fragment
source                  1..16
                        mol_type = protein
                        organism = synthetic construct
SEQUENCE: 146
LITHVLAGEP VGSRSK                                               16

SEQ ID NO: 147          moltype = AA   length = 14
FEATURE                 Location/Qualifiers
REGION                  1..14
                        note = L-lactate dehydrogenase A chain-like fragment
source                  1..14
                        mol_type = protein
                        organism = synthetic construct
SEQUENCE: 147
THVLAGEPVG SRSK                                                 14

SEQ ID NO: 148          moltype = AA   length = 9
FEATURE                 Location/Qualifiers
REGION                  1..9
                        note = L-lactate dehydrogenase A chain-like fragment
source                  1..9
                        mol_type = protein
                        organism = synthetic construct
SEQUENCE: 148
VHPVSTLVK                                                       9

SEQ ID NO: 149          moltype = AA   length = 28
FEATURE                 Location/Qualifiers
REGION                  1..28
                        note = L-lactate dehydrogenase A chain-like fragment
source                  1..28
                        mol_type = protein
                        organism = synthetic construct
SEQUENCE: 149
VVVVTAGARQ QEGESRLNLV QRNVNIFK                                  28

SEQ ID NO: 150          moltype = AA   length = 15
FEATURE                 Location/Qualifiers
REGION                  1..15
                        note = epitope
source                  1..15
                        mol_type = protein
                        organism = synthetic construct
SEQUENCE: 150
SGERLPKPDK GKMRF                                                15

SEQ ID NO: 151          moltype = AA   length = 15
FEATURE                 Location/Qualifiers
REGION                  1..15
                        note = epitope
source                  1..15
                        mol_type = protein
                        organism = synthetic construct
SEQUENCE: 151
YSKLRKDDPM GNLNT                                                15

SEQ ID NO: 152          moltype = AA   length = 15
FEATURE                 Location/Qualifiers
REGION                  1..15
                        note = epitope
source                  1..15
                        mol_type = protein
                        organism = synthetic construct
SEQUENCE: 152
SCFYHAFAGA EQAET                                                15

SEQ ID NO: 153          moltype = AA   length = 15
FEATURE                 Location/Qualifiers
REGION                  1..15
                        note = epitope
```

-continued

```
source                  1..15
                        mol_type = protein
                        organism = synthetic construct
SEQUENCE: 153
TKLRLSNRPA FMPSE                                                      15

SEQ ID NO: 154          moltype = AA  length = 15
FEATURE                 Location/Qualifiers
REGION                  1..15
                        note = epitope
source                  1..15
                        mol_type = protein
                        organism = synthetic construct
SEQUENCE: 154
SDKTYITVEE LRREL                                                      15

SEQ ID NO: 155          moltype = AA  length = 15
FEATURE                 Location/Qualifiers
REGION                  1..15
                        note = epitope
source                  1..15
                        mol_type = protein
                        organism = synthetic construct
SEQUENCE: 155
LDNRLYYMVA EHDSS                                                      15

SEQ ID NO: 156          moltype = AA  length = 15
FEATURE                 Location/Qualifiers
REGION                  1..15
                        note = epitope
source                  1..15
                        mol_type = protein
                        organism = synthetic construct
SEQUENCE: 156
GGYIQAVLDR NLCEN                                                      15

SEQ ID NO: 157          moltype = AA  length = 15
FEATURE                 Location/Qualifiers
REGION                  1..15
                        note = epitope
source                  1..15
                        mol_type = protein
                        organism = synthetic construct
SEQUENCE: 157
DRFKVFADYE AYIKS                                                      15

SEQ ID NO: 158          moltype = AA  length = 15
FEATURE                 Location/Qualifiers
REGION                  1..15
                        note = epitope
source                  1..15
                        mol_type = protein
                        organism = synthetic construct
SEQUENCE: 158
AIMDKKSNIR NMSVI                                                      15

SEQ ID NO: 159          moltype = AA  length = 15
FEATURE                 Location/Qualifiers
REGION                  1..15
                        note = epitope
source                  1..15
                        mol_type = protein
                        organism = synthetic construct
SEQUENCE: 159
GKSTLTDSLV SKAGI                                                      15

SEQ ID NO: 160          moltype = AA  length = 15
FEATURE                 Location/Qualifiers
REGION                  1..15
                        note = epitope
source                  1..15
                        mol_type = protein
                        organism = synthetic construct
SEQUENCE: 160
SMVLVKMKEI AEAYL                                                      15

SEQ ID NO: 161          moltype = AA  length = 15
FEATURE                 Location/Qualifiers
REGION                  1..15
```

-continued

```
                                note = heat shock cognate 70 kDa protein epitope
source                          1..15
                                mol_type = protein
                                organism = synthetic construct
SEQUENCE: 161
EAEQYKAADD VQRDK                                                      15

SEQ ID NO: 162                  moltype = AA  length = 15
FEATURE                         Location/Qualifiers
REGION                          1..15
                                note = epitope
source                          1..15
                                mol_type = protein
                                organism = synthetic construct
SEQUENCE: 162
KLSDEDKQKI LDKCN                                                      15

SEQ ID NO: 163                  moltype = AA  length = 15
FEATURE                         Location/Qualifiers
REGION                          1..15
                                note = epitope
source                          1..15
                                mol_type = protein
                                organism = synthetic construct
SEQUENCE: 163
DTCYYAVAVA KKGTE                                                      15

SEQ ID NO: 164                  moltype = AA  length = 15
FEATURE                         Location/Qualifiers
REGION                          1..15
                                note = epitope
source                          1..15
                                mol_type = protein
                                organism = synthetic construct
SEQUENCE: 164
YSGAFQCLKD GAGEV                                                      15

SEQ ID NO: 165                  moltype = AA  length = 15
FEATURE                         Location/Qualifiers
REGION                          1..15
                                note = epitope
source                          1..15
                                mol_type = protein
                                organism = synthetic construct
SEQUENCE: 165
IYSKLMAVTN FNLFS                                                      15

SEQ ID NO: 166                  moltype = AA  length = 15
FEATURE                         Location/Qualifiers
REGION                          1..15
                                note = epitope
source                          1..15
                                mol_type = protein
                                organism = synthetic construct
SEQUENCE: 166
MSTIRSLTKA QATGV                                                      15

SEQ ID NO: 167                  moltype = AA  length = 15
FEATURE                         Location/Qualifiers
REGION                          1..15
                                note = epitope
source                          1..15
                                mol_type = protein
                                organism = synthetic construct
SEQUENCE: 167
YYGYNGAFRC LVEDA                                                      15

SEQ ID NO: 168                  moltype = AA  length = 15
FEATURE                         Location/Qualifiers
REGION                          1..15
                                note = epitope
source                          1..15
                                mol_type = protein
                                organism = synthetic construct
SEQUENCE: 168
RYVKKVGEKI NIVIP                                                      15

SEQ ID NO: 169                  moltype = AA  length = 15
FEATURE                         Location/Qualifiers
```

-continued

```
REGION                    1..15
                          note = epitope
source                    1..15
                          mol_type = protein
                          organism = synthetic construct
SEQUENCE: 169
SYEMCVKVDD FEDKA                                              15

SEQ ID NO: 170            moltype = AA  length = 15
FEATURE                   Location/Qualifiers
REGION                    1..15
                          note = epitope
source                    1..15
                          mol_type = protein
                          organism = synthetic construct
SEQUENCE: 170
KEVIDYKPTP FVEHD                                              15

SEQ ID NO: 171            moltype = AA  length = 15
FEATURE                   Location/Qualifiers
REGION                    1..15
                          note = epitope
source                    1..15
                          mol_type = protein
                          organism = synthetic construct
SEQUENCE: 171
NNMDNPKYRM ISTGG                                              15

SEQ ID NO: 172            moltype = AA  length = 15
FEATURE                   Location/Qualifiers
REGION                    1..15
                          note = epitope
source                    1..15
                          mol_type = protein
                          organism = synthetic construct
SEQUENCE: 172
NDRFASYIEK VRFLE                                              15

SEQ ID NO: 173            moltype = AA  length = 15
FEATURE                   Location/Qualifiers
REGION                    1..15
                          note = epitope
source                    1..15
                          mol_type = protein
                          organism = synthetic construct
SEQUENCE: 173
YKSKVSDLNQ AVNKN                                              15

SEQ ID NO: 174            moltype = AA  length = 15
FEATURE                   Location/Qualifiers
REGION                    1..15
                          note = epitope
source                    1..15
                          mol_type = protein
                          organism = synthetic construct
SEQUENCE: 174
DVGRSAEVHS KKTVL                                              15

SEQ ID NO: 175            moltype = AA  length = 15
FEATURE                   Location/Qualifiers
REGION                    1..15
                          note = epitope
source                    1..15
                          mol_type = protein
                          organism = synthetic construct
SEQUENCE: 175
VILIKKAGDG SKKIK                                              15

SEQ ID NO: 176            moltype = AA  length = 15
FEATURE                   Location/Qualifiers
REGION                    1..15
                          note = epitope
source                    1..15
                          mol_type = protein
                          organism = synthetic construct
SEQUENCE: 176
IHVVEVQEKS SGRTA                                              15

SEQ ID NO: 177            moltype = AA  length = 15
```

-continued

```
FEATURE               Location/Qualifiers
REGION                1..15
                      note = epitope
source                1..15
                      mol_type = protein
                      organism = synthetic construct
SEQUENCE: 177
IYFGKTKDIV NGLRS                                                 15

SEQ ID NO: 178        moltype = AA  length = 15
FEATURE               Location/Qualifiers
REGION                1..15
                      note = epitope
source                1..15
                      mol_type = protein
                      organism = synthetic construct
SEQUENCE: 178
DNQKYRQLQK ELSQV                                                 15

SEQ ID NO: 179        moltype = AA  length = 15
FEATURE               Location/Qualifiers
REGION                1..15
                      note = epitope
source                1..15
                      mol_type = protein
                      organism = synthetic construct
SEQUENCE: 179
TVTALDFREG KEFKD                                                 15

SEQ ID NO: 180        moltype = AA  length = 15
FEATURE               Location/Qualifiers
REGION                1..15
                      note = epitope
source                1..15
                      mol_type = protein
                      organism = synthetic construct
SEQUENCE: 180
YNSMEQLCIN FTNEK                                                 15

SEQ ID NO: 181        moltype = AA  length = 15
FEATURE               Location/Qualifiers
REGION                1..15
                      note = epitope
source                1..15
                      mol_type = protein
                      organism = synthetic construct
SEQUENCE: 181
LYPPPPPEDK AKKGG                                                 15

SEQ ID NO: 182        moltype = AA  length = 15
FEATURE               Location/Qualifiers
REGION                1..15
                      note = myosin heavy chain, fast skeletal muscle-like epitope
source                1..15
                      mol_type = protein
                      organism = synthetic construct
SEQUENCE: 182
ASMDESVAKL TKEKK                                                 15

SEQ ID NO: 183        moltype = AA  length = 15
FEATURE               Location/Qualifiers
REGION                1..15
                      note = epitope
source                1..15
                      mol_type = protein
                      organism = synthetic construct
SEQUENCE: 183
EEDKVNTLTK AKTKL                                                 15

SEQ ID NO: 184        moltype = AA  length = 15
FEATURE               Location/Qualifiers
REGION                1..15
                      note = epitope
source                1..15
                      mol_type = protein
                      organism = synthetic construct
SEQUENCE: 184
KLRMDLERSK RKLEG                                                 15
```

-continued

```
SEQ ID NO: 185          moltype = AA   length = 15
FEATURE                 Location/Qualifiers
REGION                  1..15
                        note = epitope
source                  1..15
                        mol_type = protein
                        organism = synthetic construct
SEQUENCE: 185
DIVQEARNAE EKAKK                                              15

SEQ ID NO: 186          moltype = AA   length = 15
FEATURE                 Location/Qualifiers
REGION                  1..15
                        note = epitope
source                  1..15
                        mol_type = protein
                        organism = synthetic construct
SEQUENCE: 186
GGYIQAVLDR NLCEN                                              15

SEQ ID NO: 187          moltype = AA   length = 15
FEATURE                 Location/Qualifiers
REGION                  1..15
                        note = epitope
source                  1..15
                        mol_type = protein
                        organism = synthetic construct
SEQUENCE: 187
LKATKKKKKP VVDEE                                              15

SEQ ID NO: 188          moltype = AA   length = 15
FEATURE                 Location/Qualifiers
REGION                  1..15
                        note = epitope
source                  1..15
                        mol_type = protein
                        organism = synthetic construct
SEQUENCE: 188
YEKIAFEYGI TDLRG                                              15

SEQ ID NO: 189          moltype = AA   length = 15
FEATURE                 Location/Qualifiers
REGION                  1..15
                        note = epitope
source                  1..15
                        mol_type = protein
                        organism = synthetic construct
SEQUENCE: 189
TDLRGLLKRL KKMKT                                              15

SEQ ID NO: 190          moltype = AA   length = 15
FEATURE                 Location/Qualifiers
REGION                  1..15
                        note = epitope
source                  1..15
                        mol_type = protein
                        organism = synthetic construct
SEQUENCE: 190
KKMKTVEPKH SDAFL                                              15

SEQ ID NO: 191          moltype = AA   length = 15
FEATURE                 Location/Qualifiers
REGION                  1..15
                        note = epitope
source                  1..15
                        mol_type = protein
                        organism = synthetic construct
SEQUENCE: 191
AYSVDKGKKI VLQVE                                              15

SEQ ID NO: 192          moltype = AA   length = 15
FEATURE                 Location/Qualifiers
REGION                  1..15
                        note = epitope
source                  1..15
                        mol_type = protein
                        organism = synthetic construct
SEQUENCE: 192
LSRDTHKYRF KKDGL                                              15
```

-continued

```
SEQ ID NO: 193          moltype = AA   length = 15
FEATURE                 Location/Qualifiers
REGION                  1..15
                        note = epitope
source                  1..15
                        mol_type = protein
                        organism = synthetic construct
SEQUENCE: 193
YTFIPDGYAL SLSAK                                                  15

SEQ ID NO: 194          moltype = AA   length = 15
FEATURE                 Location/Qualifiers
REGION                  1..15
                        note = epitope
source                  1..15
                        mol_type = protein
                        organism = synthetic construct
SEQUENCE: 194
GAPVTGYLME RKKKG                                                  15

SEQ ID NO: 195          moltype = AA   length = 15
FEATURE                 Location/Qualifiers
REGION                  1..15
                        note = epitope
source                  1..15
                        mol_type = protein
                        organism = synthetic construct
SEQUENCE: 195
RQKYIRRVGD KINLT                                                  15

SEQ ID NO: 196          moltype = AA   length = 15
FEATURE                 Location/Qualifiers
REGION                  1..15
                        note = epitope
source                  1..15
                        mol_type = protein
                        organism = synthetic construct
SEQUENCE: 196
YTIQKADKKT NEWFT                                                  15

SEQ ID NO: 197          moltype = AA   length = 15
FEATURE                 Location/Qualifiers
REGION                  1..15
                        note = epitope
source                  1..15
                        mol_type = protein
                        organism = synthetic construct
SEQUENCE: 197
NVAKAHGGYS VFAGV                                                  15

SEQ ID NO: 198          moltype = AA   length = 15
FEATURE                 Location/Qualifiers
REGION                  1..15
                        note = epitope
source                  1..15
                        mol_type = protein
                        organism = synthetic construct
SEQUENCE: 198
VLAGEPVGSR SKVTV                                                  15

SEQ ID NO: 199          moltype = AA   length = 15
FEATURE                 Location/Qualifiers
REGION                  1..15
                        note = epitope
source                  1..15
                        mol_type = protein
                        organism = synthetic construct
SEQUENCE: 199
SYGRALQASA LKAWG                                                  15

SEQ ID NO: 200          moltype = AA   length = 15
FEATURE                 Location/Qualifiers
REGION                  1..15
                        note = epitope
source                  1..15
                        mol_type = protein
                        organism = synthetic construct
SEQUENCE: 200
```

```
DGDKSRYLGK GTVKA                                              15

SEQ ID NO: 201            moltype = AA  length = 15
FEATURE                   Location/Qualifiers
REGION                    1..15
                          note = epitope
source                    1..15
                          mol_type = protein
                          organism = synthetic construct
SEQUENCE: 201
YRHIADLAGH KDVIL                                              15

SEQ ID NO: 202            moltype = AA  length = 15
FEATURE                   Location/Qualifiers
REGION                    1..15
                          note = epitope
source                    1..15
                          mol_type = protein
                          organism = synthetic construct
SEQUENCE: 202
NLKNVIKAKY GKDAT                                              15

SEQ ID NO: 203            moltype = AA  length = 15
FEATURE                   Location/Qualifiers
REGION                    1..15
                          note = epitope
source                    1..15
                          mol_type = protein
                          organism = synthetic construct
SEQUENCE: 203
YMVYMFKYDS THGRF                                              15

SEQ ID NO: 204            moltype = AA  length = 15
FEATURE                   Location/Qualifiers
REGION                    1..15
                          note = epitope
source                    1..15
                          mol_type = protein
                          organism = synthetic construct
SEQUENCE: 204
PASYDAIKKV VKAAA                                              15

SEQ ID NO: 205            moltype =   length =
SEQUENCE: 205
000

SEQ ID NO: 206            moltype = AA  length = 10
FEATURE                   Location/Qualifiers
REGION                    1..10
                          note = epitope
REGION                    2..6
                          note = misc_feature - X can be any amino acid
source                    1..10
                          mol_type = protein
                          organism = synthetic construct
SEQUENCE: 206
SXXXXXKPDK                                                    10

SEQ ID NO: 207            moltype = AA  length = 10
FEATURE                   Location/Qualifiers
REGION                    1..10
                          note = epitope
source                    1..10
                          mol_type = protein
                          organism = synthetic construct
SEQUENCE: 207
SGERLPKPDK                                                    10

SEQ ID NO: 208            moltype =   length =
SEQUENCE: 208
000

SEQ ID NO: 209            moltype =   length =
SEQUENCE: 209
000

SEQ ID NO: 210            moltype = AA  length = 6
FEATURE                   Location/Qualifiers
REGION                    1..6
```

```
                                     note = epitope
source                               1..6
                                     mol_type = protein
                                     organism = synthetic construct
SEQUENCE: 210
DKGKMR                                                                          6

SEQ ID NO: 211          moltype =   length =
SEQUENCE: 211
000

SEQ ID NO: 212          moltype = AA  length = 10
FEATURE                 Location/Qualifiers
REGION                  1..10
                        note = epitope
REGION                  2..5
                        note = misc_feature - X can be any amino acid
source                  1..10
                        mol_type = protein
                        organism = synthetic construct
SEQUENCE: 212
YXXXXKDDPM                                                                     10

SEQ ID NO: 213          moltype = AA  length = 10
FEATURE                 Location/Qualifiers
REGION                  1..10
                        note = epitope
source                  1..10
                        mol_type = protein
                        organism = synthetic construct
SEQUENCE: 213
YSKLRKDDPM                                                                     10

SEQ ID NO: 214          moltype =   length =
SEQUENCE: 214
000

SEQ ID NO: 215          moltype = AA  length = 10
FEATURE                 Location/Qualifiers
REGION                  1..10
                        note = epitope
REGION                  3..6
                        note = misc_feature - X can be any amino acid
SITE                    8
                        note = misc_feature - X can be any amino acid
source                  1..10
                        mol_type = protein
                        organism = synthetic construct
SEQUENCE: 215
YSXXXXDXPM                                                                     10

SEQ ID NO: 216          moltype =   length =
SEQUENCE: 216
000

SEQ ID NO: 217          moltype = AA  length = 7
FEATURE                 Location/Qualifiers
REGION                  1..7
                        note = epitope
SITE                    2
                        note = misc_feature - X can be any amino acid
source                  1..7
                        mol_type = protein
                        organism = synthetic construct
SEQUENCE: 217
PXGNLNT                                                                         7

SEQ ID NO: 218          moltype = AA  length = 7
FEATURE                 Location/Qualifiers
REGION                  1..7
                        note = epitope
source                  1..7
                        mol_type = protein
                        organism = synthetic construct
SEQUENCE: 218
PMGNLNT                                                                         7

SEQ ID NO: 219          moltype = AA  length = 15
FEATURE                 Location/Qualifiers
```

-continued

```
REGION                1..15
                      note = epitope
SITE                  2
                      note = misc_feature - X can be any amino acid
source                1..15
                      mol_type = protein
                      organism = synthetic construct
SEQUENCE: 219
SXFYHAFAGA EQAET                                                15

SEQ ID NO: 220        moltype = AA  length = 15
FEATURE               Location/Qualifiers
REGION                1..15
                      note = epitope
SITE                  2
                      note = misc_feature - X can be any amino acid
REGION                4..6
                      note = misc_feature - X can be any amino acid
SITE                  8
                      note = misc_feature - X can be any amino acid
REGION                10..13
                      note = misc_feature - X can be any amino acid
source                1..15
                      mol_type = protein
                      organism = synthetic construct
SEQUENCE: 220
TXLXXXNXPX XXXSE                                                15

SEQ ID NO: 221        moltype = AA  length = 15
FEATURE               Location/Qualifiers
REGION                1..15
                      note = epitope
SITE                  2
                      note = misc_feature - X can be any amino acid
SITE                  6
                      note = misc_feature - X can be any amino acid
REGION                10..13
                      note = misc_feature - X can be any amino acid
source                1..15
                      mol_type = protein
                      organism = synthetic construct
SEQUENCE: 221
TXLRLXNRPX XXXSE                                                15

SEQ ID NO: 222        moltype = AA  length = 12
FEATURE               Location/Qualifiers
REGION                1..12
                      note = epitope
SITE                  2
                      note = misc_feature - X can be any amino acid
REGION                5..9
                      note = misc_feature - X can be any amino acid
SITE                  11
                      note = misc_feature - X can be any amino acid
source                1..12
                      mol_type = protein
                      organism = synthetic construct
SEQUENCE: 222
SXKTXXXXXE XR                                                   12

SEQ ID NO: 223        moltype = AA  length = 12
FEATURE               Location/Qualifiers
REGION                1..12
                      note = epitope
REGION                5..9
                      note = misc_feature - X can be any amino acid
source                1..12
                      mol_type = protein
                      organism = synthetic construct
SEQUENCE: 223
SDKTXXXXXE LR                                                   12

SEQ ID NO: 224        moltype = AA  length = 12
FEATURE               Location/Qualifiers
REGION                1..12
                      note = epitope
source                1..12
                      mol_type = protein
                      organism = synthetic construct
```

-continued

```
SEQUENCE: 224
SDKTYITVEE LR                                                          12

SEQ ID NO: 225           moltype =   length =
SEQUENCE: 225
000

SEQ ID NO: 226           moltype =   length =
SEQUENCE: 226
000

SEQ ID NO: 227           moltype = AA  length = 4
FEATURE                  Location/Qualifiers
REGION                   1..4
                         note = epitope
source                   1..4
                         mol_type = protein
                         organism = synthetic construct
SEQUENCE: 227
LRRE                                                                  4

SEQ ID NO: 228           moltype = AA  length = 11
FEATURE                  Location/Qualifiers
REGION                   1..11
                         note = epitope
REGION                   1..2
                         note = misc_feature - X can be any amino acid
SITE                     5
                         note = misc_feature - X can be any amino acid
REGION                   8..10
                         note = misc_feature - X can be any amino acid
source                   1..11
                         mol_type = protein
                         organism = synthetic construct
SEQUENCE: 228
XXNRXYYXXX E                                                          11

SEQ ID NO: 229           moltype = AA  length = 11
FEATURE                  Location/Qualifiers
REGION                   1..11
                         note = epitope
SITE                     8
                         note = misc_feature - X can be any amino acid
source                   1..11
                         mol_type = protein
                         organism = synthetic construct
SEQUENCE: 229
LDNRLYYXVA E                                                          11

SEQ ID NO: 230           moltype = AA  length = 11
FEATURE                  Location/Qualifiers
REGION                   1..11
                         note = epitope
source                   1..11
                         mol_type = protein
                         organism = synthetic construct
SEQUENCE: 230
LDNRLYYMVA E                                                          11

SEQ ID NO: 231           moltype =   length =
SEQUENCE: 231
000

SEQ ID NO: 232           moltype = AA  length = 8
FEATURE                  Location/Qualifiers
REGION                   1..8
                         note = epitope
source                   1..8
                         mol_type = protein
                         organism = synthetic construct
SEQUENCE: 232
YIQAVLDR                                                              8

SEQ ID NO: 233           moltype = AA  length = 10
FEATURE                  Location/Qualifiers
REGION                   1..10
                         note = epitope
SITE                     4
                         note = misc_feature - X can be any amino acid
```

```
REGION                  6..7
                        note = misc_feature - X can be any amino acid
SITE                    9
                        note = misc_feature - X can be any amino acid
source                  1..10
                        mol_type = protein
                        organism = synthetic construct SEQUENCE: 233
GGYXQXXLXR                                                              10

SEQ ID NO: 234          moltype = AA  length = 10
FEATURE                 Location/Qualifiers
REGION                  1..10
                        note = epitope
REGION                  6..7
                        note = misc_feature - X can be any amino acid
source                  1..10
                        mol_type = protein
                        organism = synthetic construct SEQUENCE: 234
GGYIQXXLDR                                                              10

SEQ ID NO: 235          moltype = AA  length = 10
FEATURE                 Location/Qualifiers
REGION                  1..10
                        note = epitope
source                  1..10
                        mol_type = protein
                        organism = synthetic construct SEQUENCE: 235
GGYIQAVLDR                                                              10

SEQ ID NO: 236          moltype = AA  length = 8
FEATURE                 Location/Qualifiers
REGION                  1..8
                        note = epitope
SITE                    2
                        note = misc_feature - X can be any amino acid
REGION                  4..6
                        note = misc_feature - X can be any amino acid
source                  1..8
                        mol_type = protein
                        organism = synthetic construct SEQUENCE: 236
RXKXXXDY                                                                 8

SEQ ID NO: 237          moltype = AA  length = 8
FEATURE                 Location/Qualifiers
REGION                  1..8
                        note = epitope
source                  1..8
                        mol_type = protein
                        organism = synthetic construct SEQUENCE: 237
RFKVFADY                                                                 8

SEQ ID NO: 238          moltype =    length =
SEQUENCE: 238
000

SEQ ID NO: 239          moltype = AA  length = 6
FEATURE                 Location/Qualifiers
REGION                  1..6
                        note = epitope
source                  1..6
                        mol_type = protein
                        organism = synthetic construct SEQUENCE: 239
KKSNIR                                                                   6

SEQ ID NO: 240          moltype = AA  length = 7
FEATURE                 Location/Qualifiers
REGION                  1..7
                        note = epitope
REGION                  3..5
                        note = misc_feature - X can be any amino acid
source                  1..7
                        mol_type = protein
                        organism = synthetic construct
```

```
SEQUENCE: 240
KKXXXRN                                                                      7

SEQ ID NO: 241            moltype = AA   length = 7
FEATURE                   Location/Qualifiers
REGION                    1..7
                          note = epitope
SITE                      5
                          note = misc_feature - X can be any amino acid
source                    1..7
                          mol_type = protein
                          organism = synthetic construct
SEQUENCE: 241
KKSNXRN                                                                      7

SEQ ID NO: 242            moltype = AA   length = 7
FEATURE                   Location/Qualifiers
REGION                    1..7
                          note = epitope
source                    1..7
                          mol_type = protein
                          organism = synthetic construct
SEQUENCE: 242
KKSNIRN                                                                      7

SEQ ID NO: 243            moltype = AA   length = 11
FEATURE                   Location/Qualifiers
REGION                    1..11
                          note = epitope
REGION                    2..4
                          note = misc_feature - X can be any amino acid
REGION                    6..7
                          note = misc_feature - X can be any amino acid
REGION                    9..10
                          note = misc_feature - X can be any amino acid
source                    1..11
                          mol_type = protein
                          organism = synthetic construct
SEQUENCE: 243
LXXXLXXKXX I                                                                 11

SEQ ID NO: 244            moltype = AA   length = 11
FEATURE                   Location/Qualifiers
REGION                    1..11
                          note = epitope
SITE                      2
                          note = misc_feature - X can be any amino acid
SITE                      4
                          note = misc_feature - X can be any amino acid
REGION                    6..7
                          note = misc_feature - X can be any amino acid
REGION                    9..10
                          note = misc_feature - X can be any amino acid
source                    1..11
                          mol_type = protein
                          organism = synthetic construct
SEQUENCE: 244
LXDXLXXKXX I                                                                 11

SEQ ID NO: 245            moltype = AA   length = 11
FEATURE                   Location/Qualifiers
REGION                    1..11
                          note = epitope
source                    1..11
                          mol_type = protein
                          organism = synthetic construct
SEQUENCE: 245
LTDSLVSKAG I                                                                 11

SEQ ID NO: 246            moltype =    length =
SEQUENCE: 246
000

SEQ ID NO: 247            moltype = AA   length = 11
FEATURE                   Location/Qualifiers
REGION                    1..11
                          note = epitope
source                    1..11
                          mol_type = protein
```

-continued

```
                        organism = synthetic construct
SEQUENCE: 247
GKSTLTDSLV S                                                        11

SEQ ID NO: 248        moltype =   length =
SEQUENCE: 248
000

SEQ ID NO: 249        moltype = AA  length = 7
FEATURE               Location/Qualifiers
REGION                1..7
                      note = epitope
REGION                3..4
                      note = misc_feature - X can be any amino acid
source                1..7
                      mol_type = protein
                      organism = synthetic construct
SEQUENCE: 249
EIXXAYL                                                             7

SEQ ID NO: 250        moltype = AA  length = 7
FEATURE               Location/Qualifiers
REGION                1..7
                      note = epitope
source                1..7
                      mol_type = protein
                      organism = synthetic construct
SEQUENCE: 250
EIAEAYL                                                             7

SEQ ID NO: 251        moltype =   length =
SEQUENCE: 251
000

SEQ ID NO: 252        moltype =   length =
SEQUENCE: 252
000

SEQ ID NO: 253        moltype =   length =
SEQUENCE: 253
000

SEQ ID NO: 254        moltype = AA  length = 7
FEATURE               Location/Qualifiers
REGION                1..7
                      note = epitope
REGION                4..5
                      note = misc_feature - X can be any amino acid
source                1..7
                      mol_type = protein
                      organism = synthetic construct
SEQUENCE: 254
DDVXXDK                                                             7

SEQ ID NO: 255        moltype = AA  length = 7
FEATURE               Location/Qualifiers
REGION                1..7
                      note = epitope
source                1..7
                      mol_type = protein
                      organism = synthetic construct
SEQUENCE: 255
DDVQRDK                                                             7

SEQ ID NO: 256        moltype = AA  length = 7
FEATURE               Location/Qualifiers
REGION                1..7
                      note = epitope
SITE                  2
                      note = misc_feature - X can be any amino acid
SITE                  4
                      note = misc_feature - X can be any amino acid
SITE                  6
                      note = misc_feature - X can be any amino acid
source                1..7
                      mol_type = protein
                      organism = synthetic construct
SEQUENCE: 256
KXSXEXK                                                             7
```

-continued

```
SEQ ID NO: 257          moltype = AA  length = 7
FEATURE                 Location/Qualifiers
REGION                  1..7
                        note = epitope
SITE                    4
                        note = misc_feature - X can be any amino acid
source                  1..7
                        mol_type = protein
                        organism = synthetic construct
SEQUENCE: 257
KLSXEDK                                                              7

SEQ ID NO: 258          moltype = AA  length = 7
FEATURE                 Location/Qualifiers
REGION                  1..7
                        note = epitope
source                  1..7
                        mol_type = protein
                        organism = synthetic construct SEQUENCE: 258
KLSDEDK                                                              7

SEQ ID NO: 259          moltype = AA  length = 7
FEATURE                 Location/Qualifiers
REGION                  1..7
                        note = epiotope
REGION                  2..4
                        note = misc_feature - X can be any amino acid
source                  1..7
                        mol_type = protein
                        organism = synthetic construct SEQUENCE: 259
QXXXDKC                                                              7

SEQ ID NO: 260          moltype = AA  length = 7
FEATURE                 Location/Qualifiers
REGION                  1..7
                        note = epitope
SITE                    4
                        note = misc_feature - X can be any amino acid
source                  1..7
                        mol_type = protein
                        organism = synthetic construct SEQUENCE: 260
QKIXDKC                                                              7

SEQ ID NO: 261          moltype = AA  length = 7
FEATURE                 Location/Qualifiers
REGION                  1..7
                        note = epitope
source                  1..7
                        mol_type = protein
                        organism = synthetic construct SEQUENCE: 261
QKILDKC                                                              7

SEQ ID NO: 262          moltype =   length =
SEQUENCE: 262
000

SEQ ID NO: 263          moltype = AA  length = 5
FEATURE                 Location/Qualifiers
REGION                  1..5
                        note = epitope
source                  1..5
                        mol_type = protein
                        organism = synthetic construct SEQUENCE: 263
DTCYY                                                                5

SEQ ID NO: 264          moltype = AA  length = 9
FEATURE                 Location/Qualifiers
REGION                  1..9
                        note = epitope
SITE                    2
                        note = misc_feature - X can be any amino acid
SITE                    4
                        note = misc_feature - X can be any amino acid
```

```
REGION                  7..9
                        note = misc_feature - X can be any amino acid
source                  1..9
                        mol_type = protein
                        organism = synthetic construct
SEQUENCE: 264
VXVXKKXXX                                                                  9

SEQ ID NO: 265          moltype = AA   length = 9
FEATURE                 Location/Qualifiers
REGION                  1..9
                        note = epitope
SITE                    8
                        note = misc_feature - X can be any amino acid
source                  1..9
                        mol_type = protein
                        organism = synthetic construct
SEQUENCE: 265
VAVAKKGXE                                                                  9

SEQ ID NO: 266          moltype = AA   length = 9
FEATURE                 Location/Qualifiers
REGION                  1..9
                        note = epitope
source                  1..9
                        mol_type = protein
                        organism = synthetic construct
SEQUENCE: 266
VAVAKKGTE                                                                  9

SEQ ID NO: 267          moltype =    length =
SEQUENCE: 267
000

SEQ ID NO: 268          moltype = AA   length = 8
FEATURE                 Location/Qualifiers
REGION                  1..8
                        note = epitope
SITE                    1
                        note = misc_feature - X can be any amino acid
SITE                    3
                        note = misc_feature - X can be any amino acid
SITE                    5
                        note = misc_feature - X can be any amino acid
SITE                    8
                        note = misc_feature - X can be any amino acid
source                  1..8
                        mol_type = protein
                        organism = synthetic construct
SEQUENCE: 268
XKXGXGEX                                                                  8

SEQ ID NO: 269          moltype = AA   length = 8
FEATURE                 Location/Qualifiers
REGION                  1..8
                        note = epitope
source                  1..8
                        mol_type = protein
                        organism = synthetic construct
SEQUENCE: 269
LKDGAGEV                                                                  8

SEQ ID NO: 270          moltype =    length =
SEQUENCE: 270
000

SEQ ID NO: 271          moltype = AA   length = 5
FEATURE                 Location/Qualifiers
REGION                  1..5
                        note = epitope
source                  1..5
                        mol_type = protein
                        organism = synthetic construct
SEQUENCE: 271
YSKLM                                                                     5

SEQ ID NO: 272          moltype = AA   length = 8
FEATURE                 Location/Qualifiers
REGION                  1..8
```

```
                              note = epitope
REGION                        5..7
                              note = misc_feature - X can be any amino acid
source                        1..8
                              mol_type = protein
                              organism = synthetic construct
SEQUENCE: 272
VTNFXXXS                                                                    8

SEQ ID NO: 273                moltype = AA  length = 8
FEATURE                       Location/Qualifiers
REGION                        1..8
                              note = epitope
source                        1..8
                              mol_type = protein
                              organism = synthetic construct
SEQUENCE: 273
VTNFNLFS                                                                    8

SEQ ID NO: 274                moltype =   length =
SEQUENCE: 274
000

SEQ ID NO: 275                moltype = AA  length = 9
FEATURE                       Location/Qualifiers
REGION                        1..9
                              note = epitope
SITE                          2
                              note = misc_feature - X can be any amino acid
REGION                        5..6
                              note = misc_feature - X can be any amino acid
SITE                          8
                              note = misc_feature - X can be any amino acid
source                        1..9
                              mol_type = protein
                              organism = synthetic construct
SEQUENCE: 275
YXYNXXFXC                                                                   9

SEQ ID NO: 276                moltype = AA  length = 9
FEATURE                       Location/Qualifiers
REGION                        1..9
                              note = epitope
source                        1..9
                              mol_type = protein
                              organism = synthetic construct
SEQUENCE: 276
YGYNGAFRC                                                                   9

SEQ ID NO: 277                moltype =   length =
SEQUENCE: 277
000

SEQ ID NO: 278                moltype = AA  length = 5
FEATURE                       Location/Qualifiers
REGION                        1..5
                              note = epitope
SITE                          2
                              note = misc_feature - X can be any amino acid
source                        1..5
                              mol_type = protein
                              organism = synthetic construct
SEQUENCE: 278
FXCLV                                                                       5

SEQ ID NO: 279                moltype = AA  length = 5
FEATURE                       Location/Qualifiers
REGION                        1..5
                              note = epitope
source                        1..5
                              mol_type = protein
                              organism = synthetic construct
SEQUENCE: 279
FRCLV                                                                       5

SEQ ID NO: 280                moltype = AA  length = 9
FEATURE                       Location/Qualifiers
REGION                        1..9
                              note = epitope
```

-continued

```
REGION                  4..7
                        note = misc_feature - X can be any amino acid
source                  1..9
                        mol_type = protein
                        organism = synthetic construct
SEQUENCE: 280
YVKXXXXKI                                                               9

SEQ ID NO: 281          moltype = AA  length = 9
FEATURE                 Location/Qualifiers
REGION                  1..9
                        note = epitope
SITE                    4
                        note = misc_feature - X can be any amino acid
SITE                    6
                        note = misc_feature - X can be any amino acid
source                  1..9
                        mol_type = protein
                        organism = synthetic construct
SEQUENCE: 281
YVKXVXEKI                                                               9

SEQ ID NO: 282          moltype = AA  length = 9
FEATURE                 Location/Qualifiers
REGION                  1..9
                        note = epitope
source                  1..9
                        mol_type = protein
                        organism = synthetic construct
SEQUENCE: 282
YVKKVGEKI                                                               9

SEQ ID NO: 283          moltype = AA  length = 5
FEATURE                 Location/Qualifiers
REGION                  1..5
                        note = epitope
SITE                    3
                        note = misc_feature - X can be any amino acid
source                  1..5
                        mol_type = protein
                        organism = synthetic construct
SEQUENCE: 283
NIXIP                                                                   5

SEQ ID NO: 284          moltype = AA  length = 5
FEATURE                 Location/Qualifiers
REGION                  1..5
                        note = epitope
source                  1..5
                        mol_type = protein
                        organism = synthetic construct
SEQUENCE: 284
NIVIP                                                                   5

SEQ ID NO: 285          moltype = AA  length = 11
FEATURE                 Location/Qualifiers
REGION                  1..11
                        note = epitope
SITE                    2
                        note = misc_feature - X can be any amino acid
REGION                  4..6
                        note = misc_feature - X can be any amino acid
REGION                  8..10
                        note = misc_feature - X can be any amino acid
source                  1..11
                        mol_type = protein
                        organism = synthetic construct
SEQUENCE: 285
SXEXXXKXXX F                                                            11

SEQ ID NO: 286          moltype = AA  length = 11
FEATURE                 Location/Qualifiers
REGION                  1..11
                        note = epitope
SITE                    2
                        note = misc_feature - X can be any amino acid
SITE                    4
                        note = misc_feature - X can be any amino acid
SITE                    6
```

```
                            note = misc_feature - X can be any amino acid
REGION                      8..10
                            note = misc_feature - X can be any amino acid
source                      1..11
                            mol_type = protein
                            organism = synthetic construct
SEQUENCE: 286
SXEXCXKXXX F                                                                      11

SEQ ID NO: 287              moltype = AA  length = 11
FEATURE                     Location/Qualifiers
REGION                      1..11
                            note = epitope
source                      1..11
                            mol_type = protein
                            organism = synthetic construct
SEQUENCE: 287
SYEMCVKVDD F                                                                      11

SEQ ID NO: 288              moltype = AA  length = 8
FEATURE                     Location/Qualifiers
REGION                      1..8
                            note = epitope
SITE                        2
                            note = misc_feature - X can be any amino acid
SITE                        4
                            note = misc_feature - X can be any amino acid
REGION                      6..7
                            note = misc_feature - X can be any amino acid
source                      1..8
                            mol_type = protein
                            organism = synthetic construct
SEQUENCE: 288
KXDXFXXK                                                                           8

SEQ ID NO: 289              moltype = AA  length = 8
FEATURE                     Location/Qualifiers
REGION                      1..8
                            note = epitope
SITE                        2
                            note = misc_feature - X can be any amino acid
SITE                        4
                            note = misc_feature - X can be any amino acid
SITE                        6
                            note = misc_feature - X can be any amino acid
source                      1..8
                            mol_type = protein
                            organism = synthetic construct
SEQUENCE: 289
KXDXFXDK                                                                           8

SEQ ID NO: 290              moltype = AA  length = 8
FEATURE                     Location/Qualifiers
REGION                      1..8
                            note = epitope
source                      1..8
                            mol_type = protein
                            organism = synthetic construct
SEQUENCE: 290
KVDDFEDK                                                                           8

SEQ ID NO: 291              moltype =   length =
SEQUENCE: 291
000

SEQ ID NO: 292              moltype = AA  length = 14
FEATURE                     Location/Qualifiers
REGION                      1..14
                            note = epitope
source                      1..14
                            mol_type = protein
                            organism = synthetic construct
SEQUENCE: 292
EVIDYKPTPF VEHD                                                                   14

SEQ ID NO: 293              moltype =   length =
SEQUENCE: 293
000
```

-continued

```
SEQ ID NO: 294          moltype = AA  length = 10
FEATURE                 Location/Qualifiers
REGION                  1..10
                        note = epitope
REGION                  3..4
                        note = misc_feature - X can be any amino acid
REGION                  6..7
                        note = misc_feature - X can be any amino acid
SITE                    9
                        note = misc_feature - X can be any amino acid
source                  1..10
                        mol_type = protein
                        organism = synthetic construct
SEQUENCE: 294
DNXXYXXIXT                                                          10

SEQ ID NO: 295          moltype = AA  length = 10
FEATURE                 Location/Qualifiers
REGION                  1..10
                        note = epitope
source                  1..10
                        mol_type = protein
                        organism = synthetic construct SEQUENCE: 295
DNPKYRMIST                                                          10

SEQ ID NO: 296          moltype =    length =
SEQUENCE: 296
000

SEQ ID NO: 297          moltype = AA  length = 6
FEATURE                 Location/Qualifiers
REGION                  1..6
                        note = epitope
source                  1..6
                        mol_type = protein
                        organism = synthetic construct SEQUENCE: 297
YRMIST                                                              6

SEQ ID NO: 298          moltype = AA  length = 8
FEATURE                 Location/Qualifiers
REGION                  1..8
                        note = epitope
REGION                  1..3
                        note = misc_feature - X can be any amino acid
SITE                    6
                        note = misc_feature - X can be any amino acid
source                  1..8
                        mol_type = protein
                        organism = synthetic construct
SEQUENCE: 298
XXXISXGG                                                            8

SEQ ID NO: 299          moltype = AA  length = 8
FEATURE                 Location/Qualifiers
REGION                  1..8
                        note = epitope
SITE                    2
                        note = misc_feature - X can be any amino acid
SITE                    6
                        note = misc_feature - X can be any amino acid
source                  1..8
                        mol_type = protein
                        organism = synthetic construct SEQUENCE: 299
YXMISXGG                                                            8

SEQ ID NO: 300          moltype = AA  length = 8
FEATURE                 Location/Qualifiers
REGION                  1..8
                        note = epitope
source                  1..8
                        mol_type = protein
                        organism = synthetic construct
SEQUENCE: 300
YRMISTGG                                                            8

SEQ ID NO: 301          moltype =    length =
```

-continued

```
SEQUENCE: 301
000

SEQ ID NO: 302        moltype =   length =
SEQUENCE: 302
000

SEQ ID NO: 303        moltype = AA  length = 6
FEATURE               Location/Qualifiers
REGION                1..6
                      note = epitope
source                1..6
                      mol_type = protein
                      organism = synthetic construct
SEQUENCE: 303
KSKVSD                                                                 6

SEQ ID NO: 304        moltype =   length =
SEQUENCE: 304
000

SEQ ID NO: 305        moltype = AA  length = 9
FEATURE               Location/Qualifiers
REGION                1..9
                      note = epitope
SITE                  5
                      note = misc_feature - X can be any amino acid
source                1..9
                      mol_type = protein
                      organism = synthetic construct
SEQUENCE: 305
YKSKXSDLN                                                              9

SEQ ID NO: 306        moltype = AA  length = 9
FEATURE               Location/Qualifiers
REGION                1..9
                      note = epitope
source                1..9
                      mol_type = protein
                      organism = synthetic construct
SEQUENCE: 306
YKSKVSDLN                                                              9

SEQ ID NO: 307        moltype =   length =
SEQUENCE: 307
000

SEQ ID NO: 308        moltype = AA  length = 4
FEATURE               Location/Qualifiers
REGION                1..4
                      note = epitope
source                1..4
                      mol_type = protein
                      organism = synthetic construct
SEQUENCE: 308
VNKN                                                                   4

SEQ ID NO: 309        moltype = AA  length = 7
FEATURE               Location/Qualifiers
REGION                1..7
                      note = epitope
SITE                  2
                      note = misc_feature - X can be any amino acid
REGION                5..6
                      note = misc_feature - X can be any amino acid
source                1..7
                      mol_type = protein
                      organism = synthetic construct
SEQUENCE: 309
DXGRXXE                                                                7

SEQ ID NO: 310        moltype = AA  length = 7
FEATURE               Location/Qualifiers
REGION                1..7
                      note = epitope
source                1..7
                      mol_type = protein
                      organism = synthetic construct
SEQUENCE: 310
```

```
DVGRSAE                                                              7

SEQ ID NO: 311          moltype =   length =
SEQUENCE: 311
000

SEQ ID NO: 312          moltype = AA  length = 6
FEATURE                 Location/Qualifiers
REGION                  1..6
                        note = epitope
source                  1..6
                        mol_type = protein
                        organism = synthetic construct
SEQUENCE: 312
KKAGDG                                                               6

SEQ ID NO: 313          moltype =   length =
SEQUENCE: 313
000

SEQ ID NO: 314          moltype = AA  length = 5
FEATURE                 Location/Qualifiers
REGION                  1..5
                        note = epitope
source                  1..5
                        mol_type = protein
                        organism = synthetic construct
SEQUENCE: 314
SKKIK                                                                5

SEQ ID NO: 315          moltype =   length =
SEQUENCE: 315
000

SEQ ID NO: 316          moltype = AA  length = 11
FEATURE                 Location/Qualifiers
REGION                  1..11
                        note = epitope
REGION                  2..5
                        note = misc_feature - X can be any amino acid
SITE                    7
                        note = misc_feature - X can be any amino acid
source                  1..11
                        mol_type = protein
                        organism = synthetic construct
SEQUENCE: 316
HXXXXQXKSS G                                                         11

SEQ ID NO: 317          moltype = AA  length = 11
FEATURE                 Location/Qualifiers
REGION                  1..11
                        note = epitope
source                  1..11
                        mol_type = protein
                        organism = synthetic construct
SEQUENCE: 317
HVVEVQEKSS G                                                         11

SEQ ID NO: 318          moltype =   length =
SEQUENCE: 318
000

SEQ ID NO: 319          moltype = AA  length = 9
FEATURE                 Location/Qualifiers
REGION                  1..9
                        note = epitope
SITE                    3
                        note = misc_feature - X can be any amino acid
SITE                    7
                        note = misc_feature - X can be any amino acid
source                  1..9
                        mol_type = protein
                        organism = synthetic construct
SEQUENCE: 319
IYXGKTXDI                                                            9

SEQ ID NO: 320          moltype = AA  length = 9
FEATURE                 Location/Qualifiers
REGION                  1..9
```

```
                                note = epitope
source                          1..9
                                mol_type = protein
                                organism = synthetic construct
SEQUENCE: 320
IYFGKTKDI                                                                         9

SEQ ID NO: 321                  moltype = AA   length = 9
FEATURE                         Location/Qualifiers
REGION                          1..9
                                note = epitiope
SITE                            1
                                note = misc_feature - X can be any amino acid
REGION                          3..4
                                note = misc_feature - X can be any amino acid
REGION                          6..7
                                note = misc_feature - X can be any amino acid
source                          1..9
                                mol_type = protein
                                organism = synthetic construct
SEQUENCE: 321
XDXXNXXRS                                                                         9

SEQ ID NO: 322                  moltype = AA   length = 9
FEATURE                         Location/Qualifiers
REGION                          1..9
                                note = epitope
REGION                          3..4
                                note = misc_feature - X can be any amino acid
SITE                            6
                                note = misc_feature - X can be any amino acid
source                          1..9
                                mol_type = protein
                                organism = synthetic construct
SEQUENCE: 322
KDXXNXLRS                                                                         9

SEQ ID NO: 323                  moltype = AA   length = 9
FEATURE                         Location/Qualifiers
REGION                          1..9
                                note = epitope
source                          1..9
                                mol_type = protein
                                organism = synthetic construct
SEQUENCE: 323
KDIVNGLRS                                                                         9

SEQ ID NO: 324                  moltype = AA   length = 12
FEATURE                         Location/Qualifiers
REGION                          1..12
                                note = epitope
REGION                          6..7
                                note = misc_feature - X can be any amino acid
REGION                          9..12
                                note = misc_feature - X can be any amino acid
source                          1..12
                                mol_type = protein
                                organism = synthetic construct
SEQUENCE: 324
QKYRQXXKXX XX                                                                     12

SEQ ID NO: 325                  moltype = AA   length = 12
FEATURE                         Location/Qualifiers
REGION                          1..12
                                note = epitope
REGION                          6..7
                                note = misc_feature - X can be any amino acid
SITE                            9
                                note = misc_feature - X can be any amino acid
SITE                            11
                                note = misc_feature - X can be any amino acid
source                          1..12
                                mol_type = protein
                                organism = synthetic construct
SEQUENCE: 325
QKYRQXXKXL XQ                                                                     12

SEQ ID NO: 326                  moltype = AA   length = 12
FEATURE                         Location/Qualifiers
```

-continued

```
REGION                 1..12
                       note = epitope
source                 1..12
                       mol_type = protein
                       organism = synthetic construct SEQUENCE: 326
QKYRQLQKEL SQ                                                          12

SEQ ID NO: 327         moltype = AA  length = 11
FEATURE                Location/Qualifiers
REGION                 1..11
                       note = epitope
REGION                 2..5
                       note = misc_feature - X can be any amino acid
REGION                 7..8
                       note = misc_feature - X can be any amino acid
source                 1..11
                       mol_type = protein
                       organism = synthetic construct SEQUENCE: 327
TXXXXDXXEG K                                                           11

SEQ ID NO: 328         moltype = AA  length = 11
FEATURE                Location/Qualifiers
REGION                 1..11
                       note = epitope
REGION                 2..4
                       note = misc_feature - X can be any amino acid
source                 1..11
                       mol_type = protein
                       organism = synthetic construct SEQUENCE: 328
TXXXLDFREG K                                                           11

SEQ ID NO: 329         moltype = AA  length = 11
FEATURE                Location/Qualifiers
REGION                 1..11
                       note = epitope
source                 1..11
                       mol_type = protein
                       organism = synthetic construct SEQUENCE: 329
TVTALDFREG K                                                           11

SEQ ID NO: 330         moltype =    length =
SEQUENCE: 330
000

SEQ ID NO: 331         moltype = AA  length = 9
FEATURE                Location/Qualifiers
REGION                 1..9
                       note = epitope
REGION                 4..5
                       note = misc_feature - X can be any amino acid
REGION                 7..8
                       note = misc_feature - X can be any amino acid
source                 1..9
                       mol_type = protein
                       organism = synthetic construct
SEQUENCE: 331
FREXXEXXD                                                              9

SEQ ID NO: 332         moltype = AA  length = 9
FEATURE                Location/Qualifiers
REGION                 1..9
                       note = epitope
source                 1..9
                       mol_type = protein
                       organism = synthetic construct SEQUENCE: 332
FREGKEFKD                                                              9

SEQ ID NO: 333         moltype = AA  length = 9
FEATURE                Location/Qualifiers
REGION                 1..9
                       note = epitope
REGION                 2..3
                       note = misc_feature - X can be any amino acid
REGION                 7..8
```

-continued

```
                              note = misc_feature - X can be any amino acid
source                        1..9
                              mol_type = protein
                              organism = synthetic construct
SEQUENCE: 333
LXXNFTXXK                                                                        9

SEQ ID NO: 334                moltype = AA  length = 9
FEATURE                       Location/Qualifiers
REGION                        1..9
                              note = epitope
SITE                          2
                              note = misc_feature - X can be any amino acid
source                        1..9
                              mol_type = protein
                              organism = synthetic construct
SEQUENCE: 334
LXINFTNEK                                                                        9

SEQ ID NO: 335                moltype = AA  length = 9
FEATURE                       Location/Qualifiers
REGION                        1..9
                              note = epitope
source                        1..9
                              mol_type = protein
                              organism = synthetic construct
SEQUENCE: 335
LCINFTNEK                                                                        9

SEQ ID NO: 336                moltype = AA  length = 10
FEATURE                       Location/Qualifiers
REGION                        1..10
                              note = epitope
SITE                          1
                              note = misc_feature - X can be any amino acid
SITE                          3
                              note = misc_feature - X can be any amino acid
REGION                        7..9
                              note = misc_feature - X can be any amino acid
source                        1..10
                              mol_type = protein
                              organism = synthetic construct
SEQUENCE: 336
XYXPPPXXXK                                                                       10

SEQ ID NO: 337                moltype = AA  length = 10
FEATURE                       Location/Qualifiers
REGION                        1..10
                              note = epitope
SITE                          3
                              note = misc_feature - X can be any amino acid
REGION                        7..9
                              note = misc_feature - X can be any amino acid
source                        1..10
                              mol_type = protein
                              organism = synthetic construct
SEQUENCE: 337
LYXPPPXXXK                                                                       10

SEQ ID NO: 338                moltype = AA  length = 10
FEATURE                       Location/Qualifiers
REGION                        1..10
                              note = epitope
source                        1..10
                              mol_type = protein
                              organism = synthetic construct
SEQUENCE: 338
LYPPPPPEDK                                                                       10

SEQ ID NO: 339                moltype = AA  length = 8
FEATURE                       Location/Qualifiers
REGION                        1..8
                              note = epitope
REGION                        1..2
                              note = misc_feature - X can be any amino acid
SITE                          5
                              note = misc_feature - X can be any amino acid
SITE                          7
                              note = misc_feature - X can be any amino acid
```

```
source                    1..8
                          mol_type = protein
                          organism = synthetic construct SEQUENCE: 339
XXDEXVXK                                                                    8

SEQ ID NO: 340           moltype = AA  length = 8
FEATURE                  Location/Qualifiers
REGION                   1..8
                         note = epitope
SITE                     2
                         note = misc_feature - X can be any amino acid
SITE                     5
                         note = misc_feature - X can be any amino acid
SITE                     7
                         note = misc_feature - X can be any amino acid
source                   1..8
                         mol_type = protein
                         organism = synthetic construct SEQUENCE: 340
SXDEXVXK                                                                    8

SEQ ID NO: 341           moltype = AA  length = 8
FEATURE                  Location/Qualifiers
REGION                   1..8
                         note = epitope
source                   1..8
                         mol_type = protein
                         organism = synthetic construct SEQUENCE: 341
SMDESVAK                                                                    8

SEQ ID NO: 342           moltype = AA  length = 10
FEATURE                  Location/Qualifiers
REGION                   1..10
                         note = epitope
REGION                   1..2
                         note = misc_feature - X can be any amino acid
REGION                   4..6
                         note = misc_feature - X can be any amino acid
SITE                     9
                         note = misc_feature - X can be any amino acid
source                   1..10
                         mol_type = protein
                         organism = synthetic construct SEQUENCE: 342
XXDXXXAKXT                                                                 10

SEQ ID NO: 343           moltype = AA  length = 10
FEATURE                  Location/Qualifiers
REGION                   1..10
                         note = epitope
SITE                     2
                         note = misc_feature - X can be any amino acid
SITE                     5
                         note = misc_feature - X can be any amino acid
SITE                     9
                         note = misc_feature - X can be any amino acid
source                   1..10
                         mol_type = protein
                         organism = synthetic construct SEQUENCE: 343
SXDEXVAKXT                                                                 10

SEQ ID NO: 344           moltype = AA  length = 10
FEATURE                  Location/Qualifiers
REGION                   1..10
                         note = epitope
source                   1..10
                         mol_type = protein
                         organism = synthetic construct SEQUENCE: 344
SMDESVAKLT                                                                 10

SEQ ID NO: 345           moltype = AA  length = 9
FEATURE                  Location/Qualifiers
REGION                   1..9
                         note = epitope
REGION                   2..5
```

```
                              note = misc_feature - X can be any amino acid
SITE                          7
                              note = misc_feature - X can be any amino acid
source                        1..9
                              mol_type = protein
                              organism = synthetic construct
SEQUENCE: 345
VXXXXKXKK                                                                    9

SEQ ID NO: 346                moltype = AA   length = 9
FEATURE                       Location/Qualifiers
REGION                        1..9
                              note = epitope
REGION                        3..5
                              note = misc_feature - X can be any amino acid
SITE                          7
                              note = misc_feature - X can be any amino acid
source                        1..9
                              mol_type = protein
                              organism = synthetic construct
SEQUENCE: 346
VAXXXKXKK                                                                    9

SEQ ID NO: 347                moltype = AA   length = 9
FEATURE                       Location/Qualifiers
REGION                        1..9
                              note = epitope
source                        1..9
                              mol_type = protein
                              organism = synthetic construct
SEQUENCE: 347
VAKLTKEKK                                                                    9

SEQ ID NO: 348                moltype =    length =
SEQUENCE: 348
000

SEQ ID NO: 349                moltype = AA   length = 6
FEATURE                       Location/Qualifiers
REGION                        1..6
                              note = epitope
REGION                        2..3
                              note = misc_feature - X can be any amino acid
source                        1..6
                              mol_type = protein
                              organism = synthetic construct
SEQUENCE: 349
KXXKEK                                                                       6

SEQ ID NO: 350                moltype = AA   length = 6
FEATURE                       Location/Qualifiers
REGION                        1..6
                              note = epitope
source                        1..6
                              mol_type = protein
                              organism = synthetic construct
SEQUENCE: 350
KLTKEK                                                                       6

SEQ ID NO: 351                moltype = AA   length = 10
FEATURE                       Location/Qualifiers
REGION                        1..10
                              note = epitope
SITE                          1
                              note = misc_feature - X can be any amino acid
REGION                        3..5
                              note = misc_feature - X can be any amino acid
SITE                          7
                              note = misc_feature - X can be any amino acid
SITE                          9
                              note = misc_feature - X can be any amino acid
source                        1..10
                              mol_type = protein
                              organism = synthetic construct
SEQUENCE: 351
XNXXXKXKXK                                                                  10

SEQ ID NO: 352                moltype = AA   length = 10
FEATURE                       Location/Qualifiers
```

-continued

```
REGION                   1..10
                         note = epitope
SITE                     1
                         note = misc_feature - X can be any amino acid
REGION                   3..5
                         note = misc_feature - X can be any amino acid
SITE                     7
                         note = misc_feature - X can be any amino acid
source                   1..10
                         mol_type = protein
                         organism = synthetic construct
SEQUENCE: 352
XNXXXKXKTK                                                                    10

SEQ ID NO: 353           moltype = AA  length = 10
FEATURE                  Location/Qualifiers
REGION                   1..10
                         note = epitope
source                   1..10
                         mol_type = protein
                         organism = synthetic construct
SEQUENCE: 353
VNTLTKAKTK                                                                    10

SEQ ID NO: 354           moltype =   length =
SEQUENCE: 354
000

SEQ ID NO: 355           moltype = AA  length = 8
FEATURE                  Location/Qualifiers
REGION                   1..8
                         note = epitope
REGION                   2..4
                         note = misc_feature - X can be any amino acid
SITE                     6
                         note = misc_feature - X can be any amino acid
source                   1..8
                         mol_type = protein
                         organism = synthetic construct
SEQUENCE: 355
DXXXSXRK                                                                       8

SEQ ID NO: 356           moltype = AA  length = 8
FEATURE                  Location/Qualifiers
REGION                   1..8
                         note = epitope
source                   1..8
                         mol_type = protein
                         organism = synthetic construct
SEQUENCE: 356
DLERSKRK                                                                       8

SEQ ID NO: 357           moltype =   length =
SEQUENCE: 357
000

SEQ ID NO: 358           moltype = AA  length = 7
FEATURE                  Location/Qualifiers
REGION                   1..7
                         note = epitope
SITE                     2
                         note = misc_feature - X can be any amino acid
SITE                     5
                         note = misc_feature - X can be any amino acid
source                   1..7
                         mol_type = protein
                         organism = synthetic construct
SEQUENCE: 358
SXRKXEG                                                                        7

SEQ ID NO: 359           moltype = AA  length = 7
FEATURE                  Location/Qualifiers
REGION                   1..7
                         note = epitope
source                   1..7
                         mol_type = protein
                         organism = synthetic construct
SEQUENCE: 359
SKRKLEG                                                                        7
```

-continued

```
SEQ ID NO: 360          moltype =    length =
SEQUENCE: 360
000

SEQ ID NO: 361          moltype = AA   length = 8
FEATURE                 Location/Qualifiers
REGION                  1..8
                        note = epitope
SITE                    2
                        note = misc_feature - X can be any amino acid
REGION                  4..5
                        note = misc_feature - X can be any amino acid
source                  1..8
                        mol_type = protein
                        organism = synthetic construct
SEQUENCE: 361
EXRXXEEK                                                                      8

SEQ ID NO: 362          moltype = AA   length = 8
FEATURE                 Location/Qualifiers
REGION                  1..8
                        note = epitope
source                  1..8
                        mol_type = protein
                        organism = synthetic construct
SEQUENCE: 362
EARNAEEK                                                                      8

SEQ ID NO: 363          moltype = AA   length = 9
FEATURE                 Location/Qualifiers
REGION                  1..9
                        note = epitope
REGION                  1..3
                        note = misc_feature - X can be any amino acid
SITE                    5
                        note = misc_feature - X can be any amino acid
SITE                    7
                        note = misc_feature - X can be any amino acid
source                  1..9
                        mol_type = protein
                        organism = synthetic construct
SEQUENCE: 363
XXXEXKXKK                                                                     9

SEQ ID NO: 364          moltype = AA   length = 9
FEATURE                 Location/Qualifiers
REGION                  1..9
                        note = epitope
REGION                  2..3
                        note = misc_feature - X can be any amino acid
SITE                    7
                        note = misc_feature - X can be any amino acid
source                  1..9
                        mol_type = protein
                        organism = synthetic construct
SEQUENCE: 364
RXXEEKXKK                                                                     9

SEQ ID NO: 365          moltype = AA   length = 9
FEATURE                 Location/Qualifiers
REGION                  1..9
                        note = epitope
source                  1..9
                        mol_type = protein
                        organism = synthetic construct
SEQUENCE: 365
RNAEEKAKK                                                                     9

SEQ ID NO: 366          moltype =    length =
SEQUENCE: 366
000

SEQ ID NO: 367          moltype = AA   length = 10
FEATURE                 Location/Qualifiers
REGION                  1..10
                        note = epitope
source                  1..10
                        mol_type = protein
```

```
SEQUENCE: 367
GGYIQAVLDR                                                            10

SEQ ID NO: 368          moltype =   length =
SEQUENCE: 368
000

SEQ ID NO: 369          moltype = AA   length = 5
FEATURE                 Location/Qualifiers
REGION                  1..5
                        note = epitope
SITE                    3
                        note = misc_feature - X can be any amino acid
source                  1..5
                        mol_type = protein
                        organism = synthetic construct
SEQUENCE: 369
NLXEN                                                                 5

SEQ ID NO: 370          moltype = AA   length = 5
FEATURE                 Location/Qualifiers
REGION                  1..5
                        note = epitope
source                  1..5
                        mol_type = protein
                        organism = synthetic construct
SEQUENCE: 370
NLCEN                                                                 5

SEQ ID NO: 371          moltype = AA   length = 10
FEATURE                 Location/Qualifiers
REGION                  1..10
                        note = epitope
SITE                    2
                        note = misc_feature - X can be any amino acid
REGION                  4..5
                        note = misc_feature - X can be any amino acid
REGION                  9..10
                        note = misc_feature - X can be any amino acid
source                  1..10
                        mol_type = protein
                        organism = synthetic construct
SEQUENCE: 371
KXTXXKKKXX                                                            10

SEQ ID NO: 372          moltype = AA   length = 10
FEATURE                 Location/Qualifiers
REGION                  1..10
                        note = epitope
SITE                    2
                        note = misc_feature - X can be any amino acid
REGION                  4..5
                        note = misc_feature - X can be any amino acid
source                  1..10
                        mol_type = protein
                        organism = synthetic construct
SEQUENCE: 372
KXTXXKKKPV                                                            10

SEQ ID NO: 373          moltype = AA   length = 10
FEATURE                 Location/Qualifiers
REGION                  1..10
                        note = epitope
source                  1..10
                        mol_type = protein
                        organism = synthetic construct
SEQUENCE: 373
KATKKKKKPV                                                            10

SEQ ID NO: 374          moltype = AA   length = 8
FEATURE                 Location/Qualifiers
REGION                  1..8
                        note = epitope
SITE                    2
                        note = misc_feature - X can be any amino acid
REGION                  7..8
                        note = misc_feature - X can be any amino acid
source                  1..8
```

-continued

```
                              mol_type = protein
                              organism = synthetic construct
SEQUENCE: 374
KXKPVVXX                                                          8

SEQ ID NO: 375           moltype = AA   length = 8
FEATURE                  Location/Qualifiers
REGION                   1..8
                         note = epitope
SITE                     2
                         note = misc_feature - X can be any amino acid
source                   1..8
                         mol_type = protein
                         organism = synthetic construct
SEQUENCE: 375
KXKPVVDE                                                          8

SEQ ID NO: 376           moltype = AA   length = 8
FEATURE                  Location/Qualifiers
REGION                   1..8
                         note = epitope
source                   1..8
                         mol_type = protein
                         organism = synthetic construct
SEQUENCE: 376
KKKPVVDE                                                          8

SEQ ID NO: 377           moltype =    length =
SEQUENCE: 377
000

SEQ ID NO: 378           moltype = AA   length = 10
FEATURE                  Location/Qualifiers
REGION                   1..10
                         note = epitope
REGION                   2..3
                         note = misc_feature - X can be any amino acid
SITE                     5
                         note = misc_feature - X can be any amino acid
SITE                     9
                         note = misc_feature - X can be any amino acid
source                   1..10
                         mol_type = protein
                         organism = synthetic construct
SEQUENCE: 378
YXXIXFEYXI                                                        10

SEQ ID NO: 379           moltype = AA   length = 10
FEATURE                  Location/Qualifiers
REGION                   1..10
                         note = epitope
source                   1..10
                         mol_type = protein
                         organism = synthetic construct
SEQUENCE: 379
YEKIAFEYGI                                                        10

SEQ ID NO: 380           moltype = AA   length = 8
FEATURE                  Location/Qualifiers
REGION                   1..8
                         note = epitope
REGION                   1..2
                         note = misc_feature - X can be any amino acid
SITE                     4
                         note = misc_feature - X can be any amino acid
SITE                     6
                         note = misc_feature - X can be any amino acid
source                   1..8
                         mol_type = protein
                         organism = synthetic construct
SEQUENCE: 380
XXIXDXRG                                                          8

SEQ ID NO: 381           moltype = AA   length = 8
FEATURE                  Location/Qualifiers
REGION                   1..8
                         note = epitope
SITE                     2
                         note = misc_feature - X can be any amino acid
```

```
SITE                     4
                         note = misc_feature - X can be any amino acid
SITE                     6
                         note = misc_feature - X can be any amino acid
source                   1..8
                         mol_type = protein
                         organism = synthetic construct SEQUENCE: 381
YXIXDXRG                                                             8

SEQ ID NO: 382           moltype = AA  length = 8
FEATURE                  Location/Qualifiers
REGION                   1..8
                         note = epitope
source                   1..8
                         mol_type = protein
                         organism = synthetic construct SEQUENCE: 382
YGITDLRG                                                             8

SEQ ID NO: 383           moltype = AA  length = 7
FEATURE                  Location/Qualifiers
REGION                   1..7
                         note = epitope
SITE                     2
                         note = misc_feature - X can be any amino acid
REGION                   5..6
                         note = misc_feature - X can be any amino acid
source                   1..7
                         mol_type = protein
                         organism = synthetic construct SEQUENCE: 383
DXRGXXK                                                              7

SEQ ID NO: 384           moltype = AA  length = 7
FEATURE                  Location/Qualifiers
REGION                   1..7
                         note = epitope
source                   1..7
                         mol_type = protein
                         organism = synthetic construct SEQUENCE: 384
DLRGLLK                                                              7

SEQ ID NO: 385           moltype = AA  length = 8
FEATURE                  Location/Qualifiers
REGION                   1..8
                         note = epitope
REGION                   3..6
                         note = misc_feature - X can be any amino acid
source                   1..8
                         mol_type = protein
                         organism = synthetic construct SEQUENCE: 385
KMXXXXPK                                                             8

SEQ ID NO: 386           moltype = AA  length = 8
FEATURE                  Location/Qualifiers
REGION                   1..8
                         note = epitope
source                   1..8
                         mol_type = protein
                         organism = synthetic construct SEQUENCE: 386
KMKTVEPK                                                             8

SEQ ID NO: 387           moltype = AA  length = 10
FEATURE                  Location/Qualifiers
REGION                   1..10
                         note = epitope
REGION                   2..3
                         note = misc_feature - X can be any amino acid
REGION                   5..7
                         note = misc_feature - X can be any amino acid
source                   1..10
                         mol_type = protein
                         organism = synthetic construct SEQUENCE: 387
KXXKXXXPKH                                                          10
```

-continued

```
SEQ ID NO: 388          moltype = AA  length = 10
FEATURE                 Location/Qualifiers
REGION                  1..10
                        note = epitope
source                  1..10
                        mol_type = protein
                        organism = synthetic construct
SEQUENCE: 388
KKMKTVEPKH                                                      10

SEQ ID NO: 389          moltype =   length =
SEQUENCE: 389
000

SEQ ID NO: 390          moltype = AA  length = 7
FEATURE                 Location/Qualifiers
REGION                  1..7
                        note = epitope
source                  1..7
                        mol_type = protein
                        organism = synthetic construct
SEQUENCE: 390
KHSDAFL                                                         7

SEQ ID NO: 391          moltype = AA  length = 6
FEATURE                 Location/Qualifiers
REGION                  1..6
                        note = epitope
REGION                  5..6
                        note = misc_feature - X can be any amino acid
source                  1..6
                        mol_type = protein
                        organism = synthetic construct
SEQUENCE: 391
KGKKXX                                                          6

SEQ ID NO: 392          moltype = AA  length = 6
FEATURE                 Location/Qualifiers
REGION                  1..6
                        note = epitope
source                  1..6
                        mol_type = protein
                        organism = synthetic construct
SEQUENCE: 392
KGKKIV                                                          6

SEQ ID NO: 393          moltype = AA  length = 10
FEATURE                 Location/Qualifiers
REGION                  1..10
                        note = epitope
SITE                    2
                        note = misc_feature - X can be any amino acid
REGION                  4..6
                        note = misc_feature - X can be any amino acid
REGION                  8..9
                        note = misc_feature - X can be any amino acid
source                  1..10
                        mol_type = protein
                        organism = synthetic construct
SEQUENCE: 393
KXKXXXLXXE                                                      10

SEQ ID NO: 394          moltype = AA  length = 10
FEATURE                 Location/Qualifiers
REGION                  1..10
                        note = epitope
SITE                    2
                        note = misc_feature - X can be any amino acid
REGION                  4..6
                        note = misc_feature - X can be any amino acid
SITE                    9
                        note = misc_feature - X can be any amino acid
source                  1..10
                        mol_type = protein
                        organism = synthetic construct
SEQUENCE: 394
KXKXXXLQXE                                                      10
```

-continued

```
SEQ ID NO: 395          moltype = AA  length = 10
FEATURE                 Location/Qualifiers
REGION                  1..10
                        note = epitope
source                  1..10
                        mol_type = protein
                        organism = synthetic construct
SEQUENCE: 395
KGKKIVLQVE                                                        10

SEQ ID NO: 396          moltype =   length =
SEQUENCE: 396
000

SEQ ID NO: 397          moltype = AA  length = 4
FEATURE                 Location/Qualifiers
REGION                  1..4
                        note = epitope
source                  1..4
                        mol_type = protein
                        organism = synthetic construct
SEQUENCE: 397
THKY                                                              4

SEQ ID NO: 398          moltype = AA  length = 9
FEATURE                 Location/Qualifiers
REGION                  1..9
                        note = epitope
REGION                  3..4
                        note = misc_feature - X can be any amino acid
REGION                  7..9
                        note = misc_feature - X can be any amino acid
source                  1..9
                        mol_type = protein
                        organism = synthetic construct
SEQUENCE: 398
KYXXKKXXX                                                         9

SEQ ID NO: 399          moltype = AA  length = 9
FEATURE                 Location/Qualifiers
REGION                  1..9
                        note = epitope
REGION                  3..4
                        note = misc_feature - X can be any amino acid
source                  1..9
                        mol_type = protein
                        organism = synthetic construct
SEQUENCE: 399
KYXXKKDGL                                                         9

SEQ ID NO: 400          moltype = AA  length = 9
FEATURE                 Location/Qualifiers
REGION                  1..9
                        note = epitope
source                  1..9
                        mol_type = protein
                        organism = synthetic construct
SEQUENCE: 400
KYRFKKDGL                                                         9

SEQ ID NO: 401          moltype = AA  length = 7
FEATURE                 Location/Qualifiers
REGION                  1..7
                        note = epitope
REGION                  2..4
                        note = misc_feature - X can be any amino acid
source                  1..7
                        mol_type = protein
                        organism = synthetic construct
SEQUENCE: 401
YXXXPDG                                                           7

SEQ ID NO: 402          moltype = AA  length = 7
FEATURE                 Location/Qualifiers
REGION                  1..7
                        note = epitope
source                  1..7
                        mol_type = protein
                        organism = synthetic construct
```

```
SEQUENCE: 402
YTFIPDG                                                                      7

SEQ ID NO: 403            moltype = AA  length = 10
FEATURE                   Location/Qualifiers
REGION                    1..10
                          note = epitope
REGION                    4..5
                          note = misc_feature - X can be any amino acid
SITE                      7
                          note = misc_feature - X can be any amino acid
SITE                      9
                          note = misc_feature - X can be any amino acid
source                    1..10
                          mol_type = protein
                          organism = synthetic construct
SEQUENCE: 403
DGYXXSXSXK                                                                    10

SEQ ID NO: 404            moltype = AA  length = 10
FEATURE                   Location/Qualifiers
REGION                    1..10
                          note = epitope
SITE                      4
                          note = misc_feature - X can be any amino acid
SITE                      9
                          note = misc_feature - X can be any amino acid
source                    1..10
                          mol_type = protein
                          organism = synthetic construct
SEQUENCE: 404
DGYXLSLSXK                                                                    10

SEQ ID NO: 405            moltype = AA  length = 10
FEATURE                   Location/Qualifiers
REGION                    1..10
                          note = epitope
source                    1..10
                          mol_type = protein
                          organism = synthetic construct
SEQUENCE: 405
DGYALSLSAK                                                                    10

SEQ ID NO: 406            moltype =   length =
SEQUENCE: 406
000

SEQ ID NO: 407            moltype = AA  length = 5
FEATURE                   Location/Qualifiers
REGION                    1..5
                          note = epitope
source                    1..5
                          mol_type = protein
                          organism = synthetic construct
SEQUENCE: 407
PVTGY                                                                         5

SEQ ID NO: 408            moltype = AA  length = 12
FEATURE                   Location/Qualifiers
REGION                    1..12
                          note = epitope
REGION                    2..8
                          note = misc_feature - X can be any amino acid
SITE                      11
                          note = misc_feature - X can be any amino acid
source                    1..12
                          mol_type = protein
                          organism = synthetic construct
SEQUENCE: 408
QXXXXXXXDK XN                                                                 12

SEQ ID NO: 409            moltype = AA  length = 12
FEATURE                   Location/Qualifiers
REGION                    1..12
                          note = epitope
source                    1..12
                          mol_type = protein
                          organism = synthetic construct
SEQUENCE: 409
```

-continued

```
QKYIRRVGDK IN                                                       12

SEQ ID NO: 410        moltype = AA  length = 10
FEATURE               Location/Qualifiers
REGION                1..10
                      note = epitope
REGION                2..6
                      note = misc_feature - X can be any amino acid
SITE                  8
                      note = misc_feature - X can be any amino acid
source                1..10
                      mol_type = protein
                      organism = synthetic construct
SEQUENCE: 410
YXXXXXDXKT                                                          10

SEQ ID NO: 411        moltype = AA  length = 10
FEATURE               Location/Qualifiers
REGION                1..10
                      note = epitope
source                1..10
                      mol_type = protein
                      organism = synthetic construct
SEQUENCE: 411
YTIQKADKKT                                                          10

SEQ ID NO: 412        moltype =   length =
SEQUENCE: 412
000

SEQ ID NO: 413        moltype = AA  length = 8
FEATURE               Location/Qualifiers
REGION                1..8
                      note = epitope
source                1..8
                      mol_type = protein
                      organism = synthetic construct
SEQUENCE: 413
YTIQKADK                                                            8

SEQ ID NO: 414        moltype =   length =
SEQUENCE: 414
000

SEQ ID NO: 415        moltype = AA  length = 4
FEATURE               Location/Qualifiers
REGION                1..4
                      note = epitope
source                1..4
                      mol_type = protein
                      organism = synthetic construct
SEQUENCE: 415
GGYS                                                                4

SEQ ID NO: 416        moltype =   length =
SEQUENCE: 416
000

SEQ ID NO: 417        moltype = AA  length = 6
FEATURE               Location/Qualifiers
REGION                1..6
                      note = epitope
source                1..6
                      mol_type = protein
                      organism = synthetic construct
SEQUENCE: 417
YSVFAG                                                              6

SEQ ID NO: 418        moltype = AA  length = 9
FEATURE               Location/Qualifiers
REGION                1..9
                      note = epitope
SITE                  1
                      note = misc_feature - X can be any amino acid
SITE                  6
                      note = misc_feature - X can be any amino acid
SITE                  9
                      note = misc_feature - X can be any amino acid
source                1..9
```

-continued

```
                             mol_type = protein
                             organism = synthetic construct
SEQUENCE: 418
XPVGSXSKX                                                               9

SEQ ID NO: 419          moltype = AA   length = 9
FEATURE                 Location/Qualifiers
REGION                  1..9
                        note = epitope
SITE                    6
                        note = misc_feature - X can be any amino acid
source                  1..9
                        mol_type = protein
                        organism = synthetic construct
SEQUENCE: 419
EPVGSXSKV                                                               9

SEQ ID NO: 420          moltype = AA   length = 9
FEATURE                 Location/Qualifiers
REGION                  1..9
                        note = epitope
source                  1..9
                        mol_type = protein
                        organism = synthetic construct
SEQUENCE: 420
EPVGSRSKV                                                               9

SEQ ID NO: 421          moltype =    length =
SEQUENCE: 421
000

SEQ ID NO: 422          moltype = AA   length = 12
FEATURE                 Location/Qualifiers
REGION                  1..12
                        note = epitope
SITE                    3
                        note = misc_feature - X can be any amino acid
SITE                    5
                        note = misc_feature - X can be any amino acid
REGION                  7..9
                        note = misc_feature - X can be any amino acid
SITE                    11
                        note = misc_feature - X can be any amino acid
source                  1..12
                        mol_type = protein
                        organism = synthetic construct
SEQUENCE: 422
SYXRXLXXXA XK                                                          12

SEQ ID NO: 423          moltype = AA   length = 12
FEATURE                 Location/Qualifiers
REGION                  1..12
                        note = epitope
source                  1..12
                        mol_type = protein
                        organism = synthetic construct
SEQUENCE: 423
SYGRALQASA LK                                                          12

SEQ ID NO: 424          moltype =    length =
SEQUENCE: 424
000

SEQ ID NO: 425          moltype = AA   length = 7
FEATURE                 Location/Qualifiers
REGION                  1..7
                        note = epitope
source                  1..7
                        mol_type = protein
                        organism = synthetic construct
SEQUENCE: 425
SALKAWG                                                                 7

SEQ ID NO: 426          moltype = AA   length = 8
FEATURE                 Location/Qualifiers
REGION                  1..8
                        note = epitope
REGION                  6..8
                        note = misc_feature - X can be any amino acid
```

-continued

```
source                  1..8
                        mol_type = protein
                        organism = synthetic construct
SEQUENCE: 426
RYLGKXXX                                                              8

SEQ ID NO: 427          moltype = AA  length = 8
FEATURE                 Location/Qualifiers
REGION                  1..8
                        note = epitope
SITE                    7
                        note = misc_feature - X can be any amino acid
source                  1..8
                        mol_type = protein
                        organism = synthetic construct
SEQUENCE: 427
RYLGKGXV                                                              8

SEQ ID NO: 428          moltype = AA  length = 8
FEATURE                 Location/Qualifiers
REGION                  1..8
                        note = epitope
source                  1..8
                        mol_type = protein
                        organism = synthetic construct
SEQUENCE: 428
RYLGKGTV                                                              8

SEQ ID NO: 429          moltype = AA  length = 10
FEATURE                 Location/Qualifiers
REGION                  1..10
                        note = epitope
REGION                  2..3
                        note = misc_feature - X can be any amino acid
SITE                    5
                        note = misc_feature - X can be any amino acid
REGION                  7..9
                        note = misc_feature - X can be any amino acid
source                  1..10
                        mol_type = protein
                        organism = synthetic construct
SEQUENCE: 429
YXXIXDXXXH                                                           10

SEQ ID NO: 430          moltype = AA  length = 10
FEATURE                 Location/Qualifiers
REGION                  1..10
                        note = epitope
REGION                  2..3
                        note = misc_feature - X can be any amino acid
SITE                    5
                        note = misc_feature - X can be any amino acid
SITE                    8
                        note = misc_feature - X can be any amino acid
source                  1..10
                        mol_type = protein
                        organism = synthetic construct
SEQUENCE: 430
YXXIXDLXGH                                                           10

SEQ ID NO: 431          moltype = AA  length = 10
FEATURE                 Location/Qualifiers
REGION                  1..10
                        note = epitope
source                  1..10
                        mol_type = protein
                        organism = synthetic construct
SEQUENCE: 431
YRHIADLAGH                                                           10

SEQ ID NO: 432          moltype = AA  length = 10
FEATURE                 Location/Qualifiers
REGION                  1..10
                        note = epitope
REGION                  2..4
                        note = misc_feature - X can be any amino acid
SITE                    6
                        note = misc_feature - X can be any amino acid
SITE                    9
```

```
                              note = misc_feature - X can be any amino acid
source                        1..10
                              mol_type = protein
                              organism = synthetic construct
SEQUENCE: 432
DXXXHXDVXL                                                                    10

SEQ ID NO: 433                moltype = AA  length = 10
FEATURE                       Location/Qualifiers
REGION                        1..10
                              note = epitope
REGION                        2..4
                              note = misc_feature - X can be any amino acid
source                        1..10
                              mol_type = protein
                              organism = synthetic construct
SEQUENCE: 433
DXXXHKDVIL                                                                    10

SEQ ID NO: 434                moltype = AA  length = 10
FEATURE                       Location/Qualifiers
REGION                        1..10
                              note = epitope
source                        1..10
                              mol_type = protein
                              organism = synthetic construct
SEQUENCE: 434
DLAGHKDVIL                                                                    10

SEQ ID NO: 435                moltype = AA  length = 10
FEATURE                       Location/Qualifiers
REGION                        1..10
                              note = epitope
REGION                        3..6
                              note = misc_feature - X can be any amino acid
source                        1..10
                              mol_type = protein
                              organism = synthetic construct
SEQUENCE: 435
IKXXXXKDAT                                                                    10

SEQ ID NO: 436                moltype = AA  length = 10
FEATURE                       Location/Qualifiers
REGION                        1..10
                              note = epitope
source                        1..10
                              mol_type = protein
                              organism = synthetic construct
SEQUENCE: 436
IKAKYGKDAT                                                                    10

SEQ ID NO: 437                moltype = AA  length = 15
FEATURE                       Location/Qualifiers
REGION                        1..15
                              note = epitope
REGION                        2..8
                              note = misc_feature - X can be any amino acid
REGION                        10..12
                              note = misc_feature - X can be any amino acid
source                        1..15
                              mol_type = protein
                              organism = synthetic construct
SEQUENCE: 437
YXXXXXXXDX XXGRF                                                              15

SEQ ID NO: 438                moltype = AA  length = 15
FEATURE                       Location/Qualifiers
REGION                        1..15
                              note = epitope
REGION                        2..8
                              note = misc_feature - X can be any amino acid
SITE                          12
                              note = misc_feature - X can be any amino acid
source                        1..15
                              mol_type = protein
                              organism = synthetic construct
SEQUENCE: 438
YXXXXXXXDS TXGRF                                                              15
```

-continued

```
SEQ ID NO: 439          moltype = AA  length = 15
FEATURE                 Location/Qualifiers
REGION                  1..15
                        note = epitope
source                  1..15
                        mol_type = protein
                        organism = synthetic construct
SEQUENCE: 439
YMVYMFKYDS THGRF                                                      15

SEQ ID NO: 440          moltype = AA  length = 8
FEATURE                 Location/Qualifiers
REGION                  1..8
                        note = epitope
REGION                  3..4
                        note = misc_feature - X can be any amino acid
REGION                  6..7
                        note = misc_feature - X can be any amino acid
source                  1..8
                        mol_type = protein
                        organism = synthetic construct
SEQUENCE: 440
SYXXIXXV                                                               8

SEQ ID NO: 441          moltype = AA  length = 8
FEATURE                 Location/Qualifiers
REGION                  1..8
                        note = epitope
source                  1..8
                        mol_type = protein
                        organism = synthetic construct
SEQUENCE: 441
SYDAIKKV                                                               8

SEQ ID NO: 442          moltype = AA  length = 6
FEATURE                 Location/Qualifiers
REGION                  1..6
                        note = epitope
REGION                  4..5
                        note = misc_feature - X can be any amino acid
source                  1..6
                        mol_type = protein
                        organism = synthetic construct
SEQUENCE: 442
IKKXXK                                                                 6

SEQ ID NO: 443          moltype = AA  length = 6
FEATURE                 Location/Qualifiers
REGION                  1..6
                        note = epitope
SITE                    5
                        note = misc_feature - X can be any amino acid
source                  1..6
                        mol_type = protein
                        organism = synthetic construct
SEQUENCE: 443
IKKVXK                                                                 6

SEQ ID NO: 444          moltype = AA  length = 6
FEATURE                 Location/Qualifiers
REGION                  1..6
                        note = epitope
source                  1..6
                        mol_type = protein
                        organism = synthetic construct
SEQUENCE: 444
IKKVVK                                                                 6

SEQ ID NO: 445          moltype = AA  length = 363
FEATURE                 Location/Qualifiers
REGION                  1..363
                        note = aldolase a, fructose-bisphosphate 2
source                  1..363
                        mol_type = protein
                        organism = synthetic construct
SEQUENCE: 445
MPHAFPFLTP DQKKELSDIA HKIVAQGKGI LAADESTGSV AKRFQSINTE NTEENRRLYR   60
QLLFTADERA GPCIGGVIFF HETLYQKTDA GKTFPQHVKS RGWLVGIKVD KGVVPLAGTN  120
GETTTQGLDG LYERCAQYKK DGCDFAKWRC VLKITSTTPS RLAIMENCNV LARYASICQM  180
```

```
HGIVPIVEPE ILPDGDHDLK RTQYVTEKVL AAMYKALSDH HVYLEGTLLK PNMVTAGHSC   240
SHKYTHQDIA MATITALRRT VPPAVPGITF LSGGQSEEEA SINLNVMNQC PLHRPWAITF   300
SYGRALQASA LKAWGGKPKN GKAAQEEFIK RALANSLACQ GKYVSSGDSA AAGDSLFVAN   360
HAY                                                                363

SEQ ID NO: 446           moltype = AA  length = 434
FEATURE                  Location/Qualifiers
REGION                   1..434
                         note = beta-enolase
source                   1..434
                         mol_type = protein
                         organism = synthetic construct
SEQUENCE: 446
MSITKIHARE ILDSRGNPTV EVDLYTAKGR FRAAVPSGAS TGVHEALELR DGDKSRYLGK   60
GTVKAVDHVN KDIAAKLIEK KFSVVDQEKI DHFMLELDGT ENKSKFGANA ILGVSLAVCK   120
AGAAEKGVPL YRHIADLAGH KDVILPCPAF NVINGGSHAG NKLAMQEFMI LPIGASNFHE   180
AMRIGAEVYH NLKNVIKAKY GKDATNVGDE GGFAPNILEN NEALELLKTA IEKAGYPDKI   240
IIGMDVAASE FYKAGKYDLD FKSPDDPARY ITGDQLGDLY KSFIKGYPVQ SIEDPFDQDD   300
WAAWTKFTAA VDIQVVGDDL TVTNPKRIQQ AVEKKACNCL LLKVNQIGSV TESIKACKLA   360
QSNGWGVMVS HRSGETEDTF IADLVVGLCT GQIKTGAPCR SERLAKYNQL MRIEEELGAK   420
AKFAGKDYRH PKIN                                                     434

SEQ ID NO: 447           moltype = AA  length = 334
FEATURE                  Location/Qualifiers
REGION                   1..334
                         note = glyceraldehyde-3-phosphate dehydrogenase
source                   1..334
                         mol_type = protein
                         organism = synthetic construct
SEQUENCE: 447
MVKVGVNGFG RIGRLVTRAA FHSKKGVEIV AINDPFIDLD YMVYMFKYDS THGRFHGEVK   60
AEGGKLVIDG HKITVFHERD PANIKWGDAG ATYVVESTGV FTTIEKASTH LEGGAKRVVI   120
SAPSADAPMF VMGVNHEKYD NSLKVVSNAS CTTNCLAPLA KVIHDNYHII EGLMSTVHGV   180
TATQKTVDGP SGKLWRDGRG ASQNIIPAST GAAKAVGKVI PELNGKITGM AFRVPTPNVS   240
VVDLTVRLEK PASYDAIKKV VKAAADGPMK GILGYTEQQV VSSDFNGDTH SSIFDAGAGI   300
ALNDHFVKLV TWYDNEFGYS NRVIDLMAHM ATKE                               334

SEQ ID NO: 448           moltype = DNA  length = 1092
FEATURE                  Location/Qualifiers
misc_feature             1..1092
                         note = aldolase a, fructose-bisphosphate 2
source                   1..1092
                         mol_type = other DNA
                         organism = synthetic construct
SEQUENCE: 448
atgcctcacg cattcccctt cctcactcct gaccagaaga aggagcttag tgacattgct   60
cacaagatcg tcgcccaggg caagggaatc ctcgccgctg atgagtctac cggcagcgtt   120
gccaagcgct tccagagcat caacactgag aacacagagg agaacaggag actgtaccgt   180
cagctgctct tcaccgctga cgagcgtgcc ggtccttgca ttggtggcgt catcttcttc   240
cacgagaccc tgtaccagaa aaccgatgcc ggcaagacct cccccagca cgtcaagtcc   300
agaggctgac ttgtaggcat caaggttgac aaaggtgtcg tcccccctgg cggaaccaac   360
ggagagacca ccacccaggg tttggatggc ctgtatgagc gttgcgccca gtataagaag   420
gacggttgcg acttcgccaa gtggcgttgt gtgctgaaaa tcacctccac caccccctct   480
cgccttgcta tcatggagaa ttgcaatgtc ctggcccgtt atgccagcat ctgccagatg   540
cacggcattg tccccattgt tgagcccgag atcctccccg acggtgacca tgacctgaag   600
cgcacccagt acgtgactga gaaggtcctg gccgcaatgt acaaggctct gtccgaccac   660
cacgtctacc tggagggtac cctcctgaag cccaacatgg tcactgctgg acattcctgc   720
tcacacaagt acacccacca ggacatcgcc atggccacta ttaccgccct gcgccgtacc   780
gtgcccccag cagtccctgg catcaccttc ctgtccggtg gccagtctga ggaggaagcc   840
tccatcaacc tgaatgtcat gaaccagtgc cccctgcaca ggccatgggc cattactttc   900
tcctatggcc gtgccctcca ggcctccgcc cttaaggcat ggggtggcaa gcccaagaac   960
ggcaaggctg cccaggagga gttcatcaag agagctctgg ccaacagcct ggcctgccaa   1020
ggcaagtatg tttcttccgg agacagcgcc gctgctggag attcactgtt cgtggccaac   1080
catgcttatt aa                                                      1092

SEQ ID NO: 449           moltype = DNA  length = 1305
FEATURE                  Location/Qualifiers
misc_feature             1..1305
                         note = beta-enolase
source                   1..1305
                         mol_type = other DNA
                         organism = synthetic construct
SEQUENCE: 449
atgtctatca ctaagatcca tgcccgagag atcctcgact ccagaggaaa ccccaccgtg   60
gaggtggacc tctacaccgc caaaggccgt ttcagagcag ccgtgcccag cggtgcttct   120
accggtgtcc atgaggctct gggagctgaga gatggagaca gtcacgcta cctgggaaaa   180
ggtaccgtta aggctgtgga tcacgtaaac aaggacatcg ctgccaaact gatcgagaag   240
aagttcagcg ttgttgacca ggagaagatc gaccatttca tgctggagtt ggacggaact   300
gagaacaagt ctaagtttgg agccaacgcc atcctgggcg tttctctggc agtctgcaag   360
```

-continued

```
gcaggagcag cagagaaggg agtgcccctg taccgtcaca tcgctgacct ggccggacac   420
aaggacgtca tcctgccctg ccccgccttc aatgtgatca acggtggtag ccatgctggg   480
aacaagctgg ccatgcagga gttcatgatc ctgcccatcg gagcgtctaa cttccacgag   540
gccatgagga tcgagctga  ggtttaccac aacctgaaga acgtgatcaa ggccaagtac   600
ggaaaggatg ccaccaacgt aggcgatgag ggcggcttcg cccccaacat cctggagaac   660
aacgaggctc tggagctcct gaagacagcc attgagaagg ccggctaccc agacaagatc   720
atcatcggca tggacgtggc tgcctctgag ttctacaagg caggaaagta cgacctggac   780
ttcaagtcac ctgacgaccc tgccaggtac atcaccgggg atcagctggg agatctgtac   840
aagagcttca tcaagggata tcccgtccag tccattgagg atcccttcga tcaggatgat   900
tgggctgcat ggacaaagtt caccgccgcc gtcgacatcc aggtggtggg tgatgatctg   960
accgtgacca accccaagcg tatccagcag gccgtggaga agaaggcctg taactgcctg  1020
ctcctcaagg tcaaccagat tggctccgtc acagagtcca tcaaggcgtg taaactggcc  1080
cagtctaacg gatggggtgt gatggtgtct catcgttccg gagagacaga ggataccttc  1140
atcgctgacc tggtggtcgg actctgcact ggacagatca agactggtgc cccctgtaga  1200
tcagagcgtc tggccaaata caaccagctg atgaggattg aagaggagct tggagccaag  1260
gccaagttcg caggcaagga ctaccgtcac cccaaaatca actaa                  1305

SEQ ID NO: 450          moltype = DNA   length = 1005
FEATURE                 Location/Qualifiers
misc_feature            1..1005
                        note = glyceraldehyde-3-phosphate dehydrogenase
source                  1..1005
                        mol_type = other DNA
                        organism = synthetic construct SEQUENCE: 450
atggtgaaag taggtgtcaa tggattcggc cgtatcggc  gtctggtgac ccgtgctgca    60
ttccactcca agaagggagt tgagattgtg gccatcaacg accccttcat cgacctggac   120
tacatggtct acatgttcaa gtatgactcc acccacggac gtttccatgg tgaggtcaag   180
gctgagggtg gcaagctggt catcgatgga cacaaaatca ctgtgttcca cgagagagac   240
ccagctaaca tcaagtgatg agatgctggt gccacctatg tagttgagtc aacaggtgtc   300
ttcaccacca ttgagaaggc ctctacccat cttgaaggtg gtgccaagag ggttgtcatc   360
tccgctccca gcgctgatgc acccatgttc gtcatgggcg tcaaccacga gaagtacgat   420
aactccctca aggttgtcag caatgcttca tgcacaacca actgcctggc tccctggcc   480
aaggtcatcc acgataacta ccacatcatt gagggtctga tgagcacagt tcacggcgtc   540
accgccaccc agaagactgt tgatggtcct tctggaaagc tgtggaggga tggacgtggc   600
gccagccaga acatcatccc tgcctccacc ggagcagcaa aggctgtcgg caaggtcatc   660
cccgagctga acggcaagat cactggcatg gccttccgtg tccccacccc caacgtctca   720
gtggtggacc tgaccgtccg tctggagaag cctgccagct acgacgccat caagaaggtt   780
gtcaaggctg ccgctgatgg acccatgaag ggaattcttg gatacacgga gcaacaggtt   840
gtgtcttcag acttcaacgg cgacacccac tcctccatct ttgatgccgg cgctggcatt   900
gctctgaacg accacttcgt caagctggtt acatggtatg acaacgagtt cggctacagc   960
aaccgcgtca ttgacctgat ggctcacatg gccaccaagg agtaa               1005

SEQ ID NO: 451          moltype = AA   length = 15
FEATURE                 Location/Qualifiers
REGION                  1..15
                        note = epitope
source                  1..15
                        mol_type = protein
                        organism = synthetic construct
SEQUENCE: 451
AMVLVKMKET AEAYL                                                      15
```

1

ALLERGY ANTIGEN AND EPITOPE FOR SAME

CROSS-REFERENCE TO RELATED APPLICATIONS

This application is a divisional application of U.S. application Ser. No. 16/608,361, filed on Oct. 25, 2019, which is a U.S. national stage filing, under 35 U.S.C. § 371(c), of International Application No. PCT/JP2017/045832, filed on Dec. 20, 2017, which claims foreign priority to International Patent Application No. PCT/JP2017/017018, filed on Apr. 28, 2017. The entire contents of each of the aforementioned applications are incorporated herein by reference.

REFERENCE TO SEQUENCE LISTING

The instant application contains a Sequence Listing XML filed which has been submitted electronically in XML format and is hereby incorporated by reference in its entirety. The Sequence Listing XML file, created on Dec. 28, 2022, is named FA1621-17254US-01.xml and is 650,038 bytes in size. The Sequence Listing XML file is part of the specification, and is incorporated in its entirety by reference herein.

TECHNICAL FIELD

The present invention relates to a novel antigen of an allergy to fish. The present invention also relates to a kit, a composition, and a method for diagnosing allergy to fish. The present invention also relates to a pharmaceutical composition comprising such an antigen, fish, fish egg or processed products of such fish or fish egg in which such an antigen is eliminated or reduced, and fish that delivers such fish egg or is born from such fish egg. The present invention further relates to a tester for determining the presence or absence of a fish antigen in an object of interest.

The present invention also relates to a polypeptide comprising an epitope of an antigen. The present invention also relates to a kit, a composition and a method for diagnosing an allergy, comprising such a polypeptide. The present invention also relates to a pharmaceutical composition comprising such a polypeptide, and a raw material or a processed product in which such a polypeptide is eliminated or reduced. The present invention further relates to a method for producing a processed product in which such a polypeptide is eliminated or reduced. The present invention further relates to a tester for determining the presence or absence of an antigen comprising such a polypeptide in an object of interest.

BACKGROUND ART

In blood and tissues of allergic patients, IgE antibodies specific to particular antigens are produced. Physiological consequences caused by interaction between such IgE antibodies and such particular antigens elicit allergic reactions.

In the process of production of conventional allergy testing agents, antigen reagents are commonly prepared simply by grinding a candidate allergenic food, cooking ingredients or the like (Patent Literature 1). Hence, the reagents contain an enormous number of proteins and contain these individual proteins in very small amounts. For this reason, the only case where conventional allergy tests have permitted detection of a positive allergic reaction is when in a conventional antigen reagent containing many types of proteins, a protein acting as a particular antigen protein (an allergen component) that causes such allergic reaction is present in an amount exceeding a threshold that allows determination of a positive reaction for binding to an IgE antibody. However, no determination of a positive reaction was possible and diagnosis efficiency was not sufficiently high when using a conventional allergy testing agent in patients possessing an IgE antibody binding to an allergen component present in small amounts in an allergen such as food and cooking ingredients.

The severity and symptoms of an allergic reaction do not necessarily correlate with the content of an allergen component. Even when a patient's IgE antibody reacts with an allergen component present in trace amounts in a candidate allergic food, cooking ingredients or the like, the allergic reaction may develop allergic symptoms or may affect the severity of those symptoms.

An attempt to increase the diagnostic efficiency is being made by examining IgE antibodies to protein composing food and cooking ingredients to distinguish sensitization that directly contributes to a diagnosis from sensitization based on cross-antigenicity by a pan-allergen or the like. Fish allergens shown in the table below, etc. are currently known (Non Patent Literature 1-4).

TABLE 1

| Species | Allergen | Biochemical name | MW (SDS-PAGE) | Food Allergen | Entry Date | Modified Date |
|---|---|---|---|---|---|---|
| *Clupea harengus* (Atlantic herring) | Clu h 1 | Beta-parvalbumin | 12 kDa | Yes | 2016 Apr. 4 | 2014 Nov. 3 |
| *Cyprinus carpio* (Common carp) | Cyp c 1 | beta-parvalbumin | 12 | Yes | 2016 Apr. 4 | 2013 Sep. 10 |
| *Gadus callarias* (Baltic cod) | Gad c 1 | Beta-parvalbumin | 12 | Yes | 2016 Apr. 4 | 2010 Apr. 29 |
| *Gadus morhua* (Atlantic cod) | Gad m 1 | Beta-parvalbumin | 12 | Yes | 2016 Apr. 4 | 2011 Jan. 25 |
| | Gad m 2 | Beta-enolase | 47.3 kDa | Yes | 2016 Apr. 4 | 2012 Jul. 30 |
| | Gad m 3 | Aldolase A | 40 kDa | Yes | 2016 Apr. 4 | 2012 Jul. 30 |
| *Lates calcarifer* (Barramundi) | Lat c 1 | Beta-parvalbumin | 11.5 kDa | Yes | 2016 Apr. 4 | 2014 Nov. 13 |
| *Lepidorhombus whiffiagonis* (Megrim, Whiff, Gallo) | Lep w 1 | Beta-parvalbumin | 11.5 kDa | Yes | 2016 Apr. 4 | 2010 Apr. 29 |
| *Oncorhynchus keta* (Chum salmon) | Onc k 5 | beta-prime-component of vitellogenin | 18 kDa | Yes | 2016 Apr. 4 | 2012 Dec. 18 |
| *Oncorhynchus mykiss* (Rainbow trout) | Onc m 1 | Beta-parvalbumin | 12 kDa | Yes | 2016 Apr. 4 | 2011 Apr. 14 |
| *Oreochromis mossambicus* (Mozambique tilapia) | Ore m 4 | Tropomyosin | 33 kDa | Yes | 2016 Apr. 4 | 2012 Jul. 30 |

TABLE 1-continued

| Species | Allergen | Biochemical name | MW (SDS-PAGE) | Food Allergen | Entry Date | Modified Date |
|---|---|---|---|---|---|---|
| *Salmo salar* | Sal s 1 | Beta-parvalbumin 1 | 12 | Yes | 2016 Apr. 4 | 2010 Apr. 29 |
| (Atlantic salmon) | Sal s 2 | Beta-Enolase | 47.3 kDa | Yes | 2016 Apr. 4 | 2011 Aug. 26 |
| | Sal s 3 | Aldolase A | 40 | Yes | 2016 Apr. 4 | 2012 Jul. 30 |
| *Sardinops sagax* | Sar sa 1 | Beta-parvalbumin | 12 kDa | Yes | 2016 Apr. 4 | 2010 Apr. 29 |
| (Pacific pilchard) | | | | | | |
| *Sebastes marinus* | Seb m 1 | Beta-parvalbumin | 11 kDa | Yes | 2016 Apr. 4 | 2010 Apr. 29 |
| (Ocean perch, redfish, snapper) | | | | | | |
| *Thunnus albacares* | Thu a 1 | Beta-parvalbumin | 11 kDa | Yes | 2016 Apr. 4 | 2010 Apr. 29 |
| (Yellowfin tuna) | Thu a 2 | Beta-enolase | 50 | Yes | 2016 Apr. 4 | 2012 Jul. 30 |
| | Thu a 3 | Aldolase A | 40 | Yes | 2016 Apr. 4 | 2012 Jul. 30 |
| *Xiphias gladius* | Xip g 1 | Beta-parvalbumin | 11.5 kDa | Yes | 2016 Apr. 4 | 2010 Apr. 29 |
| (Swordfish) | | | | | | |

However, while it is necessary to exhaustively identify allergen components in candidate allergic foods and cooking ingredients in order to enhance the reliability of allergy tests, the patient detection rate by the measurement of such allergenic components is far insufficient. Identification of novel allergens in fish is very important not only for increasing the precision of diagnosis, but also for determining targets of therapeutic agents, low allergenic foods, and low allergenic cooking ingredients.

Meanwhile, in the field of protein separation and purification, various efforts have conventionally been made to develop methods for separating and purifying a protein or nucleic acid of interest from cell extracts or the like. Such methods may well be exemplified by dialysis based on salt concentration, and centrifugal separation.

Other efforts have been made to develop many purification methods based on electric charges of protein or nucleic acid residues or on the difference in molecular weight. Electric charge-based purification methods can be exemplified by column chromatography using ion exchange resins, and isoelectric focusing. Purifications based on molecular weight difference can be exemplified by centrifugal separation, molecular-sieve column chromatography, and SDS-PAGE (sodium dodecyl sulfate-polyacrylamide gel electrophoresis).

In recent years, a method for separating and purifying many different proteins from a small amount of sample has been used, which is more specifically a two-dimensional electrophoresis consisting of isoelectric focusing in the first dimension, followed by SDS-PAGE in the second dimension. The present applicant has conventionally developed some 2D electrophoresis methods with high separation ability (Patent Literature 2-5).

Allergen-specific IgE antibodies recognize and bind to epitopes that are particular amino acid sequences in allergen components. However, only a slight number of analyses have been made on epitopes as to the allergen components (Non Patent Literature 5), but such analyses are still totally quite rare. Furthermore, any kit for diagnosing an allergy using a polypeptide comprising an epitope has not yet emerged in the market.

CITATION LIST

Patent Literature

PTL1: Japanese Patent Application Publication No. JP 2002-286716
PTL2: Japanese Patent Application Publication No. JP 2011-33544

PTL3: Japanese Patent Application Publication No. JP 2011-33546
PTL4: Japanese Patent Application Publication No. JP 2011-33547
PTL5: Japanese Patent Application Publication No. JP 2011-33548

Non Patent Literature

NPL 1: Allergen Nomenclature, WHO/IUIS Allergen Nomenclature Sub-Committee, [searched on Jun. 9, 2016], Internet <URL: http://www.allergen.org/search. php?allergenname=&allergensource=&TaxSource= Animalia+Chordata&TaxOrder=&foodallerg= 1&bioname=>
NPL 2: Kuehn, A., et al., Clin. Exp. Allergy, (2013), Vol. 43, No. 7, pp. 811-22
NPL 3: Gonzalez-Mancebo, E., et al., Ann. Allergy Asthma Immunol., (2014), Vol. 113, No. 1, pp. 114-115
NPL 4: van der Ventel, M. L., et al., Mol. Immunol., (2011), Vol. 48, No. 4, pp. 637-646
NPL 5: Matsuo, H., et al., J. Biol. Chem., (2004), Vol. 279, No. 13, pp. 12135-12140

SUMMARY OF INVENTION

Technical Problem

The present invention provides novel antigens of an allergy to fish. The present invention also provides methods and kits for diagnosing allergy to fish. The present invention also provides pharmaceutical compositions comprising such an antigen, fish, fish egg or processed products of such fish or fish egg in which such an antigen is eliminated or reduced, and fish that delivers such fish egg or is born from such fish egg. The present invention further provides testers for determining the presence or absence of a fish antigen in an object of interest.

The present invention also provides polypeptides comprising an epitope of an antigen. The present invention also provides kits, compositions and methods for diagnosing an allergy including such a polypeptides. The present invention also provides pharmaceutical compositions comprising such a polypeptide, and raw materials or processed products in which an antigen comprising such a polypeptide is eliminated or reduced The present invention further relates to methods for producing a processed product in which such an antigen is eliminated or reduced. The present invention further relates to testers for determining the presence or absence of an antigen comprising such a polypeptide in an object of interest.

Solution to Problem

In order to solve the aforementioned problems, the present inventors had made intensive studies to identify causative antigens of an allergy to fish. As a result, the inventors succeeded in identifying novel antigens to which an IgE antibody in the serum of a fish allergic patient specifically binds. The present invention has been completed based on this finding.

Thus, in one embodiment, the present invention can be as defined below.

[1] A kit for diagnosing an allergy to a fish, the kit comprising, as an antigen, at least one of proteins as defined below in any one of (10) to (14):

(10) (10A) myosin heavy chain, fast skeletal muscle-like or a variant thereof, which is an antigen of an allergy to a fish and is defined below in any of (10A-a) to (10A-e):

(10A-a) a protein comprising an amino acid sequence with deletion, substitution, insertion or addition of one or several amino acids in SEQ ID NO: 70;

(10A-b) a protein comprising an amino acid sequence having at least 70% identity to the amino acid sequence of SEQ ID NO: 70;

(10A-c) a protein comprising an amino acid sequence encoded by a nucleotide sequence with deletion, substitution, insertion or addition of one or several nucleotides in SEQ ID NO: 69;

(10A-d) a protein comprising an amino acid sequence encoded by a nucleotide sequence having at least 70% identity to the nucleotide sequence of SEQ ID NO: 69; or (10A-e) a protein comprising an amino acid sequence encoded by a nucleic acid that hybridizes under stringent conditions with a nucleic acid having a nucleotide sequence complementary to the nucleotide sequence of SEQ ID NO: 69; or (10B) a protein comprising at least one amino acid sequence selected from the group consisting of SEQ ID NOs: 70-108;

(11) (11A) glycogen phosphorylase, muscle form-like or a variant thereof, which is an antigen of an allergy to a fish and is defined below in any of (11A-a) to (11A-e):

(11A-a) a protein comprising an amino acid sequence with deletion, substitution, insertion or addition of one or several amino acids in SEQ ID NO: 110;

(11A-b) a protein comprising an amino acid sequence having at least 70% identity to the amino acid sequence of SEQ ID NO: 110;

(11A-c) a protein comprising an amino acid sequence encoded by a nucleotide sequence with deletion, substitution, insertion or addition of one or several nucleotides in SEQ ID NO: 109;

(11A-d) a protein comprising an amino acid sequence encoded by a nucleotide sequence having at least 70% identity to the nucleotide sequence of SEQ ID NO: 109; or (11A-e) a protein comprising an amino acid sequence encoded by a nucleic acid that hybridizes under stringent conditions with a nucleic acid having a nucleotide sequence complementary to the nucleotide sequence of SEQ ID NO: 109; or (11B) a protein comprising at least one amino acid sequence selected from the group consisting of SEQ ID NOs: 110-119;

(12) (12A) myosin-binding protein C, fast-type-like or a variant thereof, which is an antigen of an allergy to a fish and is defined below in any of (12A-a) to (12A-e):

(12A-a) a protein comprising an amino acid sequence with deletion, substitution, insertion or addition of one or several amino acids in SEQ ID NO: 121;

(12A-b) a protein comprising an amino acid sequence having at least 70% identity to the amino acid sequence of SEQ ID NO: 121;

(12A-c) a protein comprising an amino acid sequence encoded by a nucleotide sequence with deletion, substitution, insertion or addition of one or several nucleotides in SEQ ID NO: 120;

(12A-d) a protein comprising an amino acid sequence encoded by a nucleotide sequence having at least 70% identity to the nucleotide sequence of SEQ ID NO: 120; or (12A-e) a protein comprising an amino acid sequence encoded by a nucleic acid that hybridizes under stringent conditions with a nucleic acid having a nucleotide sequence complementary to the nucleotide sequence of SEQ ID NO: 120; or (12B) a protein comprising at least one amino acid sequence selected from the group consisting of SEQ ID NOs: 121-136;

(13) (13A) ATP synthase subunit beta, mitochondrial or a variant thereof, which is an antigen of an allergy to a fish and is defined below in any of (13A-a) to (13A-e):

(13A-a) a protein comprising an amino acid sequence with deletion, substitution, insertion or addition of one or several amino acids in SEQ ID NO: 138;

(13A-b) a protein comprising an amino acid sequence having at least 70% identity to the amino acid sequence of SEQ ID NO: 138;

(13A-c) a protein comprising an amino acid sequence encoded by a nucleotide sequence with deletion, substitution, insertion or addition of one or several nucleotides in SEQ ID NO: 137;

(13A-d) a protein comprising an amino acid sequence encoded by a nucleotide sequence having at least 70% identity to the nucleotide sequence of SEQ ID NO: 137; or (13A-e) a protein comprising an amino acid sequence encoded by a nucleic acid that hybridizes under stringent conditions with a nucleic acid having a nucleotide sequence complementary to the nucleotide sequence of SEQ ID NO: 137; or (13B) a protein comprising at least one amino acid sequence selected from the group consisting of SEQ ID NOs: 138-142; and

(14) (14A) L-lactate dehydrogenase A chain-like or a variant thereof, which is an antigen of an allergy to a fish and is defined below in any of (14A-a) to (14A-e):

(14A-a) a protein comprising an amino acid sequence with deletion, substitution, insertion or addition of one or several amino acids in SEQ ID NO: 144;

(14A-b) a protein comprising an amino acid sequence having at least 70% identity to the amino acid sequence of SEQ ID NO: 144;

(14A-c) a protein comprising an amino acid sequence encoded by a nucleotide sequence with deletion, substitution, insertion or addition of one or several nucleotides in SEQ ID NO: 143;

(14A-d) a protein comprising an amino acid sequence encoded by a nucleotide sequence having at least 70% identity to the nucleotide sequence of SEQ ID NO: 143; or (14A-e) a protein comprising an amino acid sequence encoded by a nucleic acid that hybridizes under stringent conditions with a nucleic acid having a nucleotide sequence complementary to the nucleotide sequence of SEQ ID NO: 143; or (14B) a protein comprising at least one amino acid sequence selected from the group consisting of SEQ ID NOs: 144-149;

[2] A composition for diagnosing an allergy to fish, comprising, as an antigen, at least one of proteins as defined above in any of (10) to (14) of [1].

[3] A method for providing an indicator for diagnosing an allergy to fish in a subject, the method comprising the steps of:

(i) contacting a sample obtained from the subject with an antigen, wherein the sample is a solution comprising an IgE antibody;

(ii) detecting binding between the IgE antibody present in the sample from the subject and the antigen; and (iii) when the binding between the IgE antibody in the subject and the antigen is detected, an indicator of the fact that the subject is allergic to fish is provided;

wherein the antigen is at least one of proteins as defined above in any of (10) to (14) of [1].

[4] A pharmaceutical composition comprising at least one of proteins as defined above in any of (10) to (14) of [1].

[5] The pharmaceutical composition as set forth in [4], wherein the pharmaceutical composition is intended for the treatment of an allergy to fish.

[6] Fish or processed products of fish in which an antigen is eliminated or reduced, wherein the antigen is at least one of proteins as defined above in any of (10) to (14) of [1].

[7] A tester for determining the presence or absence of a fish antigen in an object of interest, comprising an antibody that binds to at least one of proteins as defined above in any of (10) to (14) of [1].

[8] A tester for determining the presence or absence of an antigen causative of an allergy to fish in an object of interest, comprising a primer having a nucleotide sequence complementary to a portion of at least one of the nucleotide sequences of SEQ ID NOs: 69, 109, 120, 137 and 143.

[9] A fish-derived antigen which is at least one of proteins as defined above in any of (10) to (14) of [1] and is causative of an allergy to fish.

The present inventors also succeeded in finding epitopes as to fish-derived antigens including the antigens described above.

Since the epitopes have a relatively short amino acid sequence, the IgE antibodies are capable of binding to different allergen components if the same amino acid sequence is present in the different allergen components. Since different allergen components have a common epitope so that IgE antibodies from allergic patients bind to both of them, the antigens have cross-reactivity. Thus, the epitopes defined in the present invention enable diagnosis or treatment of an allergy including cross-reactivity, and detection of a plurality of allergen components comprising the epitopes, etc.

The present invention has been completed based on this finding. Thus, in another embodiment, the present invention can be as defined below.

[10] A polypeptide specifically binding to an IgE antibody from an allergic patient, the polypeptide being any one of the following:

(1α) a polypeptide comprising at least one amino acid sequence selected from the group consisting of SEQ ID NOs: 150-154 and 205-227;

(2α) a polypeptide comprising at least one amino acid sequence selected from the group consisting of SEQ ID NOs: 155 and 228-230;

(3α) a polypeptide comprising at least one amino acid sequence selected from the group consisting of SEQ ID NOs: 156, 157 and 231-237;

(4α) a polypeptide comprising at least one amino acid sequence selected from the group consisting of SEQ ID NOs: 158, 159 and 238-247;

(5α) a polypeptide comprising at least one amino acid sequence selected from the group consisting of SEQ ID NOs: 160-162 and 248-261;

(6α) a polypeptide comprising at least one amino acid sequence selected from the group consisting of SEQ ID NOs: 163-167 and 262-279;

(7α) a polypeptide comprising at least one amino acid sequence selected from the group consisting of SEQ ID NOs: 168-171 and 280-300;

(8α) a polypeptide comprising at least one amino acid sequence selected from the group consisting of SEQ ID NOs: 172-174 and 301-310;

(9α) a polypeptide comprising at least one amino acid sequence selected from the group consisting of SEQ ID NOs: 175-178 and 311-326;

(10α) a polypeptide comprising at least one amino acid sequence selected from the group consisting of SEQ ID NOs: 179-185 and 327-365;

(11α) a polypeptide comprising at least one amino acid sequence selected from the group consisting of SEQ ID NOs: 186 and 366-370;

(12α) a polypeptide comprising at least one amino acid sequence selected from the group consisting of SEQ ID NOs: 187-196 and 371-413;

(13α) a polypeptide comprising at least one amino acid sequence selected from the group consisting of SEQ ID NOs: 197 and 414-417;

(14α) a polypeptide comprising at least one amino acid sequence selected from the group consisting of SEQ ID NOs: 198 and 418-420;

(15α) a polypeptide comprising at least one amino acid sequence selected from the group consisting of SEQ ID NOs: 199 and 421-425;

(16α) a polypeptide comprising at least one amino acid sequence selected from the group consisting of SEQ ID NOs: 200-202 and 426-436; and (17α) a polypeptide comprising at least one amino acid sequence selected from the group consisting of SEQ ID NOs: 203, 204 and 437-444.

[11] The polypeptide according to the above [10], wherein the number of amino acid residues is 500 or less.

[12] A kit for diagnosing an allergy, comprising at least one of polypeptides according to the above [10] or [11].

[13] A composition for diagnosing an allergy, the composition comprising at least one of polypeptides according to the above [10] or [11] as an antigen.

[14] A method for providing an indicator for diagnosing an allergy in a subject, the method comprising the steps of:

(i) contacting a sample obtained from the subject with an antigen, wherein the sample is a solution comprising an IgE antibody;

(ii) detecting binding between the IgE antibody present in the sample obtained from the subject and the antigen; and (iii) when the binding between the IgE antibody in the subject and the antigen is detected, an indicator of the fact that the subject is allergic is provided;

wherein the antigen is at least one of polypeptides according to any one of the above [10] or [11].

[15] A pharmaceutical composition comprising at least one of polypeptides according to the above [10] or [11].

[16] The pharmaceutical composition according to the above [15], wherein the pharmaceutical composition is intended for the treatment of an allergy.

[17] A tester for determining the presence or absence of an antigen in an object of interest, the tester comprising an antibody that binds to at least one of polypeptides according to the above [10] or [11].

[18] A tester for determining the presence or absence of an antigen in an object of interest, the tester comprising any of the following primers:

(a) a primer comprising a portion of the nucleotide sequence of a nucleic acid encoding a polypeptide according to the above [10] or [11], and/or a portion of a complementary strand thereof; and (b) a primer which is a portion of at least one of the nucleotide sequences of SEQ ID NOs: 69, 109, 120, 137 and 143 and/or a primer which is a portion of a sequence complementary to at least one of the nucleotide sequences of SEQ ID NOs: 69, 109, 120, 137 and 143.

[19] A raw material or a processed product in which an antigen is eliminated or reduced, wherein the antigen is at least one of polypeptides according to the above [10] or [11].

[20] A method for producing a processed product in which an antigen is eliminated or reduced, the method comprising the step of confirming that the antigen is eliminated or reduced in a production process of the processed product, wherein the antigen is at least one of polypeptides according to the above [10] or [11].

Advantageous Effects of Invention

The present invention can provide novel antigens of an allergy to fish. Since the novel antigens (allergen components) that trigger a fish allergy were identified according to this invention, this invention can provide highly sensitive methods and kits for diagnosing an allergy to fish, pharmaceutical compositions comprising such an antigen, fish, fish egg, or processed products of such fish or fish egg in which such an antigen is eliminated or reduced, fish that delivers such fish egg or is born from such fish egg, and testers for determining the presence or absence of a fish antigen in an object of interest.

The present invention can provide novel polypeptides comprising an epitope of an antigen. Use of the polypeptide of the present invention enables provision of highly sensitive kits, compositions and methods for diagnosing an allergy, pharmaceutical compositions comprising such a polypeptide, testers for determining the presence or absence of an antigen comprising such a polypeptide in an object of interest, raw materials or processed products in which such a polypeptide is eliminated or reduced, and a method for producing the processed products.

BRIEF DESCRIPTION OF DRAWINGS

FIG. 1B is a photograph of an immunoblot of a two-dimensional electrophoretic pattern of proteins contained in an extract of salmon meat using the serum of fish-allergic patient 2 (left diagram) and using the serum of fish-allergic patient 3 (right diagram). The numeric values at the top of each photograph represent isoelectric points.

DESCRIPTION OF EMBODIMENTS

Figure 1A:
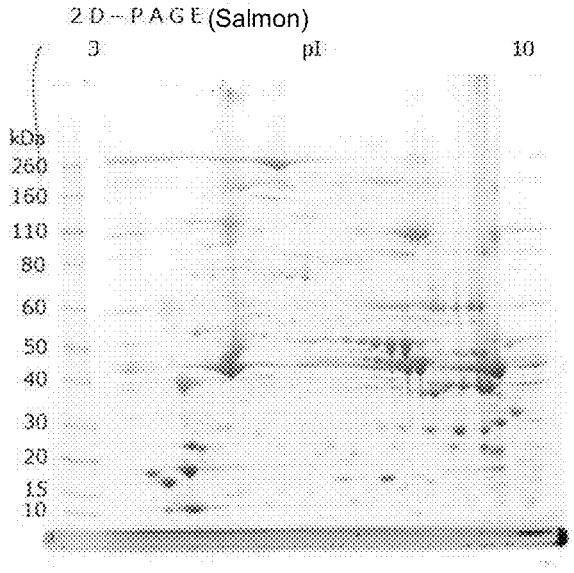
FIG. 1A is a photograph of a gel showing a protein electrophoretic pattern in two-dimensional electrophoresis of proteins contained in an extract of salmon meat (left diagram) and a photograph of an immunoblot of the two-dimensional electrophoretic pattern using the serum of fish-allergic patient 1 (right diagram). The bands at the left of the photograph of the gel are bands of molecular weight markers, and the numeric values at the left of the photograph of the gel are respective molecular weights (KDa) of the molecular weight markers. The numeric values at the top of the photograph represent isoelectric points.
Figure 1A:
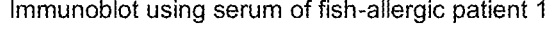
Figure 1A:
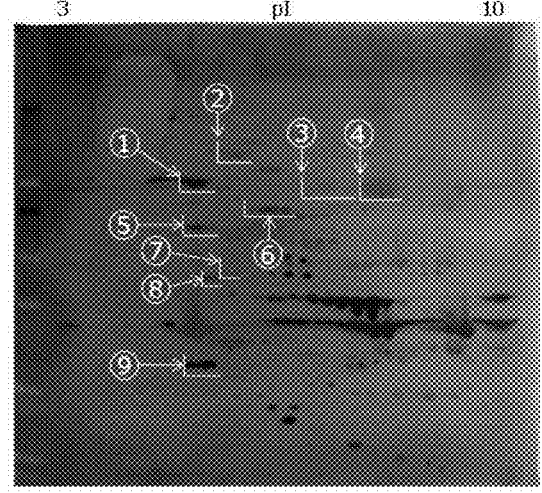

The present invention will be described in detail below, but the present invention is not limited to them.

Unless otherwise defined herein, all scientific and technical terms used in relation to the present invention shall have meanings commonly understood by those skilled in the art.

As referred to herein, the "allergy" refers to the state in which, when a certain antigen enters the body of a living individual sensitized to said antigen, the living individual shows a hypersensitive reaction detrimental to him/her. An allergic reaction can be produced upon contact with an antigen or consumption of the antigen. Here, the contact refers to touch to an object and, particularly, as for the human body, refers to attachment to the skin, the mucosa (eyes, lips, etc.) or the like. The consumption refers to incorporation into the body and refers to incorporation by inhalation, through an oral route, or the like. In general, allergic reactions caused by consumption of foods are particularly referred to as food allergies. In a preferred mode, the allergy may be a food allergy. In blood and tissues of individuals with many food-allergic diseases, IgE antibodies specific to antigens are produced. IgE antibodies bind to mast cells or basophils. When an antigen specific to such an IgE antibody enters again the body of a patient with an allergic disease, said antigen combines with the IgE antibody bound to mast cells or basophils, and the IgE antibody crosslinks said antigen on the cell surface, resulting in physiological effects of IgE antibody-antigen interaction. Examples of such physiological effects include release of histamine, serotonin, heparin, eosinophil chemotactic factors, leucotrienes, or the like. These released substances provoke an allergic reaction resulting from the combination of an IgE antibody with particular antigens. Specifically, IgE antibodies recognize and bind to epitopes that are particular amino acid sequences in particular antigens. Allergic reactions caused by such antigens occur through the aforementioned pathway.

In the present invention, the allergy of interest is not particularly limited as long as it is an allergy to an allergen comprising an epitope to be used. Such an allergy may include allergies to plants of the family Oleaceae, the family Compositae, the family Poaceae, the family Bromeliaceae, the family Juglandaceae, the family Cucurbitaceae, and the family Leguminosae, allergies to animals of the family Phasianidae and the family Bovidae, allergies to seafood of the family Carangidae, the family Sparidae, the family Salmonidae, the family Penaeidae, the family Lithodidae, the family Octopodidae, and the family Veneridae, and parasites of the family Anisakidae. Examples of the plant of the family Oleaceae include olive (scientific name: *Olea europaea*). Examples of the plant of the family Compositae include artichoke (scientific name: *Cynara scolymus*). Examples of the plant of the family Poaceae include bread wheat (scientific name: *Triticum aestivum*) and Tausch's goatgrass (scientific name: *Aegilops tauschii*). Examples of the plant of the family Bromeliaceae include pineapple (scientific name: *Ananas comosus*). Examples of the plant of the family Juglandaceae include walnut (scientific name: *Juglans regia*). Examples of the plant of the family Cucurbitaceae include squash (scientific name: *Cucurbita moschata*). Examples of the plant of the family Leguminosae include soybean (scientific name: *Glycine max*). Examples of the animal of the family Phasianidae include Japanese quail (scientific name: *Coturnix japonica*) and wild turkey (scientific name: *Meleagris gallopavo*). Examples of the animal of the family Bovidae include cattle (scientific name: *Bos taurus*). Examples of the seafood of the family Carangidae include greater amberjack (scientific name: *Seriola dumerili*). Examples of the seafood of the family Sparidae include red seabream (scientific name: *Pagrus major*). Examples of the seafood of the family Salmonidae include rainbow trout (scientific name: *Oncorhynchus mykiss*). Examples of the seafood of the family Penaeidae include whiteleg shrimp (scientific name: *Litopenaeus vannamei*). Examples of the seafood of the family Lithodidae include red king crab (scientific name: *Paralithodes camtschaticus*). Examples of the seafood of the family Octopodidae include North Pacific giant octopus (scientific name: *Enteroctopus dofleini*). Examples of the seafood of the family Veneridae include Manila clam (scientific name: *Ruditapes philippinarum*). Examples of the parasite of the family Anisakidae include anisakis (*Anisakis simplex*).

As referred to herein, the fish means, among fishes, a bony fish or a cartilage fish, preferably a bony fish, more preferably a fish belonging to the order Salmoniformes, the order Perciformes, the order Anguilliformes, the order Gadiformes, or the order Pleuronectiformes, further preferably a fish belonging to the family Salmonidae, the family Carangidae, the family Congridae, the family Sparidae, the family Scombridae, the family Gadidae, the family Anguillidae, or the family Paralichthyidae, still further preferably salmon, horse mackerel, conger, blackhead seabream, mackerel, sea bream, cod, amberjack, eel, or bastard halibut. The fish may be edible.

As referred to herein, the "fish egg" means an egg of a fish and is discriminated from the "egg", which typically means an egg of a bird. The fish egg may be edible.

As referred to herein, the allergy to fish refers to the state in which an individual has an allergic reaction caused by proteins, etc. present in fish which act as an antigen. The allergy to fish can produce an allergic reaction upon contact with an antigen present in fish or consumption of the antigen. In general, allergic reactions caused by consumption of foods are particularly referred to as food allergies. The allergy to fish may be a food allergy.

As referred to herein, the "antigen" refers to a substance that provokes an allergic reaction, and is also referred to as an "allergen component". The antigen is preferably a protein.

As referred to herein, the "protein" refers to a molecule having a structure in which naturally occurring amino acids are joined together by peptide bond. The number of amino acids present in a protein is not particularly limited. As referred to herein, the term "polypeptide" also means a molecule having a structure in which naturally occurring amino acids are joined together by peptide bond. The number of amino acids present in a polypeptide is not particularly limited. The "polypeptide" conceptually includes the "protein". Also, polypeptides having about 2 to 50 amino acids joined together by peptide bond are in some cases called "peptides", especially. In the case where amino acids can form different enantiomers, the amino acids are understood to form an L-enantiomer, unless otherwise indicated. The amino acid sequences of proteins, polypeptides, or peptides as used herein are represented by one-letter symbols of amino acids in accordance with standard usage and the notational convention commonly used in the art. The leftward direction represents the amino-terminal direction, and the rightward direction represents the carboxy-terminal direction. In the one-letter symbols of amino acids, X can be any substance having an amino group and a carboxyl group that can bind to amino acids at both ends, and particularly represents that any of 20 types of naturally occurring amino acids are acceptable. The residue of X is an amino acid residue at a site where binding activity against IgE antibodies from allergic patients was maintained even after substitution by alanine in alanine scanning described in Example 10. It is well known to those skilled in the art that even when such a site is substituted by any other amino acids, it is highly probable that this binding activity against IgE antibodies is maintained.

Identification of Antigens

Proteins contained in fish were analyzed by the aforementioned technique to identify antigens of an allergy to fish. To be specific, proteins were extracted from fish meat and subjected to two-dimensional electrophoresis under the conditions described below.

The electrophoresis in the first dimension was isoelectric focusing, which was performed using isoelectric focusing gels with a gel-strip length of 5 to 10 cm and a gel pH range of 3 to 10. The pH gradient of the gels in the direction of electrophoresis was as follows: with the total gel-strip length being taken as 1, the gel-strip length up to pH 5 was "a=0.15 to 0.3", the gel-strip length from pH 5 to 7 was "b=0.4 to 0.7", and the gel-strip length above pH 7 was "c=0.15 to 0.3". More specifically, the isoelectric focusing was performed using the IPG gels, Immobiline Drystrip (pH3-10NL), produced by GE Healthcare Bio-Sciences Corporation (hereinafter abbreviated as "GE"). The electrophoresis system used was IPGphor produced by GE. The maximum current of the electrophoresis system was limited to 75 μA per gel strip. The voltage program adopted to perform the first-dimensional isoelectric focusing was as follows: (1) a constant voltage step was performed at a constant voltage of 300 V until the volt-hours reached 750 Vhr (the current variation width during electrophoresis for 30 minutes before the end of this step was 5 µA); (2) the voltage was increased gradually to 1000 V for 300 Vhr; (3) the voltage was further increased gradually to 5000 V for 4500 Vhr; and then (4) the voltage was held at a constant voltage of 5000 V until the total Vhr reached 12000.

The electrophoresis in the second dimension was SDS-PAGE, which was performed using polyacrylamide gels whose gel concentration at the distal end in the direction of electrophoresis was set to 3 to 6% and whose gel concentration at the proximal end was set to a higher value than that at the distal end. More specifically, the SDS-PAGE was performed using NuPAGE 4-12% Bris-Tris Gels (IPG well, Mini, 1 mm) produced by Life Technologies. The electrophoresis system used was XCell SureLock Mini-Cell produced by Life Technologies. The electrophoresis was run at a constant voltage of 200 V for about 45 minutes using an electrophoresis buffer composed of 50 mM MOPS, 50 mM Tris base, 0.1% (w/v) SDS and 1 mM EDTA.

As a result, the following spots in a two-dimensional electrophoresis gel run under the conditions described above for proteins in fish have been revealed to exhibit specific binding to IgE antibodies from fish-allergic patients diagnosed with immediate-type allergy.

Spot 1: Molecular weight 80 to 160 kDa, pI 3.0 to 7.0
Spot 2: Molecular weight 110 to 260 kDa, pI 4.0 to 8.0
Spot 3: Molecular weight 80 to 160 kDa, pI 4.0 to 10.0
Spot 4: Molecular weight 80 to 160 kDa, pI 5.0 to 11.0
Spot 5: Molecular weight 50 to 110 kDa, pI 3.0 to 7.0
Spot 6: Molecular weight 60 to 110 kDa, pI 4.0 to 8.0
Spot 7: Molecular weight 40 to 80 kDa, pI 4.0 to 8.0
Spot 8: Molecular weight 40 to 80 kDa, pI 3.0 to 7.0
Spot 9: Molecular weight 20 to 50 kDa, pI 3.0 to 7.0
Spot 10: Molecular weight 160 to 300, pI 3.0 to 7.0
Spot 11: Molecular weight 80 to 160, pI 4.0 to 8.0
Spot 12: Molecular weight 100 to 160, pI 4.0 to 7.0
Spot 13: Molecular weight 30 to 70, pI 3.0 to 7.0
Spot 14: Molecular weight 20 to 50, pI 5.0 to 9.0
Antigen
(10) Antigen in Spot 10

As the result of sequence identification of the antigen in spot 10 by mass spectroscopy, the amino acid sequences of SEQ ID NOs: 71-108 were detected.

Also, the mass spectroscopic data (SEQ ID NOs: 71-108) obtained for spot 10 on a mass spectrometer was analyzed by comparing the data against the NCBI protein data, and as a result, myosin heavy chain, fast skeletal muscle-like (amino acid sequence: SEQ ID NO: 70, encoding nucleotide sequence: SEQ ID NO: 69) was identified. SEQ ID NO: 71 corresponds to amino acids 13-19 of SEQ ID NO: 70, SEQ ID NO: 72 corresponds to amino acids 262-271 of SEQ ID NO: 70, SEQ ID NO: 73 corresponds to amino acids 996-1014 of SEQ ID NO: 70, SEQ ID NO: 74 corresponds to amino acids 951-961 of SEQ ID NO: 70, SEQ ID NO: 75 corresponds to amino acids 1293-1303 of SEQ ID NO: 70, SEQ ID NO: 76 corresponds to amino acids 1082-1091 of SEQ ID NO: 70, SEQ ID NO: 77 corresponds to amino acids 1847-1856 of SEQ ID NO: 70, SEQ ID NO: 78 corresponds to amino acids 172-186 of SEQ ID NO: 70, SEQ ID NO: 79 corresponds to amino acids 919-937 of SEQ ID NO: 70, SEQ ID NO: 80 corresponds to amino acids 249-258 of SEQ ID NO: 70, SEQ ID NO: 81 corresponds to amino acids 706-717 of SEQ ID NO: 70, SEQ ID NO: 82 corresponds to amino acids 50-59 of SEQ ID NO: 70, SEQ ID NO: 83 corresponds to amino acids 415-430 of SEQ ID NO: 70, SEQ ID NO: 84 corresponds to amino acids 834-845 of SEQ ID NO: 70, SEQ ID NO: 85 corresponds to amino acids 617-630 of SEQ ID NO: 70, SEQ ID NO: 86 corresponds to amino acids 1556-1567 of SEQ ID NO: 70, SEQ ID NO: 87 corresponds to amino acids 1391-1408 of SEQ ID NO: 70, SEQ ID NO: 88 corresponds to amino acids 1025-1040 of SEQ ID NO: 70, SEQ ID NO: 89 corresponds to amino acids 1813-1836 of SEQ ID NO: 70, SEQ ID NO: 90 corresponds to amino acids 743-755 of SEQ ID NO: 70, SEQ ID NO: 91 corresponds to amino acids 1172-1192 of SEQ ID NO: 70, SEQ ID NO: 92 corresponds to amino acids 353-364 of SEQ ID NO: 70, SEQ ID NO: 93 corresponds to amino acids 1261-1292 of SEQ ID NO: 70, SEQ ID NO: 94 corresponds to amino acids 1783-1789 of SEQ ID NO: 70, SEQ ID NO: 95 corresponds to amino acids 1502-1519 of SEQ ID NO: 70, SEQ ID NO: 96 corresponds to amino acids 1484-1497 of SEQ ID NO: 70, SEQ ID NO: 97 corresponds to amino acids 1194-1212 of SEQ ID NO: 70, SEQ ID NO: 98 corresponds to amino acids 1304-1314 of SEQ ID NO: 70, SEQ ID NO: 99 corresponds to amino acids 369-384 of SEQ ID NO: 70, SEQ ID NO: 100 corresponds to amino acids 1315-1322 of SEQ ID NO: 70, SEQ ID NO: 101 corresponds to amino acids 1536-1555 of SEQ ID NO: 70, SEQ ID NO: 102 corresponds to amino acids 237-248 of SEQ ID NO: 70, SEQ ID NO: 103 corresponds to amino acids 1699-1725 of SEQ ID NO: 70, SEQ ID NO: 104 corresponds to amino acids 1092-1104 of SEQ ID NO: 70, SEQ ID NO: 105 corresponds to amino acids 407-414 of SEQ ID NO: 70, SEQ ID NO: 106 corresponds to amino acids 1897-1917 of SEQ ID NO: 70, SEQ ID NO: 107 corresponds to amino acids 1458-1470 of SEQ ID NO: 70, and SEQ ID NO: 108 corresponds to amino acids 1373-1388 of SEQ ID NO: 70.

Accordingly, the antigen in spot 10 in the present invention can be any of below in (10A-a) to (10A-e), and (10B):

(10A-a) a protein comprising an amino acid sequence with deletion, substitution, insertion or addition of one or several amino acids in SEQ ID NO: 70;

(10A-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 70;

(10A-c) a protein comprising an amino acid sequence encoded by a nucleotide sequence with deletion, substitution, insertion or addition of one or several nucleotides in SEQ ID NO: 69;

(10A-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 69;

(10A-e) a protein comprising an amino acid sequence encoded by a nucleic acid that hybridizes under stringent conditions with a nucleic acid having a nucleotide sequence complementary to the nucleotide sequence of SEQ ID NO: 69;

(10B) a protein comprising at least one amino acid sequence selected from the group consisting of SEQ ID NOs: 70-108, preferably a protein comprising at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, or 38 types or all sequences of the amino acid sequences. As referred to above, the amino acid sequence of any of SEQ ID NOs: 70 to 108 may be an amino acid sequence derived therefrom by deletion, substitution, insertion or addition of one or several amino acids;

The proteins as defined above in (10A-a) to (10A-e) and (10B) include those proteins whose amino acid residues are modified by phosphorylation, sugar chain modification, aminoacylation, ring-opening, deamination or the like.

The proteins as defined above in (10A-a) to (10A-e) and (10B) can be proteins that are found in a protein spot with a molecular weight of around 160 kDa to 300 kDa, preferably around 160 kDa to 260 kDa, more preferably around 200 kDa to 230 kDa and an isoelectric point of 3.0 to 7.0, preferably 4.0 to 6.0, more preferably 4.5 to 5.5 on gels used in the two-dimensional electrophoresis performed under the conditions described above in the subsection titled "Identification of antigens".

Preferably, a protein that is an antigen in spot 10 is an antigen of an allergy to fish.

Epitopes of the aforementioned antigens (10A-a) to (10A-e) and (10B) reside in amino acids 61-75 (SEQ ID NO: 179), amino acids 471-485 (SEQ ID NO: 180), amino acids 621-635 (SEQ ID NO: 181), amino acids 981-995 (SEQ ID NO: 182), amino acids 1011-1025 (SEQ ID NO: 183), amino acids 1041-1055 (SEQ ID NO: 184), and amino acids 1741-1755 (SEQ ID NO: 185) of SEQ ID NO: 70. When the antigen in spot 10 contains a variation in the amino acid sequence of SEQ ID NO: 70, amino acids corresponding to at least one of these epitopes may retain the sequence in SEQ ID NO: 70.

From the viewpoint that binding activity against IgE antibodies such as sensitivity (a degree to which a patient can be diagnosed as being positive) or specificity (a degree to which a healthy subject is not diagnosed as being positive) remains even if the amino acid sequence is varied, the antigen in spot 10 may be the following variant.

In the epitope having the sequence of SEQ ID NO: 179, sites of amino acids other than X in SEQ ID NO: 327 or 328 corresponding to the positions of the amino acids at positions 1-11 or SEQ ID NO: 330 or 331 corresponding to the positions of the amino acids at positions 1-9 in SEQ ID NO: 179 are important for binding to IgE antibodies from allergic patients. Thus, in another preferred mode, when the antigen in spot 10 contains a variation in the amino acid sequence of SEQ ID NO: 70, the antigen may have an amino acid sequence of SEQ ID NO: 70 in which the amino acids at positions 1-11 of amino acids 61-75 are SEQ ID NO: 327 or 328 or the amino acids at positions 1-9 thereof are SEQ ID NO: 330 or 331.

In the epitope having the sequence of SEQ ID NO: 180, sites of amino acids other than X in SEQ ID NO: 333 or 334 corresponding to the positions of the amino acids at positions 7-15 in SEQ ID NO: 180 are important for binding to IgE antibodies from allergic patients. Thus, in another preferred mode, when the antigen in spot 10 contains a variation in the amino acid sequence of SEQ ID NO: 70, the antigen may have an amino acid sequence of SEQ ID NO: 70 in which the amino acids at positions 7-15 of amino acids 471-485 are SEQ ID NO: 333 or 334.

In the epitope having the sequence of SEQ ID NO: 181, sites of amino acids other than X in SEQ ID NO: 336 or 337 corresponding to the positions of the amino acids at positions 1-10 in SEQ ID NO: 181 are important for binding to IgE antibodies from allergic patients. Thus, in another preferred mode, when the antigen in spot 10 contains a variation in the amino acid sequence of SEQ ID NO: 70, the antigen may have an amino acid sequence of SEQ ID NO:

70 in which the amino acids at positions 1-10 of amino acids 621-635 are SEQ ID NO: 336 or 337.

In the epitope having the sequence of SEQ ID NO: 182, sites of amino acids other than X in SEQ ID NO: 339 or 340 corresponding to the positions of the amino acids at positions 2-9, SEQ ID NO: 342 or 343 corresponding to the positions of the amino acids at positions 2-11, SEQ ID NO: 345 or 346 corresponding to the positions of the amino acids at positions 7-15, or SEQ ID NO: 348 or 349 corresponding to the positions of the amino acids at positions 9-14 in SEQ ID NO: 182 are important for binding to IgE antibodies from allergic patients. Thus, in another preferred mode, when the antigen in spot 10 contains a variation in the amino acid sequence of SEQ ID NO: 70, the antigen may have an amino acid sequence of SEQ ID NO: 70 in which the amino acids at positions 2-9 of amino acids 981-995 are SEQ ID NO: 339 or 340, the amino acids at positions 2-11 thereof are SEQ ID NO: 342 or 343, the amino acids at positions 7-15 thereof are SEQ ID NO: 345 or 346, or the amino acids at positions 9-14 thereof are SEQ ID NO: 348 or 349.

In the epitope having the sequence of SEQ ID NO: 183, sites of amino acids other than X in SEQ ID NO: 351 or 352 corresponding to the positions of the amino acids at positions 5-14 in SEQ ID NO: 183 are important for binding to IgE antibodies from allergic patients. Thus, in another preferred mode, when the antigen in spot 10 contains a variation in the amino acid sequence of SEQ ID NO: 70, the antigen may have an amino acid sequence of SEQ ID NO: 70 in which the amino acids at positions 5-14 of amino acids 1011-1025 are SEQ ID NO: 351 or 352.

In the epitope having the sequence of SEQ ID NO: 184, sites of amino acids other than X in SEQ ID NO: 354 or 355 corresponding to the positions of the amino acids at positions 5-12 or SEQ ID NO: 357 or 358 corresponding to the positions of the amino acids at positions 9-15 in SEQ ID NO: 184 are important for binding to IgE antibodies from allergic patients. Thus, in another preferred mode, when the antigen in spot 10 contains a variation in the amino acid sequence of SEQ ID NO: 70, the antigen may have an amino acid sequence of SEQ ID NO: 70 in which the amino acids at positions 5-12 of amino acids 1041-1055 are SEQ ID NO: 354 or 355 or the amino acids at positions 9-15 thereof are SEQ ID NO: 357 or 358.

In the epitope having the sequence of SEQ ID NO: 185, sites of amino acids other than X in SEQ ID NO: 360 or 361 corresponding to the positions of the amino acids at positions 5-12 or SEQ ID NO: 363 or 364 corresponding to the positions of the amino acids at positions 7-15 in SEQ ID NO: 185 are important for binding to IgE antibodies from allergic patients. Thus, in another preferred mode, when the antigen in spot 10 contains a variation in the amino acid sequence of SEQ ID NO: 70, the antigen may have an amino acid sequence of SEQ ID NO: 70 in which the amino acids at positions 5-12 of amino acids 1741-1755 are SEQ ID NO: 360 or 361 or the amino acids at positions 7-15 thereof are SEQ ID NO: 363 or 364.

(11) Antigen in Spot 11

As the result of sequence identification of the antigen in spot 11 by mass spectroscopy, the amino acid sequences of SEQ ID NOs: 111-119 were detected.

Also, the mass spectroscopic data (SEQ ID NOs: 111-119) obtained for spot 11 on a mass spectrometer was analyzed by comparing the data against the NCBI protein data, and as a result, glycogen phosphorylase, muscle form-like (amino acid sequence: SEQ ID NO: 110, encoding nucleotide sequence: SEQ ID NO: 109) was identified. SEQ ID NO: 111 corresponds to amino acids 471-479 of SEQ ID NO: 110, SEQ ID NO: 112 corresponds to amino acids 547-555 of SEQ ID NO: 110, SEQ ID NO: 113 corresponds to amino acids 203-215 of SEQ ID NO: 110, SEQ ID NO: 114 corresponds to amino acids 727-741 of SEQ ID NO: 110, SEQ ID NO: 115 corresponds to amino acids 508-520 of SEQ ID NO: 110, SEQ ID NO: 116 corresponds to amino acids 742-755 of SEQ ID NO: 110, SEQ ID NO: 117 corresponds to amino acids 13-29 of SEQ ID NO: 110, SEQ ID NO: 118 corresponds to amino acids 775-784 of SEQ ID NO: 110, and SEQ ID NO: 119 corresponds to amino acids 643-656 of SEQ ID NO: 110.

Accordingly, the antigens in spot 11 in the present invention can be any of below in (11A-a) to (11A-e) and (11B):

(11A-a) a protein comprising an amino acid sequence with deletion, substitution, insertion or addition of one or several amino acids in SEQ ID NO: 110;

(11A-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 110;

(11A-c) a protein comprising an amino acid sequence encoded by a nucleotide sequence with deletion, substitution, insertion or addition of one or several nucleotides in SEQ ID NO: 109;

(11A-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 109;

(11A-e) a protein comprising an amino acid sequence encoded by a nucleic acid that hybridizes under stringent conditions with a nucleic acid having a nucleotide sequence complementary to the nucleotide sequence of SEQ ID NO: 109;

(11B) a protein comprising at least one amino acid sequence selected from the group consisting of SEQ ID NOs: 110-119, preferably a protein comprising at least 2, 3, 4, 5, 6, 7, 8, or 9 types or all sequences of the amino acid sequences. As referred to above, the amino acid sequence of any of SEQ ID NOs: 110 to 119 may be an amino acid sequence derived therefrom by deletion, substitution, insertion or addition of one or several amino acids.

The proteins as defined above in (11A-a) to (11A-e) and (11B) include those proteins whose amino acid residues are modified by phosphorylation, sugar chain modification, aminoacylation, ring-opening, deamination or the like.

The proteins as defined above in (11A-a) to (11A-e) and (11B) can be proteins that are found in a protein spot with a molecular weight of around 80 kDa to 160 kDa, preferably around 80 kDa to 110 kDa, more preferably around 90 kDa to 110 kDa and an isoelectric point of 4.0 to 8.0, preferably 5.0 to 7.5, more preferably 6.5 to 7.0 on gels used in the two-dimensional electrophoresis performed under the conditions described above in the subsection titled "Identification of antigens".

Preferably, a protein that is an antigen in spot 11 is an antigen of an allergy to fish.

Epitopes of the aforementioned antigens (11A-a) to (11A-e) and (11B) reside in amino acids 261-275 (SEQ ID NO: 186) of SEQ ID NO: 110. When the antigen in spot 11 contains a variation in the amino acid sequence of SEQ ID NO: 110, amino acids corresponding to this epitope may retain the sequence in SEQ ID NO: 110.

From the viewpoint that binding activity against IgE antibodies such as sensitivity or specificity remains even if the amino acid sequence is varied, the antigen in spot 11 may be the following variant.

In the epitope having the sequence of SEQ ID NO: 186, sites of amino acids other than X in SEQ ID NO: 366 corresponding to the positions of the amino acids at positions 1-10 or SEQ ID NO: 368 or 369 corresponding to the positions of the amino acids at positions 11-15 in SEQ ID NO: 186 are important for binding to IgE antibodies from allergic patients. Thus, in another preferred mode, when the antigen in spot 11 contains a variation in the amino acid sequence of SEQ ID NO: 110, the antigen may have an amino acid sequence of SEQ ID NO: 110 in which the amino acids at positions 1-10 of amino acids 261-275 are SEQ ID NO: 366 or the amino acids at positions 11-15 thereof are SEQ ID NO: 368 or 369.

(12) Antigen in Spot 12

As the result of sequence identification of the antigen in spot 12 by mass spectroscopy, the amino acid sequences of SEQ ID NOs: 122-136 were detected.

Also, the mass spectroscopic data (SEQ ID NOs: 122-136) obtained for spot 12 on a mass spectrometer was analyzed by comparing the data against the NCBI protein data, and as a result, myosin-binding protein C, fast-type-like (amino acid sequence: SEQ ID NO: 121, encoding nucleotide sequence: SEQ ID NO: 120) was identified. SEQ ID NO: 122 corresponds to amino acids 197-204 of SEQ ID NO: 121, SEQ ID NO: 123 corresponds to amino acids 421-434 of SEQ ID NO: 121, SEQ ID NO: 124 corresponds to amino acids 329-336 of SEQ ID NO: 121, SEQ ID NO: 125 corresponds to amino acids 413-420 of SEQ ID NO: 121, SEQ ID NO: 126 corresponds to amino acids 240-246 of SEQ ID NO: 121, SEQ ID NO: 127 corresponds to amino acids 214-228 of SEQ ID NO: 121, SEQ ID NO: 128 corresponds to amino acids 1014-1024 of SEQ ID NO: 121, SEQ ID NO: 129 corresponds to amino acids 842-855 of SEQ ID NO: 121, SEQ ID NO: 130 corresponds to amino acids 260-274 of SEQ ID NO: 121, SEQ ID NO: 131 corresponds to amino acids 672-685 of SEQ ID NO: 121, SEQ ID NO: 132 corresponds to amino acids 506-512 of SEQ ID NO: 121, SEQ ID NO: 133 corresponds to amino acids 205-213 of SEQ ID NO: 121, SEQ ID NO: 134 corresponds to amino acids 165-182 of SEQ ID NO: 121, SEQ ID NO: 135 corresponds to amino acids 321-328 of SEQ ID NO: 121, and SEQ ID NO: 136 corresponds to amino acids 70-82 of SEQ ID NO: 121.

Accordingly, the antigen in spot 12 in the present invention can be any of below in (12A-a) to (12A-e), and (12B):

(12A-a) a protein comprising an amino acid sequence with deletion, substitution, insertion or addition of one or several amino acids in SEQ ID NO: 121;

(12A-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 121;

(12A-c) a protein comprising an amino acid sequence encoded by a nucleotide sequence with deletion, substitution, insertion or addition of one or several nucleotides in SEQ ID NO: 119;

(12A-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 119;

(12A-e) a protein comprising an amino acid sequence encoded by a nucleic acid that hybridizes under stringent conditions with a nucleic acid having a nucleotide sequence complementary to the nucleotide sequence of SEQ ID NO: 119;

(12B) a protein comprising at least one amino acid sequence selected from the group consisting of SEQ ID NOs: 121-136, preferably a protein comprising at least 2, 3, 4, 5, 6, 7, 8, 9, 10, 11, 12, 13, 14, or 15 types or all sequences of the amino acid sequences. As referred to above, the amino acid sequence of any of SEQ ID NOs: 121 to 136 may be an amino acid sequence derived therefrom by deletion, substitution, insertion or addition of one or several amino acids.

The proteins as defined above in (12A-a) to (12A-e) and (12B) include those proteins whose amino acid residues are modified by phosphorylation, sugar chain modification, aminoacylation, ring-opening, deamination or the like.

The proteins as defined above in (12A-a) to (12A-e) and (12B) can be proteins that are found in a protein spot with a molecular weight of around 100 kDa to 160 kDa, preferably around 110 kDa to 150 kDa, more preferably around 120 kDa to 140 kDa and an isoelectric point of 4.0 to 7.0, preferably 4.0 to 6.0, more preferably 5.0 to 6.0 on gels used in the two-dimensional electrophoresis performed under the conditions described above in the subsection titled "Identification of antigens".

Preferably, a protein that is an antigen in spot 12 is an antigen of an allergy to fish.

Epitopes of the aforementioned antigens (12A-a) to (12A-e) and (12B) reside in amino acids 181-195 (SEQ ID NO: 187), amino acids 211-225 (SEQ ID NO: 188), amino acids 221-235 (SEQ ID NO: 189), amino acids 231-245 (SEQ ID NO: 190), amino acids 251-265 (SEQ ID NO: 191), amino acids 371-385 (SEQ ID NO: 192), amino acids 491-505 (SEQ ID NO: 193), amino acids 651-665 (SEQ ID NO: 194), amino acids 831-845 (SEQ ID NO: 195), and amino acids 951-965 (SEQ ID NO: 196) of SEQ ID NO: 121. When the antigen in spot 12 contains a variation in the amino acid sequence of SEQ ID NO: 121, amino acids corresponding to at least one of these epitopes may retain the sequence in SEQ ID NO: 121.

From the viewpoint that binding activity against IgE antibodies such as sensitivity or specificity remains even if the amino acid sequence is varied, the antigen in spot 12 may be the following variant.

In the epitope having the sequence of SEQ ID NO: 187, sites of amino acids other than X in SEQ ID NO: 371 or 372 corresponding to the positions of the amino acids at positions 2-11 or SEQ ID NO: 374 or 375 corresponding to the positions of the amino acids at positions 7-14 in SEQ ID NO: 187 are important for binding to IgE antibodies from allergic patients. Thus, in another preferred mode, when the antigen in spot 12 contains a variation in the amino acid sequence of SEQ ID NO: 121, the antigen may have an amino acid sequence of SEQ ID NO: 121 in which the amino acids at positions 2-11 of amino acids 181-195 are SEQ ID NO: 371 or 372 or the amino acids at positions 7-14 thereof are SEQ ID NO: 374 or 375.

In the epitope having the sequence of SEQ ID NO: 188, sites of amino acids other than X in SEQ ID NO: 377 or 378 corresponding to the positions of the amino acids at positions 1-10 or SEQ ID NO: 380 or 381 corresponding to the positions of the amino acids at positions 8-15 in SEQ ID NO: 188 are important for binding to IgE antibodies from allergic patients. Thus, in another preferred mode, when the antigen in spot 12 contains a variation in the amino acid sequence of SEQ ID NO: 121, the antigen may have an amino acid sequence of SEQ ID NO: 121 in which the amino acids at positions 1-10 of amino acids 211-225 are SEQ ID NO: 377 or 378 or the amino acids at positions 8-15 thereof are SEQ ID NO: 380 or 381.

In the epitope having the sequence of SEQ ID NO: 189, sites of amino acids other than X in SEQ ID NO: 383 corresponding to the positions of the amino acids at positions 2-8 in SEQ ID NO: 189 are important for binding to IgE antibodies from allergic patients. Thus, in another preferred mode, when the antigen in spot 12 contains a variation in the amino acid sequence of SEQ ID NO: 121, the antigen may have an amino acid sequence of SEQ ID NO: 121 in which the amino acids at positions 2-8 of amino acids 221-235 are SEQ ID NO: 383.

In the epitope having the sequence of SEQ ID NO: 190, sites of amino acids other than X in SEQ ID NO: 385 corresponding to the positions of the amino acids at positions 2-9, SEQ ID NO: 387 corresponding to the positions of the amino acids at positions 1-10, or SEQ ID NO: 389 corresponding to the positions of the amino acids at positions 9-15 in SEQ ID NO: 190 are important for binding to IgE antibodies from allergic patients. Thus, in another preferred mode, when the antigen in spot 12 contains a variation in the amino acid sequence of SEQ ID NO: 121, the antigen may have an amino acid sequence of SEQ ID NO: 121 in which the amino acids at positions 2-9 of amino acids 231-245 are SEQ ID NO: 385, the amino acids at positions 1-10 thereof are SEQ ID NO: 387, or the amino acids at positions 9-15 thereof are SEQ ID NO: 389.

In the epitope having the sequence of SEQ ID NO: 191, sites of amino acids other than X in SEQ ID NO: 391 corresponding to the positions of the amino acids at positions 6-11 or SEQ ID NO: 393 or 394 corresponding to the positions of the amino acids at positions 6-12 in SEQ ID NO: 191 are important for binding to IgE antibodies from allergic patients. Thus, in another preferred mode, when the antigen in spot 12 contains a variation in the amino acid sequence of SEQ ID NO: 121, the antigen may have an amino acid sequence of SEQ ID NO: 121 in which the amino acids at positions 6-11 of amino acids 251-265 are SEQ ID NO: 391 or the amino acids at positions 6-12 thereof are SEQ ID NO: 393 or 394.

In the epitope having the sequence of SEQ ID NO: 192, sites of amino acids other than X in SEQ ID NO: 396 corresponding to the positions of the amino acids at positions 5-8 or SEQ ID NO: 398 or 399 corresponding to the positions of the amino acids at positions 7-15 in SEQ ID NO: 192 are important for binding to IgE antibodies from allergic patients. Thus, in another preferred mode, when the antigen in spot 12 contains a variation in the amino acid sequence of SEQ ID NO: 121, the antigen may have an amino acid sequence of SEQ ID NO: 121 in which the amino acids at positions 5-8 of amino acids 371-385 are SEQ ID NO: 396 or the amino acids at positions 7-15 thereof are SEQ ID NO: 398 or 399.

In the epitope having the sequence of SEQ ID NO: 193, sites of amino acids other than X in SEQ ID NO: 401 corresponding to the positions of the amino acids at positions 1-7 or SEQ ID NO: 403 or 404 corresponding to the positions of the amino acids at positions 6-15 in SEQ ID NO: 193 are important for binding to IgE antibodies from allergic patients. Thus, in another preferred mode, when the antigen in spot 12 contains a variation in the amino acid sequence of SEQ ID NO: 121, the antigen may have an amino acid sequence of SEQ ID NO: 121 in which the amino acids at positions 1-7 of amino acids 491-505 are SEQ ID NO: 401 or the amino acids at positions 6-15 thereof are SEQ ID NO: 403 or 404.

In the epitope having the sequence of SEQ ID NO: 194, sites of amino acids other than X in SEQ ID NO: 406 corresponding to the positions of the amino acids at positions 3-7 in SEQ ID NO: 194 are important for binding to IgE antibodies from allergic patients. Thus, in another preferred mode, when the antigen in spot 12 contains a variation in the amino acid sequence of SEQ ID NO: 121, the antigen may have an amino acid sequence of SEQ ID NO: 121 in which the amino acids at positions 3-7 of amino acids 651-665 are SEQ ID NO: 406.

In the epitope having the sequence of SEQ ID NO: 195, sites of amino acids other than X in SEQ ID NO: 408 corresponding to the positions of the amino acids at positions 2-13 in SEQ ID NO: 195 are important for binding to IgE antibodies from allergic patients. Thus, in another preferred mode, when the antigen in spot 12 contains a variation in the amino acid sequence of SEQ ID NO: 121, the antigen may have an amino acid sequence of SEQ ID NO: 121 in which the amino acids at positions 2-13 of amino acids 831-845 are SEQ ID NO: 408.

In the epitope having the sequence of SEQ ID NO: 196, sites of amino acids other than X in SEQ ID NO: 410 corresponding to the positions of the amino acids at positions 1-10 or SEQ ID NO: 412 corresponding to the positions of the amino acids at positions 1-8 in SEQ ID NO: 196 are important for binding to IgE antibodies from allergic patients. Thus, in another preferred mode, when the antigen in spot 12 contains a variation in the amino acid sequence of SEQ ID NO: 121, the antigen may have an amino acid sequence of SEQ ID NO: 121 in which the amino acids at positions 1-10 of amino acids 951-965 are SEQ ID NO: 410 or the amino acids at positions 1-8 thereof are SEQ ID NO: 412.

(13) Antigen in Spot 13

As the result of sequence identification of the antigen in spot 13 by mass spectroscopy, the amino acid sequences of SEQ ID NOs: 139-142 were detected.

Also, the mass spectroscopic data (SEQ ID NOs: 139-142) obtained for spot 13 on a mass spectrometer was analyzed by comparing the data against the NCBI protein data, and as a result, ATP synthase subunit beta, mitochondrial (amino acid sequence: SEQ ID NO: 138, encoding nucleotide sequence: SEQ ID NO: 137) was identified. SEQ ID NO: 139 corresponds to amino acids 191-201 of SEQ ID NO: 138, SEQ ID NO: 140 corresponds to amino acids 449-469 of SEQ ID NO: 138, SEQ ID NO: 141 corresponds to amino acids 202-214 of SEQ ID NO: 138, and SEQ ID NO: 142 corresponds to amino acids 178-187 of SEQ ID NO: 138.

Accordingly, the antigen in spot 13 in the present invention can be any of the proteins as defined below in (13A-a) to (13A-e) and (13B).

(13A-a) a protein comprising an amino acid sequence with deletion, substitution, insertion or addition of one or several amino acids in SEQ ID NO: 138;

(13A-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 138;

(13A-c) a protein comprising an amino acid sequence encoded by a nucleotide sequence with deletion, substitution, insertion or addition of one or several nucleotides in SEQ ID NO: 137;

(13A-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 137;

(13A-e) a protein comprising an amino acid sequence encoded by a nucleic acid that hybridizes under stringent conditions with a nucleic acid having a nucleotide sequence complementary to the nucleotide sequence of SEQ ID NO: 137;

(13B) a protein comprising at least one amino acid sequence selected from the group consisting of SEQ ID NOs: 138-142, preferably a protein comprising at least 2, 3, or 4 or all sequences of the amino acid sequences. As referred to above, the amino acid sequence of any of SEQ ID NOs: 138 to 142 may be an amino acid sequence derived therefrom by deletion, substitution, insertion or addition of one or several amino acids.

The proteins as defined above in (13A-a) to (13A-e) and (13B) include those proteins whose amino acid residues are modified by phosphorylation, sugar chain modification, aminoacylation, ring-opening, deamination or the like.

The proteins as defined above in (13A-a) to (13A-e) and (13B) can be proteins that are found in a protein spot with a molecular weight of around 30 kDa to 70 kDa, preferably around 40 kDa to 60 kDa, more preferably around 45 kDa to 55 kDa and an isoelectric point of 3.0 to 7.0, preferably 3.0 to 6.0, more preferably 4.0 to 5.5 on gels used in the two-dimensional electrophoresis performed under the conditions described above in the subsection titled "Identification of antigens".

Preferably, a protein that is an antigen in spot 13 is an antigen of an allergy to fish.

Epitopes of the aforementioned antigens (13A-a) to (13A-e) and (13B) reside in amino acids 211-225 (SEQ ID NO: 197) of SEQ ID NO: 138. When the antigen in spot 13 contains a variation in the amino acid sequence of SEQ ID NO: 138, amino acids corresponding to this epitope may retain the sequence in SEQ ID NO: 138.

From the viewpoint that binding activity against IgE antibodies such as sensitivity or specificity remains even if the amino acid sequence is varied, the antigen in spot 13 may be the following variant.

In the epitope having the sequence of SEQ ID NO: 197, sites of amino acids other than X in SEQ ID NO: 414 corresponding to the positions of the amino acids at positions 7-10 or SEQ ID NO: 416 corresponding to the positions of the amino acids at positions 9-14 in SEQ ID NO: 197 are important for binding to IgE antibodies from allergic patients. Thus, in another preferred mode, when the antigen in spot 13 contains a variation in the amino acid sequence of SEQ ID NO: 138, the antigen may have an amino acid sequence of SEQ ID NO: 138 in which the amino acids at positions 7-10 of amino acids 211-225 are SEQ ID NO: 414 or the amino acids at positions 9-14 thereof are SEQ ID NO: 416.

(14) Antigen in Spot 14

As the result of sequence identification of the antigen in spot 14 by mass spectroscopy, the amino acid sequences of SEQ ID NOs: 145-149 were detected.

Also, the mass spectroscopic data (SEQ ID NOs: 145-149) obtained for spot 14 on a mass spectrometer was analyzed by comparing the data against the NCBI protein data, and as a result, L-lactate dehydrogenase A chain-like (amino acid sequence: SEQ ID NO: 144, encoding nucleotide sequence: SEQ ID NO: 143) was identified. SEQ ID NO: 145 corresponds to amino acids 119-126 of SEQ ID NO: 144, SEQ ID NO: 146 corresponds to amino acids 7-22 of SEQ ID NO: 144, SEQ ID NO: 147 corresponds to amino acids 9-22 of SEQ ID NO: 144, SEQ ID NO: 148 corresponds to amino acids 270-278 of SEQ ID NO: 144, and SEQ ID NO: 149 corresponds to amino acids 91-118 of SEQ ID NO: 144.

Accordingly, the antigen in spot 14 in the present invention can be any of the proteins as defined below in (14A-a) to (14A-e) and (14B).

(14A-a) a protein comprising an amino acid sequence with deletion, substitution, insertion or addition of one or several amino acids in SEQ ID NO: 144;

(14A-b) a protein comprising an amino acid sequence having at least 70%, preferably at least 75%, at least 80%, at least 85%, at least 90%, at least 95%, at least 97%, at least 98%, or at least 99% identity to the amino acid sequence of SEQ ID NO: 144;

(14A-c) a protein comprising an amino acid sequence encoded by a nucleotide sequence with deletion, substitution, insertion or addition of one or several nucleotides in SEQ ID NO: 143;

(14A-d) a protein comprising an amino acid sequence encoded by a nucleotide sequence having at least 70%, preferably at least 75%, at least 80%, at least 85%, at least 90%, at least 95%, at least 97%, at least 98%, or at least 99% identity to the nucleotide sequence of SEQ ID NO: 143;

(14A-e) a protein comprising an amino acid sequence encoded by a nucleic acid that hybridizes under stringent conditions with a nucleic acid having a nucleotide sequence complementary to the nucleotide sequence of SEQ ID NO: 143;

(14B) a protein comprising at least one amino acid sequence selected from the group consisting of SEQ ID NOs: 144-149, preferably a protein comprising at least 2, 3, 4, or 5 or all sequences of the amino acid sequences. As referred to above, the amino acid sequence of any of SEQ ID NOs: 144 to 149 may be an amino acid sequence derived therefrom by deletion, substitution, insertion or addition of one or several amino acids.

The proteins as defined above in (14A-a) to (14A-e) and (14B) include those proteins whose amino acid residues are modified by phosphorylation, sugar chain modification, aminoacylation, ring-opening, deamination or the like.

The proteins as defined above in (14A-a) to (14A-e) and (14B) can be proteins that are found in a protein spot with a molecular weight of around 20 kDa to 50 kDa, preferably around 30 kDa to 50 kDa, more preferably around 30 kDa to 40 kDa and an isoelectric point of 5.0 to 9.0, preferably 6.0 to 8.0, more preferably 6.5 to 7.5 on gels used in the two-dimensional electrophoresis performed under the conditions described above in the subsection titled "Identification of antigens".

Preferably, a protein that is an antigen in spot 14 is an antigen of an allergy to fish.

Epitopes of the aforementioned antigens (14A-a) to (14A-e) and (14B) reside in amino acids 11-25 (SEQ ID NO: 198) of SEQ ID NO: 144. When the antigen in spot 14 contains a variation in the amino acid sequence of SEQ ID NO: 144, amino acids corresponding to this epitope may retain the sequence in SEQ ID NO: 144.

From the viewpoint that binding activity against IgE antibodies such as sensitivity or specificity remains even if the amino acid sequence is varied, the antigen in spot 14 may be the following variant.

In the epitope having the sequence of SEQ ID NO: 198, sites of amino acids other than X in SEQ ID NO: 418 or 419 corresponding to the positions of the amino acids at positions 5-13 in SEQ ID NO: 198 are important for binding to IgE antibodies from allergic patients. Thus, in another preferred mode, when the antigen in spot 14 contains a variation in the amino acid sequence of SEQ ID NO: 144, the antigen may have an amino acid sequence of SEQ ID NO: 144 in which the amino acids at positions 5-13 of amino acids 11-25 are SEQ ID NO: 418 or 419.

By stating herein "deletion, substitution, insertion or addition of one or several amino acids" in relation to amino acid sequence, it is meant that in an amino acid sequence of interest, one or several amino acids (e.g., 30%, preferably 25%, 20%, 15%, 10%, 5%, 3%, 2% or 1%, of amino acids with respect to the total length of the amino acid sequence) are deleted, one or several amino acids are substituted by any other amino acids, any other amino acids are inserted, and/or any other amino acids are added.

Among the aforementioned modifications, substitution is preferably conservative substitution. The "conservative substitution" refers to the substitution of a certain amino acid residue by a different amino acid residue having similar physicochemical characteristics, and can be any type of substitution as long as it does not substantially change the characteristics of the structure of the original sequence for example, any type of substitution is acceptable as long as any substituted amino acids do not disrupt the helical structure of the original sequence or other secondary structures that characterize the original sequence. The following gives examples of separate groups of amino acid residues that are conservatively substitutable with each other, but substitutable amino acid residues are not limited to the examples given below.

Group A: leucine, isoleucine, valine, alanine, methionine
Group B: aspartic acid, glutamic acid
Group C: asparagine, glutamine
Group D: lysine, arginine
Group E: serine, threonine
Group F: phenylalanine, tyrosine In the case of non-conservative substitution, one member belonging to one of the aforementioned groups can be replaced with a member belong to any other group. For example, in order to eliminate the possibility of unwanted sugar-chain modification, amino acids of group B, D or E as listed above may be substituted by those of any other group. Also, cysteines may be deleted or substituted by any other amino acids to prevent them from being folded into a protein in its tertiary structure. Also, in order to maintain the balance between hydrophilicity and hydrophobicity or to increase hydrophilicity for the purpose of facilitating synthesis, any amino acids may be substituted in consideration of the hydropathy scales of amino acids, which are a measure of the hydrophilic and hydrophobic properties of amino acids (J. Kyte and R. Doolittle, J. Mol. Biol., Vol. 157, p. 105-132, 1982).

In another mode, substitution of the original amino acid by an amino acid with less steric hindrance, for example, substitution of group F by group A, B, C, D or E; or substitution of an amino acid having an electric charge by an amino acid having no electric charge, for example, substitution of group B by group C, may be performed. This may improve binding activity against IgE antibodies.

As referred to herein, the percent identity between two amino acid sequences can be determined by visual inspection and mathematical calculation. Alternatively, the percent identity can be determined using a computer program.

Examples of such computer programs include BLAST and ClustalW. In particular, various conditions (parameters) for identity searches with the BLAST program are described in Altschul, et al. (Nucl. Acids. Res., 25, p. 3389-3402, 1997), and are publicly available on the websites of the National Center for Biotechnology Information (NCBI) and DNA Data Bank of Japan (DDBJ) (Altschul, et al., BLAST Handbook, Altschul, et al., NCB/NLM/NIH Bethesda, MD 20894). Also, the percent identity can be determined using a genetic information processing software program, such as GENETYX Ver.7 (Genetyx Corporation), DINASIS Pro (Hitachi Software Engineering Co., Ltd.), or Vector NTI (Infomax Inc.).

By stating herein "deletion, substitution, insertion or addition of one or several nucleotides" in relation to nucleotide sequence, it is meant that in a nucleotide sequence of interest, one or several nucleotides (e.g., 30%, preferably 25%, 20%, 15%, 10%, 5%, 3%, 2% or 1%, of amino acid with respect to the total length of the nucleotide sequence, or e.g., 1, 5, 10, 15, 20, 25 or 30 nucleotides) are deleted, one or several nucleotides are substituted by any other nucleotides, any other nucleotides are inserted, and/or any other nucleotides are added. It is preferable that such a nucleotide deletion, substitution, insertion or addition should not give rise to a frame shift in an amino acid coding sequence.

As referred to herein, the percent identity between two nucleotide sequences can be determined by visual inspection and mathematical calculation. Alternatively, the percent identity can be determined using a computer program. Examples of such sequence comparison computer programs include the BLASTN program, version 2.2.7, available on the website of the National Library of Medicine (http://www.ncbi.nlm.nih.gov/blast/b12seq/bls.html) (Altschul, et al. (1990) J. Mol. Biol., 215: 403-10), or the WU-BLAST 2.0 algorithm. Standard default parameter settings for WU-BLAST 2.0 are found and available on the following website: http://blast.wustl.edu.

As referred to herein, "under stringent conditions" means that hybridization takes place under moderately or highly stringent conditions. To be specific, the moderately stringent conditions can be easily determined by those having ordinary skill in the art on the basis of, for example, the length of DNA. Basic conditions are described in Sambrook, et al., Molecular Cloning: A Laboratory Manual, 3rd ed., ch. 6-7, Cold Spring Harbor Laboratory Press, 2001. The moderately stringent conditions include hybridization under the conditions of preferably 1×SSC to 6×SSC at 42° C. to 55° C., more preferably 1×SSC to 3×SSC at 45° C. to 50° C., most preferably 2×SSC at 50° C. In the case of using a hybridization solution containing, for example, about 50% formamide, a temperature around 5 to 15° C. lower than the foregoing should be adopted. Washing is also carried out under the conditions of 0.5×SSC to 6×SSC at 40° C. to 60° C. In the process of hybridization and washing, generally 0.05% to 0.2% SDS, preferably about 0.1% SDS, may be added. Likewise, the highly stringent conditions can be easily determined by those having ordinary skill in the art on the basis of, for example, the length of DNA. Generally, the highly stringent (high stringent) conditions include hybridization and/or washing at a higher temperature and/or a lower salt concentration than those adopted under the moderately stringent conditions. For example, hybridization is carried out under the conditions of 0.1×SSC to 2×SSC at 55° C. to 65° C., more preferably 0.1×SSC to 1×SSC at 60° C. to 65° C., most preferably 0.2×SSC at 63° C. Washing is carried out under the conditions of 0.2×SSC to 2×SSC at 50° C. to 68° C., more preferably 0.2×SSC at 60 to 65° C.

Antigens may be obtained by separating and purifying them from fish using a combination of protein purification methods well known to those skilled in the art. Also, antigens may be obtained by expressing them as recombinant proteins using a genetic recombination technique well known to those skilled in the art and by separating and purifying them using protein purification methods well known to those skilled in the art.

Exemplary protein purification methods include: solubility-based purification methods such as salt precipitation and solvent precipitation; purification methods based on molecular weight difference, such as dialysis, ultrafiltration, gel filtration and SDS-PAGE; charge-based purification methods such as ion exchange chromatography and hydroxylapatite chromatography; specific affinity-based purification methods such as affinity chromatography; purification methods based on hydrophobicity difference, such as reverse-phase high-performance liquid chromatography; and purification methods based on isoelectric point difference, such as isoelectric focusing.

Preparation of a protein by a genetic recombination technique is carried out by preparing an expression vector comprising an antigen-encoding nucleic acid, introducing the expression vector into appropriate host cells by gene transfer or genetic transformation, culturing the host cells under suitable conditions for expression of a recombinant protein, and recovering the recombinant protein expressed in the host cells.

The "vector" refers to a nucleic acid that can be used to introduce a nucleic acid attached thereto into host cells. The "expression vector" is a vector that can induce the expression of a protein encoded by a nucleic acid introduced therethrough. Exemplary vectors include plasmid vectors and viral vectors. Those skilled in the art can select an appropriate expression vector for the expression of a recombinant protein depending on the type of host cells to be used. In order to facilitate purification, an affinity tag such as His×6 residues may be contained therein. Furthermore, the vector may be synthesized such that a protein containing a signal sequence is secreted from cells.

The "host cells" refers to cells that undergo gene transfer or genetic transformation by a vector. The host cells can be appropriately selected by those skilled in the art depending on the type of the vector to be used. The host cells can be derived from prokaryotes such as E. coli. When prokaryotic cells like E. coli are used as host cells, the antigen of the present invention may be designed to contain an N-terminal methionine residue in order to facilitate the expression of a recombinant protein in the prokaryotic cells. The N-terminal methionine can be cleaved from the recombinant protein after expression. Also, the host cells may be cells derived from eukaryotes, such as single-cell eukaryotes like yeast, plant cells and animal cells (e.g., human cells, monkey cells, hamster cells, rat cells, murine cells or insect cells) or silkworm.

Gene transfer or genetic transformation of an expression vector into host cells can be carried out as appropriate by following a technique known to those skilled in the art. Those skilled in the art can make possible the expression of a recombinant protein by selecting suitable conditions for the expression of the recombinant protein as appropriate depending on the type of host cells and culturing the host cells under the selected conditions. Then, those skilled in the art can homogenize the host cells having the expressed recombinant protein, and separate and purify an antigen expressed as the recombinant protein from the resulting homogenate by using an appropriate combination of such protein purification methods as mentioned above.

Diagnosis Kit and Method (1)

The present invention provides a method for providing an indicator for diagnosing an allergy to fish in a subject, the method comprising the steps of:

(i) contacting a sample obtained from the subject with an antigen, wherein the sample is a solution comprising an IgE antibody;

(ii) detecting binding between an IgE antibody present in the sample from the subject and the antigen; and (iii) when the binding between the IgE antibody in the subject and the antigen is detected, an indicator of the fact that the subject is allergic to fish is provided; wherein the antigen is at least one of proteins as defined above in any of (10) to (14).

The sample obtained from a subject is a solution containing an IgE antibody, as collected from the subject. Examples of such solutions include blood, saliva, sputum, snivel, urine, sweat, and tear. The sample obtained from the subject may be subjected to pretreatment for increasing the concentration of an IgE antibody in the sample before being contacted with an antigen. The pretreatment of a sample may involve, for example, collection of the serum or the plasma from the blood. Furthermore, a Fab moiety that is an antigen-binding moiety may be purified. In a particularly preferred mode, the step (i) mentioned above is carried out by contacting an IgE antibody present in the serum obtained from a subject with an antigen.

The IgE antibody may be the IgE antibody itself or may be mast cells or the like bound to IgE antibodies.

Detection of contact and binding between the sample obtained from a subject and an antigen can be carried out by using a known method. Examples of such methods that can be used include detection by ELISA (Enzyme-Linked Immunosorbent Assay), sandwich immunoassay, immuno-blotting, immunoprecipitation, or immunochromatography. These are all techniques for contacting and binding an IgE antibody from a subject with an antigen, and detecting the IgE antibody specifically bound to the antigen. Examples thereof include a method for allowing an enzymatically labelled secondary antibody to act on the IgE antibody specifically bound to the antigen, and adding an enzyme substrate (generally, chromogenic or luminescent reagent) to detect an enzymatic reaction product, a method for allowing a biotin-labeled secondary antibody to act on the IgE antibody specifically bound to the antigen, adding an avidin-bound dye, and detecting the dye, and a method for detecting a fluorescently labeled secondary antibody. Alternatively, detection by a measurement method capable of evaluating binding between an antigen and an IgE antibody, such as surface plasmon resonance (SPR), can also be used. A plurality of antigen-specific IgE antibodies may be mixed.

The antigen may be provided as an isolated antigen in a state immobilized on a carrier. In this case, the steps (i) and (ii) mentioned above can be carried out using ELISA, sandwich immunoassay, immunochromatography, surface plasmon resonance, or the like. Also, the step (i) mentioned above can be carried out by contacting the sample obtained from a subject with an antigen-immobilized surface. The isolated antigen may be obtained by separating and purifying it from fish using a combination of protein purification methods well known to those skilled in the art, or by preparing it using a genetic recombination technique. Alternatively, the antibody to bind to the antigen may be used in a state immobilized on a carrier.

The antigen may be in a state unimmobilized on a carrier. In this case, flow cytometry or the like can be used in the aforementioned steps (i) and (ii), and the presence of the antigen bound to the antibody can be confirmed with laser beam. Examples of this method include a basophil activation test (BAT) which is a method in which the amount of a surface antigen CD203c that appears when basophils in a sample are activated by the binding of the antigen to an antibody is measured. Another example includes a histamine release test (HRT) which examines whether histamine is released by contacting the antigen with blood cells through binding to an antibody in a sample.

The antigen may be detected by immunoblotting method by transferring from a state separated by two-dimensional electrophoresis. The two-dimensional electrophoresis is a technique for separating a protein sample by performing isoelectric focusing in the first dimension and performing SDS-PAGE (SDS-polyacrylamide gel electrophoresis) in the second dimension. The conditions for two-dimensional electrophoresis are not particularly limited as long as the conditions permit the separation of the antigen of the present invention. For example, the conditions for two-dimensional electrophoresis as described above in the subsection titled "Identification of antigens" can be adopted. Also, the electrophoresis conditions may be defined by reference to the descriptions in Patent Literatures 1 to 4 mentioned above. For example, two-dimensional electrophoresis can be carried out under the conditions that satisfy at least one selected from the group consisting of the following requirements:

(A) the isoelectric focusing gels used in the first dimension should have a gel-strip length of 5 to 10 cm and a gel pH range of 3 to 10, and the pH gradient of the gels in the direction of electrophoresis should be as follows: where the gel-strip length up to pH 5 is taken as "a", that length from pH 5 to 7 as "b", and that length above pH 7 as "c", the relations "a<b" and "b>c" are satisfied;

(B) in the case of (A), when the total gel-strip length is taken as 1, "a" should be in the range of 0.15 to 0.3, "b" should be in the range of 0.4 to 0.7, and "c" should be in the range of 0.15 to 0.3;

(C) in the first dimensional isoelectric focusing, a constant voltage step should be performed by applying a constant voltage ranging from 100 V to 600 V per gel strip containing a sample, and after the electrophoresis variation width during electrophoresis for 30 minutes falls within the range of 5 μA, a voltage-increasing step should be started at which the voltage is increased from the aforementioned constant voltage;

(D) in the case of (C), the final voltage at the voltage-increasing step should be in the range of 3000 V to 6000 V;

(E) the isoelectric focusing gels used in the first dimension should have a longitudinal gel-strip length of 5 to 10 cm, and the electrophoresis gels used in the second dimension should have a gel concentration at the distal end in the direction of electrophoresis, which is in the range of 3 to 6%; and (F) in the case of (E), the electrophoresis gels used in the second dimension should have a gel concentration at the proximal end in the direction of electrophoresis, which is set to a higher value than that at the distal end in the direction of electrophoresis.

The aforementioned antigens (10) to (14) are antigens that specifically bind to IgE antibodies from patients with allergy to fish. Therefore, when binding between an IgE antibody from a subject and the antigen is detected, an indicator of the fact that the subject is allergic to fish is provided.

The present invention further provides a kit for diagnosing an allergy to fish, comprising at least one of the aforementioned antigens (10) to (14). The diagnosis kit of this invention may be used in the aforementioned method for providing an indicator for diagnosing an allergy to fish or in a diagnosis method as described later. The diagnosis kit of this invention may comprise not only the at least one of the aforementioned antigens (10) to (14), but also an anti-IgE antibody labeled with an enzyme and a chromogenic or luminescent substrate serving as a substrate for the enzyme, or an anti-IgE antibody labeled with biotin and an avidin-bound dye binding to the biotin. Also, a fluorescent-labeled anti-IgE antibody may be used. In the diagnosis kit of this invention, the antigen may be provided in a state immobilized on a carrier. The diagnosis kit of this invention may also be provided together with instructions on the procedure for diagnosis or a package containing said instructions.

In another mode, the aforementioned diagnosis kit comprises a companion diagnostic agent for an allergy to fish. The companion diagnostic agent is used for identifying patients expected to respond to pharmaceutical products or identifying patients having the risk of severe adverse reactions to pharmaceutical products, or for studying the reactivity of pharmaceutical products in order to optimize treatment using the pharmaceutical products. Here, the optimization of treatment includes, for example, determination of dosage and administration, judgment regarding discontinuation of administration, and confirmation of an allergen component that is used to cause immunological tolerance.

The present invention further provides a composition for diagnosing an allergy to fish, comprising at least one of the aforementioned antigens (10) to (14). The diagnosis composition of this invention can be used in a diagnosis method as described below. The diagnosis composition of this invention may further comprise a pharmaceutically acceptable carrier and/or additives commonly used with the antigen of this invention depending on the need.

In one mode, the present invention provides a method for diagnosing an allergy to fish in a subject, the method comprising:

(i) contacting a sample obtained from the subject with an antigen;

(ii) detecting binding between an IgE antibody present in the sample from the subject and the antigen; and (iii) when the binding between the IgE antibody in the subject and the antigen is detected, diagnosing the subject as being allergic to fish;

wherein the antigen is at least one of proteins as defined above in any of (10) to (14). In this method, the steps (i) and (ii) are performed as described above regarding the corresponding steps of the method for providing an indicator for diagnosing an allergy to fish.

In another mode, the present invention provides a method for diagnosing an allergy to fish in a subject, the method comprising administering to the subject at least one of the aforementioned antigens (10) to (14). This method may be performed in the form of a skin test characterized by applying the antigen onto the skin. Examples of the skin test include various forms of tests, such as: a prick test in which a diagnosis composition is applied onto the skin and then a tiny prick to such an extent as not to provoke bleeding is made in the skin to allow an antigen to penetrate the skin, thereby observing a skin reaction; a scratch test in which a diagnosis composition is applied onto the skin and then the skin is lightly scratched to observe a reaction; a patch test in which a diagnosis composition in the form of cream, ointment, etc. is applied onto the skin to observe a reaction; and an intracutaneous test in which an antigen is administered intracutaneously to observe a reaction. The method for allowing the diagnosis composition to penetrate the skin in the prick test or the scratch test may be a method in which the tip of a lancet is contacted with the diagnosis composition, and the contact site is inserted to the skin so that a prick is made in the skin to allow the diagnosis composition to penetrate the skin. If a skin reaction such as swelling occurs in a skin portion to which the antigen has been applied, the subject of interest is diagnosed as having an allergy to fish. The amount of the antigen to be applied to the skin in such tests can be, for example, not more than 100 µg per dose.

In the process of allergy diagnosis, a load test aiming to identify an antigen is often adopted. At least one of the aforementioned antigens (10) to (14) can be used as an active ingredient for a load test to diagnose an allergy to fish. Here, the antigen protein to be used in the load test may be a protein that has been expressed and purified and may be a protein that has been expressed in food or cooking ingredients, such as rice-based vaccine expressing pollen allergens which are obtained by transforming rice with a gene of a cedar pollen antigen and expressing the antigen protein in the rice.

In yet another mode, the present invention provides at least one of the aforementioned antigens (10) to (14), intended for use in the diagnosis of an allergy to fish. This also includes the provision of at least one of the aforementioned antigens (10) to (14) mixed with a known antigen.

In still another mode, the present invention provides use of at least one of the aforementioned antigens (10) to (14) for the production of a diagnostic agent for an allergy to fish.

Pharmaceutical composition and treatment method (1)

The present invention provides a pharmaceutical composition comprising at least one of the aforementioned antigens (10) to (14).

In one mode, the aforementioned pharmaceutical composition is used for the treatment and diagnosis of an allergy to fish. The treatment of an allergy increases the limit amount of an antigen in which the allergy does not develop even if the antigen is incorporated into the body, and finally aims for the state where the allergy does not develop by the common amount of the antigen to be consumed (remission).

The present invention also provides a method for treating an allergy to fish, the method comprising administering at least one of the aforementioned antigens (10) to (14) to a patient in need of a treatment for an allergy to fish.

In another mode, the present invention provides at least one of the aforementioned antigens (10) to (14), intended for use in the treatment for an allergy to fish. In yet another mode, the present invention provides use of at least one of the aforementioned antigens (10) to (14) for the production of a therapeutic agent for an allergy to fish.

In the process of allergy treatment, a hyposensitization therapy aiming to induce immunological tolerance by administering an antigen to a patient is often adopted. The at least one of the aforementioned antigens (10) to (14) can be used as an active ingredient for a hyposensitization therapy for an allergy to fish. Here, the antigen protein to be used in the hyposensitization therapy may be a protein that has been expressed and purified and may be a protein that has been expressed in food or cooking ingredients, such as rice-based vaccine expressing pollen allergens which are obtained by transforming rice with a gene of a cedar pollen antigen and expressing the antigen protein in the rice.

The pharmaceutical composition of the present invention can be administered by common administration routes.

Examples of common administration routes include oral, sublingual, percutaneous, intracutaneous, subcutaneous, intravascular, intranasal, intramuscular, intraperitoneal, and intrarectal administrations.

The pharmaceutical composition of the present invention can be used as a pharmaceutical composition to which a commonly used pharmaceutically acceptable adjuvant or excipient or any other additives (e.g., stabilizer, solubilizer, emulsifier, buffer, preservative, colorant) are added by a conventional method together with the antigen of this invention depending on the need. The dosage form of the pharmaceutical composition can be selected by those skilled in the art as appropriate depending on the administration route. The pharmaceutical composition can be in the form of, for example, tablet, capsule, troche, sublingual tablet, parenteral injection, intranasal spray, poultice, solution, cream, lotion, or suppository. The administration dose, frequency and/or period of the pharmaceutical composition of this invention can be selected by a physician as appropriate depending on the administration route and the patient's condition and characteristics such as age and body weight. For example, the pharmaceutical composition may be administered to an adult patient at a dose of not more than 100 µg per dose. The administration interval can be, for example, once daily, once weekly, twice weekly, once per three months or so. The administration period can be, for example, several weeks to several years. The pharmaceutical composition may be administered in such a manner that the dose is increased in incremental steps over the administration period.

Tester (1)

The present invention provides a tester comprising an antibody for at least one of the aforementioned antigens (10) to (14).

The antibody can be prepared by a conventional method. For example, the antibody may be prepared by immunizing a mammal such as rabbit with one of the aforementioned antigens (10) to (14). The antibody may be an IgE antibody, a polyclonal antibody, a monoclonal antibody, or an antigen-binding fragment thereof (e.g., Fab, F(ab')$_2$, Fab').

Further, in the aforementioned tester, the antibody may be provided in a form bound to a carrier. The type of the carrier is not particularly limited as long as it is usable for detection of binding between an antibody and an antigen. Any given carrier known to those skilled in the art can be used.

Examples of a method for determining the presence or absence of an antigen include the following methods:

a method in which a prepared tester comprising an IgE antibody is contacted with a sample obtained from a food, a cooking ingredient, etc., ELISA or the like method is used to detect whether there is a binding between the IgE antibody and an antigen in the sample, and if the binding between the IgE antibody and the antigen is detected, it is determined that the antibody remains in the food, the cooking ingredient, etc. of interest;

a method in which proteins are extracted from a food or a cooking ingredient and electrophoresed, and the presence or absence of a spot band of an antigen is detected with an antibody; and a method in which filter paper is impregnated with a food or a cooking ingredient and reacted with an antibody solution so as to detect an antigen contained therein.

Another mode of the present invention includes a tester for determining the presence or absence of an antigen of an allergy to fish in an object of interest, the tester comprising a primer having a nucleotide sequence complementary to a portion of at least one of the nucleotide sequences of SEQ ID NOs: 69, 109, 120, 137, and 143. The primer has, for example, but not limited to, a nucleotide sequence complementary to, preferably, 12 residues, 15 bases, 20 bases, or 25 bases, in a 3'-terminal portion or central sequence in a sequence of at least one of the nucleotide sequences of SEQ ID NOs: 69, 109, 120, 137, and 143. Particularly, when mRNA is of interest, the tester has a complementary primer of a poly-A tail. In a preferred mode, the tester comprising the primer mentioned above may further comprise a primer comprising a 5'-terminal nucleotide sequence, preferably a nucleotide sequence of 12 bases, 15 bases, 20 bases, or 25 bases, of at least one of the nucleotide sequences of SEQ ID NOs: 69, 109, 120, 137, and 143.

For example, DNA or cDNA is amplified by PCR (Polymerase Chain Reaction) including RT-PCR using templated DNA or mRNA obtained from a fish and the aforementioned primer, and the sequence of the amplified DNA or cDNA is compared with the nucleotide sequence of SEQ ID NO: 69, 109, 120, 137 or 143 to determine the presence or absence of the antigen. mRNA amplification methods by PCR can be exemplified by RACE. In this respect, even if there exists a point mutation encoding the same amino acid in the comparison of the amplified DNA or cDNA with the nucleotide sequence of SEQ ID NO: 69, 109, 120, 137 or 143, or even if the nucleotide sequence of the amplified DNA or cDNA has insertion, deletion, substitution or addition of bases in the nucleotide sequence of SEQ ID NO: 69, 109, 120, 137 or 143, it is determined that the antigen is present when the amino acid sequence encoded by the DNA or the cDNA has at least 70%, preferably at least 80, 90, 95, 98, or 99% identity to the amino acid sequence of SEQ ID NO: 70, 110, 121, 138 or 144.

In one mode, the aforementioned tester is used to determine the presence or absence of an antigen in cooking ingredients (a fish or a fish egg) or in products of interest in a food production line. The tester may also be used for quality inspection of production lines and pre-shipment products by manufacturers, or may be used for self-checking of the presence or absence of an antigen in a food or cooking ingredients of interest by consumers.

Allergen-Free Food and the Like

The present invention provides a fish, fish egg or processed product of such fish or fish egg in which at least one of the aforementioned antigens (10) to (14) is eliminated or reduced, or a fish that delivers such fish egg or is born from such fish egg.

The method for eliminating or reducing the antigen of the present invention in a fish, fish egg or processed products of such fish or fish egg, a fish that delivers such fish egg or is born from such fish egg is not limited. The elimination or reduction of the antigen may be conducted by any method, as long as the method permits the elimination or reduction of the antigen.

For example, the fish or fish egg of the present invention whose antigen is eliminated or reduced may be obtained by preparing a fish or fish egg in which the expression of the antigen of the present invention is knocked out, using a gene knock-out technique.

Any technique known to those skilled in the art can be used as the gene knock-out technique. For example, Oishi, et al. (Scientific Reports, Vol. 6, Article number: 23980, 2016, doi:10.1038/srep23980) states that individuals with allergen protein gene deletion are obtained by applying a genome editing technique CRISPER/Cas9 to primordial germ cells. The fish or fish egg of the present invention whose antigen is eliminated may be obtained through the use of a similar technique. The fish or fish egg of the present invention whose antigen is eliminated or reduced may be obtained by mating through artificial insemination with fishes or fish eggs containing no antigen or containing the antigen in a small amount. The artificial crossing of fishes or fish eggs can be performed by a conventional method.

An antigen of the present invention may be the artefact that an antigen of the present invention assumed the removal or a reduced fish or fish egg raw material as for the removal or the reduced processed products of fish or fish egg. In the case of using an ordinary fish or fish egg as a source ingredient, a treatment for removing or reducing the antigen of this invention is performed before or after preparation of a processed product of fish or fish egg. The methods for removing or reducing the antigen of the present invention in the processed products of fish or fish egg which assumed an ordinary fish or fish egg raw material include a method to remove protein component in food or a cooking ingredient such as a high pressure treatment and elution with the neutral salt solution or the high temperature steam, and a method to perform hydrolysis, denaturation, or amino acid alteration (chemical modification, elimination, or the like of a side chain) by heat treatment and acid treatment. The fish of the present invention whose antigen is eliminated or reduced may be a fish grown from hatched fish eggs in which the aforementioned antigen of the present invention is eliminated or reduced. Also, the fish egg of the present invention whose antigen is eliminated or reduced may be obtained from fishes in which the aforementioned antigen of the present invention is eliminated or reduced.

Method for Producing Allergen-Free Processed Product (1)

The present invention provides a method for producing a processed product of fish or fish egg in which an antigen is eliminated or reduced, the method comprising the step of confirming that the antigen is eliminated or reduced, in a production process of the processed product, wherein the antigen is at least one of the aforementioned antigens (10) to (14).

The step of confirming that the antigen is eliminated or reduced, in a production process of the processed product of fish or fish egg in which an antigen is eliminated or reduced may be performed by confirming the presence or absence of an antigen by the method described above in the subsection titled "Tester (1)".

The production of the processed product of fish or fish egg in which an antigen is eliminated or reduced may be performed by the method described above in the subsection titled "Allergen-free food and the like".

Epitope of Antigen

Epitopes and amino acids important for binding activity against IgE antibodies from allergic patients within the epitopes were identified as shown in Example 10 as to antigens identified as shown in Examples 2, 3 and 5 to 8 and known antigens aldolase and β-enolase of an allergy to salmon or the like and known antigen glyceraldehyde-3-phosphate dehydrogenase of an allergy to sardine.

The present invention provides polypeptides of the following (1α) to (17α) as polypeptides comprising an amino acid sequence specifically binding to an IgE antibody from an allergic patient.

(1α) Epitope of Alpha-Actinin-3

In the present invention, the polypeptide (1α) can be any polypeptide selected from the group consisting of (1α-1) to (1α-6) as defined below:

(1α-1) a polypeptide comprising at least one amino acid sequence selected from the group consisting of SEQ ID NOs: 150-154, 207, 210, 213, 218, 224, and 227;

(1α-2) a polypeptide comprising the amino acid sequence of XXXXXXXKPDX (SEQ ID NO: 205), preferably a polypeptide comprising the amino acid sequence of SXXXXXXKPDK (SEQ ID NO: 206), more preferably a polypeptide comprising an amino acid sequence in which any 1, 2, 3, 4, 5, 6 or 7 of the amino acids at positions 1-6 and 10 of SEQ ID NO: 207 are substituted by other amino acids, preferably alanine, further preferably a polypeptide comprising an amino acid sequence in which any 1, 2, 3, 4 or 5 of the amino acids at positions 2-6 of SEQ ID NO: 207 are substituted by other amino acids, preferably alanine.

In another mode, a polypeptide comprising the amino acid sequence of DKXXXR (SEQ ID NO: 208), preferably a polypeptide comprising an amino acid sequence in which any 1, 2 or 3 of the amino acids at positions 3-5 of SEQ ID NO: 210 are substituted by other amino acids, preferably alanine.

(1α-3) a polypeptide comprising the amino acid sequence of XXXXXXXDPM (SEQ ID NO: 211), preferably a polypeptide comprising the amino acid sequence of YXXXXKDDPM (SEQ ID NO: 212), more preferably a polypeptide comprising an amino acid sequence in which any 1, 2, 3, 4, 5, 6 or 7 of the amino acids at positions 1-7 of SEQ ID NO: 213 are substituted by other amino acids, preferably alanine, further preferably a polypeptide comprising an amino acid sequence in which any 1, 2, 3 or 4 of the amino acids at positions 2-5 of SEQ ID NO: 213 are substituted by other amino acids, preferably alanine.

In another mode, a polypeptide comprising the amino acid sequence of XXXXXXDXPM (SEQ ID NO: 214), preferably a polypeptide comprising the amino acid sequence of YSXXXXDXPM (SEQ ID NO: 215), more preferably a polypeptide comprising an amino acid sequence in which any 1, 2, 3, 4, 5, 6 or 7 of the amino acids at positions 1-6 and 8 of SEQ ID NO: 213 are substituted by other amino acids, preferably alanine, further preferably a polypeptide comprising an amino acid sequence in which any 1, 2, 3, 4 or 5 of the amino acids at positions 3-6 and 8 of SEQ ID NO: 213 are substituted by other amino acids, preferably alanine.

In yet another mode, a polypeptide comprising the amino acid sequence of PXGXLXX (SEQ ID NO: 216), preferably a polypeptide comprising the amino acid sequence of PXGNLNT (SEQ ID NO: 217), more preferably a polypeptide comprising an amino acid sequence in which any 1, 2, 3 or 4 of the amino acids at positions 2, 4, 6 and 7 of SEQ ID NO: 218 are substituted by other amino acids, preferably alanine, further preferably a polypeptide comprising an amino acid sequence in which the amino acid at position 2 of SEQ ID NO: 218 is substituted by another amino acid, preferably alanine.

(1α-4) a polypeptide comprising the amino acid sequence of SXFYHAFAGAEQAET (SEQ ID NO: 219), preferably a polypeptide comprising an amino acid sequence in which the amino acid at position 2 of SEQ ID NO: 152 is substituted by another amino acid, preferably alanine.

(1α-5) a polypeptide comprising the amino acid sequence of TXLXXXNXPXXXXSE (SEQ ID NO: 220), preferably a polypeptide comprising the amino acid sequence of TXLRLXNRPXXXXSE (SEQ ID NO: 221), more preferably a polypeptide comprising an amino acid sequence in which any 1, 2, 3, 4, 5, 6, 7, 8 or 9 of the amino acids at positions 2, 4-6, 8 and 10-13 of SEQ ID NO: 153 are substituted by other amino acids, preferably alanine, further preferably a polypeptide comprising an amino acid sequence in which any 1, 2, 3, 4, 5 or 6 of the amino acids at positions 2, 6 and 10-13 of SEQ ID NO: 153 are substituted by other amino acids, preferably alanine.

(1α-6) a polypeptide comprising the amino acid sequence of SXKTXXXXXEXR (SEQ ID NO: 222), preferably a polypeptide comprising the amino acid sequence of SDKTXXXXXELR (SEQ ID NO: 223), more preferably a polypeptide comprising an amino acid sequence in which any 1, 2, 3, 4, 5, 6 or 7 of the amino acids at positions 2, 5-9 and 11 of SEQ ID NO: 224 are substituted by other amino acids, preferably alanine, further preferably a polypeptide comprising an amino acid sequence in which any 1, 2, 3, 4 or 5 of the amino acids at positions 5-9 of SEQ ID NO: 224 are substituted by other amino acids, preferably alanine.

In another mode, a polypeptide comprising the amino acid sequence of XXRE (SEQ ID NO: 225), preferably a polypeptide comprising the amino acid sequence of LXRE (SEQ ID NO: 226), more preferably a polypeptide comprising an amino acid sequence in which any 1 or 2 of the amino acids at positions 1 and 2 of SEQ ID NO: 227 are substituted by other amino acids, preferably alanine, further preferably a polypeptide comprising an amino acid sequence in which the amino acid at position 2 of SEQ ID NO: 227 is substituted by another amino acid, preferably alanine.

In one mode, the polypeptide (1α) may not comprise a variant or a homolog having 100% or at least 90%, at least 80% or at least 70% identity to the full-length amino acid sequence (SEQ ID NO: 2) of alpha-actinin-3.

(2α) Epitope of EEF1A2 Binding Protein-Like

In the present invention, the polypeptide (2α) can be any polypeptide selected from the group consisting of (2α-1) and (2α-2) as defined below:

(2α-1) a polypeptide comprising at least one amino acid sequence selected from the group consisting of SEQ ID NOs: 155 and 230.

(2α-2) a polypeptide comprising the amino acid sequence of XXNRXYYXXXE (SEQ ID NO: 228), preferably a polypeptide comprising the amino acid sequence of LDNRLYYXVAE (SEQ ID NO: 229), more preferably a polypeptide comprising an amino acid sequence in which any 1, 2, 3, 4, 5 or 6 of the amino acids at positions 1, 2, 5 and 8-10 of SEQ ID NO: 230 are substituted by other amino acids, preferably alanine, further preferably a polypeptide comprising an amino acid sequence in which the amino acid at position 8 of SEQ ID NO: 230 is substituted by another amino acid, preferably alanine.

In one mode, the polypeptide (2α) may not comprise a variant or a homolog having 100% or at least 90%, at least 80% or at least 70% identity to the full-length amino acid sequence (SEQ ID NO: 5) of EEF1A2 binding protein-like.

(3α) Epitope of Alpha-1,4-Glucan Phosphorylase

In the present invention, the polypeptide (3α) can be any polypeptide selected from the group consisting of (3α-1) to (3α-3) as defined below:

(3α-1) a polypeptide comprising at least one amino acid sequence selected from the group consisting of SEQ ID NOs: 156, 157, 232, 235, and 237.

(3α-2) a polypeptide comprising the amino acid sequence of YXXXXXXXR (SEQ ID NO: 231), preferably a polypeptide comprising an amino acid sequence in which any 1, 2, 3, 4, 5 or 6 of the amino acids at positions 2-7 of SEQ ID NO: 232 are substituted by other amino acids, preferably alanine.

In another mode, a polypeptide comprising the amino acid sequence of GGYXQXXLXR (SEQ ID NO: 233), preferably a polypeptide comprising the amino acid sequence of GGYIQXXLDR (SEQ ID NO: 234), more preferably a polypeptide comprising an amino acid sequence in which any 1, 2, 3 or 4 of the amino acids at positions 4, 6, 7 and 9 of SEQ ID NO: 235 are substituted by other amino acids, preferably alanine, further preferably a polypeptide comprising an amino acid sequence in which any 1 or 2 of the amino acids at positions 6 and 7 of SEQ ID NO: 235 are substituted by other amino acids, preferably alanine.

(3α-3) a polypeptide comprising the amino acid sequence of RXKXXXDY (SEQ ID NO: 236), preferably a polypeptide comprising an amino acid sequence in which any 1, 2, 3 or 4 of the amino acids at positions 2 and 4-6 of SEQ ID NO: 237 are substituted by other amino acids, preferably alanine.

In one mode, the polypeptide (3α) may not comprise a variant or a homolog having 100% or at least 90%, at least 80% or at least 70% identity to the full-length amino acid sequence (SEQ ID NO: 10) of alpha-1,4-glucan phosphorylase.

(4α) Epitope of Elongation Factor 2

In the present invention, the polypeptide (4α) can be any polypeptide selected from the group consisting of (4α-1) to (4α-3) as defined below:

(4α-1) a polypeptide comprising at least one amino acid sequence selected from the group consisting of SEQ ID NOs: 158, 159, 239, 242, 245, and 247.

(4α-2) a polypeptide comprising the amino acid sequence of KKXXXR (SEQ ID NO: 238), preferably a polypeptide comprising an amino acid sequence in which any 1, 2 or 3 of the amino acids at positions 3-5 of SEQ ID NO: 239 are substituted by other amino acids, preferably alanine.

In another mode, a polypeptide comprising the amino acid sequence of KKXXXRN (SEQ ID NO: 240), preferably a polypeptide comprising the amino acid sequence of KKSNXRN (SEQ ID NO: 241), more preferably a polypeptide comprising an amino acid sequence in which any 1, 2 or 3 of the amino acids at positions 3-5 of SEQ ID NO: 242 are substituted by other amino acids, preferably alanine, further preferably a polypeptide comprising an amino acid sequence in which the amino acid at position 5 of SEQ ID NO: 242 is substituted by another amino acid, preferably alanine.

(4α-3) a polypeptide comprising the amino acid sequence of LXXXLXXKXXI (SEQ ID NO: 243), preferably a polypeptide comprising the amino acid sequence of LXDXLXXKXXI (SEQ ID NO: 244), more preferably a polypeptide comprising an amino acid sequence in which any 1, 2, 3, 4, 5, 6 or 7 of the amino acids at positions 2-4, 6, 7, 9 and 10 of SEQ ID NO: 245 are substituted by other amino acids, preferably alanine, further preferably a polypeptide comprising an amino acid sequence in which any 1, 2, 3, 4, 5 or 6 of the amino acids at positions 2, 4, 6, 7, 9 and 10 of SEQ ID NO: 245 are substituted by other amino acids, preferably alanine.

In another mode, a polypeptide comprising the amino acid sequence of GKXXXXXXXXS (SEQ ID NO: 246), preferably a polypeptide comprising an amino acid sequence in which any 1, 2, 3, 4, 5, 6, 7 or 8 of the amino acids at positions 3-10 of SEQ ID NO: 247 are substituted by other amino acids, preferably alanine.

In one mode, the polypeptide (4α) may not comprise a variant or a homolog having 100% or at least 90%, at least 80% or at least 70% identity to the full-length amino acid sequence (SEQ ID NO: 19) of elongation factor 2.

(5α) Epitope of Heat Shock Cognate 70 kDa Protein

In the present invention, the polypeptide (5α) can be any polypeptide selected from the group consisting of (5α-1) to (5α-4) as defined below:

(5α-1) a polypeptide comprising at least one amino acid sequence selected from the group consisting of SEQ ID NOs: 160-162, 250, 252 (amino acid sequence: QYK), 255, 258, and 261.

(5α-2) a polypeptide comprising the amino acid sequence of EXXXXYL (SEQ ID NO: 248), preferably a polypeptide comprising the amino acid sequence of EIXXAYL (SEQ ID NO: 249), more preferably a polypeptide comprising an amino acid sequence in which any 1, 2, 3 or 4 of the amino acids at positions 2-5 of SEQ ID NO: 250 are substituted by other amino acids, preferably alanine, further preferably a polypeptide comprising an amino acid sequence in which any 1 or 2 of the amino acids at positions 3 and 4 of SEQ ID NO: 250 are substituted by other amino acids, preferably alanine.

(5α-3) a polypeptide comprising the amino acid sequence of QXK (SEQ ID NO: 251), preferably a polypeptide comprising an amino acid sequence in which the amino acid at position 2 of SEQ ID NO: 252 is substituted by another amino acid, preferably alanine.

In another mode, a polypeptide comprising the amino acid sequence of XDXXXDK (SEQ ID NO: 253), preferably a polypeptide comprising the amino acid sequence of DDVXXDK (SEQ ID NO: 254), more preferably a polypeptide comprising an amino acid sequence in which any 1, 2, 3 or 4 of the amino acids at positions 1 and 3-5 of SEQ ID NO: 255 are substituted by other amino acids, preferably alanine, further preferably a polypeptide comprising an amino acid sequence in which any 1 or 2 of the amino acids at positions 4 and 5 of SEQ ID NO: 255 are substituted by other amino acids, preferably alanine.

(5α-4) a polypeptide comprising the amino acid sequence of KXSXEXK (SEQ ID NO: 256), preferably a polypeptide comprising the amino acid sequence of KLSXEDK (SEQ ID NO: 257), more preferably a polypeptide comprising an amino acid sequence in which any 1, 2 or 3 of the amino acids at positions 2, 4 and 6 of SEQ ID NO: 258 are substituted by other amino acids, preferably alanine, further preferably a polypeptide comprising an amino acid sequence in which the amino acid at position 4 of SEQ ID NO: 258 is substituted by another amino acid, preferably alanine.

In another mode, a polypeptide comprising the amino acid sequence of QXXXDKC (SEQ ID NO: 259), preferably a polypeptide comprising the amino acid sequence of QKIXDKC (SEQ ID NO: 260), more preferably a polypeptide comprising an amino acid sequence in which any 1, 2 or 3 of the amino acids at positions 2-4 of SEQ ID NO: 261 are substituted by other amino acids, preferably alanine, further preferably a polypeptide comprising an amino acid sequence in which the amino acid at position 4 of SEQ ID NO: 261 is substituted by another amino acid, preferably alanine.

In one mode, the polypeptide (5α) may not comprise a variant or a homolog having 100% or at least 90%, at least 80% or at least 70% identity to the full-length amino acid sequence (SEQ ID NO: 26) of heat shock cognate 70 kDa protein.

(6α) Epitope of Serotransferrin

In the present invention, the polypeptide (6α) can be any polypeptide selected from the group consisting of (6α-1) to (6α-5) as defined below:

(6α-1) a polypeptide comprising at least one amino acid sequence selected from the group consisting of SEQ ID NOs: 163-167, 263, 266, 269, 271, 273, 276, and 279.

(6α-2) a polypeptide comprising the amino acid sequence of XXCYY (SEQ ID NO: 262), preferably a polypeptide comprising an amino acid sequence in which any 1 or 2 of the amino acids at positions 1 and 2 of SEQ ID NO: 263 are substituted by other amino acids, preferably alanine.

In another mode, a polypeptide comprising the amino acid sequence of VXVXKKXXX (SEQ ID NO: 264), preferably a polypeptide comprising the amino acid sequence of VAVAKKGXE (SEQ ID NO: 265), more preferably a polypeptide comprising an amino acid sequence in which any 1, 2, 3, 4 or 5 of the amino acids at positions 2, 4 and 7-9 of SEQ ID NO: 266 are substituted by other amino acids, preferably alanine, further preferably a polypeptide comprising an amino acid sequence in which the amino acid at position 8 of SEQ ID NO: 266 is substituted by another amino acid, preferably alanine.

(6α-3) a polypeptide comprising the amino acid sequence of XKXXXXEX (SEQ ID NO: 267), preferably a polypeptide comprising the amino acid sequence of XKXGXGEX (SEQ ID NO: 268), more preferably a polypeptide comprising an amino acid sequence in which any 1, 2, 3, 4, 5 or 6 of the amino acids at positions 1, 3-6 and 8 of SEQ ID NO: 269 are substituted by other amino acids, preferably alanine, further preferably a polypeptide comprising an amino acid sequence in which any 1, 2, 3 or 4 of the amino acids at positions 1, 3, 5 and 8 of SEQ ID NO: 269 are substituted by other amino acids, preferably alanine.

(6α-4) a polypeptide comprising the amino acid sequence of XXKXM (SEQ ID NO: 270), preferably a polypeptide comprising an amino acid sequence in which any 1, 2 or 3 of the amino acids at positions 1, 2 and 4 of SEQ ID NO: 271 are substituted by other amino acids, preferably alanine.

In another mode, a polypeptide comprising the amino acid sequence of VTNFXXXS (SEQ ID NO: 272), preferably a polypeptide comprising an amino acid sequence in which any 1, 2 or 3 of the amino acids at positions 5-7 of SEQ ID NO: 273 are substituted by other amino acids, preferably alanine.

(6α-5) a polypeptide comprising the amino acid sequence of YXYXXXXXC (SEQ ID NO: 274), preferably a polypeptide comprising the amino acid sequence of YXYNXXFXC (SEQ ID NO: 275), more preferably a polypeptide comprising an amino acid sequence in which any 1, 2, 3, 4, 5 or 6 of the amino acids at positions 2 and 4-8 of SEQ ID NO: 276 are substituted by other amino acids, preferably alanine, further preferably a polypeptide comprising an amino acid sequence in which any 1, 2, 3 or 4 of the amino acids at positions 2, 5, 6 and 8 of SEQ ID NO: 276 are substituted by other amino acids, preferably alanine.

In another mode, a polypeptide comprising the amino acid sequence of XXCLV (SEQ ID NO: 277), preferably a polypeptide comprising the amino acid sequence of FXCLV (SEQ ID NO: 278), more preferably a polypeptide comprising an amino acid sequence in which any 1 or 2 of the amino acids at positions 1 and 2 of SEQ ID NO: 279 are substituted by other amino acids, preferably alanine, further preferably a polypeptide comprising an amino acid sequence in which the amino acid at position 2 of SEQ ID NO: 279 is substituted by another amino acid, preferably alanine.

In one mode, the polypeptide (6α) may not comprise a variant or a homolog having 100% or at least 90%, at least 80% or at least 70% identity to the full-length amino acid sequence (SEQ ID NO: 33) of serotransferrin.

(7α) Epitope of Myosin Binding Protein H-Like

In the present invention, the polypeptide (7α) can be any polypeptide selected from the group consisting of (7α-1) to (7α-5) as defined below:

(7α-1) a polypeptide comprising at least one amino acid sequence selected from the group consisting of SEQ ID NOs: 168-171, 282, 284, 287, 290, 292, 295, 297 and 300.

(7α-2) a polypeptide comprising the amino acid sequence of YVKXXXXKI (SEQ ID NO: 280), preferably polypeptide comprising the amino acid sequence of YVKXVXEKI (SEQ ID NO: 281), more preferably a polypeptide comprising an amino acid sequence in which any 1, 2, 3 or 4 of the amino acids at positions 4-7 of SEQ ID NO: 282 are substituted by other amino acids, preferably alanine, further preferably a polypeptide comprising an amino acid sequence in which any 1 or 2 of the amino acids at positions 4 and 6 of SEQ ID NO: 282 are substituted by other amino acids, preferably alanine.

In another mode, a polypeptide comprising the amino acid sequence of NIXIP (SEQ ID NO: 283), preferably a polypeptide comprising an amino acid sequence in which the amino acid at position 3 of SEQ ID NO: 284 is substituted by another amino acid, preferably alanine.

(7α-3) a polypeptide comprising the amino acid sequence of SXEXXXKXXXF (SEQ ID NO: 285), preferably a polypeptide comprising the amino acid sequence of SXEXCXKXXXF (SEQ ID NO: 286), more preferably a polypeptide comprising an amino acid sequence in which any 1, 2, 3, 4, 5, 6 or 7 of the amino acids at positions 2, 4-6 and 8-10 of SEQ ID NO: 287 are substituted by other amino acids, preferably alanine, further preferably a polypeptide comprising an amino acid sequence in which any 1, 2, 3, 4, 5 or 6 of the amino acids at positions 2, 4, 6, and 8-10 of SEQ ID NO: 287 are substituted by other amino acids, preferably alanine.

In another mode, a polypeptide comprising the amino acid sequence of KXDXFXXK (SEQ ID NO: 288), preferably a polypeptide comprising the amino acid sequence of KXDXFXDK (SEQ ID NO: 289), more preferably a polypeptide comprising an amino acid sequence in which any 1, 2, 3 or 4 of the amino acids at positions 2, 4, 6 and 7 of SEQ ID NO: 290 are substituted by other amino acids, preferably alanine, further preferably a polypeptide comprising an amino acid sequence in which any 1, 2 or 3 of the amino acids at positions 2, 4 and 6 of SEQ ID NO: 290 are substituted by other amino acids, preferably alanine.

(7α-4) a polypeptide comprising the amino acid sequence of EXXXYXXXXXXXXD (SEQ ID NO: 291), preferably a polypeptide comprising an amino acid sequence in which any 1, 2, 3, 4, 5, 6, 7, 8, 9, 10 or 11 of the amino acids at positions 2-4 and 6-13 of SEQ ID NO: 292 are substituted by other amino acids, preferably alanine.

(7α-5) a polypeptide comprising the amino acid sequence of XNXXYXXIXX (SEQ ID NO: 293), preferably a polypeptide comprising the amino acid sequence of DNXXYXXIXT (SEQ ID NO: 294), more preferably a polypeptide comprising an amino acid sequence in which any 1, 2, 3, 4, 5, 6 or 7 of the amino acids at positions 1, 3, 4, 6, 7, 9 and 10 of SEQ ID NO: 295 are substituted by other amino acids, preferably alanine, further preferably a polypeptide comprising an amino acid sequence in which any 1, 2, 3, 4 or 5 of the amino acids at positions 3, 4, 6, 7 and 9 of SEQ ID NO: 295 are substituted by other amino acids, preferably alanine.

In another mode, a polypeptide comprising the amino acid sequence of YXXIXT (SEQ ID NO: 296), preferably a polypeptide comprising an amino acid sequence in which any 1, 2 or 3 of the amino acids at positions 2, 3 and 5 of SEQ ID NO: 297 are substituted by other amino acids, preferably alanine.

In another mode, a polypeptide comprising the amino acid sequence of XXXISXGG (SEQ ID NO: 298), preferably a polypeptide comprising the amino acid sequence of YXMISXGG (SEQ ID NO: 299), more preferably a polypeptide comprising an amino acid sequence in which any 1, 2, 3 or 4 of the amino acids at positions 1-3 and 6 of SEQ ID NO: 300 are substituted by other amino acids, preferably alanine, further preferably a polypeptide comprising an amino acid sequence in which any 1 or 2 of the amino acids at positions 2 and 6 of SEQ ID NO: 300 are substituted by other amino acids, preferably alanine.

In one mode, the polypeptide (7α) may not comprise a variant or a homolog having 100% or at least 90%, at least 80% or at least 70% identity to the full-length amino acid sequence (SEQ ID NO: 43) of myosin binding protein H-like.

(8α) Epitope of Desmin (Fragment)

In the present invention, the polypeptide (8α) can be any polypeptide selected from the group consisting of (8α-1) to (8α-4) as defined below:

(8α-1) a polypeptide comprising at least one amino acid sequence selected from the group consisting of SEQ ID NOs: 172, 173, 174, 303, 306, 308, and 310.

(8α-2) a polypeptide comprising the amino acid sequence of KXXXSX (SEQ ID NO: 301), preferably a polypeptide comprising the amino acid sequence of KXXXSD (SEQ ID NO: 302), more preferably a polypeptide comprising an amino acid sequence in which any 1, 2, 3 or 4 of the amino acids at positions 2-4 and 6 of SEQ ID NO: 303 are substituted by other amino acids, preferably alanine, further preferably a polypeptide comprising an amino acid sequence in which any 1, 2 or 3 of the amino acids at positions 2-4 of SEQ ID NO: 303 are substituted by other amino acids, preferably alanine.

In another mode, a polypeptide comprising the amino acid sequence of XKXKXXXXN (SEQ ID NO: 304), preferably a polypeptide comprising the amino acid sequence of YKSKXSDLN (SEQ ID NO: 305), more preferably a polypeptide comprising an amino acid sequence in which any 1, 2, 3, 4, 5 or 6 of the amino acids at positions 1, 3 and 5-8 of SEQ ID NO: 306 are substituted by other amino acids, preferably alanine, further preferably a polypeptide comprising an amino acid sequence in which the amino acid at position 5 of SEQ ID NO: 306 is substituted by another amino acid, preferably alanine.

In yet another mode, a polypeptide comprising the amino acid sequence of VXKN (SEQ ID NO: 307), preferably a polypeptide comprising an amino acid sequence in which the amino acid at position 2 of SEQ ID NO: 308 is substituted by another amino acid, preferably alanine.

(8α-4) a polypeptide comprising the amino acid sequence of DXGRXXE (SEQ ID NO: 309), preferably a polypeptide comprising an amino acid sequence in which any 1, 2 or 3 of the amino acids at positions 2, 5 and 6 of SEQ ID NO: 310 are substituted by other amino acids, preferably alanine.

In one mode, the polypeptide (8α) may not comprise a variant or a homolog having 100% or at least 90%, at least 80% or at least 70% identity to the amino acid sequence (SEQ ID NO: 56) of desmin (fragment).

(9α) Epitope of Capping Protein (Actin Filament) Muscle Z-Line Beta

In the present invention, the polypeptide (9α) can be any polypeptide selected from the group consisting of (9α-1) to (9α-5) as defined below:

(9α-1) a polypeptide comprising at least one amino acid sequence selected from the group consisting of SEQ ID NOs: 175-178, 312, 314, 317, 320, 323, and 326.

(9α-2) a polypeptide comprising the amino acid sequence of KKXXXG (SEQ ID NO: 311), preferably a polypeptide comprising an amino acid sequence in which any 1, 2 or 3 of the amino acids at positions 3-5 of SEQ ID NO: 312 are substituted by other amino acids, preferably alanine.

In another mode, a polypeptide comprising the amino acid sequence of SKXXK (SEQ ID NO: 313), preferably a polypeptide comprising an amino acid sequence in which any 1 or 2 of the amino acids at positions 3 and 4 of SEQ ID NO: 314 are substituted by other amino acids, preferably alanine.

(9α-3) a polypeptide comprising the amino acid sequence of XXXXXQXKXXG (SEQ ID NO: 315), preferably a polypeptide comprising the amino acid sequence of HXXXXQXKSSG (SEQ ID NO: 316), more preferably a polypeptide comprising an amino acid sequence in which any 1, 2, 3, 4, 5, 6, 7 or 8 of the amino acids at positions 1-5, 7, 9 and 10 of SEQ ID NO: 317 are substituted by other amino acids, preferably alanine, further preferably a polypeptide comprising an amino acid sequence in which any 1, 2, 3, 4 or 5 of the amino acids at positions 2-5 and 7 of SEQ ID NO: 317 are substituted by other amino acids, preferably alanine.

(9α-4) a polypeptide comprising the amino acid sequence of XYXGKXXXX (SEQ ID NO: 318), preferably a polypeptide comprising the amino acid sequence of IYXGKTXDI (SEQ ID NO: 319), more preferably a polypeptide comprising an amino acid sequence in which any 1, 2, 3, 4, 5 or 6 of the amino acids at positions 1, 3 and 6-9 of SEQ ID NO: 320 are substituted by other amino acids, preferably alanine, further preferably a polypeptide comprising an amino acid sequence in which any 1 or 2 of the amino acids at positions 3 and 7 of SEQ ID NO: 320 are substituted by other amino acids, preferably alanine.

In another mode, a polypeptide comprising the amino acid sequence of XDXXNXXRS (SEQ ID NO: 321), preferably a polypeptide comprising the amino acid sequence of KDXXNXLRS (SEQ ID NO: 322), more preferably a polypeptide comprising an amino acid sequence in which any 1, 2, 3, 4 or 5 of the amino acids at positions 1, 3, 4, 6 and 7 of SEQ ID NO: 323 are substituted by other amino acids, preferably alanine, further preferably a polypeptide comprising an amino acid sequence in which any 1, 2 or 3 of the amino acids at positions 3, 4 and 6 of SEQ ID NO: 323 are substituted by other amino acids, preferably alanine.

(9α-5) a polypeptide comprising the amino acid sequence of QKYRQXXKXXXX (SEQ ID NO: 324), preferably a polypeptide comprising the amino acid sequence of QKYRQXXKXLXQ (SEQ ID NO: 325), more preferably a polypeptide comprising an amino acid sequence in which any 1, 2, 3, 4, 5 or 6 of the amino acids at positions 6, 7 and 9-12 of SEQ ID NO: 326 are substituted by other amino acids, preferably alanine, further preferably a polypeptide comprising an amino acid sequence in which any 1, 2, 3 or 4 of the amino acids at positions 6, 7, 9 and 11 of SEQ ID NO: 326 are substituted by other amino acids, preferably alanine.

In one mode, the polypeptide (9α) may not comprise a variant or a homolog having 100% or at least 90%, at least 80% or at least 70% identity to the full-length amino acid sequence (SEQ ID NO: 61) of capping protein (actin filament) muscle Z-line beta.

(10α) Epitope of Myosin Heavy Chain, Fast Skeletal Muscle-Like

In the present invention, the polypeptide (10α) can be any polypeptide selected from the group consisting of (10α-1) to (10α-8) as defined below:

(10α-1) a polypeptide comprising at least one amino acid sequence selected from the group consisting of SEQ ID NOs: 179-185, 329, 332, 335, 338, 341, 344, 347, 350, 353, 356, 359, 362, and 365.

(10α-2) a polypeptide comprising the amino acid sequence of TXXXXDXXEGK (SEQ ID NO: 327), preferably a polypeptide comprising the amino acid sequence of TXXXLDFREGK (SEQ ID NO: 328), more preferably a polypeptide comprising an amino acid sequence in which any 1, 2, 3, 4, 5 or 6 of the amino acids at positions 2-5, 7 and 8 of SEQ ID NO: 329 are substituted by other amino acids, preferably alanine, further preferably a polypeptide comprising an amino acid sequence in which any 1, 2 or 3 of the amino acids at positions 2-4 of SEQ ID NO: 329 are substituted by other amino acids, preferably alanine.

In another mode, a polypeptide comprising the amino acid sequence of XXEXXEXXD (SEQ ID NO: 330), preferably a polypeptide comprising the amino acid sequence of FREXXEXXD (SEQ ID NO: 331), more preferably a polypeptide comprising an amino acid sequence in which any 1, 2, 3, 4, 5 or 6 of the amino acids at positions 1, 2, 4, 5, 7 and 8 of SEQ ID NO: 332 are substituted by other amino acids, preferably alanine, further preferably a polypeptide comprising an amino acid sequence in which any 1, 2, 3 or 4 of the amino acids at positions 4, 5, 7 and 8 of SEQ ID NO: 332 are substituted by other amino acids, preferably alanine.

(10α-3) a polypeptide comprising the amino acid sequence of LXXNFTXXK (SEQ ID NO: 333), preferably a polypeptide comprising the amino acid sequence of LXINFTNEK (SEQ ID NO: 334), more preferably a polypeptide comprising an amino acid sequence in which any 1, 2, 3 or 4 of the amino acids at positions 2, 3, 7 and 8 of SEQ ID NO: 335 are substituted by other amino acids, preferably alanine, further preferably a polypeptide comprising an amino acid sequence in which the amino acid at position 2 of SEQ ID NO: 335 is substituted by another amino acid, preferably alanine.

(10α-4) a polypeptide comprising the amino acid sequence of XYXPPPXXXK (SEQ ID NO: 336), preferably a polypeptide comprising the amino acid sequence of LYXPPPXXXK (SEQ ID NO: 337), more preferably a polypeptide comprising an amino acid sequence in which any 1, 2, 3, 4 or 5 of the amino acids at positions 1, 3 and 7-9 of SEQ ID NO: 338 are substituted by other amino acids, preferably alanine, further preferably a polypeptide comprising an amino acid sequence in which any 1, 2, 3 or 4 of the amino acids at positions 3 and 7-9 of SEQ ID NO: 338 are substituted by other amino acids, preferably alanine.

(10α-5) a polypeptide comprising the amino acid sequence of XXDEXVXK (SEQ ID NO: 339), preferably a polypeptide comprising the amino acid sequence of SXDEXVXK (SEQ ID NO: 340), more preferably a polypeptide comprising an amino acid sequence in which any 1, 2, 3 or 4 of the amino acids at positions 1, 2, 5 and 7 of SEQ ID NO: 341 are substituted by other amino acids, preferably alanine, further preferably a polypeptide comprising an amino acid sequence in which any 1, 2 or 3 of the amino acids at positions 2, 5 and 7 of SEQ ID NO: 341 are substituted by other amino acids, preferably alanine.

In another mode, a polypeptide comprising the amino acid sequence of XXDXXXAKXT (SEQ ID NO: 342), preferably a polypeptide comprising the amino acid sequence of SXDEXVAKXT (SEQ ID NO: 343), more preferably a polypeptide comprising an amino acid sequence in which any 1, 2, 3, 4, 5 or 6 of the amino acids at positions 1, 2, 4-6 and 9 of SEQ ID NO: 344 are substituted by other amino acids, preferably alanine, further preferably a polypeptide comprising an amino acid sequence in which any 1, 2 or 3 of the amino acids at positions 2, 5 and 9 of SEQ ID NO: 344 are substituted by other amino acids, preferably alanine.

In yet another mode, a polypeptide comprising the amino acid sequence of VXXXXKXKK (SEQ ID NO: 345), preferably a polypeptide comprising the amino acid sequence of VAXXXKXKK (SEQ ID NO: 346), more preferably a polypeptide comprising an amino acid sequence in which any 1, 2, 3, 4 or 5 of the amino acids at positions 2-5 and 7 of SEQ ID NO: 347 are substituted by other amino acids, preferably alanine, further preferably a polypeptide comprising an amino acid sequence in which any 1, 2, 3 or 4 of the amino acids at positions 3-5 and 7 of SEQ ID NO: 347 are substituted by other amino acids, preferably alanine.

In yet another mode, a polypeptide comprising the amino acid sequence of KXXKXK (SEQ ID NO: 348), preferably a polypeptide comprising the amino acid sequence of KXXKEK (SEQ ID NO: 349), more preferably a polypeptide comprising an amino acid sequence in which any 1, 2 or 3 of the amino acids at positions 2, 3 and 5 of SEQ ID NO: 350 are substituted by other amino acids, preferably alanine, further preferably a polypeptide comprising an amino acid sequence in which any 1 or 2 of the amino acids at positions 2 and 3 of SEQ ID NO: 350 are substituted by other amino acids, preferably alanine.

(10α-6) a polypeptide comprising the amino acid sequence of XNXXXKXKXK (SEQ ID NO: 351), preferably a polypeptide comprising the amino acid sequence of XNXXXKXKTK (SEQ ID NO: 352), more preferably a polypeptide comprising an amino acid sequence in which any 1, 2, 3, 4, 5 or 6 of the amino acids at positions 1, 3-5, 7 and 9 of SEQ ID NO: 353 are substituted by other amino acids, preferably alanine, further preferably a polypeptide comprising an amino acid sequence in which any 1, 2, 3, 4 or 5 of the amino acids at positions 1, 3-5 and 7 of SEQ ID NO: 353 are substituted by other amino acids, preferably alanine.

(10α-7) a polypeptide comprising the amino acid sequence of DXXXSXXK (SEQ ID NO: 354), preferably a polypeptide comprising the amino acid sequence of DXXXSXRK (SEQ ID NO: 355), more preferably a polypeptide comprising an amino acid sequence in which any 1, 2, 3, 4 or 5 of the amino acids at positions 2-4, 6 and 7 of SEQ ID NO: 356 are substituted by other amino acids, preferably alanine, further preferably a polypeptide comprising an amino acid sequence in which any 1, 2, 3 or 4 of the amino acids at positions 2-4 and 6 of SEQ ID NO: 356 are substituted by other amino acids, preferably alanine.

In another mode, a polypeptide comprising the amino acid sequence of SXXKXEX (SEQ ID NO: 357), preferably a polypeptide comprising the amino acid sequence of SXRKXEG (SEQ ID NO: 358), more preferably a polypeptide comprising an amino acid sequence in which any 1, 2, 3 or 4 of the amino acids at positions 2, 3, 5 and 7 of SEQ ID NO: 359 are substituted by other amino acids, preferably alanine, further preferably a polypeptide comprising an amino acid sequence in which any 1 or 2 of the amino acids at positions 2 and 5 of SEQ ID NO: 359 are substituted by other amino acids, preferably alanine.

(10α-8) a polypeptide comprising the amino acid sequence of XXRXXEXK (SEQ ID NO: 360), preferably a polypeptide comprising the amino acid sequence of EXRXXEEK (SEQ ID NO: 361), more preferably a polypeptide comprising an amino acid sequence in which any 1, 2, 3, 4 or 5 of the amino acids at positions 1, 2, 4, 5 and 7 of SEQ ID NO: 362 are substituted by other amino acids, preferably alanine, further preferably a polypeptide comprising an amino acid sequence in which any 1, 2 or 3 of the amino acids at positions 2, 4 and 5 of SEQ ID NO: 362 are substituted by other amino acids, preferably alanine.

In another mode, a polypeptide comprising the amino acid sequence of XXXEXKXKK (SEQ ID NO: 363), preferably a polypeptide comprising the amino acid sequence of RXXEEKXKK (SEQ ID NO: 364), more preferably a polypeptide comprising an amino acid sequence in which any 1, 2, 3, 4 or 5 of the amino acids at positions 1-3, 5 and 7 of SEQ ID NO: 365 are substituted by other amino acids, preferably alanine, further preferably a polypeptide comprising an amino acid sequence in which any 1, 2 or 3 of the amino acids at positions 2, 3 and 7 of SEQ ID NO: 365 are substituted by other amino acids, preferably alanine.

(11α) Epitope of Glycogen Phosphorylase, Muscle Form-Like

In the present invention, the polypeptide (11α) can be any polypeptide selected from the group consisting of (11α-1) and (11α-2) as defined below:

(11α-1) a polypeptide comprising at least one amino acid sequence selected from the group consisting of SEQ ID NOs: 186, 367, and 370.

(11α-2) a polypeptide comprising the amino acid sequence of GXYXXXXXXR (SEQ ID NO: 366), preferably a polypeptide comprising an amino acid sequence in which any 1, 2, 3, 4, 5, 6 or 7 of the amino acids at positions 2 and 4-9 of SEQ ID NO: 367 are substituted by other amino acids, preferably alanine.

In another mode, a polypeptide comprising the amino acid sequence of NLXXN (SEQ ID NO: 368), preferably a polypeptide comprising the amino acid sequence of NLXEN (SEQ ID NO: 369), more preferably a polypeptide comprising an amino acid sequence in which any 1 or 2 of the amino acids at positions 3 and 4 of SEQ ID NO: 370 are substituted by other amino acids, preferably alanine, further preferably a polypeptide comprising an amino acid sequence in which the amino acid at position 3 of SEQ ID NO: 370 is substituted by another amino acid, preferably alanine.

(12α) Epitope of Myosin-Binding Protein C, Fast-Type-Like

In the present invention, the polypeptide (12α) can be any polypeptide selected from the group consisting of (12α-1) to (12α-11) as defined below:

(12α-1) a polypeptide comprising at least one amino acid sequence selected from the group consisting of SEQ ID NOs: 187-196, 373, 376, 379, 382, 384, 386, 388, 390, 392, 395, 397, 400, 402, 405, 407, 409, 411, and 413.

(12α-2) a polypeptide comprising the amino acid sequence of KXTXXKKKXX (SEQ ID NO: 371), preferably a polypeptide comprising the amino acid sequence of KXTXXKKKPV (SEQ ID NO: 372), more preferably a polypeptide comprising an amino acid sequence in which any 1, 2, 3, 4 or 5 of the amino acids at positions 2, 4, 5, 9 and 10 of SEQ ID NO: 373 are substituted by other amino acids, preferably alanine, further preferably a polypeptide comprising an amino acid sequence in which any 1, 2 or 3 of the amino acids at positions 2, 4 and 5 of SEQ ID NO: 373 are substituted by other amino acids, preferably alanine.

In another mode, a polypeptide comprising the amino acid sequence of KXKPVVXX (SEQ ID NO: 374), preferably a polypeptide comprising the amino acid sequence of KXKPVVDE (SEQ ID NO: 375), more preferably a polypeptide comprising an amino acid sequence in which any 1, 2 or 3 of the amino acids at positions 2, 7 and 8 of SEQ ID NO: 376 are substituted by other amino acids, preferably alanine, further preferably a polypeptide comprising an amino acid sequence in which the amino acid at position 2 of SEQ ID NO: 376 is substituted by another amino acid, preferably alanine.

(12α-3) a polypeptide comprising the amino acid sequence of YXXXXFXXXI (SEQ ID NO: 377), preferably a polypeptide comprising the amino acid sequence of YXXIXFEYXI (SEQ ID NO: 378), more preferably a polypeptide comprising an amino acid sequence in which any 1, 2, 3, 4, 5, 6 or 7 of the amino acids at positions 2-5 and 7-9 of SEQ ID NO: 379 are substituted by other amino acids, preferably alanine, further preferably a polypeptide comprising an amino acid sequence in which any 1, 2, 3 or 4 of the amino acids at positions 2, 3, 5 and 9 of SEQ ID NO: 379 are substituted by other amino acids, preferably alanine.

In another mode, a polypeptide comprising the amino acid sequence of XXIXDXRG (SEQ ID NO: 380), preferably a polypeptide comprising the amino acid sequence of YXIXDXRG (SEQ ID NO: 381), more preferably a polypeptide comprising an amino acid sequence in which any 1, 2, 3 or 4 of the amino acids at positions 1, 2, 4 and 6 of SEQ ID NO: 382 are substituted by other amino acids, preferably alanine, further preferably a polypeptide comprising an amino acid sequence in which any 1, 2 or 3 of the amino acids at positions 2, 4 and 6 of SEQ ID NO: 382 are substituted by other amino acids, preferably alanine.

(12α-4) a polypeptide comprising the amino acid sequence of DXRGXXK (SEQ ID NO: 383), preferably a polypeptide comprising an amino acid sequence in which any 1, 2 or 3 of the amino acids at positions 2, 5 and 6 of SEQ ID NO: 384 are substituted by other amino acids, preferably alanine.

(12α-5) a polypeptide comprising the amino acid sequence of KMXXXXPK (SEQ ID NO: 385), preferably a polypeptide comprising an amino acid sequence in which any 1, 2, 3 or 4 of the amino acids at positions 3-6 of SEQ ID NO: 386 are substituted by other amino acids, preferably alanine.

In another mode, a polypeptide comprising the amino acid sequence of KXXKXXXPKH (SEQ ID NO: 387), preferably a polypeptide comprising an amino acid sequence in which any 1, 2, 3, 4 or 5 of the amino acids at positions 2, 3 and 5-7 of SEQ ID NO: 388 are substituted by other amino acids, preferably alanine.

In yet another mode, a polypeptide comprising the amino acid sequence of KXXXXFL (SEQ ID NO: 389), preferably a polypeptide comprising an amino acid sequence in which any 1, 2, 3 or 4 of the amino acids at positions 2-5 of SEQ ID NO: 390 are substituted by other amino acids, preferably alanine.

(12α-6) a polypeptide comprising the amino acid sequence of KGKKXX (SEQ ID NO: 391), preferably a polypeptide comprising an amino acid sequence in which any 1 or 2 of the amino acids at positions 5 and 6 of SEQ ID NO: 392 are substituted by other amino acids, preferably alanine.

In another mode, a polypeptide comprising the amino acid sequence of KXKXXXLXXE (SEQ ID NO: 393), preferably a polypeptide comprising the amino acid sequence of KXKXXXLQXE (SEQ ID NO: 394), more preferably a polypeptide comprising an amino acid sequence in which any 1, 2, 3, 4, 5 or 6 of the amino acids at positions 2, 4-6, 8 and 9 of SEQ ID NO: 395 are substituted by other amino acids, preferably alanine, further preferably a polypeptide comprising an amino acid sequence in which any 1, 2, 3, 4 or 5 of the amino acids at positions 2, 4-6 and 9 of SEQ ID NO: 395 are substituted by other amino acids, preferably alanine.

(12α-7) a polypeptide comprising the amino acid sequence of TXKX (SEQ ID NO: 396), preferably a polypeptide comprising an amino acid sequence in which any 1 or 2 of the amino acids at positions 2 and 4 of SEQ ID NO: 397 are substituted by other amino acids, preferably alanine.

In another mode, a polypeptide comprising the amino acid sequence of KYXXKKXXX (SEQ ID NO: 398), preferably a polypeptide comprising the amino acid sequence of KYXXKKDGL (SEQ ID NO: 399), more preferably a polypeptide comprising an amino acid sequence in which any 1, 2, 3, 4 or 5 of the amino acids at positions 3, 4 and 7-9 of SEQ ID NO: 400 are substituted by other amino acids, preferably alanine, further preferably a polypeptide comprising an amino acid sequence in which any 1 or 2 of the amino acids at positions 3 and 4 of SEQ ID NO: 400 are substituted by other amino acids, preferably alanine.

(12α-8) a polypeptide comprising the amino acid sequence of YXXXPDG (SEQ ID NO: 401), preferably a polypeptide comprising an amino acid sequence in which any 1, 2 or 3 of the amino acids at positions 2-4 of SEQ ID NO: 402 are substituted by other amino acids, preferably alanine.

In another mode, a polypeptide comprising the amino acid sequence of DGYXXSXSXK (SEQ ID NO: 403), preferably a polypeptide comprising the amino acid sequence of DGYXLSLSXK (SEQ ID NO: 404), more preferably a polypeptide comprising an amino acid sequence in which any 1, 2, 3 or 4 of the amino acids at positions 4, 5, 7 and 9 of SEQ ID NO: 405 are substituted by other amino acids, preferably alanine, further preferably a polypeptide comprising an amino acid sequence in which any 1 or 2 of the amino acids at positions 4 and 9 of SEQ ID NO: 405 are substituted by other amino acids, preferably alanine.

(12α-9) a polypeptide comprising the amino acid sequence of PVTXX (SEQ ID NO: 406), preferably a polypeptide comprising an amino acid sequence in which any 1 or 2 of the amino acids at positions 4 and 5 of SEQ ID NO: 407 are substituted by other amino acids, preferably alanine.

(12α-10) a polypeptide comprising the amino acid sequence of QXXXXXXXXDKXN (SEQ ID NO: 408), preferably a polypeptide comprising an amino acid sequence in which any 1, 2, 3, 4, 5, 6, 7 or 8 of the amino acids at positions 2-8 and 11 of SEQ ID NO: 409 are substituted by other amino acids, preferably alanine.

(12α-11) a polypeptide comprising the amino acid sequence of YXXXXXDXKT (SEQ ID NO: 410), preferably a polypeptide comprising an amino acid sequence in which any 1, 2, 3, 4, 5 or 6 of the amino acids at positions 2-6 and 8 of SEQ ID NO: 411 are substituted by other amino acids, preferably alanine.

In another mode, a polypeptide comprising the amino acid sequence of YXXQXXXK (SEQ ID NO: 412), preferably a polypeptide comprising an amino acid sequence in which any 1, 2, 3, 4 or 5 of the amino acids at positions 2, 3 and 5-7 of SEQ ID NO: 413 are substituted by other amino acids, preferably alanine.

(13α) Epitope of ATP Synthase Subunit Beta, Mitochondrial

In the present invention, the polypeptide (13α) can be any polypeptide selected from the group consisting of (13α-1) and (13α-2) as defined below:

(13α-1) a polypeptide comprising at least one amino acid sequence selected from the group consisting of SEQ ID NOs: 197, 415, and 417.

(13α-2) a polypeptide comprising the amino acid sequence of GXYS (SEQ ID NO: 414), preferably a polypeptide comprising an amino acid sequence in which the amino acid at position 2 of SEQ ID NO: 415 is substituted by another amino acid, preferably alanine.

In another mode, a polypeptide comprising the amino acid sequence of YXXXXG (SEQ ID NO: 416), preferably a polypeptide comprising an amino acid sequence in which any 1, 2, 3 or 4 of the amino acids at positions 2-5 of SEQ ID NO: 417 are substituted by other amino acids, preferably alanine.

(14α) Epitope of L-Lactate Dehydrogenase a Chain-Like

In the present invention, the polypeptide (14α) can be any polypeptide selected from the group consisting of (14α-1) and (14α-2) as defined below:

(14α-1) a polypeptide comprising at least one amino acid sequence selected from the group consisting of SEQ ID NOs: 198 and 420.

(14α-2) a polypeptide comprising the amino acid sequence of XPVGSXSKX (SEQ ID NO: 418), preferably a polypeptide comprising the amino acid sequence of EPVGSXSKV (SEQ ID NO: 419), more preferably a polypeptide comprising an amino acid sequence in which any 1, 2 or 3 of the amino acids at positions 1, 6 and 9 of SEQ ID NO: 420 are substituted by other amino acids, preferably alanine, further preferably a polypeptide comprising an amino acid sequence in which the amino acid at position 6 of SEQ ID NO: 420 is substituted by another amino acid, preferably alanine.

(15α) Epitope of Aldolase

In the present invention, the polypeptide (15α) can be any polypeptide selected from the group consisting of (15α-1) and (15α-2) as defined below:

(15α-1) a polypeptide comprising at least one amino acid sequence selected from the group consisting of SEQ ID NOs: 199, 423, and 425.

(15α-2) a polypeptide comprising the amino acid sequence of XYXRXXXXXXXK (SEQ ID NO: 421), preferably a polypeptide comprising the amino acid sequence of SYXRXLXXXAXK (SEQ ID NO: 422), more preferably a polypeptide comprising an amino acid sequence in which any 1, 2, 3, 4, 5, 6, 7, 8 or 9 of the amino acids at positions 1, 3 and 5-11 of SEQ ID NO: 423 are substituted by other amino acids, preferably alanine, further preferably a polypeptide comprising an amino acid sequence in which any 1, 2, 3, 4, 5 or 6 of the amino acids at positions 3, 5, 7-9 and 11 of SEQ ID NO: 423 are substituted by other amino acids, preferably alanine.

In another mode, a polypeptide comprising the amino acid sequence of SXXKXXG (SEQ ID NO: 424), preferably a polypeptide comprising an amino acid sequence in which any 1, 2, 3 or 4 of the amino acids at positions 2, 3, 5 and 6 of SEQ ID NO: 425 are substituted by other amino acids, preferably alanine.

In one mode, the polypeptide (15α) may not comprise a variant or a homolog having 100% or at least 90%, at least 80% or at least 70% identity to the full-length amino acid sequence (NCBI protein accession number: NP_001133180.1, SEQ ID NO: 445) of aldolase.

(16α) Epitope of β-Enolase

In the present invention, the polypeptide (16α) can be any polypeptide selected from the group consisting of (16α-1) to (16α-4) as defined below:

(16α-1) a polypeptide comprising at least one amino acid sequence selected from the group consisting of SEQ ID NOs: 200-202, 428, 431, 434, and 436.

(16α-2) a polypeptide comprising the amino acid sequence of RYLGKXXX (SEQ ID NO: 426), preferably a polypeptide comprising the amino acid sequence of RYLGKGXV (SEQ ID NO: 427), more preferably a polypeptide comprising an amino acid sequence in which any 1, 2 or 3 of the amino acids at positions 6-8 of SEQ ID NO: 428 are substituted by other amino acids, preferably alanine, further preferably a polypeptide comprising an amino acid sequence in which the amino acid at position 7 of SEQ ID NO: 428 is substituted by another amino acid, preferably alanine.

(16α-3) a polypeptide comprising the amino acid sequence of YXXIXDXXXH (SEQ ID NO: 429), preferably a polypeptide comprising the amino acid sequence of YXXIXDLXGH (SEQ ID NO: 430), more preferably a polypeptide comprising an amino acid sequence in which any 1, 2, 3, 4, 5 or 6 of the amino acids at positions 2, 3, 5 and 7-9 of SEQ ID NO: 431 are substituted by other amino acids, preferably alanine, further preferably a polypeptide comprising an amino acid sequence in which any 1, 2, 3 or 4 of the amino acids at positions 2, 3, 5 and 8 of SEQ ID NO: 431 are substituted by other amino acids, preferably alanine.

In another mode, a polypeptide comprising the amino acid sequence of DXXXHXDVXL (SEQ ID NO: 432), preferably a polypeptide comprising the amino acid sequence of DXXXHKDVIL (SEQ ID NO: 433), more preferably a polypeptide comprising an amino acid sequence in which any 1, 2, 3, 4 or 5 of the amino acids at positions 2-4, 6 and 9 of SEQ ID NO: 434 are substituted by other amino acids, preferably alanine, further preferably a polypeptide comprising an amino acid sequence in which any 1, 2 or 3 of the amino acids at positions 2-4 of SEQ ID NO: 434 are substituted by other amino acids, preferably alanine.

(16α-4) a polypeptide comprising the amino acid sequence of IKXXXXKDAT (SEQ ID NO: 435), preferably a polypeptide comprising an amino acid sequence in which any 1, 2, 3 or 4 of the amino acids at positions 3-6 of SEQ ID NO: 436 are substituted by other amino acids, preferably alanine.

In one mode, the polypeptide (16α) may not comprise a variant or a homolog having 100% or at least 90%, at least 80% or at least 70% identity to the full-length amino acid sequence (NCBI protein accession number: NP_001133193.1, SEQ ID NO: 446) of β-enolase.

(17α) Epitope of Glyceraldehyde-3-Phosphate Dehydrogenase

In the present invention, the polypeptide (17α) can be any polypeptide selected from the group consisting of (17α-1) to (17α-3) as defined below:

(17α-1) a polypeptide comprising at least one amino acid sequence selected from the group consisting of SEQ ID NOs: 203, 204, 441, and 444.

(17α-2) a polypeptide comprising the amino acid sequence of YXXXXXXXDXXXGRF (SEQ ID NO: 437), preferably a polypeptide comprising the amino acid sequence of YXXXXXXXDSTXGRF (SEQ ID NO: 438), more preferably a polypeptide comprising an amino acid sequence in which any 1, 2, 3, 4, 5, 6, 7, 8, 9 or 10 of the amino acids at positions 2-8 and 10-12 of SEQ ID NO: 203 are substituted by other amino acids, preferably alanine, further preferably a polypeptide comprising an amino acid sequence in which any 1, 2, 3, 4, 5, 6, 7 or 8 of the amino acids at positions 2-8 and 12 of SEQ ID NO: 203 are substituted by other amino acids, preferably alanine.

(17α-3) a polypeptide comprising the amino acid sequence of SYXXIXXV (SEQ ID NO: 440), preferably a polypeptide comprising an amino acid sequence in which any 1, 2, 3 or 4 of the amino acids at positions 3, 4, 6 and 7 of SEQ ID NO: 441 are substituted by other amino acids, preferably alanine.

In another mode, a polypeptide comprising the amino acid sequence of IKKXXK (SEQ ID NO: 442), preferably a polypeptide comprising the amino acid sequence of IKKVXK (SEQ ID NO: 443), more preferably a polypeptide comprising an amino acid sequence in which any 1 or 2 of the amino acids at positions 4 and 5 of SEQ ID NO: 444 are substituted by other amino acids, preferably alanine, further preferably a polypeptide comprising an amino acid sequence in which the amino acid at position 5 of SEQ ID NO: 444 is substituted by another amino acid, preferably alanine.

In one mode, the polypeptide (17α) may not comprise a variant or a homolog having 100% or at least 90%, at least 80% or at least 70% identity to the full-length amino acid sequence (NCBI protein accession number: NP_001117033.1, SEQ ID NO: 447) of glyceraldehyde-3-phosphate dehydrogenase.

The lengths of the aforementioned polypeptides (1α) to (17α) are not particularly limited. In a preferred mode, the lengths of the aforementioned polypeptides (1α) to (17α) can be 500 amino acids or less, 300 amino acids or less, 200 amino acids or less, 100 amino acids or less, 50 amino acids or less, 30 amino acids or less, 20 amino acids or less, 15 amino acids or less, 10 amino acids or less, or 5 amino acids or less.

The aforementioned polypeptides (1α) to (17α) may be prepared by a technique of chemical synthesis such as solid-phase peptide synthesis. Alternatively, polypeptides comprising an epitope may be obtained by expressing them as recombinant proteins using a genetic recombination technique well known to those skilled in the art and by separating and producing them using protein producing methods well known to those skilled in the alt Diagnosis Kit and Method (2)

The present invention provides a method for providing an indicator for diagnosing an allergy in a subject, the method comprising the steps of:

(i) contacting a sample obtained from the subject with an antigen, wherein the sample is a solution comprising an IgE antibody;

(ii) detecting binding between the IgE antibody present in the sample obtained from the subject and the antigen; and (iii) when the binding between the IgE antibody in the subject and the antigen is detected, an indicator of the fact that the subject is allergic is provided; wherein the antigen is a polypeptide that is at least one of the aforementioned polypeptides (1α) to (17α), or a polypeptide in which two or more of the aforementioned polypeptides (1α) to (17α) are joined together via or without a spacer.

Hereinafter, the polypeptide that is at least one of the aforementioned polypeptides (1α) to (17α), or the polypeptide in which two or more of the aforementioned polypeptides (1α) to (17α) are joined together via or without a spacer is referred to as the "antigen including (1α) to (17α)" in the present specification. The type of the spacer is not particularly limited, and an ordinary spacer that is used by those skilled in the art for joining together two or more peptides can be used. The spacer may be, for example, a hydrocarbon chain such as Acp(6)-OH.

The sample obtained from a subject is as described above in the subsection titled "Diagnosis kit and method (1)".

Detection of contact and binding between the sample obtained from a subject and the antigen can be carried out by using a known method described above in the subsection titled "Diagnosis kit and method (1)", such as ELISA (Enzyme-Linked Immunosorbent Assay), sandwich immunoassay, immunoblotting, immunoprecipitation, or immunochromatography.

The antigen including (1α) to (17α) may be provided in a state immobilized on a carrier. In this case, the steps (i) and (ii) mentioned above can be carried out using ELISA, sandwich immunoassay, immunochromatography, surface plasmon resonance, or the like. The step (i) mentioned above can be carried out by contacting the sample obtained from a subject with a surface on which the antigen including (1α) to (17α) is immobilized. The IgE antibody from the subject may be used in a state immobilized on a carrier, and binding to the antigen including (1α) to (17α) may be detected by the aforementioned technique.

The antigen including (1α) to (17α) may be in a state unimmobilized on a carrier. In this case, flow cytometry or the like can be used in the aforementioned steps (i) and (ii), and the presence of IgE antibody-bound antigen including (1α) to (17α) can be confirmed with laser beam. Examples of this method include a basophil activation test (BAT) which is a method in which a surface antigen CD203c that appears when basophils are activated by the contact of the antigen including (1α) to (17α) is detected. Another example includes a histamine release test (HRT) which examines whether histamine is released by further contacting the antigen including (1α) to (17α) with blood cells in a sample.

The antigen including (1α) to (17α) is an antigen specifically binding to IgE antibodies from allergic patients. Therefore, when binding between an IgE antibody from a subject and the antigen is detected, an indicator of the fact that the subject is allergic to fish is provided.

The present invention further provides a kit for diagnosing an allergy, comprising at least one antigen including (1α) to (17α). The diagnosis kit of this invention may be used in the aforementioned method for providing an indicator for diagnosing an allergy or in a diagnosis method as described later. The diagnosis kit of this invention may comprise not only the at least one antigen including (1α) to (17α), but also an anti-IgE antibody labeled with an enzyme and a chromogenic or luminescent substrate serving as a substrate for the enzyme. Also, a fluorescent-labeled anti-IgE antibody may be used. In the diagnosis kit of this invention, the antigen including (1α) to (17α) may be provided in a state immobilized on a carrier. The diagnosis kit of this invention may also be provided together with instructions on the procedure for diagnosis or a package containing said instructions.

In another mode, the aforementioned diagnosis kit comprises a companion diagnostic agent for an allergy. The companion diagnostic agent is used for identifying patients expected to respond to pharmaceutical products or identifying patients having the risk of severe adverse reactions to pharmaceutical products, or for studying the reactivity of pharmaceutical products in order to optimize treatment using the pharmaceutical products. Here, the optimization of treatment includes, for example, determination of dosage and administration, judgment regarding discontinuation of administration, and confirmation of an allergen component that is used to cause immunological tolerance.

The present invention further provides a composition for diagnosing an allergy, comprising at least one antigen including (1α) to (17α). The diagnosis composition of this invention can be used in a diagnosis method as described below. The diagnosis composition of this invention may further comprise a pharmaceutically acceptable carrier and/or additives commonly used with the antigen of this invention depending on the need.

In one mode, the present invention provides a method for diagnosing an allergy in a subject, the method comprising:
(i) contacting a sample obtained from the subject with an antigen;
(ii) detecting binding between an IgE antibody present in the sample obtained from the subject and the antigen; and
(iii) when the binding between the IgE antibody in the subject and the antigen is detected, diagnosing the subject as being allergic;
wherein the antigen is at least one of the proteins defined as the antigen including (1α) to (17α). In this method, the steps (i) and (ii) are performed as described above regarding the corresponding steps of the method for providing an indicator for diagnosing an allergy.

In another mode, the present invention provides a method for diagnosing an allergy in a subject, the method comprising administering to the subject at least one antigen including (1α) to (17α). This method may be performed in the form of a skin test characterized by applying the antigen including (1α) to (17α) onto the skin. Examples of the skin test include various forms of tests, such as: a prick test in which a diagnosis composition is applied onto the skin and then a tiny prick to such an extent as not to provoke bleeding is made in the skin to allow the antigen including (1α) to (17α) to penetrate the skin, thereby observing a skin reaction; a scratch test in which a diagnosis composition is applied onto the skin and then the skin is lightly scratched to observe a reaction; a patch test in which a diagnosis composition in the form of cream, ointment, etc. is applied onto the skin to observe a reaction; and an intracutaneous test in which the antigen including (1α) to (17α) is administered intracutaneously to observe a reaction. If a skin reaction such as swelling occurs in a skin portion to which the antigen including (1α) to (17α) has been applied, the subject of interest is diagnosed as having an allergy. The amount of the antigen including (1α) to (17α) to be applied to the skin in such tests can be, for example, not more than 100 μg per dose.

In the process of allergy diagnosis, a load test aiming to identify an antigen is often adopted. At least one antigen including (1α) to (17α) can be used as an active ingredient for a load test to diagnose an allergy. Here, the allergen component to be used in the load test may be a polypeptide that has been expressed and purified and may be a protein that has been expressed in food or cooking ingredients, such as rice-based vaccine expressing pollen allergens which are obtained by transforming rice with a gene of a cedar pollen antigen and expressing the antigen protein in the rice.

In still another mode, the present invention provides at least one antigen including (1α) to (17α), intended for use in the diagnosis of an allergy.

In still another mode, the present invention provides use of at least one antigen including (1α) to (17α) for the production of a diagnostic agent for an allergy.

In this subsection, the allergy to be diagnosed or detected can be allergies to the antigen including (1α) to (17α). Thus, detection of the allergy can be detection of not only an allergy to a single antigen including (1α) to (17α), but also allergies including cross-reactivity.

Pharmaceutical Composition and Treatment Method (2)

The present invention provides a pharmaceutical composition comprising at least one antigen including (1α) to (17α). In one mode, the aforementioned pharmaceutical composition is used for the treatment of an allergy. The treatment of an allergy increases the limit amount of an antigen in which the allergy does not develop even if the antigen is incorporated into the body, and finally aims for the state where the allergy does not develop by the common amount of the antigen to be consumed (remission).

The present invention also provides a method for treating an allergy, the method comprising administering at least one antigen including (1α) to (17α) to a patient in need of a treatment for an allergy.

In another mode, the present invention provides at least one antigen including (1α) to (17α), intended for use in the treatment for an allergy. In yet another mode, the present invention provides use of at least one antigen including (1α) to (17α) for the production of a therapeutic agent for an allergy.

In the process of allergy treatment, a hyposensitization therapy aiming to induce immunological tolerance by administering an antigen to a patient is often adopted. The at least one antigen including (1α) to (17α) can be used as an active ingredient for hyposensitization therapy for an allergy. Here, the allergen component to be used in the hyposensitization therapy may be a polypeptide that has been expressed and purified and may be a polypeptide that has been expressed in food or a cooking ingredient, such as rice-based vaccine expressing pollen allergens.

The administration route, administration dose, frequency and/or period of the pharmaceutical composition of this invention, and other ingredients to be contained in the pharmaceutical composition, and the dosage form can be as described above in the subsection titled "Pharmaceutical composition and treatment method (1)". In the case of using the antigen including (1α) to (17α), for example, the dose to an adult patient may be a dose of not more than 100 μg per dose.

In this subsection, the allergy to be treated can be allergies to the antigen including (1α) to (17α). Thus, treatment of the allergy can be treatment of not only an allergy to a single antigen including (1α) to (17α), but also allergies including cross-reactivity.

Tester (2)

The present invention provides a tester comprising an antibody for at least one antigen including (1α) to (17α).

The antibody can be prepared by a conventional method. For example, the antibody may be prepared by immunizing a mammal such as rabbit with the aforementioned antigen including (1α) to (17α). The antibody may be an Ig antibody, a polyclonal antibody, a monoclonal antibody, or an antigen-binding fragment thereof (e.g., Fab, F(ab')₂, Fab').

Further, in the aforementioned tester, the antibody may be provided in a form bound to a carrier. The type of the carrier is not particularly limited as long as it is usable for detection of binding between an antibody and the antigen including (1α) to (17α). Any given carrier known to those skilled in the art can be used. Also, the antibody for the antigen including (1α) to (17α) is preferably an antibody for the epitopes described above in the subsection titled "Epitope of antigen". This can attain a tester that can also detect cross-reactivity.

Examples of a method for determining the presence or absence of the antigen including (1α) to (17α) include the following methods:

a method in which a prepared tester comprising an antibody is contacted with a sample obtained from a raw material, a processed product, etc., ELISA or the like is used to detect whether there is a binding between the antibody and the antigen including (1α) to (17α) in the sample, and if the binding between the antibody and the antigen including (1α) to (17α) is detected, it is determined that the antigen remains in the raw material, the processed product, etc. of interest; and a method in which filter paper is impregnated with a raw material, a processed product, etc. and reacted with an antibody solution so as to detect the antigen including (1α) to (17α) contained therein.

Another mode of the present invention includes a tester for determining the presence or absence of the antigen including (1α) to (17α) of an allergy in an object of interest, the tester comprising a primer appropriate for an epitope. The primer is not limited and may be designed so as to comprise, for example, a portion of the nucleotide sequence of a nucleic acid encoding any of the amino acid sequences defined above in (1α) to (17α), or a complementary strand thereof. Alternatively, the primer may be designed so as to be the nucleotide sequence of a region upstream of a portion encoding an epitope that is any of the amino acid sequences defined above in (1α) to (17α), in a nucleic acid encoding a protein comprising the epitope, or the nucleotide sequence of a complementary strand of a region downstream of the portion encoding the epitope. Examples of such a primer include a primer which is a portion of at least one of the nucleotide sequences of SEQ ID NOs: 1, 4, 9, 18, 25, 32, 42, 55, 60, 69, 109, 120, 137, 143, 448, 449 and 450 and/or a primer which is a portion of a sequence complementary to at least one of the nucleotide sequences of SEQ ID NOs: 1, 4, 9, 18, 25, 32, 42, 55, 60, 69, 109, 120, 137, 143, 448, 449 and 450. Here, the position of the epitope in the full-length sequence of an antigen is as defined in Table 2 of Example 10 given below. Particularly, when mRNA is of interest, the tester has a complementary primer of a poly-A tail.

For example, DNA is amplified by PCR (Polymerase Chain Reaction) including RT-PCR using templated DNA or mRNA obtained from a sample and the aforementioned primer, and the presence or absence of a nucleic acid encoding the amino acid sequences defined above in (1α) to (17α) in the sequence of the amplified DNA is determined to determine the presence or absence of the antigen including (1α) to (17α). Amplification methods by PCR for mRNA of interest can be exemplified by RACE. When one of amino acid sequences encoded by three possible open reading frames in the amplified DNA comprises any of the amino acid sequences defined above in (1α) to (17α), it is determined that the antigen is present. When no DNA is amplified, it is determined that the antigen is absent.

In one mode, the aforementioned tester is used to determine the presence or absence of the antigen including (1α) to (17α) in raw materials or processed products of interest in a food production line. The raw material may be a cooking ingredient or may be a cosmetic raw material, a pharmaceutical raw material or the like. The processed product may be an edible processed product or may be a cosmetic, a pharmaceutical product or the like. The tester may also be used for search for organism species contained in raw materials, may be used for quality inspection of production lines and pre-shipment products by manufacturers, or may be used for self-checking of the presence or absence of an antigen in raw materials or processed products of interest by consumers or users.

Allergen-Free Raw Material and the Like

The present invention provides a raw material or a processed product in which at least one antigen including (1α) to (17α) is eliminated or reduced.

The method for eliminating or reducing the antigen of the present invention in a raw material or a processed product is not limited. The elimination or reduction of the antigen may be conducted by any method, as long as the method permits the elimination or reduction of the antigen including (1α) to (17α). For example, the techniques described above in the subsection titled "Allergen-free food and the like" may be used.

Elimination or reduction of at least one antigen including (1α) to (17α) may be achieved by eliminating or reducing the whole antigen or may be achieved by cleaving or removing the sequence moiety defined in (1α) to (17α) from the antigen protein. The "removal" includes deletion and modification of the whole or a portion of a sequence moiety defined above in (1α) to (17α).

For example, the raw material in which the antigen including (1α) to (17α) is eliminated or reduced may be obtained by preparing a raw material in which the expression of the antigen including (1α) to (17α) is knocked out, using a gene knock-out technique. Any technique known to those skilled in the art such as genetic modification can be used as the gene knock-out technique.

The processed product in which the antigen including (1α) to (17α) is eliminated or reduced may be a processed product of the raw material in which the antigen including (1α) to (17α) is eliminated or reduced, such as powdered milk obtained with purified peptide as a raw material. In the case of using an ordinary raw material, a treatment for eliminating or reducing the antigen including (1α) to (17α) is performed before or after preparation of a processed product. The techniques described in the subsection titled "Allergen-free food and the like" may be used as methods for eliminating or reducing the antigen including (1α) to (17α) in a processed product obtained with an ordinary raw material. Examples of the method for cleaving the antigen including (1α) to (17α) include a method in which the antigen is treated by cleavage with a particular digestive enzyme.

Method for Producing Allergen-Free Processed Product (2)

The present invention provides a method for producing a processed product in which an antigen is eliminated or reduced, the method comprising the step of confirming that the antigen is eliminated or reduced, in a production process of the processed product, wherein the antigen is at least one of the aforementioned antigens including (1α) to (17α).

In the production method, elimination or reduction of an antigen means that at least one antigen including (1α) to (17α) is eliminated or reduced, or the sequence moiety defined in (1α) to (17α) are cleaved or removed from the antigen.

A technique of confirming that the antigen is eliminated or reduced in the production process of the processed product is not particularly limited, and any technique capable of detecting at least one of the aforementioned antigen including (1α) to (17α) may be used. For example, the presence or absence of the polypeptide or the antigen in the processed product may be confirmed from the binding activity of an antibody for at least one of the aforementioned antigen including (1α) to (17α) against a sample containing a material resulting from the production process of the processed product. Details of such a method are as described above in the subsection titled "Diagnosis kit and method (2)". Thus, in the production method, the "IgE antibody from a subject" described above in the subsection titled "Diagnosis kit and method (2)" is replaced with the "antibody for at least one of the aforementioned antigen including (1α) to (17α)", and the "antigen" described above in the subsection titled "Diagnosis kit and method (2)" is replaced with the "sample containing a material resulting from the production process of the processed product". The techniques described above in the subsection titled "Diagnosis kit and method (2)" can be used to confirm that the antigen is eliminated or reduced in the production process of the processed product. The testers described above in the subsection titled "Tester (2)" can also be used.

EXAMPLES

The following describes examples of the present invention. The technical scope of this invention is not limited by these examples.

Example 1: Confirmation of a Protein Pattern

Proteins contained in salmons were investigated using a two-dimensional electrophoresis method described below.

Protein Extraction

Extraction and purification of proteins contained in salmons were carried out as follows. The proteins were extracted by adding a solubilizer (Mammalian Lysis Buffer (MCLI), Sigma-Aldrich Co. LLC) to salmon meat. Then, a urea buffer was added thereto to obtain a liquid protein extract. The constituents of the urea buffer are as mentioned below.

30 mM Tris
2 M thiourea
7 M urea
4% (w/v) CHAPS:

3-[(3-cholamidopropyl)dimethylammonio]propane-sulfonate
Moderate amount of dilute hydrochloric acid The total amount was adjusted to 100 mL by the addition of distilled water. The pH was 8.5.

Then, 25 μg (by weight) each of the proteins was mixed to obtain a liquid extract.

Thereafter, the precipitation procedure was repeated twice using a 2D-CleanUP Kit (produced by GE). In the first round of precipitation, the collected liquid protein extract was precipitated by adding TCA (trichloroacetic acid) thereto and the precipitated product produced by this procedure (TCA-precipitated product) was collected. In the second round of precipitation, the TCA-precipitated product collected above was further precipitated by adding acetone thereto and the precipitated product (sample) produced by this procedure was collected.

Preparation of a Sample Solution

Part of the collected sample (40 μg on a protein weight basis) was dissolved in 150 μL of a DeStreak Rehydration Solution (produced by GE), which is a swelling buffer for first-dimensional isoelectric focusing gels, thereby obtaining a sample solution for first-dimensional isoelectric focusing (sample solution for swelling). The constituents of the DeStreak Rehydration Solution are as mentioned below.

7M thiourea
2M urea
4% (w/v) of CHAPS
0.5% (v/v) IPG buffer; produced by GE
Moderate amount of BPB (bromophenol blue)

Penetration of the sample into first-dimensional isoelectric focusing gels First-dimensional isoelectric focusing gel strips (Immobiline Drystrip IPG gels (pH3-10NL); produced by GE) were immersed in 140 μL of the foregoing sample solution for first-dimensional isoelectric focusing (sample solution for swelling) and impregnated with the solution at room temperature overnight.

In this example, an IPGphor electrophoresis system produced by GE was used.

An electrophoresis tray was filled with silicone oil. Filter paper moisten with water was positioned at both ends of the gel strips impregnated with the sample, and the gel strips were set in the electrophoresis tray such that the gel strips were covered with silicone oil. Electrodes were placed on the gel strips with the filter paper intervening therebetween.

The maximum current of the isoelectric focusing system was set to 75 μA per gel strip, and the first-dimensional isoelectric focusing was carried out according to the following voltage program: (1) a constant voltage step was performed at a constant voltage of 300 V until the volt-hours reached 750 Vhr (the current variation width during electrophoresis for 30 minutes before the end of this step was 5 μA); (2) the voltage was increased gradually to 1000 V for 300 Vhr; (3) the voltage was further increased gradually to 5000 V for 4500 Vhr; and then (4) the voltage was held at a constant voltage of 5000 V until the total Vhr reached 12000.

SDS Equilibration of Isoelectric Focusing Gels

After the aforementioned first-dimensional isoelectric focusing was done, the gel strips were taken out of the isoelectric focusing system, immersed in an equilibration buffer containing a reducing agent, and shaken at room temperature for 15 minutes. The constituents of the equilibration buffer containing the reducing agent are as mentioned below.

100 mM Tris-HCl (pH 8.0)
6M urea

30% (v/v) glycerol

2% (w/v) SDS

1% (w/v) DTT

Next, the equilibration buffer containing the reducing agent was removed, and then the gel strips were immersed in an equilibration buffer containing an alkylating agent and shaken at room temperature for 15 minutes to obtain SDS-equilibrated gels. The constituents of the equilibration buffer containing the alkylating agent are as mentioned below.

100 mM Tris-HCl (pH 8.0)

6M urea

30% (v/v) glycerol

2% (w/v) SDS 2.5% (w/v) iodoacetamide

Second-Dimensional SDS-PAGE

In this example, the XCell SureLock Mini-Cell electrophoresis system produced by Life Technologies was used. The second-dimensional electrophoresis gels used were NuPAGE 4-12% Bis-Tris Gels produced by Life Technologies. Also, an electrophoresis buffer composed of the following constituents was prepared and used.

50 mM MOPS 50 mM Tris base 0.1% (w/v) SDS 1 mM EDTA

Further, an agarose solution for gel adhesion was used in this example, which was prepared by dissolving 0.5% (w/v) Agarose S (produced by Nippon Gene Co., Ltd.) and a moderate amount of BPB (bromophenol blue) in the electrophoresis buffer.

SDS-PAGE wells were washed well with the electrophoresis buffer, and then the buffer used for the washing was removed. Next, the washed wells were charged with the fully dissolved agarose solution for gel adhesion. Next, the SDS-equilibrated gel strips were immersed in agarose and closely adhered to second-dimensional electrophoresis gels using tweezers. After it was confirmed that agarose was fully fixed with the gels being closely adhered to each other, electrophoresis was performed at a constant voltage of 200 V for about 45 minutes.

Fluorescent Staining of Gels

The gels were fluorescently stained with SYPRO Ruby (produced by Life Technologies).

First, an airtight container to be used was washed well in advance with 98% (v/v) ethanol. The electrophoresed second-dimensional electrophoresis gel strips were taken out of the SDS-PAGE system, placed onto the washed airtight container, and treated twice by immersion in 50% (v/v) methanol and 7% (v/v) aqueous solution containing acetic acid for 30 minutes. Then, a further immersion treatment was done for 10 minutes, with the solution being replaced by water. Next, the second-dimensional electrophoresis gel strips were immersed in 40 mL of SYPRO Ruby and shaken at room temperature overnight. Thereafter, the SYPRO Ruby was removed, and then the second-dimensional electrophoresis gel strips were washed with water and shaken in 10% (v/v) methanol and 7% (v/v) aqueous solution containing acetic acid for 30 minutes. Further shaking was done for at least 30 minutes, with the solution being replaced by water.

Analysis

The second-dimensional electrophoresis gels obtained through the foregoing series of treatments were subjected to fluorescent image scanning on Typhoon9500 (produced by GE). The results of the two-dimensional electrophoresis as to the proteins contained in the salmon meat are shown in the left diagram FIG. 1A. Molecular weight marker bands are found at the left of the photograph of the gel. The positions of the bands denote particular molecular weights (in KDa).

Example 2: Identification of Antigens by Immunoblotting (1)

Identification of antigens by immunoblotting was carried out by taking all the steps up to the step of "Second-dimensional SDS-PAGE" as described above in Example 1, followed by the steps of "Transfer to membrane", "Immunoblotting" and "Analysis" as described below.

Transfer to Membrane

Transfer to membrane was done using the following transfer system and transfer buffer.

Transfer system: XCell SureLock Mini-Cell and XCell II Blot Module (produced by Life Technologies)

Transfer buffer: NuPAGE Transfer Buffer (X20) (produced by Life Technologies), used in a form diluted 20-fold with milliQ water.

To be specific, proteins in the second-dimensional electrophoresis gels were transferred to a membrane (PVDF membrane) according to the following procedure.

(1) The PVDF membrane was immersed in 100% methanol followed by milliQ water, and then moved into the transfer buffer to hydrophilize the PVDF membrane.

(2) After sponge, filter paper, the second-dimensional electrophoresis gels treated by second-dimensional SDS-PAGE, the hydrophilized PVDF membrane, filter paper, and sponge were put in place in this order, the transfer system was energized at a constant voltage of 30 V for one hour.

Immunoblotting

Immunoblotting of the membrane was carried out using, as a primary antibody, a serum sample from patient 1 with a fish allergy or a serum sample from a non-fish-allergic subject. This fish-allergic patient 1 was a patient diagnosed with immediate-type allergy to fish. This patient developed allergy symptoms to salmon, horse mackerel, conger, black-head seabream, mackerel, sea bream, cod, and amberjack and exhibited positivity in the prick test.

Immunoblotting of the membrane was carried out according to the following procedure.

(1) The transferred membrane was shaken in a 5% skim milk/PBST solution (a PBS buffer containing 0.1% Tween 20 nonionic surfactant) at room temperature for one hour.

(2) The membrane was left to stand in a solution of 5% primary antibody serum in 5% skim milk/PBST at room temperature for one hour.

(3) The membrane was washed with a PBST solution (5 min.×3 times).

(4) The membrane was left to stand in a 1:5000 dilution of the secondary antibody, anti-human IgE-HRP (horseradish peroxidase), with a 5% skim milk/PBST solution at room temperature for one hour.

(5) The membrane was washed with a PBST solution (5 min.×3 times).

(6) The membrane was left to stand in Pierce Western Blotting Substrate Plus (produced by Thermo Fisher Scientific) for 5 minutes.

Analysis

The membrane obtained through the foregoing series of treatments was subjected to fluorescent image scanning on Typhoon9500 (produced by GE).

Figure 3:
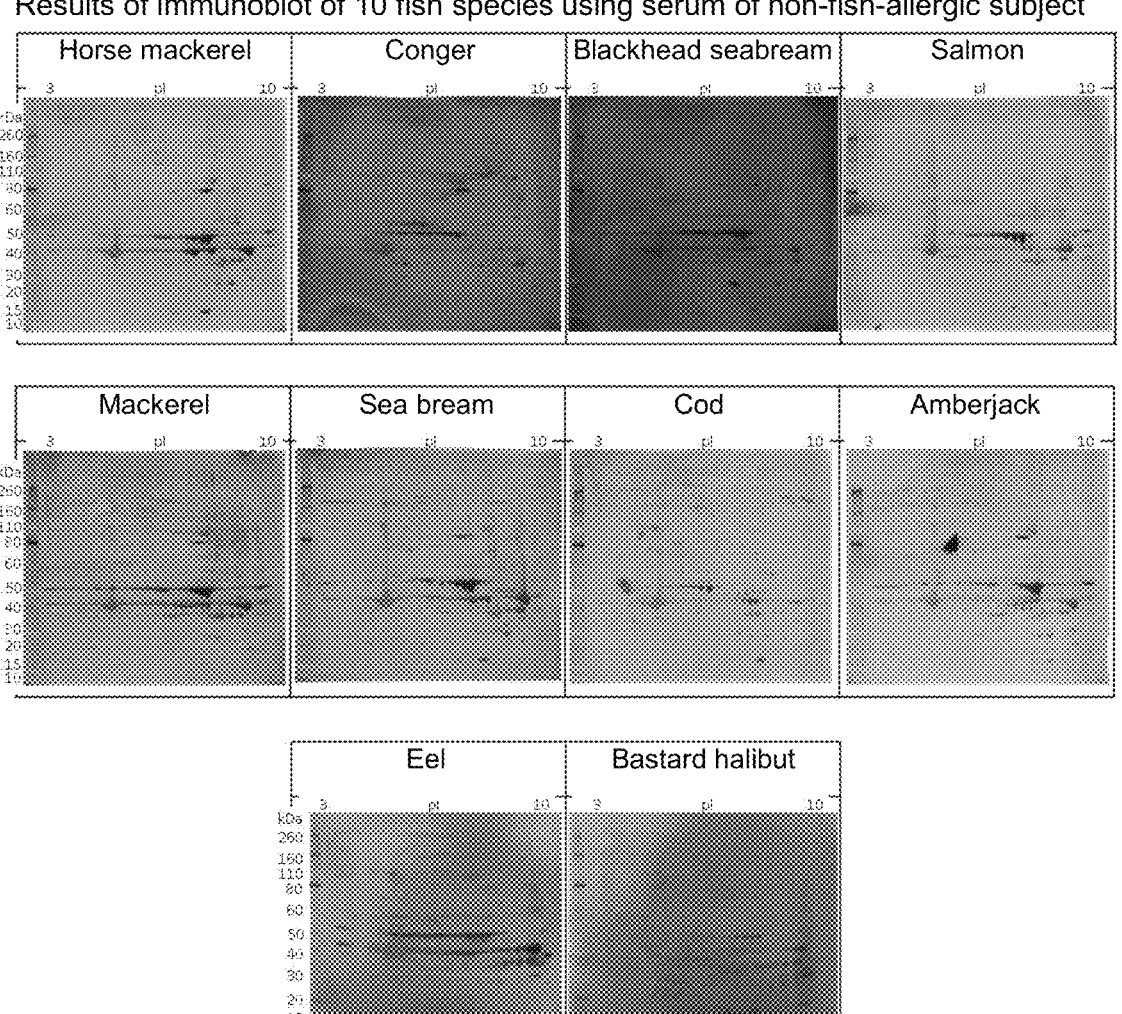
FIG. 3 is a photograph of an immunoblot of a two-dimensional electrophoretic pattern of proteins contained in meat extracts of 10 types of fishes using the serum of a subject having no symptom of a fish allergy (non-fish-allergic subject).

The immunoblots obtained with the serum from the fish-allergic patient 1 were compared with those obtained with the control serum from the non-fish-allergic subject. By immunoblotting of the proteins contained in the salmon meat using the serum from the fish-allergic patient 1 (the right diagram of FIG. 1A), spots were detected, which are different from the spots detected when the serum of the non-fish-allergic subject was used (FIG. 3) and different from those of the known salmon allergen proteins. The detected spots are shown in the immunoblot (the right diagram of FIG. 1A).

The molecular weights and isoelectric points of the 9 spots are as follows.

Spot 1: Molecular weight 90 to 120 kDa, pI 3.0 to 6.0
Spot 2: Molecular weight 120 to 160 kDa, pI 4.0 to 7.0
Spot 3: Molecular weight 90 to 120 kDa, pI 5.0 to 8.0
Spot 4: Molecular weight 90 to 120 kDa, pI 6.0 to 8.0
Spot 5: Molecular weight 60 to 90 kDa, pI 3.0 to 6.0
Spot 6: Molecular weight 70 to 100 kDa, pI 5.0 to 7.0
Spot 7: Molecular weight 40 to 70 kDa, pI 4.0 to 7.0
Spot 8: Molecular weight 40 to 70 kDa, pI 4.0 to 7.0
Spot 9: Molecular weight 20 to 50 kDa, pI 4.0 to 7.0

Example 3: Mass Spectrometry and Identification of Antigens (1)

The amino acid sequences of the antigens that form the 9 protein spots were identified by mass spectroscopy.

To be specific, protein extraction and mass spectroscopy were done by the following procedure.

(1) Salmon meat was subjected to protein extraction, two-dimensional electrophoresis and transfer to membrane by following the procedures described in Example 1 and 2, and the resulting membrane was stained by shaking in a solution of 0.008% Direct blue in 40% ethanol and 10% acetic acid.

(2) Then, the membrane was decolorized by repeating a 5-minute treatment with 40% ethanol and 10% acetic acid three times, washed with water for 5 minutes, and then dried by air.

(3) A protein spot of interest was cut out with a clean cutter blade and put into a centrifugal tube. The cut membrane was subjected to hydrophilization with 50 μL of methanol, followed by washing with 100 μL of water twice and then centrifugal cleaning. Thereafter, 20 μL of 20 mM $NH_4HCO_3$ and 50% acetonitrile were added.

(4) 1 μL of 1 μmol/μL lysyl endopeptidase (produced by WAKO) was added, and the solution was left to stand at 37° C. for 60 minutes and then collected in a new centrifugal tube. After 20 μL of 20 mM $NH_4HCO_3$ and 70% acetonitrile were added to the membrane, the membrane was immersed therein at room temperature for 10 minutes, and the resulting solution was further collected. The solution was dissolved with 0.1% formic acid and 10 μL of 4% acetonitrile and transferred to a tube.

(5) The collected solution was dried under reduced pressure, dissolved with 15 μL of solution A (a 0.1% formic acid/4% acetonitrile solution), and analyzed by mass spectroscopy (ESI-TOF6600, produced by AB Sciex).

(6) Identification of proteins based on the MS data obtained with the mass spectrometer was done by searching the NCBI or UniProt database.

Results

The mass spectrometry of the spots resulted in the detection of the following amino acid sequences.

Spot 1: Amino acid sequence of SEQ ID NO: 3
Spot 2: Amino acid sequences of SEQ ID NOs: 6-8
Spot 3: Amino acid sequences of SEQ ID NOs: 11-17

Spot 4: Amino acid sequences of SEQ ID NOs: 20-24
Spot 5: Amino acid sequences of SEQ ID NOs: 27-31
Spot 6: Amino acid sequences of SEQ ID NOs: 34-41
Spot 7: Amino acid sequences of SEQ ID NOs: 44-54
Spot 8: Amino acid sequences of SEQ ID NOs: 57-59
Spot 9: Amino acid sequences of SEQ ID NOs: 62-68

Furthermore, the spots were identified as the following proteins by the analysis of the mass data obtained from the mass spectrometer for the spots at NCBI for spot 1 and at UniProt for spots 2 to 9.

Spot 1: Alpha-actinin-3 (NCBI protein accession number: XP_014051545.1, DNA accession number: XM_014196070.1) (amino acid sequence: SEQ ID NO: 2, encoding nucleotide sequence: SEQ ID NO: 1)

Spot 2: EEF1A2 binding protein-like (UniProt protein accession number: B5RI29, DNA accession number: ACH85270.1) (amino acid sequence: SEQ ID NO: 5, encoding nucleotide sequence: SEQ ID NO: 4)

Spot 3: Alpha-1,4-glucan phosphorylase (UniProt protein accession number: B5DG55, DNA accession number: ACH70729.1) (amino acid sequence: SEQ ID NO: 10, encoding nucleotide sequence: SEQ ID NO: 9)

Spot 4: Elongation factor 2 (UniProt protein accession number: C0H9N2, DNA accession number: ACN10751.1) (amino acid sequence: SEQ ID NO: 19, encoding nucleotide sequence: SEQ ID NO: 18)

Spot 5: Heat shock cognate 70 kDa protein (UniProt protein accession number: B5X3U6, DNA accession number: ACI33977.1) (amino acid sequence: SEQ ID NO: 26, encoding nucleotide sequence: SEQ ID NO: 25)

Spot 6: Serotransferrin (UniProt protein accession number: P79815, DNA accession number: BAA13759.1) (amino acid sequence: SEQ ID NO: 33, encoding nucleotide sequence: SEQ ID NO: 32)

Spot 7: Myosin binding protein H-like (UniProt protein accession number: B5DG45, DNA accession number: ACH70719.1) (amino acid sequence: SEQ ID NO: 43, encoding nucleotide sequence: SEQ ID NO: 42)

Spot 8: Desmin (fragment) (UniProt protein accession number: Q8UWF1, DNA accession number: CAC83053.1) (amino acid sequence: SEQ ID NO: 56, encoding nucleotide sequence: SEQ ID NO: 55) Spot 9: Capping protein (actin filament) muscle Z-line beta (UniProt protein accession number: B5DFX6, DNA accession number: ACH70650.1) (amino acid sequence: SEQ ID NO: 61, encoding nucleotide sequence: SEQ ID NO: 60)

Example 4: Identification of Antigens in Other Fish Species (1)

Identification of antigens were carried out by the same procedure as described in Example 1 and Example 2 using meat of 9 fish species other than salmon, i.e., horse mackerel, conger, blackhead seabream, mackerel, sea bream, cod, amberjack, eel, and bastard halibut.

Figure 2:
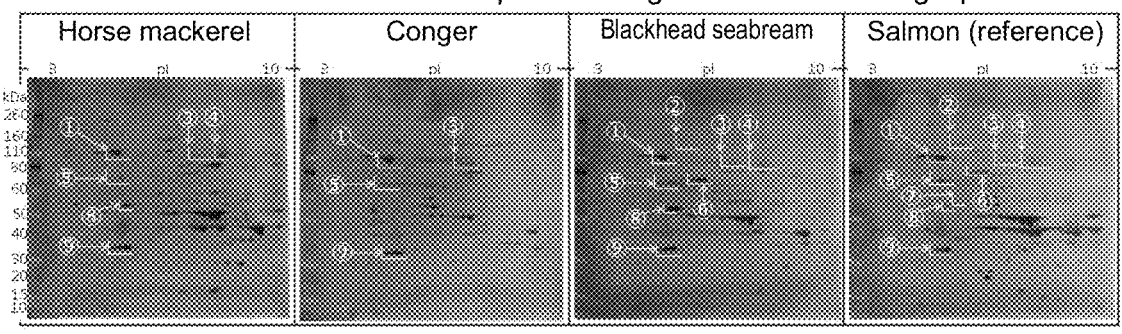
FIG. 2 is a photograph of an immunoblot of a two-dimensional electrophoretic pattern of proteins contained in meat extracts of 10 types of fishes using the serum of fish-allergic patient 1.
Figure 2:
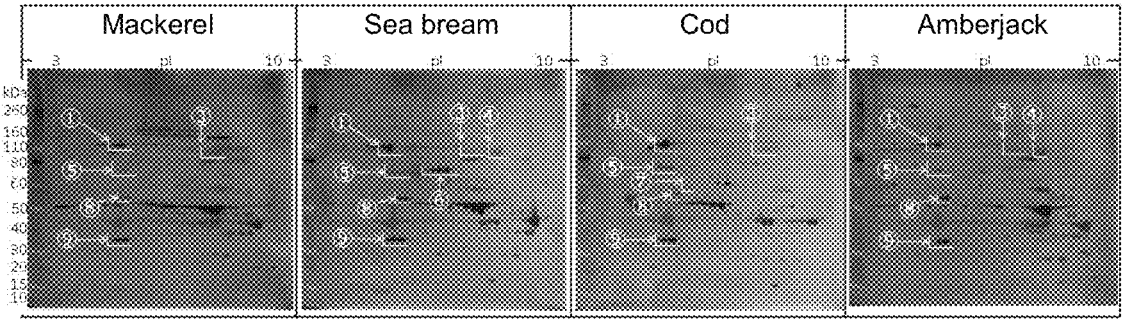
Figure 2:
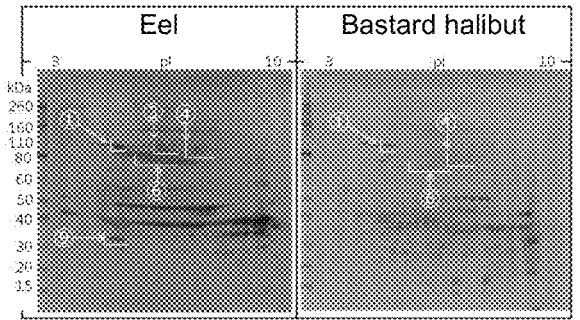

The immunoblots obtained with the serum from the fish-allergic patient 1 were compared with those obtained with the control serum from the non-fish-allergic subject. By immunoblotting of the proteins contained in the meat of each of the 9 fish species using the serum from the fish-allergic patient 1 (FIG. 2), spots were detected, which are different from the spots detected when the serum of the non-fish-allergic subject was used (FIG. 3) and corresponded to some of the 9 spots obtained in salmon.

The following spots were detected in each of the fish species.

Horse mackerel: Spots 1, 3 to 5, 8, and 9

Conger: Spots 1, 3, 5, and 9

Blackhead seabream: Spots 1 to 6, 8, and 9

Mackerel: Spots 1, 3, 5, 8, and 9

Sea bream: Spots 1, 3 to 6, 8, and 9

Cod: Spots 1, 3, 5, and 7 to 9

Amberjack: Spots 1, 3 to 5, 8, and 9

Eel: Spots 1, 3, 4, 6, and 9

Bastard halibut: Spots 1, 4, and 6

Example 5: Identification of Antigens by Immunoblotting (2)

The immunoblots obtained with the serum from a fish-allergic patient were compared with those obtained with the control serum from the non-fish-allergic subject in the same manner as in Example 2. By immunoblotting of the proteins contained in the salmon meat using the serum from the fish-allergic patient 2 (the left diagram of FIG. 1B), 3 spots (spots 11, 12 and 14) were newly detected, which are different from the spots detected when the serum of the non-fish-allergic subject was used (FIG. 3) and different from those of the known salmon allergen proteins, in addition to 7 (spots 1 to 6 and 9) out of the 9 spots detected in Example 2. A total of 10 spots are shown in the immunoblot (the left diagram of FIG. 1B).

The molecular weights and isoelectric points of the newly detected 3 spots are as follows.

Spot 11: Molecular weight 90 to 110, pI 6.5 to 7.0

Spot 12: Molecular weight 120 to 140, pI 5.0 to 6.0

Spot 14: Molecular weight 30 to 40, pI 6.5 to 7.5

Example 6: Mass Spectrometry and Identification of Antigens (2)

The amino acid sequences of the antigens that form the newly detected 3 protein spots were identified by mass spectroscopy in the same manner as in Example 3.

The mass spectrometry of the spots resulted in the detection of the following amino acid sequences.

Spot 11: Amino acid sequences of SEQ ID NOs: 111-119

Spot 12: Amino acid sequences of SEQ ID NOs: 122-136

Spot 14: Amino acid sequences of SEQ ID NOs: 145-149

Furthermore, the spots were identified as the following proteins by the analysis of the mass data obtained from the mass spectrometer for the spots at NCBI. Spot 11: Glycogen phosphorylase, muscle form-like (NCBI protein accession number: XP_013984904.1, DNA accession number: XM_014129429.1) (amino acid sequence: SEQ ID NO: 110, encoding nucleotide sequence: SEQ ID NO: 109) Spot 12: Myosin-binding protein C, fast-type-like (NCBI protein accession number: XP_014014310.1, DNA accession number: XM_014158835.1) (amino acid sequence: SEQ ID NO: 121, encoding nucleotide sequence: SEQ ID NO: 120) Spot 14: L-lactate dehydrogenase A chain-like (NCBI protein accession number: XP_014003141.1, DNA accession number: XM_014147666.1) (amino acid sequence: SEQ ID NO: 144, encoding nucleotide sequence: SEQ ID NO: 143)

Example 7: Identification of Antigens by Immunoblotting (3)

The immunoblots obtained with the serum from a fish-allergic patient were compared with those obtained with the control serum from the non-fish-allergic subject in the same manner as in Example 2. By immunoblotting of the proteins contained in the salmon meat using the serum from the fish-allergic patient 3 (the right diagram of FIG. 1B), 2 spots (spots 10 and 13) were newly detected, which are different from the spots detected when the serum of the non-fish-allergic subject was used (FIG. 3) and different from those of the known salmon allergen proteins, in addition to 2 (spots 7 and 8) out of the 9 spots detected in Example 2. A total of 4 spots are shown in the immunoblot (the right diagram of FIG. 1B).

The molecular weights and isoelectric points of the newly detected 2 spots are as follows.

Spot 10: Molecular weight 200 to 230, pI 4.5 to 5.5

Spot 13: Molecular weight 45 to 55, pI 4.0 to 5.5

Example 8: Mass Spectrometry and Identification of Antigens (3)

The amino acid sequences of the antigens that form the newly detected 2 protein spots were identified by mass spectroscopy in the same manner as in Example 3.

The mass spectrometry of the spots resulted in the detection of the following amino acid sequences.

Spot 10: Amino acid sequences of SEQ ID NOs: 71-108

Spot 13: Amino acid sequences of SEQ ID NOs: 139-142

Furthermore, the spots were identified as the following proteins by the analysis of the mass data obtained from the mass spectrometer for the spots at NCBI.

Spot 10: Myosin heavy chain, fast skeletal muscle-like (NCBI protein accession number: XP_014039990.1, DNA accession number: XM_014184515.1) (amino acid sequence: SEQ ID NO: 70, encoding nucleotide sequence: SEQ ID NO: 69) Spot 13: ATP synthase subunit beta, mitochondrial (NCBI protein accession number: XP_014007238.1, DNA accession number: XM_014151763.1) (amino acid sequence: SEQ ID NO: 138, encoding nucleotide sequence: SEQ ID NO: 137)

Example 9: Identification of Antigens in Other Fish Species (2)

Figure 4:
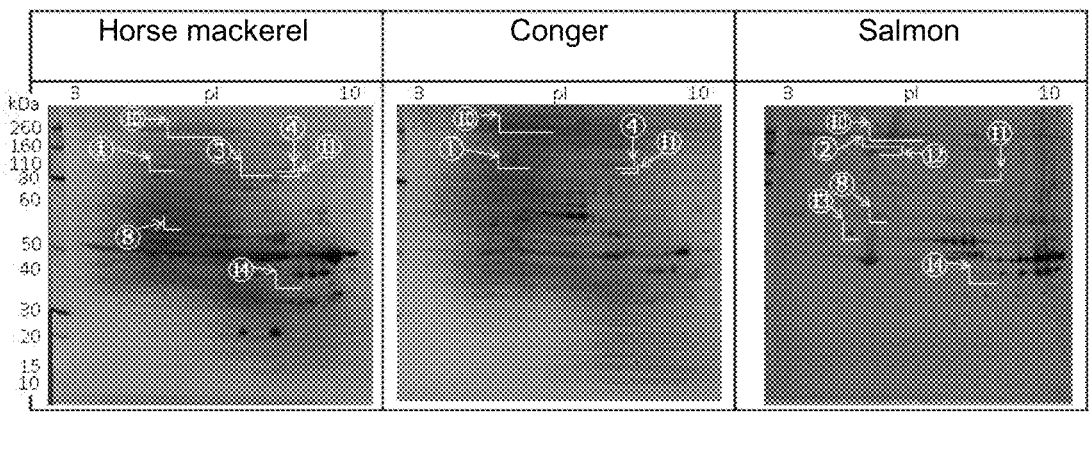
FIG. 4 is a photograph of an immunoblot of a two-dimensional electrophoretic pattern of proteins contained in meat extracts of 6 types of fishes using the serum of fish-allergic patient 4.
Figure 4:
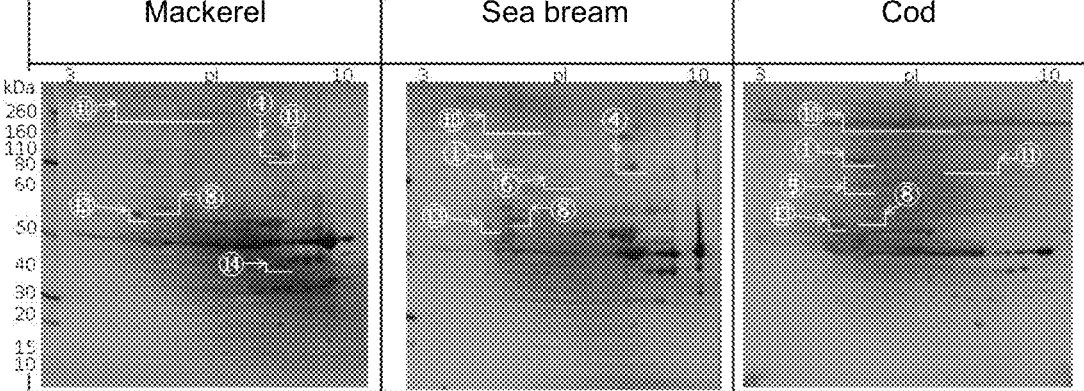

Identification of antigens were carried out in the same manner as in Example 4 using meat of 6 fish species, i.e., horse mackerel, conger, salmon, mackerel, sea bream, and cod. The immunoblots obtained with the serum from the fish-allergic patient 4 were compared with those obtained with the control serum from the non-fish-allergic subject. By immunoblotting of the proteins contained in the meat of each of the 6 fish species using the serum from the fish-allergic patient 4 (FIG. 4), spots were detected, which are different from the spots detected when the serum of the non-fish-allergic subject was used (FIG. 3) and corresponded to some of a total of 14 spots obtained with the serum from the fish-allergic patients 1 to 3.

The following spots were detected in each of the fish species.

Horse mackerel: Spots 1, 3, 4, 8, 10, 11, and 14

Conger: Spots 1, 4, 10, and 11

Salmon: Spots 2, 8, and 10 to 14

Mackerel: Spots 4, 8, 10, 11, 13, and 14

Sea bream: Spots 1, 4, 6, 8, 10, and 13

Cod: Spots 1, 5, 8, 10, 11, and 13

Example 10: Identification of Epitopes

Epitopes of Fish Allergen Components

Identification of epitopes was carried out by the following procedure as to the fish allergen components.

(A) Epitope Mapping (1)

Epitope mapping was carried out using a library of overlapping peptides (length: 15 amino acids) correspond-ing to the amino acid sequences identified as allergy com-ponents of fish and the amino acid sequences of known fish allergy antigens aldolase, β-enolase, and glyceraldehyde-3-phosphate dehydrogenase (Non Patent Literature 2-4). Spe-cifically, the library of overlapping peptides was prepared on the basis of the amino acid sequences of SEQ ID NO: 2 for alpha-actinin-3, SEQ ID NO: 5 for EEF1A2 binding protein-like, SEQ ID NO: 10 for alpha-1,4-glucan phosphorylase, SEQ ID NO: 19 for elongation factor 2, SEQ ID NO: 26 for heat shock cognate 70 kDa protein, SEQ ID NO: 33 for serotransferrin, SEQ ID NO: 43 for myosin binding protein H-like, SEQ ID NO: 56 for desmin (fragment), SEQ ID NO: 61 for capping protein (actin filament) muscle Z-line beta, SEQ ID NO: 70 for myosin heavy chain, fast skeletal muscle-like, SEQ ID NO: 110 for glycogen phosphorylase, muscle form-like, SEQ ID NO: 121 for myosin-binding protein C, fast-type-like, SEQ ID NO: 138 for ATP synthase subunit beta, mitochondrial, SEQ ID NO: 144 for L-lactate dehydrogenase A chain-like, SEQ ID NO: 445 for aldolase, SEQ ID NO: 446 for β-enolase, and SEQ ID NO: 447 for glyceraldehyde-3-phosphate dehydrogenase.

The peptides to be synthesized were shifted by 10 amino acids. Thus, each peptide had an overlap of 5 amino acids with each of the peptides previous and subsequent thereto.

For preparation of peptide arrays, the Intavis CelluS-pots™ technique was used. Specifically, the peptide arrays were prepared by the following procedure: (1) synthesizing peptides of interest on amino-modified cellulose disks using an automated chemical synthesis apparatus (Intavis Multi-Pep RS), (2) dissolving the amino-modified cellulose disks to obtain a cellulose-bound peptide solution, and (3) spotting the cellulose-bound peptides onto coated glass slides. The details of each procedure are as described below.

(1) Synthesis of Peptide

Peptide synthesis was carried out in incremental steps through 9-fluorenylmethoxycarbonyl (Fmoc) chemical reac-tion on amino-modified cellulose disks in 384-well synthesis plates. Specifically, amino acids in which a Fmoc group is bonded to an amino group were activated in a solution of N,N'-diisopropylcarbodiimide (DIC) and 1-hydroxybenzo-triazole (HOBt) in dimethylformamide (DMF) and added dropwise to the cellulose disks so that the Fmoc group-bound amino acids were bound to the amino groups on the cellulose disks (coupling). Unreacted amino groups were capped with acetic anhydride and washed with DMF. Fur-thermore, the Fmoc groups were eliminated from the amino groups of the amino acids bound to the amino groups on the cellulose disks by treatment with piperidine and washing with DMF. The amino acids bound to the amino groups on the cellulose disks were repetitively subjected to the cou-pling, the capping, and the Fmoc group elimination described above to elongate the amino terminus for peptide synthesis.

(2) Dissolution of Amino-Modified Cellulose Disk

The peptides-bound cellulose disks of interest obtained above in the subsection titled "(1) Synthesis of peptide" were transferred to 96-well plates and treated with a side chain deprotection mixed solution of trifluoroacetic acid (TFA), dichloromethane, triisopropylsilane (TIPS), and water for deprotection of amino acid side chains. Then, the deprotected cellulose-bound peptides were dissolved in a mixed solution of TFA, perfluoromethanesulfonic acid (TFMSA), TIPS, and water and precipitated in tetrabutyl methyl ether (TBME), and the precipitate was resuspended in dimethyl sulfoxide (DMSO) and mixed with a mixed solution of NaCl, sodium citrate, and water to obtain a peptide solution for slide spotting.

(3) Spotting of Cellulose-Bound Peptide Solution

The peptide solution for slide spotting obtained above in the subsection titled "(2) Dissolution of amino-modified cellulose disk" was spotted onto Intavis CelluSpots™ slides using Intavis Slide Spotting Robot, and the slides were dried to prepare peptide arrays.

The presence or absence of binding, to each peptide fragment, of an IgE antibody present in the serum of a fish-allergic patient was measured through antigen-antibody reaction using the peptide arrays. The measurement was carried out according to the following procedure.

(1) The peptides were shaken at room temperature for 1 hour in PBST.

(2) The peptide arrays were shaken at overnight at room temperature in 5% serum/PBST.

(3) The peptide arrays were washed with a PBST solution (a PBS buffer containing 0.1% Tween 20 nonionic surfactant) for 5 minutes (×3).

(4) Anti-human IgE antibody-HRP(1:5,000, PBST) was added thereto, and the peptide arrays were shaken at room temperature for 1 hour.

(5) The peptide arrays were washed with a PBST solution for 5 minutes (×3).

(6) Pierce ECL Plus Western Blotting Substrate (produced by Thermo Fisher Scientific) was added thereto, and the peptide arrays were shaken at room temperature for 5 minutes.

(7) The chemiluminescence of the peptides treated as described above in (1) to (6) was measured using Amersham Imager 600.

Chemiluminescence intensity in images obtained by the measurement described above in (7) was converted into a numeric value using ImageQuant TL (GE Healthcare). The average value of numeric values determined from images obtained from results about the serum of 5 patients was divided by the average value of numeric values determined from images obtained from results about the serum of 4 non-fish-allergic subjects. It was determined that a peptide having a calculated value (average value of the patient group/average value of the non-fish-allergic subject group) of at least 1.5 and a significant difference of at least 0.05 in the Mann-Whitney U test was a peptide bound to an IgE antibody in a patient-specific manner.

(B) Epitope Mapping (2): Overlapping

On the basis of the sequences (SEQ ID NOs: 150-154 for alpha-actinin-3, SEQ ID NO: 155 for EEF1A2 binding protein-like, SEQ ID NOs: 156 and 157 for alpha-1,4-glucan phosphorylase, SEQ ID NOs: 158 and 159 for elongation factor 2, SEQ ID NOs: 160-162 for heat shock cognate 70 kDa protein, SEQ ID NOs: 163-167 for serotransferrin, SEQ ID NOs: 168-171 for myosin binding protein H-like, SEQ ID NOs: 172-174 for desmin (fragment), SEQ ID NOs: 175-178 for capping protein (actin filament) muscle Z-line beta, SEQ ID NOs: 179-185 for myosin heavy chain, fast skeletal muscle-like, SEQ ID NO: 186 for glycogen phos-phorylase, muscle form-like, SEQ ID NOs: 187-196 for myosin-binding protein C, fast-type-like, SEQ ID NO: 197 for ATP synthase subunit beta, mitochondrial, SEQ ID NO: 198 for L-lactate dehydrogenase A chain-like, SEQ ID NO:

199 for aldolase, SEQ ID NOs: 200-202 for β-enolase, and SEQ ID NOs: 203 and 204 for glyceraldehyde-3-phosphate dehydrogenase) of the peptides bound to an IgE antibody in serum in a patient-specific manner as described above in (A), a library of overlapping peptide fragments (length: 10 amino acids) was prepared using the sequences of the peptides and sequences in which sequences were added so as to flank each peptide in the amino acid sequences of allergen components (SEQ ID NO: 2 for alpha-actinin-3, SEQ ID NO: 5 for EEF1A2 binding protein-like, SEQ ID NO: 10 for alpha-1,4-glucan phosphorylase, SEQ ID NO: 19 for elongation factor 2, SEQ ID NO: 26 for heat shock cognate 70 kDa protein, SEQ ID NO: 33 for serotransferrin, SEQ ID NO: 43 for myosin binding protein H-like, SEQ ID NO: 56 for desmin (fragment), SEQ ID NO: 61 for capping protein (actin filament) muscle Z-line beta, SEQ ID NO: 70 for myosin heavy chain, fast skeletal muscle-like, SEQ ID NO: 110 for glycogen phosphorylase, muscle form-like, SEQ ID NO: 121 for myosin-binding protein C, fast-type-like, SEQ ID NO: 138 for ATP synthase subunit beta, mitochondrial, SEQ ID NO: 144 for L-lactate dehydrogenase A chain-like, SEQ ID NO: 445 for aldolase, SEQ ID NO: 446 for β-enolase, and SEQ ID NO: 447 for glyceraldehyde-3-phosphate dehydrogenase) comprising the sequences of the peptide. Epitope mapping was carried out using the library.

The peptides to be synthesized were shifted by one amino acid. Thus, each peptide had an overlap of 9 amino acids with each of the peptides previous and subsequent thereto.

The library was prepared by the same procedure as described above in (A), and the presence or absence of binding of an IgE antibody present in the serum of a patient and a non-fish-allergic subject to each peptide fragment was measured by the same technique as described above. Amino acids at positions where the binding activity against IgE antibodies from patients were lost or decreased in the peptides shifted by one amino acid while binding activity against IgE antibodies from non-fish-allergic subjects arose were confirmed as amino acids adversely affecting the specificity of binding to IgE antibodies.

Chemiluminescence intensity in images obtained by measurement was converted into a numeric value in the same manner as in (A) using ImageQuant TL (GE Healthcare). When values obtained using the sequences (SEQ ID NOs: 150-204) that were of the peptides confirmed to bind to an IgE antibody in a patient specific manner from the images obtained from results about the serum of 5 patients and served as the basis of overlapping were defined as 100%, it was determined that: a peptide having a value of less than 20% had no binding activity against IgE antibodies; a peptide having a value of 20% or more and less than 50% had binding activity, albeit poor, against IgE antibodies; a peptide having a value of 50% or more and less than 70% had binding activity, albeit somewhat poor, against IgE antibodies; a peptide having a value of 70% or more and less than 90% had equivalent binding activity against IgE antibodies; and a peptide having a value of 90% or more had almost equivalent or good binding activity against IgE antibodies and was thus a peptide had remaining binding activity against IgE antibodies.

This analysis found regions important for binding to IgE antibodies from patients, in the sequences serving as the basis of overlapping.

(C) Epitope Mapping (3): Alanine Scanning

From the amino acid sequences identified above in (A), a library of peptide fragments in which N-terminal amino acids were substituted one by one by alanine according to a technique called alanine scanning (Non Patent Literature 5)

was prepared by the same technique as described above. The presence or absence of binding of an IgE antibody present in the serum of a patient and a non-fish-allergic subject to each peptide fragment was measured by the same technique as described above. Amino acids at positions where the binding activity against IgE antibodies from patients were lost or decreased by the substitution by alanine while binding activity against IgE antibodies from non-fish-allergic subjects arose were confirmed as amino acids important for exertion of original antigenicity, or amino acids influencing exertion of original antigenicity. Also, amino acids at positions where the binding activity against IgE antibodies from patients was maintained even after the substitution by alanine while binding activity against IgE antibodies from non-fish-allergic subjects did not arise were confirmed as substitutable positions that were not important for exertion of original antigenicity, Chemiluminescence intensity in images obtained by measurement was converted into a numeric value in the same manner as in (A) using ImageQuant TL (GE Healthcare). When values obtained using the sequences (SEQ ID NOs: 150-204) that were of the peptides confirmed to bind to an IgE antibody in a patient specific manner from the images obtained from results about the serum of 5 patients and served as the basis of overlapping were defined as 100%, it was determined that: a peptide having a value of less than 20% had no binding activity against IgE antibodies; a peptide having a value of 20% or more and less than 50% had binding activity, albeit poor, against IgE antibodies; a peptide having a value of 50% or more and less than 70% had binding activity, albeit somewhat poor, against IgE antibodies; a peptide having a value of 70% or more and less than 90% had equivalent binding activity against IgE antibodies; and a peptide having a value of 90% or more had almost equivalent or good binding activity against IgE antibodies and was thus a peptide had remaining binding activity against IgE antibodies.

By this analysis, common sequences important for exertion of original antigenicity were found in regions important for binding to IgE antibodies from patients, in the sequences serving as the basis of overlapping.

(D) Results

As a result of the epitope mapping described above in (A), an IgE antibody was confirmed to bind in a patient-specific manner to each of epitope Nos. 1-5 (peptides having the amino acid sequences of SEQ ID NOs: 150-154, respectively) for alpha-actinin-3, epitope No. 6 (a peptide having the amino acid sequence of SEQ ID NO: 155) for EEF1A2 binding protein-like, epitope Nos. 7 and 8 (peptides having the amino acid sequences of SEQ ID NOs: 156 and 157, respectively) for alpha-1,4-glucan phosphorylase, epitope Nos. 9 and 10 (peptides having the amino acid sequences of SEQ ID NOs: 158 and 159, respectively) for elongation factor 2, epitope Nos. 11-13 (peptides having the amino acid sequences of SEQ ID NOs: 160-162, respectively) for heat shock cognate 70 kDa protein, epitope Nos. 14-18 (peptides having the amino acid sequences of SEQ ID NOs: 163-167, respectively) for serotransferrin, epitope Nos. 19-22 (peptides having the amino acid sequences of SEQ ID NOs: 168-171, respectively) for myosin binding protein H-like, epitope Nos. 23-25 (peptides having the amino acid sequences of SEQ ID NOs: 172-174, respectively) for desmin (fragment), epitope Nos. 26-29 (peptides having the amino acid sequences of SEQ ID NOs: 175-178, respectively) for capping protein (actin filament) muscle Z-line beta, epitope Nos. 30-36 (peptides having the amino acid sequences of SEQ ID NOs: 179-185, respectively) for myosin heavy chain, fast skeletal muscle-like, epitope No. 37 (a peptide having the amino acid sequence of SEQ ID NO: 186) for glycogen phosphorylase, muscle form-like, epitope Nos. 38-47 (peptides having the amino acid sequences of SEQ ID NOs: 187-196, respectively) for myosin-binding protein C, fast-type-like, epitope No. 48 (a peptide having the amino acid sequence of SEQ ID NO: 197) for ATP synthase subunit beta, mitochondrial, epitope No. 49 (a peptide having the amino acid sequence of SEQ ID NO: 198) for L-lactate dehydrogenase A chain-like, epitope No. 50 (a peptide having the amino acid sequence of SEQ ID NO: 199) for aldolase, epitope Nos. 51-53 (peptides having the amino acid sequences of SEQ ID NOs: 200-202, respectively) for β-enolase, and epitope Nos. 54 and 55 (peptides having the amino acid sequences of SEQ ID NOs: 203 and 204, respectively) for glyceraldehyde-3-phosphate dehydrogenase. Portions to which the peptide sequences of these epitopes correspond in the sequences of the allergen components identified in Examples 2, 3 and 5 to 8 and the known allergen components aldolase, β-enolase, and glyceraldehyde-3-phosphate dehydrogenase are shown in Table 2.

TABLE 2

| Epitope No. | Protein name | Sequence of epitope | Position in sequence of allergen component |
|---|---|---|---|
| 1 | Alpha-actinin-3 | SEQ ID NO: 150 | Amino acids 81-95 of SEQ ID NO: 2 |
| 2 | Alpha-actinin-3 | SEQ ID NO: 151 | Amino acids 201-215 of SEQ ID NO: 2 |
| 3 | Alpha-actinin-3 | SEQ ID NO: 152 | Amino acids 251-265 of SEQ ID NO: 2 |
| 4 | Alpha-actinin-3 | SEQ ID NO: 153 | Amino acids 351-365 of SEQ ID NO: 2 |
| 5 | Alpha-actinin-3 | SEQ ID NO: 154 | Amino acids 841-855 of SEQ ID NO: 2 |
| 6 | EEF1A2 binding protein-like | SEQ ID NO: 155 | Amino acids 1021-1035 of SEQ ID NO: 5 |
| 7 | Alpha-1,4-glucan phosphorylase | SEQ ID NO: 156 | Amino acids 261-275 of SEQ ID NO: 10 |
| 8 | Alpha-1,4-glucan phosphorylase | SEQ ID NO: 157 | Amino acids 771-785 of SEQ ID NO: 10 |
| 9 | Elongation factor 2 | SEQ ID NO: 158 | Amino acids 11-25 of SEQ ID NO: 19 |
| 10 | Elongation factor 2 | SEQ ID NO: 159 | Amino acids 31-45 of SEQ ID NO: 19 |
| 11 | Heat shock cognate 70 kDa protein | SEQ ID NO: 160 | Amino acids 121-135 of SEQ ID NO: 26 |
| 12 | Heat shock cognate 70 kDa protein | SEQ ID NO: 161 | Amino acids 521-535 of SEQ ID NO: 26 |
| 13 | Heat shock cognate 70 kDa protein | SEQ ID NO: 162 | Amino acids 561-575 of SEQ ID NO: 26 |
| 14 | Serotransferrin | SEQ ID NO: 163 | Amino acids 101-115 of SEQ ID NO: 33 |
| 15 | Serotransferrin | SEQ ID NO: 164 | Amino acids 201-215 of SEQ ID NO: 33 |
| 16 | Serotransferrin | SEQ ID NO: 165 | Amino acids 271-285 of SEQ ID NO: 33 |
| 17 | Serotransferrin | SEQ ID NO: 166 | Amino acids 321-335 of SEQ ID NO: 33 |
| 18 | Serotransferrin | SEQ ID NO: 167 | Amino acids 521-535 of SEQ ID NO: 33 |
| 19 | Myosin binding protein H-like | SEQ ID NO: 168 | Amino acids 201-215 of SEQ ID NO: 43 |
| 20 | Myosin binding protein H-like | SEQ ID NO: 169 | Amino acids 261-275 of SEQ ID NO: 43 |
| 21 | Myosin binding protein H-like | SEQ ID NO: 170 | Amino acids 381-395 of SEQ ID NO: 43 |
| 22 | Myosin binding protein H-like | SEQ ID NO: 171 | Amino acids 441-455 of SEQ ID NO: 43 |
| 23 | Desmin (fragment) | SEQ ID NO: 172 | Amino acids 101-115 of SEQ ID NO: 56 |
| 24 | Desmin (fragment) | SEQ ID NO: 173 | Amino acids 281-295 of SEQ ID NO: 56 |
| 25 | Desmin (fragment) | SEQ ID NO: 174 | Amino acids 431-445 of SEQ ID NO: 56 |
| 26 | Capping protein (actin filament) muscle Z-line beta | SEQ ID NO: 175 | Amino acids 131-145 of SEQ ID NO: 61 |
| 27 | Capping protein (actin filament) muscle Z-line beta | SEQ ID NO: 176 | Amino acids 151-165 of SEQ ID NO: 61 |
| 28 | Capping protein (actin filament) muscle Z-line beta | SEQ ID NO: 177 | Amino acids 231-245 of SEQ ID NO: 61 |
| 29 | Capping protein (actin filament) muscle Z-line beta | SEQ ID NO: 178 | Amino acids 251-265 of SEQ ID NO: 61 |
| 30 | Myosin heavy chain, fast skeletal muscle-like | SEQ ID NO: 179 | Amino acids 61-75 of SEQ ID NO: 70 |
| 31 | Myosin heavy chain, fast skeletal muscle-like | SEQ ID NO: 180 | Amino acids 471-485 of SEQ ID NO: 70 |
| 32 | Myosin heavy chain, fast skeletal muscle-like | SEQ ID NO: 181 | Amino acids 621-635 of SEQ ID NO: 70 |
| 33 | Myosin heavy chain, fast skeletal muscle-like | SEQ ID NO: 182 | Amino acids 981-995 of SEQ ID NO: 70 |
| 34 | Myosin heavy chain, fast skeletal muscle-like | SEQ ID NO: 183 | Amino acids 1011-1025 of SEQ ID NO: 70 |
| 35 | Myosin heavy chain, fast skeletal muscle-like | SEQ ID NO: 184 | Amino acids 1041-1055 of SEQ ID NO: 70 |
| 36 | Myosin heavy chain, fast skeletal muscle-like | SEQ ID NO: 185 | Amino acids 1741-1755 of SEQ ID NO: 70 |

TABLE 2-continued

| Epitope No. | Protein name | Sequence of epitope | Position in sequence of allergen component |
|---|---|---|---|
| 37 | Glycogen phosphorylase, muscle form-like | SEQ ID NO: 186 | Amino acids 261-275 of SEQ ID NO: 110 |
| 38 | Myosin-binding protein C, fast-type-like | SEQ ID NO: 187 | Amino acids 181-195 of SEQ ID NO: 121 |
| 39 | Myosin-binding protein C, fast-type-like | SEQ ID NO: 188 | Amino acids 211-225 of SEQ ID NO: 121 |
| 40 | Myosin-binding protein C, fast-type-like | SEQ ID NO: 189 | Amino acids 221-235 of SEQ ID NO: 121 |
| 41 | Myosin-binding protein C, fast-type-like | SEQ ID NO: 190 | Amino acids 231-245 of SEQ ID NO: 121 |
| 42 | Myosin-binding protein C, fast-type-like | SEQ ID NO: 191 | Amino acids 251-265 of SEQ ID NO: 121 |
| 43 | Myosin-binding protein C, fast-type-like | SEQ ID NO: 192 | Amino acids 371-385 of SEQ ID NO: 121 |
| 44 | Myosin-binding protein C, fast-type-like | SEQ ID NO: 193 | Amino acids 491-505 of SEQ ID NO: 121 |
| 45 | Myosin-binding protein C, fast-type-like | SEQ ID NO: 194 | Amino acids 651-665 of SEQ ID NO: 121 |
| 46 | Myosin-binding protein C, fast-type-like | SEQ ID NO: 195 | Amino acids 831-845 of SEQ ID NO: 121 |
| 47 | Myosin-binding protein C, fast-type-like | SEQ ID NO: 196 | Amino acids 951-965 of SEQ ID NO: 121 |
| 48 | ATP synthase subunit beta, mitochondrial | SEQ ID NO: 197 | Amino acids 211-225 of SEQ ID NO: 138 |
| 49 | L-lactate dehydrogenase A chain-like | SEQ ID NO: 198 | Amino acids 11-25 of SEQ ID NO: 144 |
| 50 | Aldolase | SEQ ID NO: 199 | Amino acids 301-315 of SEQ ID NO: 445 |
| 51 | β-enolase | SEQ ID NO: 200 | Amino acids 51-65 of SEQ ID NO: 446 |
| 52 | β-enolase | SEQ ID NO: 201 | Amino acids 131-145 of SEQ ID NO: 446 |
| 53 | β-enolase | SEQ ID NO: 202 | Amino acids 191-205 of SEQ ID NO: 446 |
| 54 | Glyceraldehyde-3-phosphate dehydrogenase | SEQ ID NO: 203 | Amino acids 41-55 of SEQ ID NO: 447 |
| 55 | Glyceraldehyde-3-phosphate dehydrogenase | SEQ ID NO: 204 | Amino acids 251-265 of SEQ ID NO: 447 |

Amino acids important for binding of the epitope sequences to IgE antibodies from allergic patients were identified by the procedures of (B) and (C) mentioned above as to each of the epitopes.

(1) Epitope 1

In epitope 1 (SEQ ID NO: 150), SEQ ID NO: 207 corresponding to the amino acids at positions 1-10 and SEQ ID NO: 210 corresponding to the amino acids at positions 9-14 were identified as regions important for binding to IgE antibodies from patients.

In the region of SEQ ID NO: 207 important for binding, the amino acids at positions 7-9 were identified as amino acids particularly important for binding to IgE antibodies from allergic patients, and the amino acids at positions 1 and 10 were identified as amino acids influencing binding to IgE antibodies from allergic patients. The amino acids at positions 2-6 of SEQ ID NO: 207 had no influence on the binding activity against IgE antibodies from allergic patients when substituted by alanine.

In the region of SEQ ID NO: 210 important for binding, the amino acids at positions 1, 2 and 6 were identified as amino acids particularly important for binding to IgE antibodies from allergic patients. The amino acids at positions 3-5 of SEQ ID NO: 210 had no influence on the binding activity against IgE antibodies from allergic patients when substituted by alanine.

Hereinafter, epitopes 2 to 55 were similarly identified, and the results were summarized below in Table 3.

TABLE 3

| Epitope No. | SEQ ID NO of epitope | Positions of amino acids of region important for binding in epitope | SEQ ID NO of region important for binding | Particularly important amino acid in region important for binding | Binding-influencing amino acid in region important for binding | Non-binding-influencing amino acid in region important for binding |
|---|---|---|---|---|---|---|
| 1 | 150 | 1-10 | 207 | 7-9 | 1, 10 | 2-6 |
| 1 | 150 | 9-14 | 210 | 1, 2, 6 | — | 3-5 |
| 2 | 151 | 1-10 | 213 | 8-10 | 1, 6, 7 | 2-5 |
| 2 | 151 | 1-10 | 213 | 7, 9, 10 | 1, 2 | 3-6, 8 |
| 2 | 151 | 9-15 | 218 | 1, 3, 5 | 4, 6, 7 | 2 |
| 3 | 152 | 1-15 | 152 | 1, 3-15 | — | 2 |
| 4 | 153 | 1-15 | 153 | 1, 3, 7, 9, 14, 15 | 4, 5, 8 | 2, 6, 10-13 |
| 5 | 154 | 1-12 | 224 | 1, 3, 4, 10, 12 | 2, 11 | 5-9 |

TABLE 3-continued

| Epitope No. | SEQ ID NO of epitope | Positions of amino acids of region important for binding in epitope | SEQ ID NO of region important for binding | Particularly important amino acid in region important for binding | Binding-influencing amino acid in region important for binding | Non-binding-influencing amino acid in region important for binding |
|---|---|---|---|---|---|---|
| 5 | 154 | 11-14 | 227 | 3, 4 | 1 | 2 |
| 6 | 155 | 1-11 | 230 | 3, 4, 6, 7, 11 | 1, 2, 5, 9, 10 | 8 |
| 7 | 156 | 3-10 | 232 | 1, 8 | — | 2-7 |
| 7 | 156 | 1-10 | 235 | 1-3, 5, 8, 10 | 4, 9 | 6, 7 |
| 8 | 157 | 2-9 | 237 | 1, 3, 7, 8 | — | 2, 4-6 |
| 9 | 158 | 5-10 | 239 | 1, 2, 6 | — | 3-5 |
| 9 | 158 | 5-11 | 242 | 1, 2, 6, 7 | 3, 4 | 5 |
| 10 | 159 | 5-15 | 245 | 1, 5, 8, 11 | 3 | 2, 4, 6, 7, 9, 10 |
| 10 | 159 | 1-11 | 247 | 1, 2, 11 | — | 3-10 |
| 11 | 160 | 9-15 | 250 | 1, 6, 7 | 2, 5 | 3, 4 |
| 12 | 161 | 4-6 | 252 | 1, 3 | — | 2 |
| 12 | 161 | 9-15 | 255 | 2, 6, 7 | 1, 3 | 4, 5 |
| 13 | 162 | 1-7 | 258 | 1, 3, 5, 7 | 2, 6 | 4 |
| 13 | 162 | 8-14 | 261 | 1, 5-7 | 2, 3 | 4 |
| 14 | 163 | 1-5 | 263 | 3-5 | — | 1, 2 |
| 14 | 163 | 1-9 | 266 | 1, 3, 5, 6 | 2, 4, 7, 9 | 8 |
| 15 | 164 | 8-15 | 269 | 2, 7 | 4, 6 | 1, 3, 5, 8 |
| 16 | 165 | 2-6 | 271 | 3, 5 | — | 1, 2, 4 |
| 16 | 165 | 8-15 | 273 | 1-4, 8 | — | 5-7 |
| 18 | 167 | 2-10 | 276 | 1, 3, 9 | 4, 7 | 2, 5, 6, 8 |
| 18 | 167 | 8-12 | 279 | 3-5 | 1 | 2 |
| 19 | 168 | 2-10 | 282 | 1-3, 8, 9 | 5, 7 | 4, 6 |
| 19 | 168 | 11-15 | 284 | 1, 2, 4, 5 | — | 3 |
| 20 | 169 | 1-11 | 287 | 1, 3, 7, 11 | 5 | 2, 4, 6, 8-10 |
| 20 | 169 | 7-14 | 290 | 1, 3, 5, 8 | 7 | 2, 4, 6 |
| 21 | 170 | 2-15 | 292 | 1, 5, 14 | — | 2-4, 6-13 |
| 22 | 171 | 4-13 | 295 | 2, 5, 8 | 1, 10 | 3, 4, 6, 7, 9 |
| 22 | 171 | 8-13 | 297 | 1, 4, 6 | — | 2, 3, 5 |
| 22 | 171 | 8-15 | 300 | 4, 5, 7, 8 | 1, 3 | 2, 6 |
| 24 | 173 | 2-7 | 303 | 1, 5 | 6 | 2-4 |
| 24 | 173 | 1-9 | 306 | 2, 4, 9 | 1, 3, 6-8 | 5 |
| 24 | 173 | 12-15 | 308 | 1, 3, 4 | — | 2 |
| 25 | 174 | 1-7 | 310 | 1, 3, 4, 7 | — | 2, 5, 6 |
| 26 | 175 | 5-10 | 312 | 1, 2, 6 | — | 3-5 |
| 26 | 175 | 11-15 | 314 | 1, 2, 5 | — | 3, 4 |
| 27 | 176 | 2-12 | 317 | 6, 8, 11 | 1, 9, 10 | 2-5, 7 |
| 28 | 177 | 1-9 | 320 | 2, 4, 5 | 1, 6, 8, 9 | 3, 7 |
| 28 | 177 | 7-15 | 323 | 2, 5, 8, 9 | 1, 7 | 3, 4, 6 |
| 29 | 178 | 3-14 | 326 | 1-5, 8 | 10, 12 | 6, 7, 9, 11 |
| 30 | 179 | 1-11 | 329 | 1, 6, 9-11 | 5, 7, 8 | 2-4 |
| 30 | 179 | 7-15 | 332 | 3, 6, 9 | 1, 2 | 4, 5, 7, 8 |
| 31 | 180 | 7-15 | 335 | 1, 4-6, 9 | 3, 7, 8 | 2 |
| 32 | 181 | 1-10 | 338 | 2, 4-6, 10 | 1 | 3, 7-9 |
| 33 | 182 | 2-9 | 341 | 3, 4, 6, 8 | 1 | 2, 5, 7 |
| 33 | 182 | 2-11 | 344 | 3, 7, 8, 10 | 1, 4, 6 | 2, 5, 9 |
| 33 | 182 | 7-15 | 347 | 1, 6, 8, 9 | 2 | 3-5, 7 |
| 33 | 182 | 9-14 | 350 | 1, 4, 6 | 5 | 2, 3 |
| 34 | 183 | 5-14 | 353 | 2, 6, 8, 10 | 9 | 1, 3-5, 7 |
| 35 | 184 | 5-12 | 356 | 1, 5, 8 | 7 | 2-4, 6 |
| 35 | 184 | 9-15 | 359 | 1, 4, 6 | 3, 7 | 2, 5 |
| 36 | 185 | 5-12 | 362 | 3, 6, 8 | 1, 7 | 2, 4, 5 |
| 36 | 185 | 7-15 | 365 | 4, 6, 8, 9 | 1, 5 | 2, 3, 7 |
| 37 | 186 | 1-10 | 367 | 1, 3, 10 | — | 2, 4-9 |
| 37 | 186 | 11-15 | 370 | 1, 2, 5 | 4 | 3 |
| 38 | 187 | 2-11 | 373 | 1, 3, 6-8 | 9, 10 | 2, 4, 5 |
| 38 | 187 | 7-14 | 376 | 1, 3-6 | 7, 8 | 2 |
| 39 | 188 | 1-10 | 379 | 1, 6, 10 | 4, 7, 8 | 2, 3, 5, 9 |
| 39 | 188 | 8-15 | 382 | 3, 5, 7, 8 | 1 | 2, 4, 6 |
| 40 | 189 | 2-8 | 384 | 1, 3, 4, 7 | — | 2, 5, 6 |
| 41 | 190 | 2-9 | 386 | 1, 2, 7, 8 | — | 3-6 |
| 41 | 190 | 1-10 | 388 | 1, 4, 8-10 | — | 2, 3, 5-7 |
| 41 | 190 | 9-15 | 390 | 1, 6, 7 | — | 2-5 |
| 42 | 191 | 6-11 | 392 | 1-4 | — | 5, 6 |
| 42 | 191 | 6-15 | 395 | 1, 3, 7, 10 | 8 | 2, 4-6, 9 |
| 43 | 192 | 5-8 | 397 | 1, 3 | — | 2, 4 |
| 43 | 192 | 7-15 | 400 | 1, 2, 5, 6 | 7, 8, 9 | 3, 4 |
| 44 | 193 | 1-7 | 402 | 1, 5-7 | — | 2-4 |
| 44 | 193 | 6-15 | 405 | 1-3, 6, 8, 10 | 5, 7 | 4, 9 |
| 45 | 194 | 3-7 | 407 | 1, 2, 3 | — | 4, 5 |
| 46 | 195 | 2-13 | 409 | 1, 9, 10, 12 | — | 2-8, 11 |
| 47 | 196 | 1-10 | 411 | 1, 7, 9, 10 | — | 2-6, 8 |
| 47 | 196 | 1-8 | 413 | 1, 4, 8 | — | 2, 3, 5-7 |

TABLE 3-continued

| Epitope No. | SEQ ID NO of epitope | Positions of amino acids of region important for binding in epitope | SEQ ID NO of region important for binding | Particularly important amino acid in region important for binding | Binding-influencing amino acid in region important for binding | Non-binding-influencing amino acid in region important for binding |
|---|---|---|---|---|---|---|
| 48 | 197 | 7-10 | 415 | 1, 3, 4 | — | 2 |
| 48 | 197 | 9-14 | 417 | 1, 6 | — | 2-5 |
| 49 | 198 | 5-13 | 420 | 2-5, 7, 8 | 1, 9 | 6 |
| 50 | 199 | 1-12 | 423 | 2, 4, 12 | 1, 6, 10 | 3, 5, 7-9, 11 |
| 50 | 199 | 9-15 | 425 | 1, 4, 7 | — | 2, 3, 5, 6 |
| 51 | 200 | 6-13 | 428 | 1-5 | 6, 8 | 7 |
| 52 | 201 | 1-10 | 431 | 1, 4, 6, 10 | 7, 9 | 2, 3, 5, 8 |
| 52 | 201 | 6-15 | 434 | 1, 5, 7, 8, 10 | 6, 9 | 2-4 |
| 53 | 202 | 6-15 | 436 | 1, 2, 7-10 | — | 3-6 |
| 54 | 203 | 1-15 | 203 | 1, 9, 13-15 | 10, 11 | 2-8, 12 |
| 55 | 204 | 3-10 | 441 | 1, 2, 5, 8 | — | 3, 4, 6, 7 |
| 55 | 204 | 7-12 | 444 | 1, 2, 3, 6 | 4 | 5 |

Example 11: Confirmation of Epitope Cross-Reactivity

Amino acids other than particularly important amino acids in the region (SEQ ID NO: 250) important for binding, in epitope No. 11 having the amino acid sequence "SMVLVKMKEIAEAYL" (SEQ ID NO: 160) found in salmon heat shock cognate 70 kDa protein in Table 3 were defined as any given amino acid (X). NCBI was searched for proteins having the resulting amino acid sequence "EXXXXYL" (SEQ ID NO: 248). As a result, the amino acid sequence "AMVLVKMKETAEAYL" (SEQ ID NO: 451) of bastard halibut heat shock 70 kDa protein (accession number: XP_019944736.1) was identified.

The binding activity of peptides comprising the amino acid sequences of SEQ ID NOs: 160 and 451 against an IgE antibody from one patient having allergies to salmons and bastard halibut, a peach and an apple was confirmed by ELISA. The peptides were synthesized such that the peptides were N-terminally biotinylated by the Fmoc method.

To be specific, ELISA was carried out according to the following procedure.

(1) The concentrations of the biotinylated peptides were adjusted to 1 µg/mL with PBST.

(2) Each peptide solution was added at 40 µL to each well of a 384-well plate coated with streptavidin, and shaken at room temperature for one hour. After collection of the solution, the wells were washed with PBS five times.

(3) A 1:5 dilution of Blocking one (diluted with MQ) was added at 40 µL thereto and shaken at room temperature for 15 minutes. After removal of the solution, the wells were washed with PBS five times.

(4) A diluted serum solution (1:10, diluting solution: Blocking one produced by Nacalai Tesque, Inc.) was added at 40 µL thereto and shaken at room temperature for one hour. After removal of the solution, the wells were washed with PBS five times.

(5) A diluted secondary antibody solution (1:5000, diluting solution: Blocking one produced by Nacalai Tesque, Inc.) was added at 40 µL thereto and shaken at room temperature for one hour. After removal of the solution, the wells were washed with PBS five times.

(6) 1-Step Ultra TMB-ELISA (Thermo Fisher Scientific) was added at 40 µL thereto and shaken at room temperature for 15 minutes.

(7) 2 M H2SO4 was added at 40 µL thereto. Absorbance at 450 nm was measured.

A peptide having this amino acid sequence "AMVLVKMKETAEAYL" of bastard halibut heat shock 70 kDa protein and a peptide having the amino acid sequence "SMVLVKMKEIAEAYL" of salmon heat shock cognate 70 kDa protein were each prepared by the same procedure as in Example 10(A), and the presence or absence of binding thereto of IgE antibodies present in the serum of a fish-allergic patient having allergy symptoms to salmon and bastard halibut and the serum of a non-fish-allergic subject (serum mixture from 4 subjects) was measured by the same technique as therein. The results are shown in FIG. 5.

Figure 5:
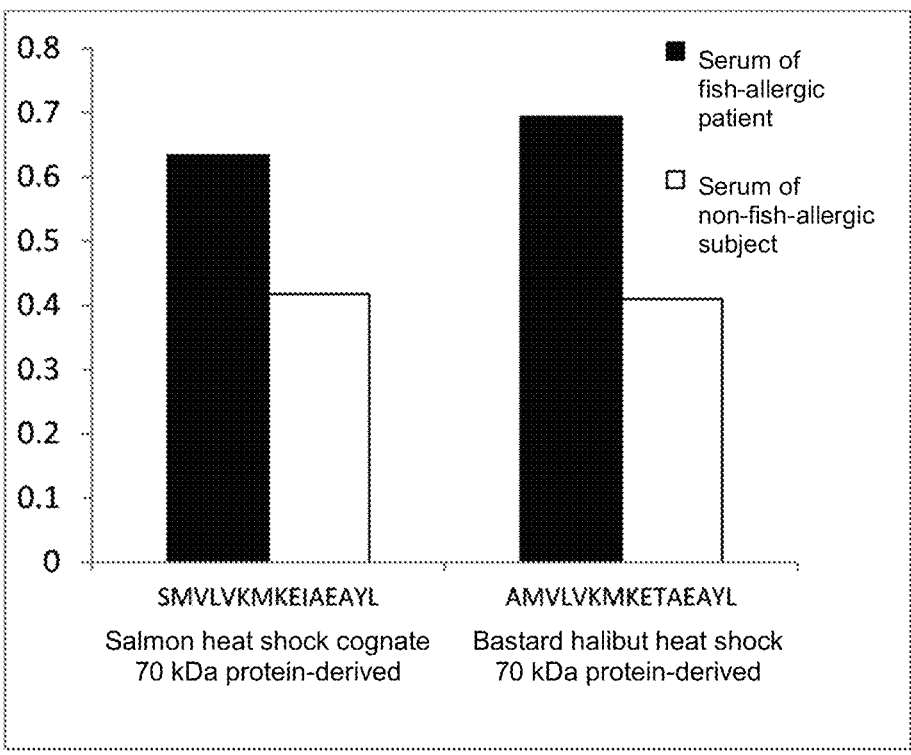
FIG. 5 is a diagram showing results of measuring chemiluminescence using the sera of a fish-allergic patient and a non-fish-allergic subject as to a peptide of epitope No. 11 (SEQ ID NO: 160) having the amino acid sequence "SMVLVKMKEIAEAYL" derived from salmon heat shock cognate 70 kDa protein, and a peptide having the amino acid sequence "AMVLVKMKETAEAYL" derived from bastard halibut heat shock cognate 70 kDa protein. The numeric values on the ordinate represent absorbance for light at a wavelength of 450 nm.

As is evident from FIG. 5, an IgE antibody bound in a patient-specific manner to the peptide having the amino acid sequence derived from bastard halibut heat shock 70 kDa protein, as in the peptide having the amino acid sequence derived from salmon heat shock cognate 70 kDa protein. Thus, epitope No. 11 was confirmed as an epitope exhibiting cross-reactivity between the fish species salmon and bastard halibut. In addition to epitope No. 11, epitope No. 1 to No. 55 (SEQ ID NOs: 150-204) identified in Example 10 were also confirmed to have cross-reactivity.

These epitopes have cross-reactivity with bastard halibut as well as horse mackerel, conger, blackhead seabream, mackerel, sea bream, cod, amberjack, eel, and the like. This indicates that these epitopes can be used for detecting antigen cross-reactivity irrespective of fish species.

The invention claimed is:

1. A method for detecting binding between an antigen and an antibody present in a sample from a fish-allergic patient, said method comprising contacting the antigen with said antibody to detect binding, wherein said antigen is a polypeptide comprising:

(a) an epitope having the amino acid sequence selected from SEQ ID NOs: 150-152 and 154, wherein (i) the polypeptide has an amino acid sequence having at least 90% sequence identity to the amino acid sequence of any one of SEQ ID NO: 2 or (ii) the polypeptide is encoded by a nucleotide sequence having at least 90% identity to the nucleotide sequence of SEQ ID NO: 1;

(b) an epitope having the amino acid sequence selected from SEQ ID NOs: 160-162, wherein (i) the polypeptide has an amino acid sequence having at least 90% sequence identity to the amino acid sequence of any one of SEQ ID NO: 26 or (ii) the polypeptide is encoded by a nucleotide sequence having at least 90% identity to the nucleotide sequence of SEQ ID NO: 25; or (c) an epitope having the amino acid sequence selected from SEQ ID NOs: 175-178, wherein (i) the polypeptide has an amino acid sequence having at least 90% sequence identity to the amino acid sequence of any one of SEQ ID NO: 61 or (ii) the polypeptide is encoded by a nucleotide sequence having at least 90% identity to the nucleotide sequence of SEQ ID NO: 60;

wherein said polypeptide as defined in any one of (a), (b) and (c) specifically binds to said antibody, and wherein said antigen is immobilized to a carrier or a surface.

2. The method according to claim 1, wherein the polypeptide is:

(a) a polypeptide comprising the epitope having the amino acid sequence selected from SEQ ID NOs: 150-152 and 154, wherein (i) the polypeptide has an amino acid sequence having at least 95% identity to the amino acid sequence of any one of SEQ ID NO: 2 or (ii) the polypeptide is encoded by a nucleotide sequence having at least 95% identity to the nucleotide sequence of SEQ ID NO: 1;

(b) a polypeptide comprising the epitope having the amino acid sequence selected from SEQ ID NOs:

160-162, wherein (i) the polypeptide has an amino acid sequence having at least 95% identity to the amino acid sequence of any one of SEQ ID NO: 26 or (ii) the polypeptide is encoded by a nucleotide sequence having at least 95% identity to the nucleotide sequence of SEQ ID NO: 25; or (c) a polypeptide comprising the epitope having the amino acid sequence selected from SEQ ID NOs: 175-178, wherein (i) the polypeptide has an amino acid sequence having at least 95% identity to the amino acid sequence of any one of SEQ ID NO: 61 or (ii) the polypeptide is encoded by a nucleotide sequence having at least 95% identity to the nucleotide sequence of SEQ ID NO: 60.

3. A method for detecting binding between an antigen and an antibody present in a sample from a fish-allergic patient, said method comprising detecting binding between said antigen and said antibody with a reagent capable of detecting binding between the antigen and the antibody, wherein said antigen is a polypeptide comprising:

(a) an epitope having the amino acid sequence selected from SEQ ID NOs: 150-152 and 154, wherein (i) the polypeptide has an amino acid sequence having at least 90% sequence identity to the amino acid sequence of any one of SEQ ID NO: 2 or (ii) the polypeptide is encoded by a nucleotide sequence having at least 90% identity to the nucleotide sequence of SEQ ID NO: 1;

(b) an epitope having the amino acid sequence selected from SEQ ID NOs: 160-162, wherein (i) the polypeptide has an amino acid sequence having at least 90% sequence identity to the amino acid sequence of any one of SEQ ID NO: 26 or (ii) the polypeptide is encoded by a nucleotide sequence having at least 90% identity to the nucleotide sequence of SEQ ID NO: 25; or (c) an epitope having the amino acid sequence selected from SEQ ID NOs: 175-178, wherein (i) the polypeptide has an amino acid sequence having at least 90% sequence identity to the amino acid sequence of any one of SEQ ID NO: 61 or (ii) the polypeptide is encoded by a nucleotide sequence having at least 90% identity to the nucleotide sequence of SEQ ID NO: 60; wherein said polypeptide as defined in any one of (a), (b) and (c) specifically binds to said antibody.

4. The method according to claim 3, wherein the polypeptide is:

(a) a polypeptide comprising the epitope having the amino acid sequence selected from SEQ ID NOs: 150-152 and 154, wherein (i) the polypeptide has an amino acid sequence having at least 95% identity to the amino acid sequence of any one of SEQ ID NO: 2 or (ii) the polypeptide is encoded by a nucleotide sequence having at least 95% identity to the nucleotide sequence of SEQ ID NO: 1;

(b) a polypeptide comprising the epitope having the amino acid sequence selected from SEQ ID NOs: 160-162, wherein (i) the polypeptide has an amino acid sequence having at least 95% identity to the amino acid sequence of any one of SEQ ID NO: 26 or (ii) the polypeptide is encoded by a nucleotide sequence having at least 95% identity to the nucleotide sequence of SEQ ID NO: 25; or (c) a polypeptide comprising the epitope having the amino acid sequence selected from SEQ ID NOs: 175-178, wherein (i) the polypeptide has an amino acid sequence having at least 95% identity to the amino acid sequence of any one of SEQ ID NO: 61 or (ii) the polypeptide is encoded by a nucleotide sequence having at least 95% identity to the nucleotide sequence of SEQ ID NO: 60.

* * * * *